US009522920B2

(12) United States Patent
Albrecht et al.

(10) Patent No.: US 9,522,920 B2
(45) Date of Patent: *Dec. 20, 2016

(54) BROMODOMAIN INHIBITORS AND USES THEREOF

(71) Applicant: Constellation Pharmaceuticals, Inc., Cambridge, MA (US)

(72) Inventors: Brian K. Albrecht, Cambridge, MA (US); James Edmund Audia, Cambridge, MA (US); Alexandre Côté, Cambridge, MA (US); Victor S. Gehling, Somerville, MA (US); Jean-Christophe Harmange, Andover, MA (US); Michael Charles Hewitt, Somerville, MA (US); Yves Leblanc, Kirkland (CA); Christopher G. Nasveschuk, Stoneham, MA (US); Alexander M. Taylor, Cambridge, MA (US); Rishi G. Vaswani, Lexington, MA (US)

(73) Assignee: CONSTELLATION PHARMACEUTICALS, INC., Cambridge, MA (US)

( * ) Notice: Subject to any disclaimer, the term of this patent is extended or adjusted under 35 U.S.C. 154(b) by 116 days.

This patent is subject to a terminal disclaimer.

(21) Appl. No.: 14/313,148

(22) Filed: Jun. 24, 2014

(65) Prior Publication Data

US 2014/0371206 A1  Dec. 18, 2014

Related U.S. Application Data

(63) Continuation of application No. 13/309,646, filed on Dec. 2, 2011, now Pat. No. 8,796,261.

(60) Provisional application No. 61/540,788, filed on Sep. 29, 2011, provisional application No. 61/540,725, filed on Sep. 29, 2011, provisional application No. 61/482,473, filed on May 4, 2011, provisional application No. 61/451,332, filed on Mar. 10, 2011, provisional application No. 61/419,119, filed on Dec. 2, 2010.

(51) Int. Cl.
| | |
|---|---|
| *A61K 31/55* | (2006.01) |
| *C07D 498/04* | (2006.01) |
| *C07D 498/14* | (2006.01) |
| *C07D 498/20* | (2006.01) |
| *C07D 498/22* | (2006.01) |
| *C07K 14/47* | (2006.01) |
| *A61K 31/424* | (2006.01) |

(52) U.S. Cl.
CPC ......... *C07D 498/04* (2013.01); *A61K 31/424* (2013.01); *A61K 31/55* (2013.01); *C07D 498/14* (2013.01); *C07D 498/20* (2013.01); *C07D 498/22* (2013.01); *C07K 14/4702* (2013.01)

(58) Field of Classification Search
CPC .............................. A61K 31/55; C07D 498/04
USPC ........................................ 514/215; 540/578
See application file for complete search history.

(56) References Cited

U.S. PATENT DOCUMENTS

| | | | |
|---|---|---|---|
| 3,523,939 A | 8/1970 | Fryer et al. |
| 3,681,343 A | 8/1972 | Hester, Jr. |
| 3,709,898 A | 1/1973 | Hester, Jr. |
| 3,763,144 A | 10/1973 | Hellerback et al. |
| 3,781,289 A | 12/1973 | Hester, Jr. |
| 3,850,942 A | 11/1974 | Hester et al. |
| 3,886,141 A | 5/1975 | Chase |
| 3,903,103 A | 9/1975 | Hester, Jr. |
| 3,966,736 A | 6/1976 | Szmuszkovicz |
| 4,110,455 A | 8/1978 | von Bebenburg et al. |
| 4,155,904 A | 5/1979 | Schlesinger |
| 4,327,026 A | 4/1982 | Branca et al. |
| 4,374,773 A | 2/1983 | Branca et al. |
| 4,377,522 A | 3/1983 | Branca et al. |
| 4,455,307 A | 6/1984 | Hester, Jr. |
| 4,820,834 A | 4/1989 | Evans et al. |
| 4,959,361 A | 9/1990 | Walser |
| 4,992,437 A | 2/1991 | Naka et al. |
| 5,004,741 A | 4/1991 | Evans et al. |
| 5,175,159 A | 12/1992 | Bock et al. |
| 5,185,331 A | 2/1993 | Freidinger et al. |
| 5,185,442 A | 2/1993 | Weber et al. |
| 5,206,234 A | 4/1993 | Bock et al. |
| 5,382,579 A | 1/1995 | Okano et al. |
| 5,409,909 A | 4/1995 | Okano et al. |

(Continued)

FOREIGN PATENT DOCUMENTS

| | | |
|---|---|---|
| CA | 2020806 A1 | 1/1991 |
| CA | 2032222 A1 | 6/1991 |

(Continued)

OTHER PUBLICATIONS

Proctor, George R., et al., "Azabenzycycloheptones, Part 19, Formation of Some Heterocyclic Annulated Compounds from 1,2,3,4-tetrahydro-1-benzazepine derivatives," Journal of the Chemical Society, Perkin Transactions 1, Chemical Society, Letchworth, GB, Jan. 1, 1978, pp. 862-879.

Venkateswarlu, Peesapati, et al., "Synthesis and Biological Activity of Some New Heterocyclic Annelated Compounds from 2,3,4,5-tetrahydro-1-benzazepines," Indian Journal of Chemistry: IJC, Council of Scientific and Industrial Research, IN., vol. 35B, Dec. 1, 1996, pp. 1287-1293.

Grey, R., et al., "Structure-Based Design of 3-Aryl-6-Amino-Triazolo[4,3-b] Pyridazine Inhibitors of Pim-1 Kinase," Bioorg. Med, Chem, Lett., vol. 19, No. 11, Jun. 1, 2009, pp. 3019-3022.

(Continued)

*Primary Examiner* — Brenda Coleman
(74) *Attorney, Agent, or Firm* — McCarter & English, LLP; Steven G. Davis; Michael J. DeGrazia

(57) ABSTRACT

The present invention relates to compounds useful as inhibitors of bromodomain-containing proteins. The invention also provides pharmaceutically acceptable compositions comprising compounds of the present invention and methods of using said compositions in the treatment of various disorders.

21 Claims, No Drawings

(56) References Cited

U.S. PATENT DOCUMENTS

| | | | |
|---|---|---|---|
| 5,428,004 A | 6/1995 | Earley et al. | |
| 5,439,905 A | 8/1995 | Naka et al. | |
| 5,550,126 A | 8/1996 | Horwell et al. | |
| 5,593,988 A | 1/1997 | Tahara et al. | |
| 5,681,833 A | 10/1997 | Castro Pineiro et al. | |
| 5,683,998 A | 11/1997 | Shibayama et al. | |
| 5,698,552 A | 12/1997 | Weber et al. | |
| 5,712,274 A | 1/1998 | Sueoka et al. | |
| 5,721,231 A | 2/1998 | Moriwaki et al. | |
| 5,733,905 A | 3/1998 | Albright et al. | |
| 5,739,129 A | 4/1998 | Aquino et al. | |
| 5,753,647 A | 5/1998 | Weber et al. | |
| 5,753,649 A | 5/1998 | Tahara et al. | |
| 5,760,031 A | 6/1998 | Albright et al. | |
| 5,795,887 A | 8/1998 | Aquino et al. | |
| 5,840,895 A | 11/1998 | Ohtsuka et al. | |
| 5,843,941 A | 12/1998 | Marsters, Jr. et al. | |
| 5,869,483 A | 2/1999 | Albright et al. | |
| 5,929,069 A | 7/1999 | Shudo | |
| 6,121,256 A | 9/2000 | Shudo | |
| 6,433,167 B1 | 8/2002 | Fujita et al. | |
| 6,458,782 B1 | 10/2002 | Kagechika et al. | |
| 6,476,017 B2 | 11/2002 | Shudo | |
| 6,649,366 B2 | 11/2003 | Chubinskaya et al. | |
| 6,777,408 B1 | 8/2004 | Liberatore et al. | |
| 7,015,213 B1 | 3/2006 | Bigg et al. | |
| 7,160,880 B1 | 1/2007 | Feldman et al. | |
| 7,250,410 B2 | 7/2007 | Bourguignon et al. | |
| 7,435,730 B2 | 10/2008 | Feldman et al. | |
| 7,442,795 B2 | 10/2008 | Bryans et al. | |
| 7,473,689 B2 | 1/2009 | Feldman et al. | |
| 7,482,337 B2 | 1/2009 | Himmelsbach et al. | |
| 7,485,635 B2 | 2/2009 | Feldman et al. | |
| 7,528,127 B2 | 5/2009 | Feldman et al. | |
| 7,696,212 B2 | 4/2010 | Himmelsbach et al. | |
| 8,796,261 B2 * | 8/2014 | Albrecht | C07D 498/04 514/215 |
| 9,249,161 B2 | 2/2016 | Albrecht et al. | |
| 2001/0039272 A1 | 11/2001 | Shudo | |
| 2002/0052358 A1 | 5/2002 | Chubinskaya et al. | |
| 2004/0053919 A1 | 3/2004 | Chubinskaya et al. | |
| 2004/0138214 A1 | 7/2004 | Himmelsbach et al. | |
| 2004/0152888 A1 | 8/2004 | Bourguignon et al. | |
| 2006/0128695 A1 | 6/2006 | Bourguignon et al. | |
| 2007/0093475 A1 | 4/2007 | Feldman et al. | |
| 2007/0105844 A1 | 5/2007 | Glick et al. | |
| 2007/0135419 A1 | 6/2007 | Feldman et al. | |
| 2007/0135420 A1 | 6/2007 | Feldman et al. | |
| 2007/0135421 A1 | 6/2007 | Feldman et al. | |
| 2009/0093457 A1 | 4/2009 | Himmelsbach et al. | |
| 2010/0041643 A1 | 2/2010 | Adachi et al. | |
| 2010/0144703 A1 | 6/2010 | Himmelsbach et al. | |
| 2010/0256123 A1 | 10/2010 | Sakuma et al. | |
| 2010/0286127 A1 | 11/2010 | Miyoshi et al. | |
| 2010/0331316 A1 | 12/2010 | Paoletti et al. | |
| 2011/0230460 A1 | 9/2011 | Kempen et al. | |
| 2014/0135316 A1 | 5/2014 | Albrecht et al. | |
| 2015/0148333 A1 | 5/2015 | Albrecht et al. | |
| 2015/0148337 A1 * | 5/2015 | Albrecht | C07D 498/04 514/215 |

FOREIGN PATENT DOCUMENTS

| | | |
|---|---|---|
| CA | 2032427 A1 | 6/1991 |
| CA | 2050268 A1 | 3/1992 |
| CA | 2056809 A1 | 6/1992 |
| CA | 2059353 A1 | 7/1992 |
| CA | 2062456 A1 | 9/1992 |
| CA | 2071092 A1 | 12/1992 |
| CA | 1327570 C | 3/1994 |
| CA | 02258053 A1 | 12/1997 |
| DE | 2640599 A1 | 3/1978 |
| DE | 3936828 A1 | 5/1990 |
| DE | 4006471 A1 | 9/1990 |
| DE | 4027470 A1 | 3/1992 |
| DE | 4107521 A1 | 9/1992 |
| DE | 4128581 A1 | 3/1993 |
| DE | 4219659 A1 | 12/1993 |
| EP | 0169392 A2 | 1/1986 |
| EP | 0315698 A1 | 5/1989 |
| EP | 0328924 A2 | 8/1989 |
| EP | 0342587 A2 | 11/1989 |
| EP | 0348523 A1 | 1/1990 |
| EP | 0367110 A1 | 5/1990 |
| EP | 0407955 A1 | 1/1991 |
| EP | 0480455 A1 | 4/1992 |
| EP | 495473 A1 | 7/1992 |
| EP | 0514125 A1 | 11/1992 |
| EP | 0559891 A1 | 9/1993 |
| EP | 0656361 A4 | 1/1995 |
| EP | 636625 A2 | 2/1995 |
| EP | 0661284 A4 | 5/1995 |
| EP | 0692483 A4 | 11/1995 |
| EP | 0989131 A1 | 3/2000 |
| EP | 1297836 A1 | 4/2003 |
| EP | 1887008 A1 | 2/2008 |
| EP | 2239264 A1 | 10/2010 |
| FR | 2154511 A1 | 5/1973 |
| FR | 2220257 A1 | 10/1974 |
| GB | 1409693 A | 10/1975 |
| GB | 2259013 A | 3/1993 |
| JP | 7179471 | 7/1995 |
| JP | 11228576 | 8/1999 |
| JP | 2959591 B2 | 10/1999 |
| JP | 3223290 B2 | 10/2001 |
| JP | 03264588 B2 | 3/2002 |
| JP | 03264589 B2 | 3/2002 |
| JP | 04226993 B2 | 2/2009 |
| WO | 9303717 A1 | 3/1993 |
| WO | 9307129 A1 | 4/1993 |
| WO | 9312791 A1 | 7/1993 |
| WO | 9313776 A1 | 7/1993 |
| WO | 9319052 A1 | 9/1993 |
| WO | 9406801 A1 | 3/1994 |
| WO | 9426723 A2 | 11/1994 |
| WO | 9514694 A1 | 6/1995 |
| WO | 9528399 A1 | 10/1995 |
| WO | 9711061 A1 | 3/1997 |
| WO | 9747622 A1 | 12/1997 |
| WO | 9811111 A1 | 3/1998 |
| WO | 9828268 A2 | 7/1998 |
| WO | 9858930 A1 | 12/1998 |
| WO | 9929324 A1 | 6/1999 |
| WO | 0006157 A1 | 2/2000 |
| WO | 0012547 A2 | 3/2000 |
| WO | 0054778 A1 | 9/2000 |
| WO | 0069836 A1 | 11/2000 |
| WO | 0147510 A2 | 7/2001 |
| WO | 02098865 A2 | 12/2002 |
| WO | 03/074525 A1 | 9/2003 |
| WO | 2004041258 A2 | 5/2004 |
| WO | 2004041820 A1 | 5/2004 |
| WO | 2004/058769 A2 | 7/2004 |
| WO | 2005/002590 A1 | 1/2005 |
| WO | 2005099759 A1 | 10/2005 |
| WO | 2006038560 A1 | 4/2006 |
| WO | 2006129623 A1 | 12/2006 |
| WO | 2007016087 A2 | 2/2007 |
| WO | 2007050587 A2 | 5/2007 |
| WO | 2007079820 A1 | 7/2007 |
| WO | 2008023847 A1 | 2/2008 |
| WO | 2008109856 A2 | 9/2008 |
| WO | 2009059191 A1 | 5/2009 |
| WO | 2009081349 A1 | 7/2009 |
| WO | 2009152589 A1 | 12/2009 |
| WO | 2010008459 A1 | 1/2010 |
| WO | 2010049466 A1 | 5/2010 |
| WO | 2010121164 A2 | 10/2010 |
| WO | 2010128685 A1 | 11/2010 |
| WO | 2011037128 A1 | 3/2011 |
| WO | 2011054553 A1 | 5/2011 |
| WO | 2011054841 A1 | 5/2011 |
| WO | 2011054843 A1 | 5/2011 |

(56) References Cited

FOREIGN PATENT DOCUMENTS

| WO | 2011054844 A1 | 5/2011 |
|---|---|---|
| WO | 2011054845 A1 | 5/2011 |
| WO | 2011054846 A1 | 5/2011 |
| WO | 2011054848 A1 | 5/2011 |
| WO | 2011054851 A1 | 5/2011 |
| WO | 2011079315 A1 | 6/2011 |
| WO | 2011123678 A2 | 10/2011 |
| WO | 2011143651 A1 | 11/2011 |
| WO | 2011143657 A1 | 11/2011 |
| WO | 2011143660 A2 | 11/2011 |
| WO | 2011143669 A2 | 11/2011 |
| WO | 2011/161031 A1 | 12/2011 |
| WO | 2012/075383 A2 | 6/2012 |
| WO | 2013024104 A1 | 2/2013 |
| WO | 2013030150 A1 | 3/2013 |
| WO | 2013033268 A2 | 3/2013 |
| WO | 2013033269 A1 | 3/2013 |
| WO | 2013033270 A2 | 3/2013 |
| WO | 2013033420 A1 | 3/2013 |

OTHER PUBLICATIONS

Filippakopoulos, et al., "Selective Inhibition of BET Bromodomains," Nature, Dec. 30, 2010, vol. 468, pp. 1067-1073.
Kosychova, L., et al., "Synthesis of Substitute 5,6-Dihydro-4H-[1,2,4]Triazolo[4,3-a][1,5]Benzodiazepines," Chemistry of Heterocyclic Compounds, vol. 40, No. 6, Jun. 2004, pp. 811-815.
Gussio, Rick, et al., "All-Atom Models for the Non-Nucleoside Binding Site of HIV-1 Reverse Transcriptase Complexed with Inhibitors: A 3D QSAR Approach," J. Med. Chem., Apr. 12, 1996, vol. 39, No. 8, pp. 1645-1650.
International Search Report and Written Opinion, dated Jul. 23, 2013, Int'l Appl'n No. PCT/US2013/044449, Int'l Filing Date Jun. 6, 2013.
International Search Report and Written Opinion, dated Feb. 21, 2013, Int'l Appl'n No. PCT/US2012/042825, Int'l Filing Date Jun. 15, 2012.
International Preliminary Report on Patentability, dated Nov. 5, 2013, Int'l Appl'n No. PCT/US2012/036569, Int'l Filing Date May 4, 2012.
International Search Report and Written Opinion, dated Jul. 23, 2013, Int'l Appl'n No. PCT/US2013/044444, Int'l Filing Date Jun. 6, 2013.
International Search Report and Written Opinion, dated Apr. 17, 2012, Int'l Appl'n No. PCT/US2011/063173, Int'l Filing Date Dec. 2, 2011.
International Preliminary Report on Patentability, mailed Jan. 3, 2014, International Application No. PCT/US2012/042825; International Filing Date: Jun. 15, 2012, 10 pages.
Di Bracco, M., et al., "1,5-Benzodiazepines. Part XII. Synthesis and Biological Evaluations of Tricyclic and Tetracyclic 1,5-benzodiazepine Derivatives as Nevirapine Analogues," European Journal of Medicinal Chemistry, vol. 36, No. 11-12, Dec. 1, 2001, pp. 935-949, XP027205317.
Jiban K. Chakrabarti, et al., "Chemistry of Adamantane. Part XI. 1,2-Disubstituted Adamantanes. Synthesis and Reactions of Adamantano[2,1-b ]- and protoadamantano-[4,5-b ][1,5]benzodiazepines," Journal of Heterocyclic Chemistry, vol. 15, No. 5, Aug. 1, 1978, pp. 705-710, XP055136791.
Kosychova, et al., "Synthesis of New [1,2,4]triazolo[4,3-a][1,5]benzodiaze-pine derivatives," Lietuvos Mokslu Akademija. Chemija, vol. 22, No. 1, Jan. 1, 2011, pp. 60-64, XP055136653.
Kosychova, et al., "Synthesis of novel 5,6-dihydro-4H-[1,2,4] triazolo[4,3-a][1,5]benzodiazepines," Rigas Tehniskas Universitates Zinatniskie Raksti. Serija 1: Materialzinatne Un Lietiska Kimija, vol. 22, Jan. 1, 2010, pp. 94-99, XP009179817.
Szarvasi, E., et al., "(4H)Dihydro-5,6(s)-triazolo-(4,3-a)benzodiazepines-1,5 a activite analgesique et anti-inflammatoire," European Journal of Medicinal Chemistry, vol. 13, No. 2, Mar. 1, 1978, pp. 113-119, XP009179828.
Terrett, N.K., et al., "Imidazoú2',3':6,5 3/4 Dipyridoú3,2-B:2',3'-E 3/4—1,4-Diazepines: Non-Nucleoside HIV-1 Reverse Transcriptase Inhibitors with Greater Enzyme Affinity than Nevirapine," Bioorganic & Medicinal Chemistry Letters, vol. 12, No. 2, Dec. 1, 1992, pp. 1745-1750, XP002912883.

* cited by examiner

BROMODOMAIN INHIBITORS AND USES THEREOF

RELATED APPLICATIONS

This application is a Continuation of U.S. patent application Ser. No. 13/309,646, filed Dec. 2, 2011, which claims the benefit of U.S. Provisional application 61/419,119, filed on Dec. 2, 2010, and U.S. Provisional application 61/540,725 filed on Sep. 29, 2011. U.S. application Ser. No. 13/309,646 also claims the benefit of U.S. Provisional application 61/451,332, filed on Mar. 10, 2011; U.S. Provisional application 61/482,473, filed on May 4, 2011; and U.S. Provisional application 61/540,788, filed on Sep. 29, 2011. The entire contents of the above-referenced applications are herein incorporated by reference.

TECHNICAL FIELD OF THE INVENTION

The present invention relates to compounds useful as inhibitors of one or more bromodomain-containing proteins.

BACKGROUND OF THE INVENTION

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin: the defining template for gene regulation. Far from serving as mere packaging modules, chromatin templates form the basis of a newly appreciated and fundamentally important set of gene control mechanisms termed epigenetic regulation. By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding proteins or chromatin-modifying enzymes. Significantly, an increasing number of these proteins have been associated with a variety of disorders such as neurodegenerative disorders, metabolic diseases, inflammation, and cancer. Thus, highly selective therapeutic agents directed against this emerging class of gene regulatory proteins promise new approaches to the treatment of human diseases.

SUMMARY OF THE INVENTION

In one aspect, the invention provides a compound of formula I:

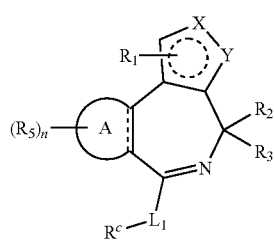

I or a pharmaceutically acceptable salt thereof, wherein:
X is O or N;
Y is O or N; wherein at least one of X or Y is O;

$R_1$ is H, alkyl, alkenyl, alkynyl, aralkyl, aryl, heteroaryl, halo, CN, $OR_A$, $NR_AR_B$, $N(R_A)S(O)_qR_AR_B$, $N(R_A)C(O)R_B$, $N(R_A)C(O)NR_AR_B$, $N(R_A)C(O)OR_A$, $N(R_A)C(S)NR_AR_B$, $S(O)_qR_A$, $C(O)R_A$, $C(O)OR_A$, $OC(O)R_A$, or $C(O)NR_AR_B$;

each $R_A$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

each $R_B^C$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or $R_A$ and $R_B$, together with the atoms to which each is attached, can form a heterocycloalkyl or a heteroaryl; each of which is optionally substituted;

Ring A is cycloalkyl, aryl, heterocycloalkyl, or heteroaryl;

$R^C$ is alkyl, alkenyl, alkynyl, cycloalkyl, aryl, heterocloalkyl, or heteroaryl, each optionally substituted with 1-5 independently selected $R_4$, and when $L_1$ is other than a covalent bond, $R^C$ is additionally selected from H;

$R_2$ and $R_3$ are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R"), or —(CH$_2$)$_p$R$_x$; or $R_2$ and $R_3$ together with the atoms to which each is attached, forms an optionally substituted 3-7 membered saturated or unsaturated spiro-fused ring having 0-3 heteroatoms independently selected from nitrogen, oxygen, or sulfur;

each $R_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R");

$L^1$ is a covalent bond or an optionally substituted bivalent C$_{1-6}$ hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—;

each R is independently hydrogen, optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group;

each R" is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group; or R' and R", together with the atoms to which each is attached, can form a cycloalkyl, a heterocycloalkyl, an aryl, or a heteroaryl; each of which is optionally substituted;

each R$_4$ is independently optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl, halogen, —OR, —SR, —N(R')(R"), —CN, —NO$_2$, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, or —OC(O)N(R')(R");

each R$_5$ is independently —R, halogen, —OR, —SR, —N(R')(R"), —CN, —NO$_2$, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, or —OC(O)N(R')(R");

n is 0-5;

each q is independently 0, 1, or 2; and p is 1-6.

In another aspect, the invention provides a method for inhibiting activity of a bromodomain-containing protein, or a mutant thereof, in a biological sample comprising the step of contacting said biological sample with a compound of the invention (e.g., Formula I).

In another aspect, the invention provides a method for inhibiting activity of a bromodomain-containing protein, or a mutant thereof, activity in a patient comprising the step of administering to said patient a compound of the invention (e.g., Formula I).

In another aspect, the invention provides a method for treating a bromodomain-containing protein-mediated disorder in a patient in need thereof, comprising the step of administering to said patient a compound of the invention (e.g., Formula I).

Provided compounds, and pharmaceutically acceptable compositions thereof, are useful for treating a variety of diseases, disorders or conditions associated with abnormal cellular responses triggered by events mediated by bromodomain-containing proteins. Such diseases, disorders, or conditions include those described herein.

Provided compounds are also useful for the study of bromodomain-containing proteins in biological and pathological phenomena, the study of intracellular signal transduction pathways mediated by bromodomain-containing proteins, and the comparative evaluation of new inhibitors of bromodomain-containing proteins.

DETAILED DESCRIPTION

Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

The number of carbon atoms in a hydrocarbyl substituent can be indicated by the prefix "$C_x$-$C_y$," where x is the minimum and y is the maximum number of carbon atoms in the substituent.

The prefix "halo" indicates that the substituent to which the prefix is attached is substituted with one or more independently selected halogen radicals. For example, "haloalkyl" means an alkyl substituent wherein at least one hydrogen radical is replaced with a halogen radical.

If a linking element in a depicted structure is "absent", then the left element in the depicted structure is directly linked to the right element in the depicted structure. For example, if a chemical structure is depicted as X-L-Y wherein L is absent, then the chemical structure is X—Y.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Aliphatic groups include, but are not limited to, alkyl, alkenyl, alkynyl, carbocycle. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic or bicyclic ring systems, as described herein, having from 3 to 18 carbon ring atoms, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

As used herein, the term "cycloalkylene" refers to a bivalent cycloalkyl group. In certain embodiments, a cycloalkylene group is a 1,1-cycloalkylene group (i.e., a spiro-fused ring). Exemplary 1,1-cycloalkylene groups include

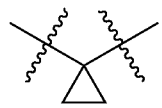

In other embodiments, a cycloalkylene group is a 1,2-cycloalkylene group or a 1,3-cycloalkylene group. Exemplary 1,2-cycloalkylene groups include

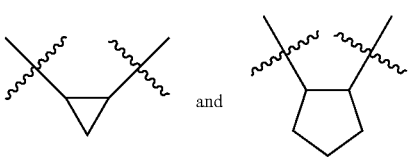

The term "alkyl" as used herein, refers to a saturated, straight- or branched-chain hydrocarbon radical typically containing from 1 to 20 carbon atoms. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds and typically from 2 to 20 carbon atoms. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds and typically from 2 to 20 carbon atoms. For example, "$C_2$-$C_8$ alkynyl" contains from two to eight carbon atoms. Representative alkynyl groups include, but are not limited to, for example, ethynyl, 1-propynyl, 1-butynyl, heptynyl, octynyl and the like.

The term "aryl" used alone or as part of a larger moiety as in "aralkyl", "aralkoxy", or "aryloxyalkyl", refers to monocyclic, bicyclic, and tricyclic ring systems having a total of five to 15 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. The term "aralkyl" or "arylalkyl" refers to an alkyl residue attached to an aryl ring. Examples of aralkyl include, but are not limited to, benzyl, phenethyl and the like. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 18 ring atoms, preferably 5, 6, or 9 ring atoms; having 6, 10, or 14 π electrons shared in a cyclic array; and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like.

As used herein, the terms "heterocycle", "heterocyclyl", "heterocyclic radical", and "heterocyclic ring" are used interchangeably and refer to a stable 3- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "bivalent hydrocarbon" refers to a bivalent saturated or unsaturated hydrocarbon group. Such bivalent hydrocarbon groups include alkylene, alkenylene, and alkynylene groups.

The term "alkylene" refers to a divalent group derived from a straight or branched saturated hydrocarbyl chain typically containing from 1 to 20 carbon atoms, more typically from 1 to 8 carbon atoms. Examples of an "alkylene" include a polymethylene group, i.e., —$(CH_2)_n$—, wherein n is a positive integer, preferably from 1 to 6, from 1 to 4, from 1 to 3, from 1 to 2, or from 2 to 3; or —$CH_2$—, —$CH_2CH_2$—, —$CH_2CH_2CH_2$—, —$CH_2CH_2CH_2CH_2$—, and —$CH_2CH(CH_3)CH_2$—. A substituted alkylene chain is a polymethylene group in which one or more methylene hydrogen atoms are replaced with a substituent. Suitable substituents include those described below for a substituted aliphatic group.

The term "alkenylene" refers to a divalent unsaturated hydrocarbyl group which may be linear or branched and which has at least one carbon-carbon double bond. An alkenylene group typically contains 2 to 20 carbon atoms, more typically from 2 to 8 carbon atoms. Non-limiting examples of alkenylene groups include —C(H)=C(H)—, —C(H)=C(H)—CH$_2$—, —C(H)=C(H)—CH$_2$—CH$_2$—, —CH$_2$—C(H)=C(H)—CH$_2$—, —C(H)=C(H)—CH(CH$_3$)—, and —CH$_2$—C(H)=C(H)—CH(CH$_2$CH$_3$)—.

The term "alkynylene" refers to a divalent unsaturated hydrocarbon group which may be linear or branched and which has at least one carbon-carbon triple bond. Representative alkynylene groups include, by way of example, —C≡C—, —C≡C—CH$_2$—, —C≡C—CH$_2$—CH$_2$—, —CH$_2$—C≡C—CH$_2$—, —C≡C—CH(CH$_3$)—, and —CH$_2$—C≡C—CH(CH$_2$CH$_3$)—.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

The terms "optionally substituted", "optionally substituted alkyl," "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with substituents including, but not limited to:

—F, —Cl, —Br, —I,

—OH, protected hydroxy, alkoxy, oxo, thiooxo,

—NO$_2$, —CN, CF$_3$, N$_3$,

—NH$_2$, protected amino, —NH-alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O-heterocyclic, —C(O)— alkyl, —C(O)— alkenyl, —C(O)— alkynyl, —C(O)— cycloalkyl, —C(O)-aryl, —C(O)-heteroaryl, —C(O)-heterocycloalkyl, —CONH$_2$, —CONH— alkyl, —CONH— alkenyl, —CONH-alkynyl, —CONH— cycloalkyl, —CONH-aryl, —CONH-heteroaryl, —CONH-heterocycloalkyl, —OCO$_2$-alkyl, —OCO$_2$-alkenyl, —OCO$_2$-alkynyl, —OCO$_2$-cycloalkyl, —OCO$_2$-aryl, —OCO$_2$-heteroaryl, —OCO$_2$-heterocycloalkyl, —OCONH$_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —NHCO$_2$-alkyl, —NHCO$_2$-alkenyl, —NHCO$_2$— alkynyl, —NHCO$_2$-cycloalkyl, —NHCO$_2$-aryl, —NHCO$_2$-heteroaryl, —NHCO$_2$-heterocycloalkyl, —NHC(O)NH$_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, NHC(S)NH$_2$, —NHC(S)NH-alkyl, —NHC(S)NH-alkenyl, —NHC(S)NH— alkynyl, —NHC(S)NH-cycloalkyl, —NHC(S)NH-aryl, —NHC(S)NH-heteroaryl, —NHC(S)NH-heterocycloalkyl, —NHC(NH)NH$_2$, —NHC(NH)NH-alkyl, —NHC(NH)NH-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl —SO$_2$NH$_2$, —SO$_2$NH-alkyl, —SO$_2$NH-alkenyl, —SO$_2$NH-alkynyl, —SO$_2$NH-cycloalkyl, —SO$_2$NH-aryl, —SO$_2$NH-heteroaryl, —SO$_2$NH-heterocycloalkyl, —NHSO$_2$-alkyl, —NHSO$_2$-alkenyl, —NHSO$_2$-alkynyl, —NHSO$_2$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

In certain embodiments, suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$—CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$C(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "suitable amino protecting group," includes those described in detail in *Protecting Groups in Organic Synthesis*, T. W. Greene and P. G. M. Wuts, 3$^{rd}$ edition, John Wiley & Sons, 1999.

Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)

ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2, 5-dimethylpyrrole, N-1,1,4,4-tetramethyldisilylazacyclopentane adduct (STABASE), 5-substituted 1,3-dimethyl-1, 3,5-triazacyclohexan-2-one, 5-substituted 1,3-dibenzyl-1,3, 5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

As used herein, the term "inhibitor" is defined as a compound that binds to and/or inhibits the target bromodomain-containing protein (such as a BET protein, e.g., BRD2, BRD3, BRD4, and/or BRDT) with measurable affinity. In certain embodiments, an inhibitor has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in activity of at least one bromodomain-containing protein between a sample comprising a provided compound, or composition thereof, and at least one histone methyltransferase, and an equivalent sample comprising at least one bromodomain-containing protein, in the absence of said compound, or composition thereof.

The term "subject" as used herein refers to a mammal A subject therefore refers to, for example, dogs, cats, horses, cows, pigs, guinea pigs, and the like. Preferably the subject is a human. When the subject is a human, the subject may be either a patient or a healthy human.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Description of Exemplary Compounds

In one aspect, the invention provides a compound of formula I:

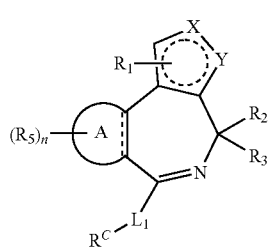

I or a pharmaceutically acceptable salt thereof, wherein:
X is O or N;
Y is O or N; wherein at least one of X or Y is O;
$R_1$ is H, alkyl, alkenyl, alkynyl, aralkyl, aryl, heteroaryl, halo, CN, $OR_A$, $NR_AR_B$, $N(R_A)S(O)_qR_AR_B$, $N(R_A)C(O)R_B$, $N(R_A)C(O)NR_AR_B$, $N(R_A)C(O)OR_A$, $N(R_A)C(S)NR_AR_B$, $S(O)_qR_A$, $C(O)R_A$, $C(O)OR_A$, $OC(O)R_A$, or $C(O)NR_AR_B$;
  each $R_A$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;
  each $R^B$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or
  $R_A$ and $R_B$, together with the atoms to which each is attached, can form a heterocycloalkyl or a heteroaryl; each of which is optionally substituted;
Ring A is cycloalkyl, aryl, heterocycloalkyl, or heteroaryl;
$R^C$ is alkyl, alkenyl, alkynyl, cycloalkyl, aryl, heterocycloalkyl, or heteroaryl, each optionally substituted with 1-5 independently selected $R^4$, and when L is other than a covalent bond, $R^C$ is additionally selected from H;
$R_2$ and $R_3$ are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R"), or —(CH$_2$)$_p$R$_x$; or
$R_2$ and $R_3$ together with the atoms to which each is attached, forms an optionally substituted 3-7 membered saturated or unsaturated spiro-fused ring having 0-3 heteroatoms independently selected from nitrogen, oxygen, or sulfur;
each $R_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R");
$L^1$ is a covalent bond or an optionally substituted bivalent $C_{1-6}$ hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—;
each R is independently hydrogen, optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl;
each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group;

each R" is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R groups on the same nitrogen are taken together with their intervening atoms to form an optionally substituted heteroaryl or heterocycloalkyl group; or R' and R", together with the atoms to which each is attached, can form a cycloalkyl, a heterocycloalkyl, an aryl, or a heteroaryl; each of which is optionally substituted;

each R$_4$ is independently optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl, halogen, —OR, —SR, —N(R')(R"), —CN, —NO$_2$, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, or —OC(O)N(R')(R");

each R$_5$ is independently —R, halogen, —OR, —SR, —N(R')(R"), —CN, —NO$_2$, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, or —OC(O)N(R')(R");

n is 0-5;
each q is independently 0, 1, or 2; and
p is 1-6.

In one embodiment, the invention provides a compound of formula II or formula III:

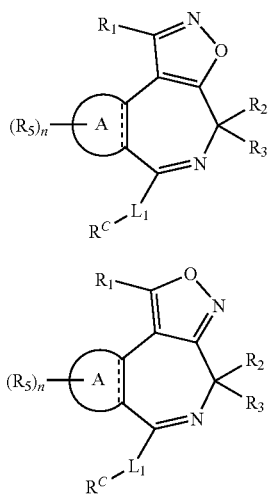

or a pharmaceutically acceptable salt thereof, wherein:

R$_1$ is H, alkyl, alkenyl, alkynyl, aralkyl, aryl, heteroaryl, halo, CN, OR$_A$, NR$_A$R$_B$, N(R$_A$)S(O)$_q$R$_A$R$_B$, N(R$_A$)C(O)R$_B$, N(R$_A$)C(O)NR$_A$R$_B$, N(R$_A$)C(O)OR$_A$, N(R$_A$)C(S)NR$_A$R$_B$, S(O)$_q$R$_A$, C(O)R$_A$, C(O)OR$_A$, OC(O)R$_A$, or C(O)NR$_A$R$_B$;

each R$_A$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

each R$_B$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or R$_A$ and R$_B$, together with the atoms to which each is attached, can form a heterocycloalkyl or a heteroaryl; each of which is optionally substituted;

Ring A is a 5-6 membered fused aryl ring; a 5-6 membered fused heteroaryl ring having 1-2 heteroatoms independently selected from nitrogen, oxygen, or sulfur; an 8-12 membered bicyclic aryl ring; or an 8-12 membered bicyclic heteroaryl ring having 1-4 heteroatoms independently selected from nitrogen, oxygen, and sulfur;

R$^C$ is alkyl, alkenyl, alkynyl, a 3-7 membered saturated, partially unsaturated or completely unsaturated carbocyclic ring; a 3-7 membered aryl ring; an 8-12 membered bicyclic saturated, partially unsaturated, or completely unsaturated carbocyclic ring; an 8-12 membered bicyclic aryl ring; a 3-7 membered saturated, partially unsaturated, or completely unsaturated heterocyclic ring having 1-2 heteroatoms independently selected from nitrogen, oxygen, and sulfur; a 3-7 membered monocyclic heteroaryl ring having 1-3 heteroatoms independently selected from nitrogen, oxygen, and sulfur; a 7-10 membered bicyclic saturated, partially unsaturated, or completely unsaturated heterocyclic ring having 1-4 heteroatoms independently selected from nitrogen, oxygen, and sulfur; or a 7-10 membered bicyclic heteroaryl ring having 1-4 heteroatoms independently selected from nitrogen, oxygen, and sulfur, each optionally substituted with 1-5 independently selected R$^4$, and when L is other than a covalent bond, R$^C$ is additionally selected from H;

R$_2$ and R$_3$ are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R"), or —(CH$_2$)$_p$R$_x$; or R$_2$ and R$_3$ together with the atoms to which each is attached, forms an optionally substituted 3-7 membered saturated or partially unsaturated spiro-fused ring having 0-3 heteroatoms independently selected from nitrogen, oxygen, or sulfur;

each R$_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R");

$L^1$ is a covalent bond or an optionally substituted bivalent $C_{1-6}$ hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—;

each R is independently hydrogen, $C_{1-6}$ aliphatic, a 5-6 membered aryl ring, a 3-7 membered saturated, partially unsaturated, or completely unsaturated carbocyclic ring, a 7-12 membered bicyclic saturated, partially unsaturated, or completely unsaturated carbocyclic ring, a 3-7 membered monocyclic heteroaryl ring having 1-3 heteroatoms independently selected from nitrogen, oxygen, and sulfur, a 3-7 membered saturated, partially unsaturated, or completely unsaturated heterocyclic ring having 1-2 heteroatoms independently selected from nitrogen, oxygen, and sulfur, a 7-12 membered bicyclic saturated, partially unsaturated, or completely unsaturated heterocyclic ring having 1-4 heteroatoms independently selected from nitrogen, oxygen, and sulfur, or a 7-12 membered bicyclic heteroaryl ring having 1-4 heteroatoms independently selected from nitrogen, oxygen, and sulfur; each of which is optionally substituted;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;

each R" is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted; or R' and R", together with the atoms to which each is attached, can form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;

each $R_4$ is independently optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl, halogen, —OR, —SR, —N(R')(R"), —CN, —NO$_2$, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, or —OC(O)N(R')(R");

each $R_5$ is independently —R, halogen, —OR, —SR, —N(R')(R"), —CN, —NO$_2$, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, or —OC(O)N(R')(R");

n is 0-5;

each q is independently 0, 1, or 2; and p is 1-6.

In certain embodiments, Ring A is benzo or a 5-6 membered fused heteroaryl ring having 1-2 heteroatoms independently selected from nitrogen, oxygen, or sulfur.

In other embodiments, $R^C$ is a 3-7 membered aryl ring; 3-7 membered saturated or partially unsaturated carbocyclic ring or a 4-7 membered saturated or partially unsaturated heterocyclic ring having 1-2 heteroatoms independently selected from nitrogen, oxygen, and sulfur, wherein $R^C$ is optionally substituted with 1-5 independently selected $R^4$.

In various embodiments, $R_2$ is H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, or —(CH$_2$)$_p$R$_x$.

In still other embodiments, $R_3$ is H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, or —(CH$_2$)$_p$R$_x$.

In certain embodiments, $R_2$ and $R_3$, together with the atoms to which each is attached, forms an optionally substituted 3-7 membered saturated or partially unsaturated spiro-fused ring having 0-3 heteroatoms independently selected from nitrogen, oxygen, or sulfur.

In other embodiments, when X is N and Y is O, $R_1$ is H, alkyl, alkenyl, alkynyl, aralkyl, aryl, heteroaryl, halo, CN, OR$_A$, NR$_A$R$_B$, N(R$_A$)S(O)$_q$R$_A$R$_B$, N(R$_A$)C(O)R$_B$, N(R$_A$)C (O)NR$_A$R$_B$, N(R$_A$)C(O)OR$_A$, N(R$_A$)C(S)NR$_A$R$_B$, S(O)$_q$R$_A$, C(O)R$_A$, C(O)OR$_A$, OC(O)R$_A$, or C(O)NR$_A$R$_B$; with the proviso that R$_1$ is not —OH.

In other embodiments, when X is N and Y is O, the compound is not 6-phenyl-4H-benzo[c]isoxazolo[4,5-e]azepin-1-ol.

In other embodiments, when X is N and Y is O, L$_1$ is a covalent bond and R$^C$ is alkyl, alkenyl, alkynyl, cycloalkyl, heterocycloalkyl, or heteroaryl, each optionally substituted with 1-5 independently selected R$^4$, or aryl substituted with 1-5 independently selected R$^4$.

In other embodiments, when X is N and Y is O, R$^C$ is aryl substituted with 1-5 independently selected R$^4$.

In another embodiment, L$_1$ is a covalent bond and the invention provides a compound of formula II-A:

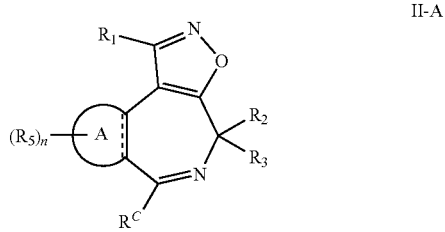

II-A or a pharmaceutically acceptable salt thereof, wherein:
R$_1$ is H, alkyl, aralkyl, aryl, heteroaryl, halo, OR$_A$, NR$_A$R$_B$, S(O)$_q$R$_A$, C(O)R$_A$, C(O)OR$_A$, OC(O)R$_A$, or C(O)NR$_A$R$_B$;
  each R$_A$ is independently optionally substituted alkyl, containing 0, 1, 2, or 3 heteroatoms selected from O, S, or N; optionally substituted aryl; optionally substituted heteroaryl; optionally substituted heterocyclic; optionally substituted carbocyclic; or hydrogen;
  each R$_B$ is independently optionally substituted alkyl, containing 0, 1, 2, or 3 heteroatoms selected from O, S, or N; optionally substituted aryl; optionally substituted heteroaryl; optionally substituted heterocyclic; optionally substituted carbocyclic; or hydrogen;
Ring A is benzo or a 5-6 membered fused heteroaryl ring having 1-2 heteroatoms independently selected from nitrogen, oxygen, or sulfur, which is optionally substituted;
R$^C$ is a 3-7 membered saturated, partially unsaturated or completely unsaturated carbocyclic ring; a 3-7 membered aryl ring; or a 3-7 membered saturated, partially unsaturated, or completely unsaturated heterocyclic ring having 1-2 heteroatoms independently selected from nitrogen, oxygen, and sulfur, wherein R$^C$ is optionally substituted with 1-5 independently selected R$^4$;
R$_2$ and R$_3$ are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R''), —C(O)R, —C(S)R, —CO$_2$R, C(O)N(R')(R''), —C(O)SR, or —(CH$_2$)$_p$R$_x$; or
R$_2$ and R$_3$ together with the atoms to which each is attached, forms an optionally substituted 3-7 membered saturated or partially unsaturated spiro-fused ring having 0-3 heteroatoms independently selected from nitrogen, oxygen, or sulfur;
each R$_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R''), —C(O)R, —C(S)R, —CO$_2$R, —C(O)N(R')(R''), —C(O) SR, —C(O)C(O)R, —C(O)CH$_2$C(O)R, —C(S)N(R')(R''), —C(S)OR, —S(O)R, —SO$_2$R, —SO$_2$N(R')(R''), —N(R')C(O)R, —N(R')C(O)N(R')(R''), —N(R')C(S)N(R')(R''), —N(R')SO$_2$R, —N(R')SO$_2$N(R')(R''), —N(R')N(R')(R''), —N(R')C(=N(R'))N(R')(R''), —C=NN(R')(R''), —C=NOR, —C(=N(R'))N(R')(R''), —OC(O)R, —OC(O)N(R')(R'');
each R is independently hydrogen, C$_{1-6}$ aliphatic, a 5-6 membered aryl ring, a 3-7 membered saturated, partially unsaturated, or completely unsaturated carbocyclic ring, a 7-12 membered bicyclic saturated, partially unsaturated, or completely unsaturated carbocyclic ring, a 3-7 membered monocyclic heteroaryl ring having 1-3 heteroatoms independently selected from nitrogen, oxygen, and sulfur, a 3-7 membered saturated, partially unsaturated, or completely unsaturated heterocyclic ring having 1-2 heteroatoms independently selected from nitrogen, oxygen, and sulfur, a 7-12 membered bicyclic saturated, partially unsaturated, or completely unsaturated heterocyclic ring having 1-4 heteroatoms independently selected from nitrogen, oxygen, and sulfur, or a 7-12 membered bicyclic heteroaryl ring having 1-4 heteroatoms independently selected from nitrogen, oxygen, and sulfur; each of which is optionally substituted;
each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;
each R'' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted; or
R' and R'', together with the atoms to which each is attached, can form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;

each R₄ is independently optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl, halogen, —OR, —SR, —N(R')(R"), —CN, —NO₂, —C(O)R, —C(S)R, —CO₂R, —C(O)N(R')(R"), —C(O)SR, —C(O)C(O)R, —C(O)CH₂C(O)R, —C(S)N(R')(R"), —C(S)OR, —S(O)R, —SO₂R, —SO₂N(R')(R"), —N(R')C(O)R, —N(R')C(O)N(R')(R"), —N(R')C(S)N(R')(R"), —N(R')SO₂R, —N(R')SO₂N(R')(R"), —N(R')N(R')(R"), —N(R')C(=N(R'))N(R')(R"), —C=NN(R')(R"), —C=NOR, —C(=N(R'))N(R')(R"), —OC(O)R, or —OC(O)N(R')(R");

each R₅ is independently —R, halogen, —OR, —SR, —N(R')(R"), —CN, or —NO₂;

n is 0-5;

q is 0, 1, or 2; and p is 1-6.

In other embodiments, L₁ is a covalent bond and the invention provides a compound of formula III-A:

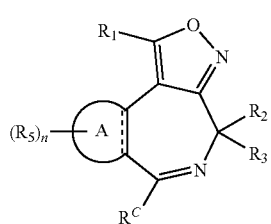

III-A or a pharmaceutically acceptable salt thereof, wherein:

R₁ is H, alkyl, aralkyl, aryl, heteroaryl, halo, OR$_A$, NR$_A$R$_B$, S(O)$_q$R$_A$, C(O)R$_A$, C(O)OR$_A$, OC(O)R$_A$, or C(O)NR$_A$R$_B$;

each R$_A$ is independently optionally substituted alkyl, containing 0, 1, 2, or 3 heteroatoms selected from O, S, or N; optionally substituted aryl; optionally substituted heteroaryl; optionally substituted heterocyclic; optionally substituted carbocyclic; or hydrogen;

each R$_B$ is independently optionally substituted alkyl, containing 0, 1, 2, or 3 heteroatoms selected from O, S, or N; optionally substituted aryl; optionally substituted heteroaryl; optionally substituted heterocyclic; optionally substituted carbocyclic; or hydrogen; or R$_A$ and R$_B$, together with the atoms to which each is attached, can form a cycloalkyl, a heterocycloalkyl, an aryl, or a heteroaryl; each of which is optionally substituted;

Ring A is benzo or a 5-6 membered fused heteroaryl ring having 1-2 heteroatoms independently selected from nitrogen, oxygen, or sulfur, which is optionally substituted;

R$^C$ is a 3-7 membered saturated, partially unsaturated or completely unsaturated carbocyclic ring; a 3-7 membered aryl ring; or a 3-7 membered saturated, partially unsaturated, or completely unsaturated heterocyclic ring having 1-2 heteroatoms independently selected from nitrogen, oxygen, and sulfur, wherein R$^C$ is optionally substituted with 1-5 independently selected R⁴;

R₂ and R₃ are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO₂R, —C(O)N(R')(R"), —C(O)SR, or —(CH₂)$_p$R$_x$; or R₂ and R₃ together with the atoms to which each is attached, forms an optionally substituted 3-7 membered saturated or partially unsaturated spiro-fused ring having 0-3 heteroatoms independently selected from nitrogen, oxygen, or sulfur;

each R$_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO₂R, —C(O)N(R')(R"), —C(O)SR, —C(O)C(O)R, —C(O)CH₂C(O)R, —C(S)N(R')(R"), —C(S)OR, —S(O)R, —SO₂R, —SO₂N(R')(R"), —N(R')C(O)R, —N(R')C(O)N(R')(R"), —N(R')C(S)N(R')(R"), —N(R')SO₂R, —N(R')SO₂N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R");

each R is independently hydrogen, C$_{1-6}$ aliphatic, a 5-6 membered aryl ring, a 3-7 membered saturated, partially unsaturated, or completely unsaturated carbocyclic ring, a 7-12 membered bicyclic saturated, partially unsaturated, or completely unsaturated carbocyclic ring, a 3-7 membered monocyclic heteroaryl ring having 1-3 heteroatoms independently selected from nitrogen, oxygen, and sulfur, a 3-7 membered saturated, partially unsaturated, or completely unsaturated heterocyclic ring having 1-2 heteroatoms independently selected from nitrogen, oxygen, and sulfur, a 7-12 membered bicyclic saturated, partially unsaturated, or completely unsaturated heterocyclic ring having 1-4 heteroatoms independently selected from nitrogen, oxygen, and sulfur, or a 7-12 membered bicyclic heteroaryl ring having 1-4 heteroatoms independently selected from nitrogen, oxygen, and sulfur; each of which is optionally substituted;

each R' is independently —R, —C(O)R, —C(S)R, —CO₂R, —C(O)N(R)₂, —C(S)N(R)₂, —S(O)R, —SO₂R, —SO₂N(R)₂, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;

each R" is independently —R, —C(O)R, —C(S)R, —CO₂R, —C(O)N(R)₂, —C(S)N(R)₂, —S(O)R, —SO₂R, —SO₂N(R)₂, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted; or R' and R", together with the atoms to which each is attached, can form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;

each $R_4$ is independently optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl, halogen, —OR, —SR, —N(R')(R"), —CN, —NO$_2$, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, or —OC(O)N(R')(R");

each $R_5$ is independently —R, halogen, —OR, —SR, —N(R')(R"), —CN, or —NO$_2$;

n is 0-5;
q is 0, 1, or 2; and
p is 1-6.

In certain embodiments, Ring A is a 6-membered fused heteroaryl ring having 1-2 nitrogen atoms. In a further embodiment, Ring A is pyrido, pyrimidino, pyrazino, or pyridazino.

In various embodiments, Ring A is a 5-membered fused heteroaryl ring having 1 heteroatom selected from nitrogen, oxygen, or sulfur. In a further embodiment, Ring A is thieno.

In other embodiments, Ring A is a 5-membered fused heteroaryl ring having 2 heteroatoms independently selected from nitrogen, oxygen, or sulfur. In a further embodiment, Ring A is isothiazolo.

In another embodiment, Ring A is benzo.

In certain embodiments, $R^C$ is phenyl or a 4-7 membered saturated or partially unsaturated heterocyclic ring having 1-2 heteroatoms independently selected from nitrogen, oxygen, and sulfur. In a further embodiment, $R^C$ is piperidinyl, morpholinyl, or piperazinyl. In each of the above embodiments, $R^C$ is optionally substituted with 1-5 independently selected $R^4$.

In other embodiments, $R_1$ is halo, alkyl, aralkyl, aryl, or heteroaryl. In a further embodiment, $R_1$ is methyl, ethyl, propyl, i-propyl, butyl, s-butyl, t-butyl, pentyl, hexyl, or heptyl.

In another embodiment, $R_2$ is H, methyl, ethyl, propyl, i-propyl, butyl, s-butyl, pentyl, hexyl, —OR, —SR, —CN, —N(R')(R"), —C(O)R, —C(S)R, —CO$_2$R, —C(O)N(R')(R"), —C(O)SR, or —(CH$_2$)$_p$R$_x$. In a further embodiment, $R_2$ is H or —(CH$_2$)$_p$R$_x$.

In certain embodiments, $R_x$ is —N(R')(R"), —C(O)R, —C(S)R, —CO$_2$R, —C(O)N(R')(R"), —C(S)N(R')(R"), —S(O)R, —SO$_2$R, —SO$_2$N(R')(R"), —N(R')C(O)R, —N(R')SO$_2$R, —OC(O)R, —OC(O)N(R')(R"), methyl, ethyl, propyl, i-propyl, butyl, s-butyl, pentyl or hexyl.

In other embodiments, $R_3$ is H, methyl, ethyl, propyl, i-propyl, butyl, s-butyl, pentyl, hexyl, —OR, —SR, —CN, —N(R')(R"), —C(O)R, —C(S)R, —CO$_2$R, —C(O)N(R')(R"), —C(O)SR, or —(CH$_2$)$_p$R$_x$. In a further embodiment, $R_2$ is H or —(CH$_2$)$_p$R$_x$.

In certain embodiments, $R_x$ is —N(R')(R"), —C(O)R, —C(S)R, —CO$_2$R, —C(O)N(R')(R"), —C(S)N(R')(R"), —S(O)R, —SO$_2$R, —SO$_2$N(R')(R"), —N(R')C(O)R, —N(R')SO$_2$R, —OC(O)R, —OC(O)N(R')(R"), methyl, ethyl, propyl, i-propyl, butyl, s-butyl, pentyl or hexyl.

In certain embodiments, $R_2$ and $R_3$ together with the atoms to which each is attached, forms an optionally substituted 3-7 membered saturated or partially unsaturated spiro-fused ring having 0-3 heteroatoms independently selected from nitrogen, oxygen, or sulfur. In a further embodiment, $R_2$ and $R_3$ together with the atoms to which each is attached, forms an optionally substituted cyclopropyl, cyclobutyl, cyclopentyl, cyclohexyl, azetidine, oxetane, tetrahydrofuran, or pyrrolidine.

In a further embodiment, $R_2$ and $R_3$ are optionally substituted by halogen, alkyl, alkenyl, alkynyl, aryl, aralkyl, cycloalkyl, heteroaryl, heterocycloalkyl, each of which is further optionally substituted; or $R_2$ and $R_3$ are optionally substituted by —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R"), or —(CH$_2$)$_p$R$_x$.

In various embodiments, $R_x$ is halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R");

each R is independently hydrogen, $C_{1-6}$ aliphatic, a 5-6 membered aryl ring, a 3-7 membered saturated, partially unsaturated, or completely unsaturated carbocyclic ring, a 7-12 membered bicyclic saturated, partially unsaturated, or completely unsaturated carbocyclic ring, a 3-7 membered monocyclic heteroaryl ring having 1-3 heteroatoms independently selected from nitrogen, oxygen, and sulfur, a 3-7 membered saturated, partially unsaturated, or completely unsaturated heterocyclic ring having 1-2 heteroatoms independently selected from nitrogen, oxygen, and sulfur, a 7-12 membered bicyclic saturated, partially unsaturated, or completely unsaturated heterocyclic ring having 1-4 heteroatoms independently selected from nitrogen, oxygen, and sulfur, or a 7-12 membered bicyclic heteroaryl ring having 1-4 heteroatoms independently selected from nitrogen, oxygen, and sulfur; each of which is optionally substituted;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;

each R" is independently —R, —C(O)R, —C(S)R, —CO$_2$R, —C(O)N(R)$_2$, —C(S)N(R)$_2$, —S(O)R, —SO₂R, —SO₂N(R)₂, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted; or R' and R", together with the atoms to which each is attached, can form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted.

In each of the embodiments of $R^C$ set forth below, $R^C$ is optionally substituted with 1-5 independently selected $R^4$.

In some embodiments, $R^C$ is phenyl.

In some embodiments, $R^C$ is a 3-7 membered saturated or partially unsaturated carbocyclic ring. In certain embodiments, $R^C$ is cyclopropyl, cyclobutyl, cyclopentyl, cyclohexyl, or cycloheptyl. In certain embodiments, $R^C$ is cyclopentenyl, cyclohexenyl, or cycloheptenyl.

In some embodiments, $R^C$ is a 4-7 membered saturated or partially unsaturated heterocyclic ring having 1-2 heteroatoms independently selected from nitrogen, oxygen, and sulfur. In certain embodiments, $R^C$ is a 5-6 membered saturated or partially unsaturated heterocyclic ring having 1-2 heteroatoms independently selected from nitrogen, oxygen, and sulfur. In certain embodiments, $R^C$ is tetrahydrofuranyl, tetrahydrothienyl, tetrahydropyranyl, tetrahydrothiopyranyl, pyrrolidinyl, pyrrolidonyl, piperidinyl, pyrrolinyl, oxazolidinyl, piperazinyl, dioxanyl, dioxolanyl, diazepinyl, oxazepinyl, thiazepinyl, or morpholinyl.

In some embodiments, $R^C$ is a 5-6 membered monocyclic heteroaryl ring having 1-3 heteroatoms independently selected from nitrogen, oxygen, and sulfur.

In certain embodiments, $R^C$ is 6-membered heteroaryl ring having 1-3 nitrogen atoms. In other embodiments, $R^C$ is a 6-membered heteroaryl ring having 1 nitrogen atom. In certain other embodiments, $R^C$ is a 6-membered heteroaryl ring having 2 nitrogen atoms. In yet other embodiments, $R^C$ is a 6-membered heteroaryl ring having 3 nitrogen atoms.

In other embodiments, $R^C$ is a 5-membered heteroaryl ring having 1-3 heteroatoms independently selected from nitrogen, oxygen, or sulfur. In certain embodiments, $R^C$ is a 5-membered heteroaryl ring having 1 heteroatom independently selected from nitrogen, oxygen, or sulfur. In certain embodiments, $R^C$ is a 5-membered heteroaryl ring having 2 heteroatoms independently selected from nitrogen, oxygen, or sulfur. In other embodiments, $R^C$ is a 5-membered heteroaryl ring having 2 heteroatoms independently selected from nitrogen and oxygen. In some embodiments, $R^C$ is a 5-membered heteroaryl ring having 2 heteroatoms independently selected from nitrogen and sulfur. In other embodiments, $R^C$ is a 5-membered heteroaryl ring having 1-3 nitrogen atoms. In certain embodiments, $R^C$ is thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, or pyrazinyl.

In some embodiments, $R^C$ is a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In certain embodiments, $R^C$ is a 5,5-fused-, 5,6-fused, or 6,6-fused saturated, partially unsaturated, or aromatic bicyclic ring. In some embodiments, $R^C$ is a 5,5-fused, 5,6-fused, or 6,6-fused aromatic bicyclic ring. In other embodiments, $R^C$ is a naphthalenyl, indanyl or indenyl group.

In some embodiments, $R^C$ is a 7-10 membered bicyclic saturated or partially unsaturated heterocyclic ring having 1-4 heteroatoms independently selected from nitrogen, oxygen, and sulfur. In certain embodiments, $R^C$ is a 7-8 membered bicyclic saturated heterocyclic ring having 1-3 heteroatoms independently selected from nitrogen, oxygen, and sulfur. In certain embodiments, $R^C$ is a 7-8 membered bicyclic partially unsaturated heterocyclic ring having 1-3 heteroatoms independently selected from nitrogen, oxygen, and sulfur. In certain embodiments, $R^C$ is a 9-10 membered bicyclic saturated heterocyclic ring having 1-3 heteroatoms independently selected from nitrogen, oxygen, and sulfur. In certain embodiments, $R^C$ is a 9-10 membered bicyclic partially unsaturated heterocyclic ring having 1-3 heteroatoms independently selected from nitrogen, oxygen, and sulfur. In certain embodiments, $R^C$ is tetrahydroquinolinyl, tetrahydroisoquinolinyl, decahydroquinolinyl, or quinuclidinyl. In certain embodiments, $R^C$ is indolinyl, 3H-indolyl, chromanyl, phenanthridinyl, 2-azabicyclo[2.2.1]heptanyl, octahydroindolyl, or tetrahydroquinolinyl.

In some embodiments, $R^C$ is a 8-10 membered bicyclic heteroaryl ring having 1-4 heteroatoms independently selected from nitrogen, oxygen, and sulfur.

In some embodiments, $R^C$ is a 5,5-fused, 5,6-fused, or 6,6-fused saturated, partially unsaturated, or aromatic bicyclic ring having 1-4 heteroatoms, independently selected from nitrogen, oxygen, or sulfur. In other embodiments, $R^C$ is a 5,5-fused, 5,6-fused, or 6,6-fused heteroaryl ring having 1-4 heteroatoms, independently selected from nitrogen, oxygen, or sulfur. In certain embodiments, $R^C$ is a 5,5-fused, 5,6-fused, or 6,6-fused heteroaryl ring having 1-4 nitrogen atoms. In other embodiments, $R^C$ is a 5,6-fused heteroaryl ring having 1-4 nitrogen atoms. In certain embodiments, $R^C$ is pyrrolizinyl, indolyl, quinolinyl, isoquinolinyl, benzimidazolyl, imidazopyridinyl, indazolyl, purinyl, cinnolinyl, quinazolinyl, phthalazinyl, naphthridinyl, quinoxalinyl, thianaphtheneyl, or benzofuranyl. In certain embodiments, $R^C$ is a indolizinyl, purinyl, naphthyridinyl, or pteridinyl.

In certain embodiments, $L_1$ is a covalent bond and the invention provides a compound of Formula IV:

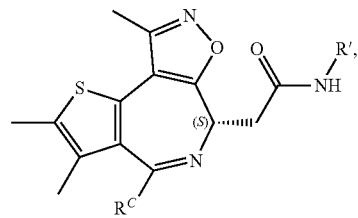

wherein:

$R^C$ is selected from phenyl, cycloalkyl, heteroaryl, saturated heterocyclyl and alkyl, wherein any ring portion of $R^C$ is optionally substituted with 1 to 2 substituents independently selected from halo, alkyl, oxo, amino, alkylcarbonylamino, carbamyl, and —CN; and R' is selected from hydrogen, alkyl and fluoroalkyl.

In certain embodiments of Formula IV, $R^C$ is selected from 1H-pyrazol-3-yl, 1-methyl-1H-pyrazol-3-yl, pyrimidin-5-yl, pyridazin-4-yl, 2-aminopyridin-5-yl, pyridin-3-yl, pyridin-4-yl, phenyl, 4-fluorophenyl, 4-chlorophenyl, 2-chlorophenyl, 2-methyl-4-chlorophenyl, 4-cyanophenyl, 4-carbamylphenyl, 3-carbamylphenyl, 4-acetylaminophenyl, 1-methylpyridin-2(1H)-one-4-yl, 1-methylpyridin-2(1H)-one-5-yl, 4-methylpiperazin-1-yl, morpholin-4-yl, 1-methyl-1,4-diazepan-4-yl, propyl, cyclopropyl, cyclohexyl, and tetrahydro-2H-pyran-4-yl.

In certain embodiments of Formula IV, R' is selected from hydrogen, ethyl, and 2-fluoroethyl.

In certain embodiments, the invention provides a compound of Formula V:

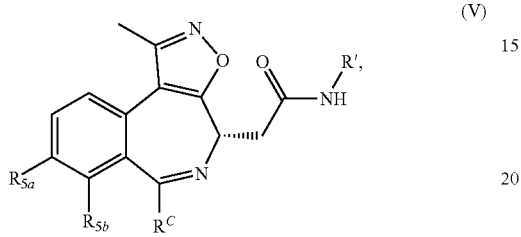

(V)

wherein:
$R_{5a}$ is selected from hydrogen, halo, and alkoxy;
$R_{5b}$ is selected from hydrogen, halo, and alkyl;
$R^C$ is selected from phenyl, heteroaryl, and saturated heterocyclyl, wherein $R^C$ is optionally substituted with 1 to 2 substituents independently selected from halo, —CN, alkyl, alkoxy, haloalkoxy, haloalkyl, and carbamyl; and
R' is selected from hydrogen, alkyl, and alkoxyalkyl.

In some embodiments of Formula V, $R_{5a}$ is selected from hydrogen, chloro, and methoxy.

In some embodiments of Formula V, $R_{5b}$ is selected from hydrogen, chloro, and methyl.

In some embodiments of Formula V, $R_{5a}$ and $R_{5b}$ are simultaneously hydrogen In some embodiments of Formula V, $R^C$ is selected from 4-chlorophenyl, 4-cyanophenyl, 4-fluorophenyl, pyridin-4-yl, 4-trifluoromethylphenyl, 5-chloropyridin-2-yl, 4-carbamylphenyl, 3-methoxyphenyl, 4-methoxyphenyl, 4-trifluoromethoxyphenyl, 2-methyl-4-chlorophenyl, and morpholin-4-yl.

In some embodiments of Formula V, R' is selected from hydrogen, ethyl, and 2-methoxyethyl.

Exemplary compounds of the invention are set forth in Tables 1-4 below.

TABLE 1

Exemplary Compounds
Compounds of the invention include the following:

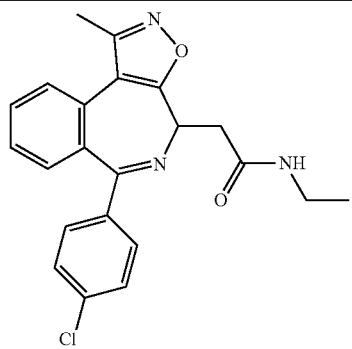

TABLE 1-continued

Exemplary Compounds
Compounds of the invention include the following:

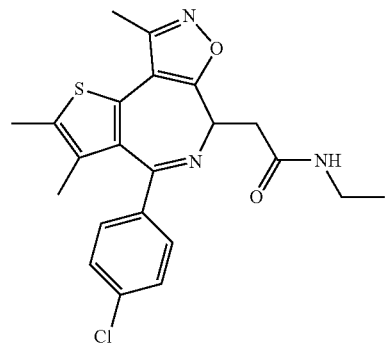 [SMILES: CCNC(=O)CC1N=C(c2ccc(Cl)cc2)c2c(sc(C)c2C)-c2c(C)noc21]

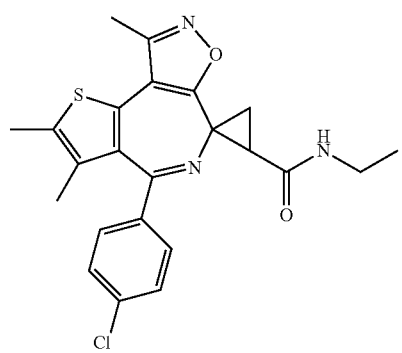 [SMILES: CCNC(=O)C1CC12N=C(c1ccc(Cl)cc1)c1c(sc(C)c1C)-c1c(C)noc12]

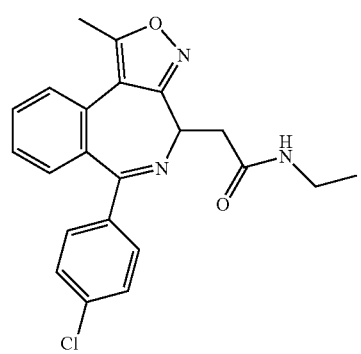 [SMILES: CCNC(=O)CC1N=C(c2ccc(Cl)cc2)c2ccccc2-c2c1noc2C]

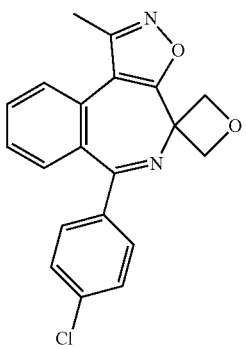 [SMILES: Cc1noc2c1-c1ccccc1C(c1ccc(Cl)cc1)=NC21COC1]

TABLE 1-continued
Exemplary Compounds
Compounds of the invention include the following:
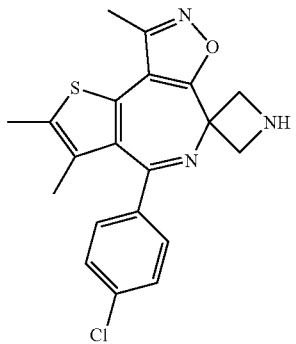 [SMILES: Cc1noc2c1-c1sc(C)c(C)c1C(c1ccc(Cl)cc1)=NC21CNC1]
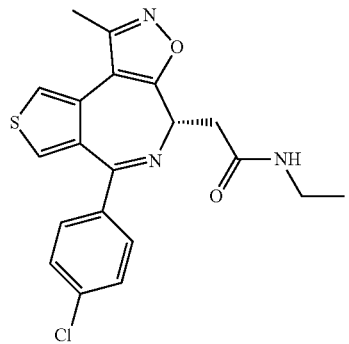
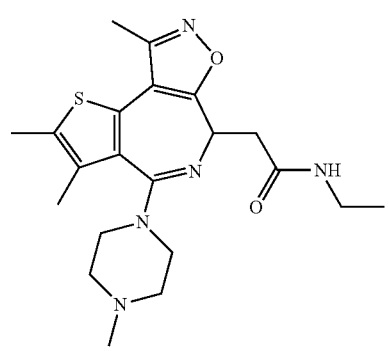 [SMILES: CCNC(=O)CC1N=C(N2CCN(C)CC2)c2c(sc(C)c2C)-c2c(C)noc21]
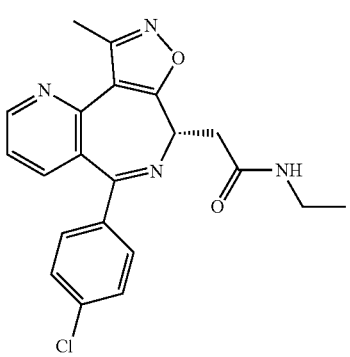
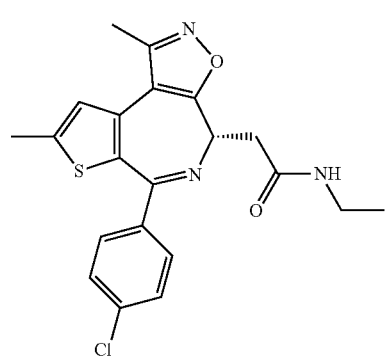 [SMILES: CCNC(=O)C[C@@H]1N=C(c2ccc(Cl)cc2)c2sc(C)cc2-c2c(C)noc21]
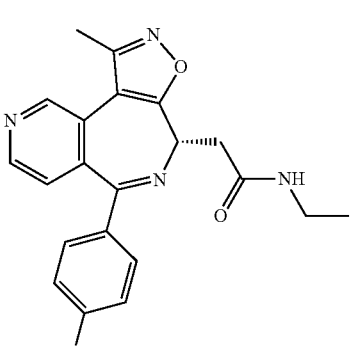
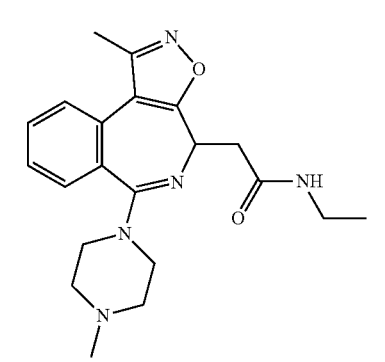 [SMILES: CCNC(=O)CC1N=C(N2CCN(C)CC2)c2ccccc2-c2c(C)noc21]
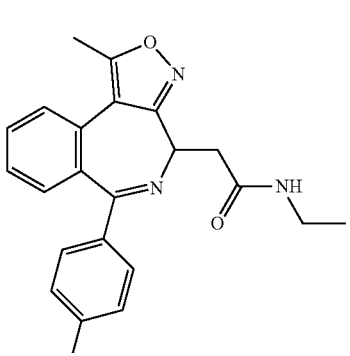

TABLE 1-continued
Exemplary Compounds
Compounds of the invention include the following:
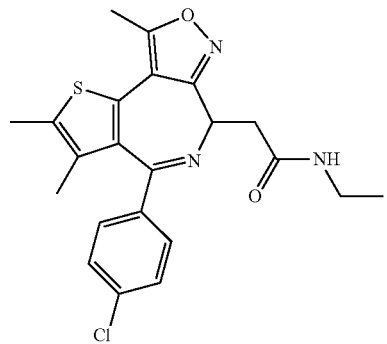 [SMILES: CCNC(=O)CC1N=C(c2ccc(Cl)cc2)c2c(sc(C)c2C)-c2c1noc2C]
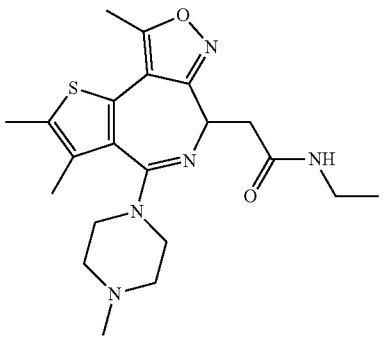
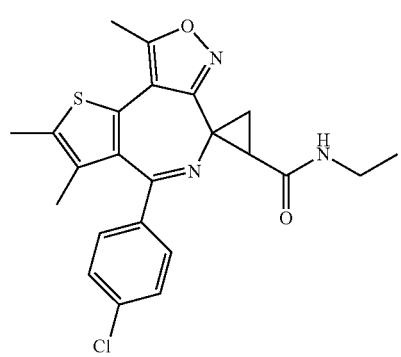 [SMILES: CCNC(=O)C1CC12N=C(c1ccc(Cl)cc1)c1c(sc(C)c1C)-c1c2noc1C]
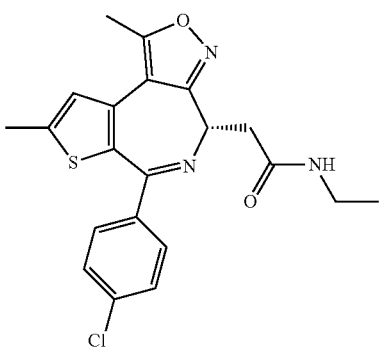
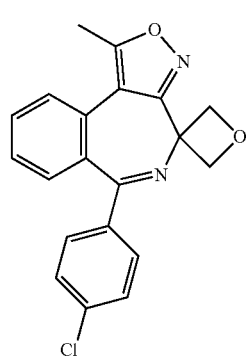 [SMILES: Cc1onc2c1-c1ccccc1C(c1ccc(Cl)cc1)=NC21COC1]
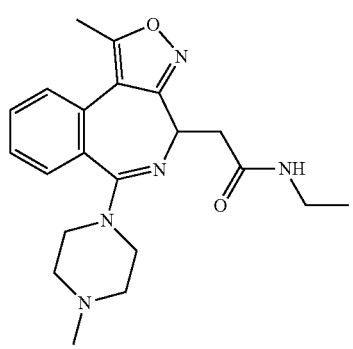
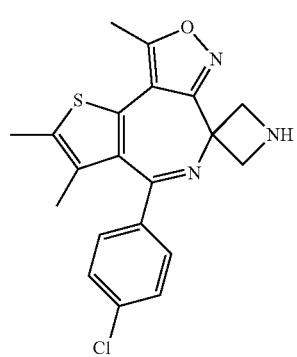 [SMILES: Cc1onc2c1-c1sc(C)c(C)c1C(c1ccc(Cl)cc1)=NC21CNC1]
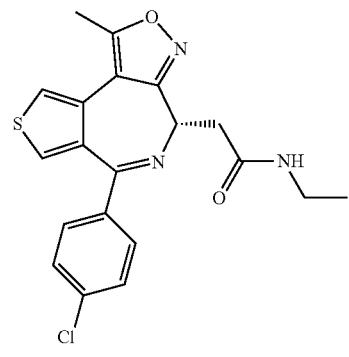 [SMILES: CCNC(=O)C[C@@H]1N=C(c2ccc(Cl)cc2)c2cscc2-c2c1noc2C]

TABLE 1-continued
Exemplary Compounds
Compounds of the invention include the following:
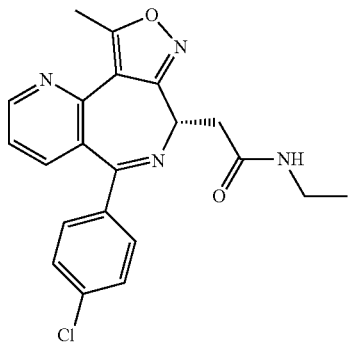 [SMILES: CCNC(=O)C[C@@H]1N=C(c2ccc(Cl)cc2)c2cccnc2-c2c1noc2C]
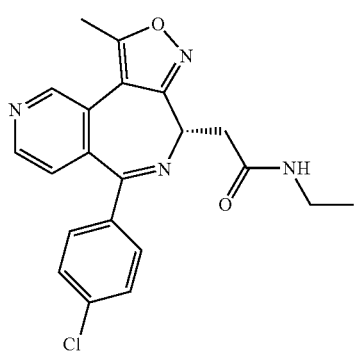 [SMILES: CCNC(=O)C[C@@H]1N=C(c2ccc(Cl)cc2)c2ccncc2-c2c1noc2C]
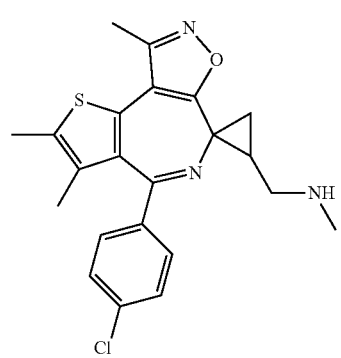
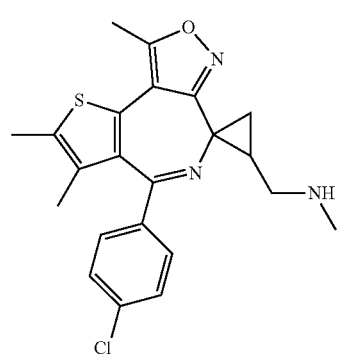
TABLE 1-continued
Exemplary Compounds
Compounds of the invention include the following:
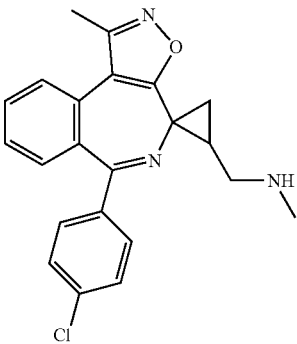 [SMILES: CNCC1CC12N=C(c1ccc(Cl)cc1)c1ccccc1-c1c(C)noc12]
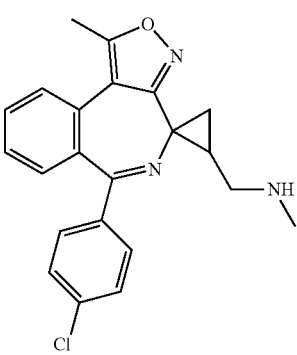 [SMILES: CNCC1CC12N=C(c1ccc(Cl)cc1)c1ccccc1-c1c2noc1C]
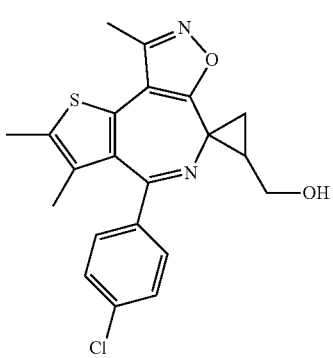 [SMILES: Cc1noc2c1-c1sc(C)c(C)c1C(c1ccc(Cl)cc1)=NC21CC1CO]
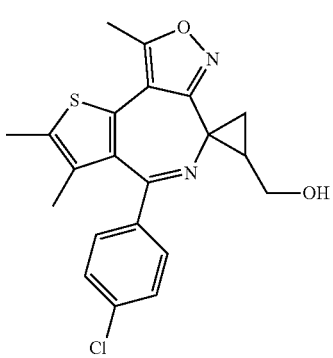 [SMILES: Cc1onc2c1-c1sc(C)c(C)c1C(c1ccc(Cl)cc1)=NC21CC1CO]

TABLE 1-continued
Exemplary Compounds
Compounds of the invention include the following:
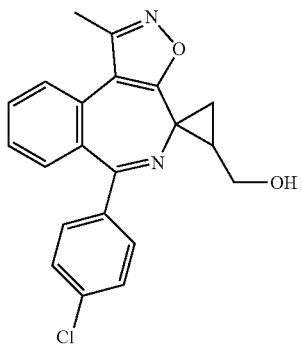 [SMILES: Cc1noc2c1-c1ccccc1C(c1ccc(Cl)cc1)=NC21CC1CO]
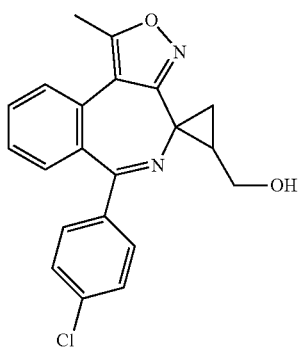 [SMILES: Cc1onc2c1-c1ccccc1C(c1ccc(Cl)cc1)=NC21CC1CO]
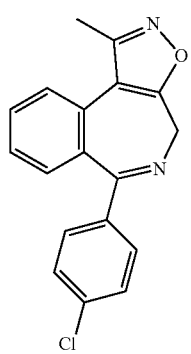 [SMILES: Cc1noc2c1-c1ccccc1C(c1ccc(Cl)cc1)=NC2]
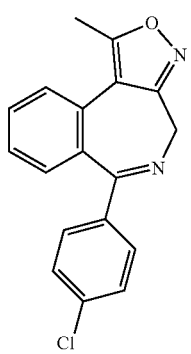 [SMILES: Cc1onc2c1-c1ccccc1C(c1ccc(Cl)cc1)=NC2]
TABLE 2
Exemplary Compounds of Formula IV:
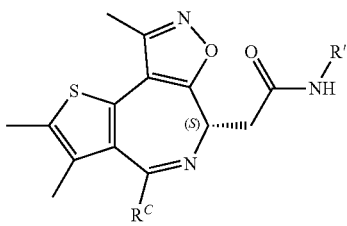
(IV)
| Cmpd No. | $R^C$ | R' |
|---|---|---|
| 100 |  | H |
| 101 |  | H |
| 102 |  | H |
| 103 |  | H |
| 104 |  | H |
| 105 |  | H |
| 106 |  | H |
| 107 |  | H |

TABLE 2-continued
Exemplary Compounds of Formula IV:
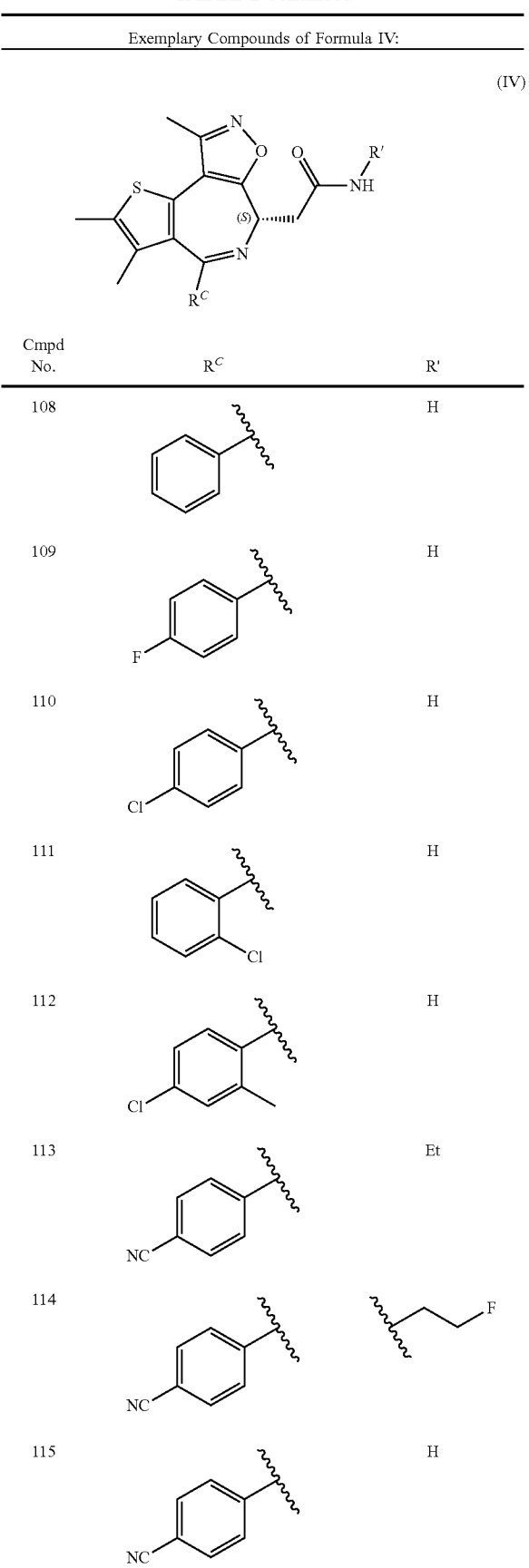
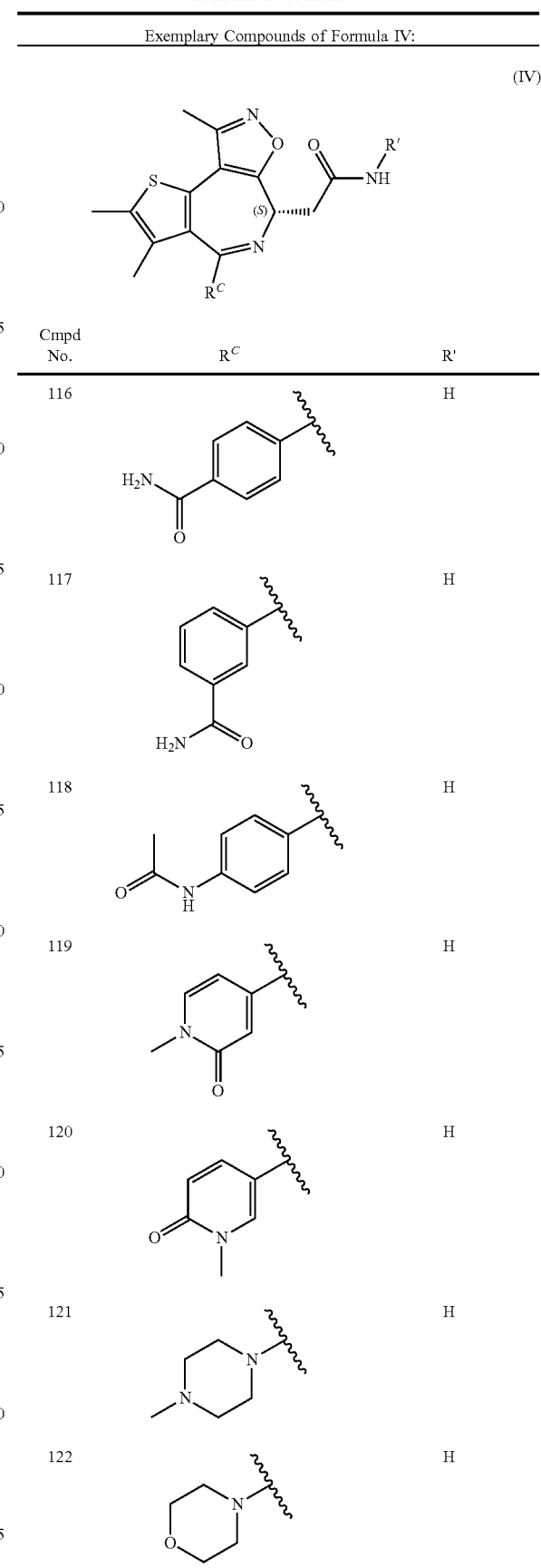

TABLE 2-continued

Exemplary Compounds of Formula IV:

(IV)

| Cmpd No. | R^C | R' |
|---|---|---|
| 123 | N-methylhomopiperazinyl | H |
| 124 | n-propyl | H |
| 125 | cyclopropyl | H |
| 126 | cyclohexyl | H |
| 165 | 4-chlorophenyl | Et |
| 168 | tetrahydropyran-4-yl | H |

TABLE 3

Exemplary Compounds of Formula V:

(V)

| Cmpd No. | $R_{5a}$ | $R_{5b}$ | $R^C$ | R' |
|---|---|---|---|---|
| 128 | H | Me | 4-chlorophenyl | H |
| 129 | H | Me | 4-fluorophenyl | H |
| 130 | H | Me | 4-cyanophenyl | H |
| 131 | H | Me | pyridin-4-yl | H |
| 132 | H | Me | 4-(trifluoromethyl)phenyl | H |
| 133 | H | Me | 5-chloropyridin-2-yl | H |
| 134 | H | Me | 4-carbamoylphenyl | H |
| 135 | H | Me | 4-methoxyphenyl | H |

TABLE 3-continued
Exemplary Compounds of Formula V:
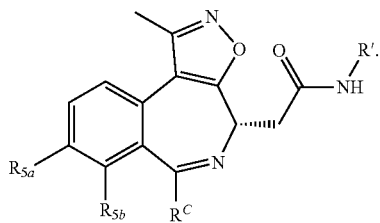
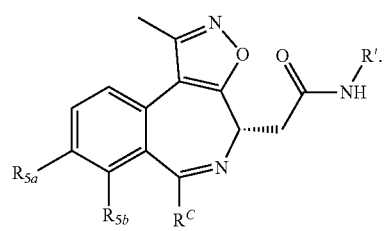
| Cmpd No. | $R_{5a}$ | $R_{5b}$ | $R^C$ | R' |
|---|---|---|---|---|
| 136 | H | Me | 4-(OCF₃)-phenyl | H |
| 137 | H | Cl | pyridin-4-yl | H |
| 138 | H | Cl | 4-F-phenyl | H |
| 139 | H | Cl | 4-Cl-phenyl | H |
| 140 | H | Cl | 4-CN-phenyl | H |
| 141 | Cl | H | 4-Cl-phenyl | H |
| 142 | Cl | H | 4-CN-phenyl | H |
| 143 | Cl | H | 4-CN-phenyl | Et |
| 144 | H | H | 4-Cl-phenyl | H |
| 145 | H | H | 4-Cl-phenyl | CH₂CH₂OMe |
| 146 | H | H | 4-OMe-phenyl | H |
| 147 | H | H | 3-OMe-phenyl | H |
| 148 | H | H | 4-CN-phenyl | H |
| 149 | H | H | 4-CN-phenyl | Et |
| 150 | H | H | 4-CN-phenyl | CH₂CH₂OMe |

TABLE 3-continued
Exemplary Compounds of Formula V:
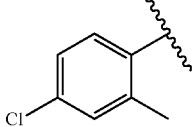 [SMILES: *c1ccc(Cl)cc1C]
(V)
| Cmpd No. | R$_{5a}$ | R$_{5b}$ | R$^C$ | R' |
|---|---|---|---|---|
| 151 | H | H | 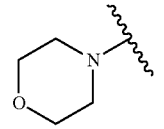 [SMILES: *N1CCOCC1] | H |
| 152 | H | H | 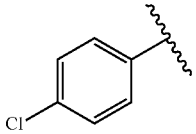 [SMILES: *c1ccc(Cl)cc1] | H |
| 159 | H | H | 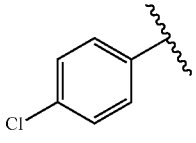 [SMILES: *c1ccc(Cl)cc1] | Et |
| 160 | OMe | H | 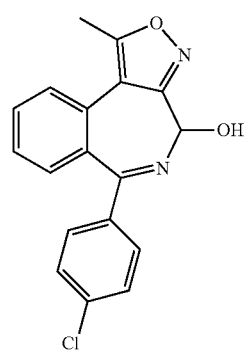 | Et |
TABLE 4
Additional Exemplary Compounds of the Invention.
| Cmpd No | Structure |
|---|---|
| 127 | 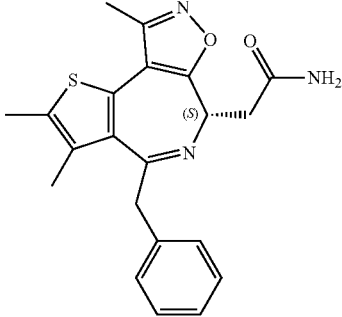 |
| 153 | 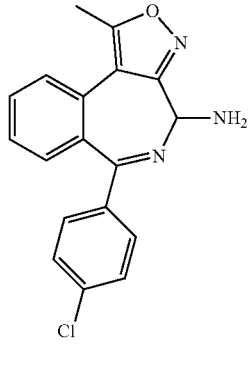 [SMILES: Cc1onc2c1-c1ccccc1C(c1ccc(Cl)cc1)=NC2N] |
| 154 | 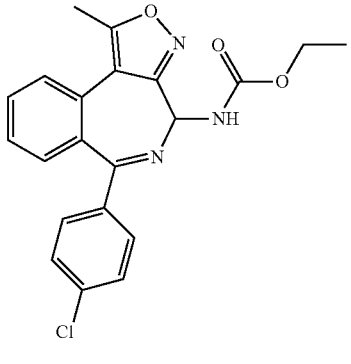 [SMILES: CCOC(=O)NC1N=C(c2ccc(Cl)cc2)c2ccccc2-c2c1noc2C] |
| 155 | 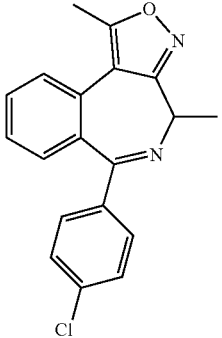 [SMILES: Cc1onc2c1-c1ccccc1C(c1ccc(Cl)cc1)=NC2C] |
| 156 | 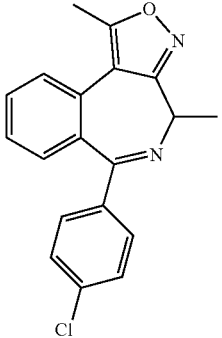 [SMILES: Cc1onc2c1-c1ccccc1C(c1ccc(Cl)cc1)=NC2C] |

TABLE 4-continued

Additional Exemplary Compounds of the Invention.

| Cmpd No | Structure |
|---|---|
| 157 | (structure) |
| 158 | (structure) |
| 161 | (structure) |
| 162 | (structure) |
| 163 | (structure) |
| 164 | (structure) |
| 166 | (structure) |
| 167 | (structure) |

TABLE 4-continued

Additional Exemplary Compounds of the Invention.

| Cmpd No | Structure |
|---|---|
| 169 | (structure) |
| 170 | (structure) |
| 171 | (structure) |
| 172 | (structure) |
| 173 | (structure) |
| 174 | (structure) |
| 175 | (structure) |
| 176 | (structure) |

TABLE 4-continued

Additional Exemplary Compounds of the Invention.

| Cmpd No | Structure |
|---|---|
| 177 | 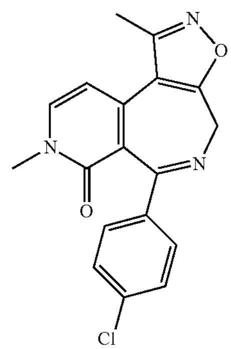 [SMILES: Cc1noc2c1-c1ccn(C)c(=O)c1C(c1ccc(Cl)cc1)=NC2] |
| 178 | 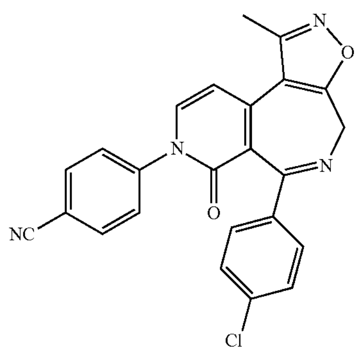 [SMILES: Cc1noc2c1-c1ccn(-c3ccc(C#N)cc3)c(=O)c1C(c1ccc(Cl)cc1)=NC2] |
| 179 | 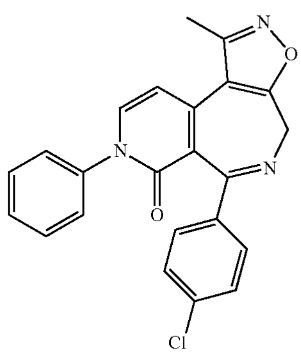 [SMILES: Cc1noc2c1-c1ccn(-c3ccccc3)c(=O)c1C(c1ccc(Cl)cc1)=NC2] |
| 180 | 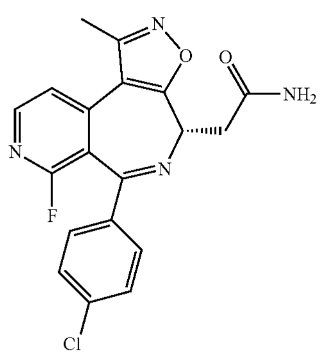 [SMILES: Cc1noc2c1-c1ccnc(F)c1C(c1ccc(Cl)cc1)=N[C@H]2CC(N)=O] |
| 181 | |
| 182 | |
| 183 | |
| 184 | |

TABLE 4-continued

Additional Exemplary Compounds of the Invention.

| Cmpd No | Structure |
|---|---|
| 185 | (structure) |
| 186 | (structure) |
| 187 | (structure) |
| 188 | (structure) |
| 189 | (structure) |

In certain embodiments, the present invention provides a method of inhibiting a bromodomain-containing protein (such as a BET protein, e.g., BRD2, BRD3, BRD4, and/or BRDT) comprising contacting said bromodomain-containing protein with any compound depicted in the tables herein, or a pharmaceutically acceptable salt or composition thereof.

Uses, Formulation and Administration

Pharmaceutically Acceptable Compositions

According to another embodiment, the present invention provides a method of inhibiting a bromodomain-containing protein (such as a BET protein, e.g., BRD2, BRD3, BRD4, and/or BRDT) using a composition comprising a compound of the invention or a pharmaceutically acceptable derivative thereof and a pharmaceutically acceptable carrier, adjuvant, or vehicle. The amount of a compound of the invention in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, the amount of compound in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, a provided composition is formulated for administration to a patient in need of such composition. In some embodiments, a provided composition is formulated for oral administration to a patient.

The term "patient," as used herein, means an animal, such as a mammal, such as a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitory active metabolite or residue thereof.

As used herein, the term "inhibitory active metabolite or residue thereof" means that a metabolite or residue thereof is also an inhibitor of one or more bromodomain-containing proteins (such as a BET protein, e.g., BRD2, BRD3, BRD4, and/or BRDT), or a mutant thereof.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promotors to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration. Provided compositions may be formulate such that a dosage of between 0.01-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for the inhibition of activity of one or more proteins involved in epigenetic regulation. Thus, in some embodiments, the present invention provides a method of inhibiting one or more proteins involved in epigenetic regulation, such as proteins containing acetyl-lysine recognition motifs, also known as bromodomains (e.g., BET proteins, such as BRD2, BRD3, BRD4, and/or BRDT), by administering a provided compound or composition.

Epigenetics is the study of heritable changes in gene expression caused by mechanisms other than changes in the underlying DNA sequence. Molecular mechanisms that play a role in epigenetic regulation include DNA methylation and chromatin/histone modifications. Chromatin recognition, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) *Curr. Opin. Genet. Dev.* 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) *Nature* 389:251-260).

Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

One type of histone modification, lysine acetylation, is recognized by bromodomain-containing proteins. Bromodomain-containing proteins are components of transcription factor complexes and determinants of epigenetic memory (Dey, et al. (2009) *Mol. Biol. Cell* 20:4899-4909). There are 46 human proteins containing a total of 57 bromodomains discovered to date. One family of bromodomain-containing proteins, BET proteins (BRD2, BRD3, BRD4, and BRDT) have been used to establish proof-of-concept for targeting protein-protein interactions of epigenetic "readers," as opposed to chromatin-modifying enzymes, or so-called epigenetic "writers" and "erasers" (Filippakopoulos, et al. "Selective Inhibition of BET Bromodomains," *Nature* (published online Sep. 24, 2010); Nicodeme, et al. "Suppression of Inflammation by a Synthetic Histone Mimic," *Nature* (published online Nov. 10, 2010)).

Examples of proteins inhibited by the compounds and compositions described herein and against which the methods described herein are useful include bromodomain-containing proteins, such as BET proteins, such as BRD2, BRD3, BRD4, and/or BRDT, or an isoform or mutant thereof.

The activity of a provided compound, or composition thereof, as an inhibitor of a bromodomain-containing protein, such as a BET protein, such as BRD2, BRD3, BRD4, and/or BRDT, or an isoform or mutant thereof, may be assayed in vitro, in vivo, or in a cell line. In vitro assays include assays that determine inhibition of bromodomain-containing proteins, such as BET proteins, such as BRD2, BRD3, BRD4, and/or BRDT, or a mutant thereof. Alternatively, inhibitor binding may be determined by running a competition experiment where a provided compound is incubated with a bromodomain-containing protein, such as a BET protein, such as BRD2, BRD3, BRD4, and/or BRDT bound to known ligands, labeled or unlabeled. Detailed conditions for assaying a provided compound as an inhibitor of a bromodomain-containing protein, such as a BET protein, such as BRD2, BRD3, BRD4, and/or BRDT or a mutant thereof, are set forth in the Examples below.

The invention provides for a method of treating a subject with a MYC-dependent cancer, comprising: identifying a subject in need of treatment; administering to the subject a BET inhibitor; determining at least one of MYC mRNA expression, MYC protein expression and tumor mass, and wherein following administration, there is a decrease in at least one of myc mRNA expression, MYC protein expression and tumor mass, thereby treating the disease.

In one embodiment, the identification step comprises determining whether the subject has at least one of a MYC translocation, a genetic rearrangement of MYC, MYC amplification, MYC over-expression and at least one cellular function that facilitates cellular and/or tumor growth and is altered upon reduction of myc mRNA or protein expression.

The invention also provides for a method of treating a subject with a MYC-dependent cancer, comprising: determining at least one of MYC mRNA expression, MYC protein expression and tumor mass; administering to the subject a BET inhibitor; and comparing at least one of MYC mRNA expression, MYC protein expression and tumor mass in the subject before and after administration of the BET inhibitor.

The invention also provides a method of treating a subject with a MYC-dependent cancer, comprising: administering to the subject a BET inhibitor that is identified as capable of decreasing at least one of myc mRNA expression, MYC protein expression and tumor mass; and determining at least one of myc mRNA expression, MYC protein expression and tumor mass; wherein following the administration, there is a decrease in at least one of myc mRNA expression, MYC protein expression and tumor mass, thereby treating the disease.

The invention also provides for a method of treating a subject with a disease, comprising: administering a BET inhibitor that is identified as capable of decreasing at least one of myc mRNA expression, MYC protein expression and tumor mass, wherein following the administration, there is a decrease in at least one of myc mRNA expression, MYC protein expression and tumor mass, thereby treating the disease.

Acetylated histone recognition and bromodomain-containing proteins (such as BET proteins) have been implicated in proliferative disease. BRD4 knockout mice die shortly after implantation and are compromised in their ability to maintain an inner cell mass, and heterozygotes display pre- and postnatal growth defects associated with reduced proliferation rates. BRD4 regulates genes expressed during M/G1, including growth-associated genes, and remains bound to chromatin throughout the cell cycle (Dey, et al. (2009) *Mol. Biol. Cell* 20:4899-4909). BRD4 also physically associates with Mediator and P-TEFb (CDK9/cyclin T1) to facilitate transcriptional elongation (Yang, et al. (2005) *Oncogene* 24:1653-1662; Yang, et al. (2005) *Mol. Cell.* 19:535-545). CDK9 is a validated target in chronic lymphocytic leukemia (CLL), and is linked to c-Myc-dependent transcription (Phelps, et al. Blood 113:2637-2645; Rahl, et al. (2010) *Cell* 141:432-445).

BRD4 is translocated to the NUT protein in patients with lethal midline carcinoma, an aggressive form of human squamous carcinoma (French, et al. (2001) *Am. J. Pathol.* 159:1987-1992; French, et al. (2003) *Cancer Res.* 63:304-307). In vitro analysis with RNAi supports a causal role for BRD4 in this recurrent t(15; 19) chromosomal translocation. Pharmacologic inhibition of the BRD4 bromodomains results in growth arrest/differentiation of BRD4-NUT cell lines in vitro and in vivo (Filippakopoulos, et al. "Selective Inhibition of BET Bromodomains," *Nature* (published online Sep. 24, 2010)).

Bromodomain-containing proteins (such as BET proteins) have also been implicated in inflammatory diseases. BET proteins (e.g., BRD2, BRD3, BRD4, and BRDT) regulate assembly of histone acetylation-dependent chromatin complexes that control inflammatory gene expression (Hargreaves, et al. (2009) *Cell* 138:129-145; LeRoy, et al. (2008) *Mol. Cell.* 30:51-60; Jang, et al. (2005) *Mol. Cell.* 19:523-534; Yang, et al. (2005) *Mol. Cell.* 19:535-545). Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shock and bacteria-induced sepsis in vivo (Nicodeme, et al. "Suppression of Inflammation by a Synthetic Histone Mimic," *Nature* (published online Nov. 10, 2010)).

Bromodomain-containing proteins (such as BET proteins) also play a role in viral disease. For example, BRD4 is implicated in human papilloma virus (HPV). In the primary phase of HPV infection of basal epithelia, the viral genome is maintained in an extra-chromosomal episome. In some strains of HPV, BRD4 binding to the HPV E2 protein functions to tether the viral genome to chromosomes. E2 is critical for both the repression of E6/E7 and to activation of HPV viral genes. Disruption of BRD4 or the BRD4-E2 interaction blocks E2-dependent gene activation. BRD4 also functions to tether other classes of viral genomes to host chromatin (e.g., Herpesvirus, Epstein-Barr virus).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In certain embodiments, a provided compound inhibits one or more of BRD2, BRD3, BRD4, BRDT, and/or another member of the bromodomain-containing proteins, or a mutant thereof. In some embodiments, a provided compound inhibits two or more of BRD2, BRD3, BRD4, BRDT, and/or another member of the bromodomain-containing proteins, or a mutant thereof. Provided compounds are inhibitors of one of more of the bromodomain-containing proteins, such as BRD2, BRD3, BRD4, and/or BRDT and are therefore useful for treating one or more disorders associated with activity of one or more of the bromodomain-containing proteins, such as BRD2, BRD3, BRD4, and/or BRDT. Thus, in certain embodiments, the present invention provides a method for treating an bromodomain-containing protein-mediated disorder, such as a BET-mediated, a BRD2-mediated, a BRD3-mediated, a BRD4-mediated disorder, and/or a BRDT-mediated disorder comprising the step of inhibiting a bromodomain-containing protein, such as a BET protein, such as BRD2, BRD3, BRD4, and/or BRDT, or a mutant thereof, by administering to a patient in need thereof a provided compound, or a pharmaceutically acceptable composition thereof.

As used herein, the terms "bromodomain-containing protein-mediated", "BET-mediated", "BRD2-mediated", "BRD3-mediated", "BRD4-mediated", and/or "BRDT-mediated" disorders or conditions means any disease or other deleterious condition in which one or more of the bromodomain-containing proteins, such as BET proteins, such as BRD2, BRD3, BRD4 and/or BRDT, or a mutant thereof, are known to play a role. Accordingly, another embodiment of the present invention relates to treating or lessening the severity of one or more diseases in which one or more of the bromodomain-containing proteins, such as BET proteins, such as BRD2, BRD3, BRD4, and/or BRDT, or a mutant thereof, are known to play a role.

Diseases and conditions treatable according to the methods of this invention include, but are not limited to, cancer and other proliferative disorders, inflammatory diseases, sepsis, autoimmune disease, and viral infection. Thus one aspect is a method of treating a subject having a disease, disorder, or symptom thereof the method including administration of a compound or composition herein to the subject. In one embodiment, a human patient is treated with a compound of the invention and a pharmaceutically acceptable carrier, adjuvant, or vehicle, wherein said compound is present in an amount to measurably inhibit bromodomain-containing protein activity (such as BET protein, e.g., BRD2, BRD3, BRD4, and/or BRDT) in the patient.

The invention further relates to a method for treating or ameliorating cancer or another proliferative disorder by administration of an effective amount of a compound according to this invention to a mammal, in particular a human in need of such treatment. In some aspects of the invention, the disease to be treated by the methods of the present invention is cancer. Examples of cancers treated using the compounds and methods described herein include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In some embodiments, the present invention provides a method of treating a benign proliferative disorder. Such benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The invention further relates to a method for treating infectious and noninfectious inflammatory events and autoimmune and other inflammatory diseases by administration of an effective amount of a provided compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleracierma, mycosis fungoides, acute inflammatory responses (such as acute respiratory distress syndrome and ischemia/reperfusion injury), and Graves' disease.

In some embodiments, the present invention provides a method of treating systemic inflammatory response syndromes such as LPS-induced endotoxic shock and/or bacteria-induced sepsis by administration of an effective amount of a provided compound to a mammal, in particular a human in need of such treatment.

The invention further relates to a method for treating viral infections and diseases by administration of an effective amount of a provided compound to a mammal, in particular a human in need of such treatment. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

The invention further provides a method of treating a subject, such as a human, suffering from one of the above-mentioned conditions, illnesses, disorders or diseases. The method comprises administering a therapeutically effective amount of one or more provided compounds, which function by inhibiting a bromodomain and, in general, by modulating gene expression, to induce various cellular effects, in particular induction or repression of gene expression, arresting cell proliferation, inducing cell differentiation and/or inducing apoptosis, to a subject in need of such treatment.

The invention further provides a therapeutic method of modulating protein methylation, gene expression, cell proliferation, cell differentiation and/or apoptosis in vivo in diseases mentioned above, in particular cancer, inflammatory disease, and/or viral disease comprising administering to a subject in need of such therapy a pharmacologically active and therapeutically effective amount of one or more provided compounds.

The invention further provides a method of regulating endogenous or heterologous promoter activity by contacting a cell with a provided compound.

In certain embodiments, the invention provides a method of treating a disorder (as described above) in a subject, comprising administering to the subject identified as in need thereof, a compound of the invention. The identification of those patients who are in need of treatment for the disorders described above is well within the ability and knowledge of one skilled in the art. Certain of the methods for identification of patients which are at risk of developing the above disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a disorder by methods well known in the art (e.g., determining tumor size or screening for tumor markers where the cell proliferative disorder is cancer) and then administering a therapeutically effective amount of a compound of the invention, to the subject. After an appropriate period of time after the administration of the compound (e.g., 1 day, 1 week, 2 weeks, one month, six months), the extent of the disorder is determined again. The modulation (e.g., decrease) of the extent or invasiveness of the disorder indicates efficacy of the treatment. The extent or invasiveness of the disorder may be determined periodically throughout treatment. For example, the extent or invasiveness of the disorder may be checked every few hours, days or weeks to assess the further efficacy of the treatment. A decrease in extent or invasiveness of the disorder indicates that the treatment is efficacious. The method described may be used to screen or select patients that may benefit from treatment with a compound of the invention.

The invention further relates to the use of provided compounds for the production of pharmaceutical compositions which are employed for the treatment and/or prophylaxis and/or amelioration of the diseases, disorders, illnesses and/or conditions as mentioned herein.

The invention further relates to the use of provided compounds for the production of pharmaceutical compositions which are employed for the treatment and/or prophylaxis of diseases and/or disorders responsive or sensitive to the inhibition of bromodomain-containing proteins, particularly those diseases mentioned above, such as e.g. cancer, inflammatory disease, viral disease.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

Compounds or compositions described herein may be administered using any amount and any route of administration effective for treating or lessening the severity of cancer or other proliferative disorder. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

According to some embodiments, the invention relates to a method of inhibiting bromodomain-containing proteins in a biological sample comprising the step of contacting said biological sample with a provided compound, or a composition thereof.

According to some embodiments, the invention relates to a method of inhibiting a bromodomain-containing protein, such as a BET protein, such as BRD2, BRD3, BRD4 and/or BRDT, or a mutant thereof, activity in a biological sample comprising the step of contacting said biological sample with a provided compound, or a composition thereof.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of activity of an protein, e.g., a bromodomain-containing protein, such as a BET protein, such as BRD2, BRD3, BRD4 and/or BRDT, or a mutant thereof, in a biological sample is useful for a variety of purposes that are known to one of skill in the art. Examples of such purposes include, but are not limited to, blood transfusion, organ-transplantation, biological specimen storage, and biological assays.

According to another embodiment, the invention relates to a method of inhibiting activity of one or more bromodomain-containing protein, such as a BET protein, such as BRD2, BRD3, BRD4, and/or BRDT, or a mutant thereof, in a patient comprising the step of administering to said patient a provided compound, or a composition comprising said compound. In certain embodiments, the present invention provides a method for treating a disorder mediated by one or more bromodomain-containing proteins, such as a BET protein, such as BRD2, BRD3, BRD4, and/or BRDT, or a mutant thereof, in a patient in need thereof, comprising the step of administering to said patient a provided compound or pharmaceutically acceptable composition thereof. Such disorders are described in detail herein.

Depending upon the particular condition, or disease, to be treated, additional therapeutic agents that are normally administered to treat that condition may also be present in the compositions of this disclosure or administered separately as a part of a dosage regimen. As used herein, additional therapeutic agents that are normally administered to treat a particular disease, or condition, are known as "appropriate for the disease, or condition, being treated."

In some embodiments, the additional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

Other therapies, chemotherapeutic agents, or other antiproliferative agents may be combined with a provided compound to treat proliferative diseases and cancer. Examples of therapies or anticancer agents that may be used in combination with compounds of formula I include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effects (e.g., an antiemetic), and any other approved chemotherapeutic drug.

A provided compound may also be used to advantage in combination with one or more antiproliferative compounds. Such antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carotenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Exemplary aromatase inhibitors include steroids, such as atamestane, exemestane and formestane, and non-steroids, such as aminoglutethimide, rogletimide, pyridoglutethimide, trilostane, testolactone, ketoconazole, vorozole, fadrozole, anastrozole and letrozole.

Exemplary anti-estrogens include tamoxifen, fulvestrant, raloxifene and raloxifene hydrochloride. Anti-androgens include, but are not limited to, bicalutamide. Gonadorelin agonists include, but are not limited to, abarelix, goserelin and goserelin acetate.

Exemplary topoisomerase I inhibitors include topotecan, gimatecan, irinotecan, camptothecin and its analogues, 9-nitrocamptothecin and the macromolecular camptothecin conjugate PNU-166148. Topoisomerase II inhibitors include, but are not limited to, the anthracyclines such as doxorubicin, daunorubicin, epirubicin, idarubicin and nemorubicin, the anthraquinones mitoxantrone and losoxantrone, and the podophillotoxins etoposide and teniposide.

Exemplary microtubule active agents include microtubule stabilizing, microtubule destabilizing compounds and microtubulin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; colchicine and epothilones and derivatives thereof.

Exemplary alkylating agents include cyclophosphamide, ifosfamide, melphalan or nitrosoureas such as carmustine and lomustine.

Exemplary cyclooxygenase inhibitors include Cox-2 inhibitors, 5-alkyl substituted 2-arylaminophenylacetic acid and derivatives, such as celecoxib, rofecoxib, etoricoxib, valdecoxib or a 5-alkyl-2-arylaminophenylacetic acid, such as lumiracoxib.

Exemplary matrix metalloproteinase inhibitors ("MMP inhibitors") include collagen peptidomimetic and non-peptidomimetic inhibitors, tetracycline derivatives, batimastat, marimastat, prinomastat, metastat, BMS-279251, BAY 12-9566, TAA211, MMI270B, and AAJ996.

Exemplary mTOR inhibitors include compounds that inhibit the mammalian target of rapamycin (mTOR) and possess antiproliferative activity such as sirolimus, everolimus, CCI-779, and ABT578.

Exemplary antimetabolites include 5-fluorouracil (5-FU), capecitabine, gemcitabine, DNA demethylating compounds, such as 5-azacytidine and decitabine, methotrexate and edatrexate, and folic acid antagonists such as pemetrexed.

Exemplary platin compounds include carboplatin, cisplatin, cisplatinum, and oxaliplatin.

Exemplary methionine aminopeptidase inhibitors include bengamide or a derivative thereof and PPI-2458.

Exemplary bisphosphonates include etidronic acid, clodronic acid, tiludronic acid, pamidronic acid, alendronic acid, ibandronic acid, risedronic acid and zoledronic acid.

Exemplary antiproliferative antibodies include trastuzumab, trastuzumab-DM1, cetuximab, bevacizumab, rituximab, PRO64553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary heparanase inhibitors include compounds that target, decrease or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras; for example, a farnesyl transferase inhibitor such as L-744832, DK8G557, tipifarnib, and lonafarnib.

Exemplary telomerase inhibitors include compounds that target, decrease or inhibit the activity of telomerase, such as compounds which inhibit the telomerase receptor, such as telomestatin.

Exemplary proteasome inhibitors include compounds that target, decrease or inhibit the activity of the proteasome including, but not limited to, bortezomib.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and busulfan; and ALK inhibitors, which are compounds which target, decrease or inhibit anaplastic lymphoma kinase.

Exemplary Flt-3 inhibitors include PKC412, midostaurin, a staurosporine derivative, SU11248 and MLN518.

Exemplary HSP90 inhibitors include compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing or inhibiting the activity of the platelet-derived growth factor-receptors (PDGFR), such as a compound which targets, decreases, or inhibits the activity of PDGFR, such as an N-phenyl-2-pyrimidine-amine derivatives, such as imatinib, SU101, SU6668 and GFB-111; b) a compound targeting, decreasing or inhibiting the activity of the fibroblast growth factor-receptors (FGFR); c) a compound targeting, decreasing or inhibiting the activity of the insulin-like growth factor receptor I (IGF-IR), such as a compound which targets, decreases, or inhibits the activity of IGF-IR; d) a compound targeting, decreasing or inhibiting the activity of the Trk receptor tyrosine kinase family, or ephrin B4 inhibitors; e) a compound targeting, decreasing or inhibiting the activity of the Axl receptor tyrosine kinase family; f) a compound targeting, decreasing or inhibiting the activity of the Ret receptor tyrosine kinase; g) a compound targeting, decreasing or inhibiting the activity of the Kit/SCFR receptor tyrosine kinase, such as imatinib; h) a compound targeting, decreasing or inhibiting the activity of the c-Kit receptor tyrosine kinases, such as imatinib; i) a compound targeting, decreasing or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; ISIS 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl) methyl]amino}-benzoic acid adamantyl ester; NSC 680410, adaphostin); l) a compound targeting, decreasing or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, CI-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing or inhibiting the activity of the c-Met receptor.

Exemplary compounds that target, decrease or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g. thalidomide and TNP-470.

Additional exemplary chemotherapeutic compounds, one or more of which may be used in combination with provided compounds, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl) phthalazine succinate, angiostatin, endostatin, anthranilic acid amides, ZD4190, ZD6474, SU5416, SU6668, bevacizumab, rhuMAb, rhuFab, macugen; FLT-4 inhibitors, FLT-3 inhibitors, VEGFR-2 IgGI antibody, RPI 4610, bevacizumab, porfimer sodium, anecortave, triamcinolone, hydrocortisone, 11-α-epihydrocotisol, cortexolone, 17α-hydroxy-progesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA or siRNA, or a miscellaneous compound or compound with other or unknown mechanism of action.

For a more comprehensive discussion of updated cancer therapies see, *The Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

The above-mentioned compounds, one or more of which can be used in combination with a provided compound, can be prepared and administered as described in the art.

Provided compounds can be administered alone or in combination with one or more other therapeutic compounds, possible combination therapy taking the form of fixed combinations or the administration of a provided compound and one or more other therapeutic compounds being staggered or given independently of one another, or the combined administration of fixed combinations and one or more other therapeutic compounds. Provided compounds can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Such additional agents may be administered separately from a composition containing a provided compound, as part of a multiple dosage regimen. Alternatively, those agents may be part of a single dosage form, mixed together with a provided compound in a single composition. If administered as part of a multiple dosage regimen, the two active agents may be submitted simultaneously, sequentially or within a period of time from one another normally within five hours from one another.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses.

As used herein, the term "combination," "combined," and related terms refers to the simultaneous or sequential administration of therapeutic agents in accordance with this invention. For example, a provided compound may be administered with another therapeutic agent simultaneously or sequentially in separate unit dosage forms or together in a single unit dosage form. Accordingly, an embodiment of the invention provides a single unit dosage form comprising a provided compound, an additional therapeutic agent, and a pharmaceutically acceptable carrier, adjuvant, or vehicle for use in the methods of the invention.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions should be formulated such that a dosage of between 0.01-100 mg/kg body weight/day of a provided compound can be administered.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Provided compounds, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a provided compound. Implantable devices coated with a compound of this invention are another embodiment of the present invention.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

In another aspect, the invention provides a method of method of synthesizing a compound of formula I. Another embodiment is a method of making a compound of any of the formulae herein using any one, or combination of, reactions delineated herein. The method can include the use of one or more intermediates or chemical reagents delineated herein.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

Synthesis of (2-Bromphenyl)(4-Chlorophenyl)Methanone

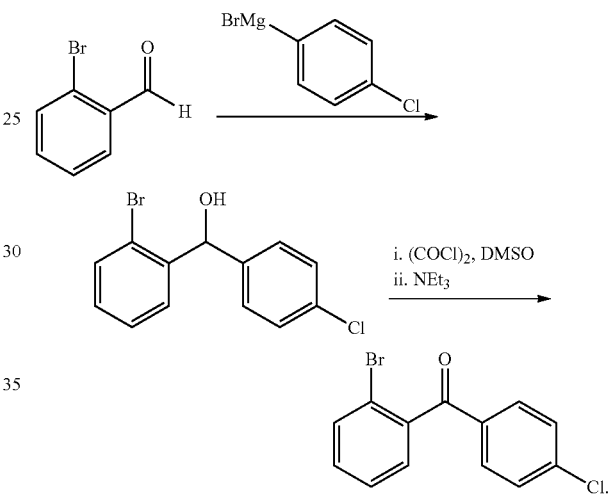

To a solution of 2-bromobenzaldehyde (3.15 mL, 27.0 mmol) and THF (135 mL) at 0° C. was added (4-chlorophenyl)magnesium bromide solution (29.7 mL, 1M in THF, 29.7 mmol). The reaction was stirred at 0° C. for 30 min before addition of a saturated solution of ammonium chloride. The layers were separated and the aqueous extracted with EtOAc. The combined organics were washed with brine, dried over $Na_2SO_4$, filtered, and concentrated. The crude residue was purified via Biotage to afford (2-bromophenyl)(4-chlorophenyl)methanol. To a solution of DCM (100 mL) and oxalyl chloride (2.471 mL, 28.2 mmol) at −78° C. was added DMSO (3.34 mL, 47.0 mmol) and the reaction stirred at −78° C. for 15 min. After 15 min a solution of (2-bromophenyl)(4-chlorophenyl)methanol in DCM (25 mL) was added dropwise and stirred for 15 min at −78° C. before addition of $Et_3N$ (9.84 mL, 70.6 mmol). The cold bath was removed and the reaction was warmed to room temperature. To this solution was added water and the layers separated. The aqueous was extracted with DCM and the combined organics were dried over $Na_2SO_4$, filtered, and concentrated. The crude residue was purified via Biotage (EtOAc/hex) to afford (2-bromophenyl)(4-chlorophenyl)methanone. LC/MS m/z 295 [M+H]$^+$.

Example 2

Synthesis of prop-2-yn-1-yl benzoate

To a solution of prop-2-yn-1-ol (3.63 mL, 62.4 mmol), DCM (180 mL), and Et$_3$N (17.40 mL, 125 mmol) at 0° C. were added benzoyl chloride (7.25 mL, 62.4 mmol) and DMAP (0.381 g, 3.12 mmol). The reaction was stirred while warming to room temperature overnight. The reaction was diluted with water and the layers separated. The aqueous was extracted with DCM and the combined organics were dried over Na$_2$SO$_4$, filtered, and concentrated to afford prop-2-yn-1-yl benzoate which was used in subsequent reactions without further purification. LC/MS m/z 161 [M+H]$^+$.

Example 3

Synthesis of (3-methylisoxazol-5-yl)methyl benzoate

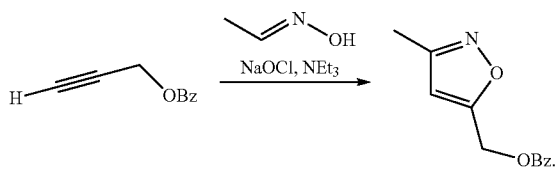

To a solution of chloroform, Et$_3$N (0.435 mL, 3.12 mmol), prop-2-ynyl benzoate (1 g, 6.24 mmol), and (E)-acetaldehyde oxime (0.571 mL, 9.37 mmol) at 0° C. was added bleach (23.12 mL, 18.73 mmol). The reaction was stirred overnight before the layers were separated and the aqueous extracted with DCM. The combined organics were dried over Na$_2$SO$_4$, filtered, and concentrated. The crude residue was purified via Biotage (EtOAc/hex) to afford (3-methyl-isoxazol-5-yl)methyl benzoate. LC/MS m/z 218 [M+H]$^+$.

Example 4

Synthesis of (4-bromo-3-methylisoxazol-5-yl)methyl benzoate

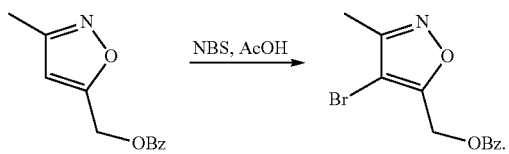

To a resealable vial was added (3-methylisoxazol-5-yl) methyl benzoate (907 mg, 4.18 mmol), AcOH (3.5 mL, 61.1 mmol), and NBS (892 mg, 5.01 mmol). The reaction was heated to 110° C. overnight. The reaction was cooled to room temperature and diluted with water. The aqueous was extracted with EtOAc and the combined organics were washed with brine, dried over Na$_2$SO$_4$, filtered, and concentrated. The crude residue was purified via Biotage (EtOAc/hex) to afford (4-bromo-3-methylisoxazol-5-yl) methyl benzoate. LC/MS m/z 296 [M+H]$^+$.

Example 5

Synthesis of (4-(2-(4-chlorobenzoyl)phenyl)-3-methylisoxazol-5-yl)methyl benzoate

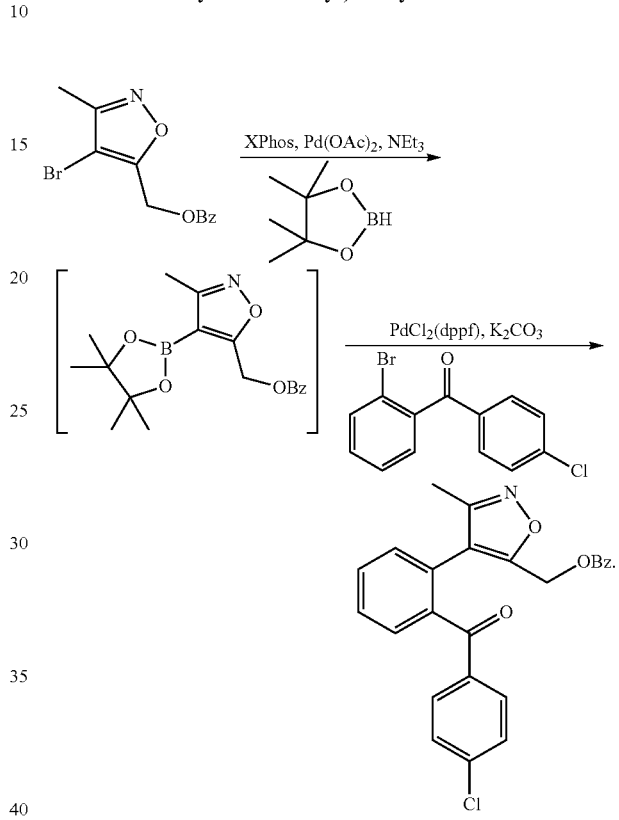

To a resealable vial was added Pd(OAc)$_2$ (3.87 mg, 0.017 mmol) and X-phos (16.42 mg, 0.034 mmol) before the vial was sealed and evacuated and purged with N$_2$ (3×). To this vial was added (4-bromo-3-methylisoxazol-5-yl)methyl benzoate (102 mg, 0.344 mmol) in dioxane (1 mL), Et$_3$N (144 μl, 1.033 mmol), and 4,4,5,5-tetramethyl-1,3,2-dioxaborolane solution (517 μl, 1M in THF, 0.517 mmol). The reaction was stirred overnight at 80° C., cooled to room temperature and filtered. The filtrate was concentrated to afford crude (3-methyl-4-(4,4,5,5-tetramethyl-1,3,2-dioxaborolan-2-yl)isoxazol-5-yl)methyl benzoate. To a resealable vial was added K$_2$CO$_3$ (47.5 mg, 0.344 mmol), PdCl$_2$(dppf)-CH$_2$Cl$_2$ Adduct (20.06 mg, 0.025 mmol), (2-bromophenyl) (4-chlorophenyl)methanone (72.6 mg, 0.246 mmol). The vial was sealed and evacuated and purged with N$_2$ (3×) before addition of crude (3-methyl-4-(4,4,5,5-tetramethyl-1,3,2-dioxaborolan-2-yl)isoxazol-5-yl)methyl benzoate (118 mg, 0.344 mmol) dissolved in dioxane (2 mL). Water (0.5 mL) was then added to this solution before the vial was heated to 110° C. overnight. The reaction was cooled to room temperature, diluted with EtOAc, filtered, and concentrated. The crude residue was purified via Biotage (EtOAc/hex) to afford (4-(2-(4-chlorobenzoyl)phenyl)-3-methylisoxazol-5-yl)methyl benzoate. LC/MS m/z 432 [M+H]$^+$.

Example 6

Synthesis of 6-(4-chlorophenyl)-1-methyl-4H-benzo[c]isoxazolo[4,5-e]azepine

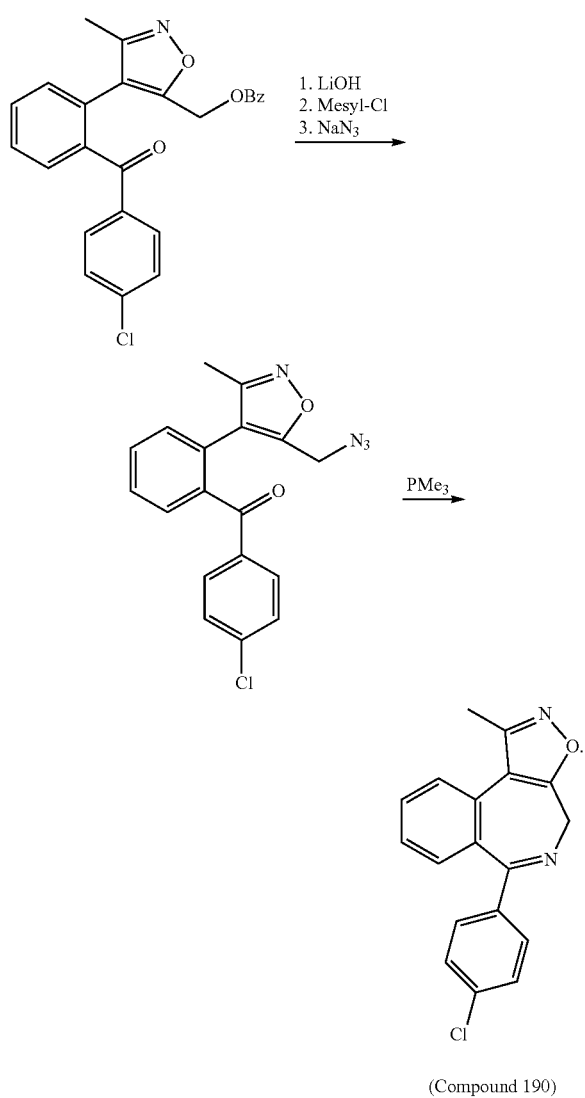

(Compound 190)

(4-chlorophenyl)(2-(5-(hydroxymethyl)-3-methylisoxazol-4-yl)phenyl)methanone To a round bottomed flask was added (4-(2-(4-chlorobenzoyl)phenyl)-3-methylisoxazol-5-yl)methyl benzoate (32.7 mg, 0.076 mmol), THF (3 mL), MeOH (3 mL), and water (1.5 mL). This solution was cooled to 0° C. before addition of Lithium Hydroxide Monohydrate (9.53 mg, 0.227 mmol) and the reaction stirred at 0° C. for 1 h before diluting with water and EtOAc. The layers were separated and the aqueous extracted with EtOAc (3×). The combined organics were washed with brine, dried over Na$_2$SO$_4$, filtered, and concentrated to afford crude (4-chlorophenyl)(2-(5-(hydroxymethyl)-3-methylisoxazol-4-yl)phenyl)methanone.

(4-(2-(4-chlorobenzoyl)phenyl)-3-methylisoxazol-5-yl)methyl methanesulfonate To a round bottomed flask was added crude (4-chlorophenyl)(2-(5-(hydroxymethyl)-3-methylisoxazol-4-yl)phenyl)methanone (24.9 mg, 0.076 mmol), DCM (2 mL), and Et$_3$N (21.18 µl, 0.152 mmol). This solution was cooled to 0° C. before addition of MsCl (7.10 µl, 0.091 mmol) and the reaction stirred at 0° C. for 30 min before diluting with water and extracting with DCM. The combined organics were dried over Na$_2$SO$_4$, filtered, and concentrated to afford crude (4-(2-(4-chlorobenzoyl)phenyl)-3-methylisoxazol-5-yl)methyl methanesulfonate.

(2-(5-(azidomethyl)-3-methylisoxazol-4-yl)phenyl)(4-chlorophenyl)methanone

To a round bottomed flask was added crude (4-(2-(4-chlorobenzoyl)phenyl)-3-methylisoxazol-5-yl)methyl methanesulfonate (30.8 mg, 0.076 mmol), DMF (2 mL), and sodium azide (4.93 mg, 0.076 mmol). The reaction was stirred at room temperature for 2 h before diluting with water and extracting with EtOAc. The combined organics were washed with brine, dried over Na$_2$SO$_4$, filtered, and concentrated to afford crude (2-(5-(azidomethyl)-3-methylisoxazol-4-yl)phenyl) (4-chlorophenyl)methanone.

6-(4-chlorophenyl)-1-methyl-4H-benzo[c]isoxazolo[4,5-e]azepine (Compound 190)

To a resealable vial was added crude (2-(5-(azidomethyl)-3-methylisoxazol-4-yl)phenyl) (4-chlorophenyl)methanone (27 mg, 0.077 mmol) and toluene. The vial was sealed and placed under N$_2$ before addition of trimethylphosphine solution (92 µl, 1 M toluene, 0.092 mmol). The reaction was stirred at room temperature for 2 h before purifying via Biotage (10 g, EtOAc/hex) to afford 6-(4-chlorophenyl)-1-methyl-4H-benzo[c]isoxazolo[4,5-e]azepine. $^1$H NMR (400 MHz, Acetone) δ 7.78-7.84 (m, 1H), 7.65-7.74 (m, 1H), 7.34-7.47 (m, 6H), 4.62 (br. s, 2H), 2.54 (s, 3H). LC/MS m/z 309 [M+H]$^+$.

Example 7

Synthesis of 3-(((4-methoxybenzyl)oxy)methyl)-5-methylisoxazole

To a resealable vial were added NaH (193 mg, 60% dispersion in mineral oil, 4.82 mmol) and THF. The vial was cooled to 0° C. before addition of (4-methoxyphenyl)methanol (639 µl, 5.14 mmol) and the reaction stirred at 0° C. for 30 min before addition of 3-(chloromethyl)-5-methylisoxazole (423 mg, 3.22 mmol) and tetrabutylammonium iodide (119 mg, 0.322 mmol). The reaction was heated to reflux overnight. The vial was cooled to room temperature before being diluted with ammonium chloride solution. The aqueous was extracted with EtOAc and the combined organics were washed with brine, dried over Na$_2$SO$_4$, filtered, and concentrated. The crude residue was purified via Biotage (EtOAc/hex) to afford 3-((4-methoxybenzyloxy)methyl)-5-methylisoxazole. LC/MS m/z 256 [M+Na]$^+$.

Example 8

Synthesis of 2-(3-(((4-methoxybenzyl)oxy)methyl)-5-methylisoxazol-4-yl)benzonitrile

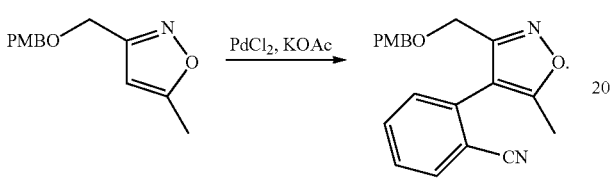

To a resealable vial was added potassium acetate (112 mg, 1.143 mmol), palladium(II) chloride (0.507 mg, 2.86 µmol), and 2-bromobenzonitrile (104 mg, 0.572 mmol). The vial was sealed and evacuated and purged with N$_2$ (3×) before addition of DMA (4 mL) and 3-((4-methoxybenzyloxy)methyl)-5-methylisoxazole (200 mg, 0.857 mmol). The vial was heated to 130° C. overnight. The reaction was cooled to room temperature and diluted with water. The aqueous was extracted with EtOAc and the combined organics were washed with brine, dried over Na$_2$SO$_4$, filtered, and concentrated. The crude residue was purified via Biotage (EtOAc/hex) to afford 2-(3-((4-methoxybenzyloxy)methyl)-5-methylisoxazol-4-yl)benzonitrile. LC/MS m/z 335 [M+H]$^+$.

Example 9

Synthesis of 2-(3-(((4-methoxybenzyl)oxy)methyl)-5-methylisoxazol-4-yl)benzaldehyde

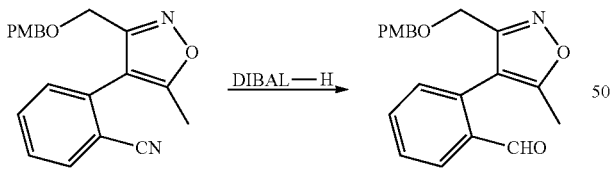

To a round bottomed flask was added 2-(3-((4-methoxybenzyloxy)methyl)-5-methylisoxazol-4-yl)benzonitrile (165.3 mg, 0.494 mmol) and DCM (3 mL). This solution was cooled to 0° C. before addition of a solution of DIBAL-H (593 µl, 1M in DCM, 0.593 mmol). The reaction was stirred at 0° C. for 1 h before addition of 1N HCl. The layers were separated and the aqueous was extracted with DCM (3×). The combined organics were washed with 1N HCl and brine before being dried over Na$_2$SO$_4$, filtered, and concentrated. The crude residue was purified via Biotage (EtOAc/hex) to afford 2-(3-((4-methoxybenzyloxy)methyl)-5-methylisoxazol-4-yl)benzaldehyde. LC/MS m/z 338 [M+H]$^+$.

Example 10

Synthesis of (4-chlorophenyl)(2-(3-(((4-methoxybenzyl)oxy)methyl)-5-methylisoxazol-4-yl)phenyl)methanol

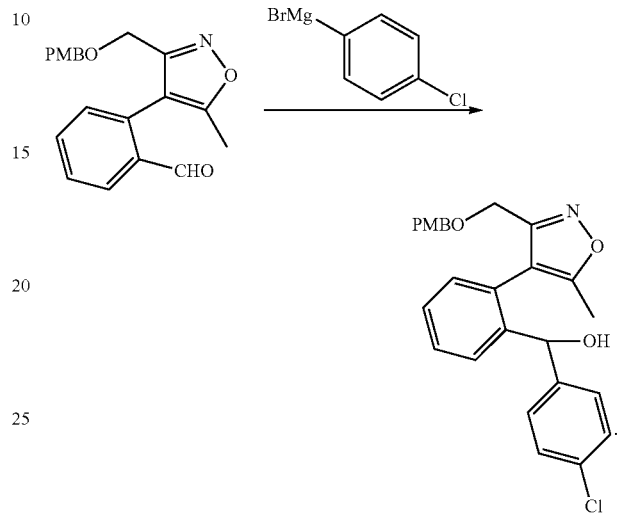

To a round bottomed flask was added 2-(3-(((4-methoxybenzyloxy)methyl)-5-methylisoxazol-4-yl)benzaldehyde (94 mg, 0.279 mmol) and THF. The solution was cooled to −78° C. before addition of (4-chlorophenyl)magnesium bromide solution (418 µl, 1M in THF, 0.418 mmol) and the reaction stirred at −78° C. for 30 min. The solution was quenched via the addition of water and warmed to room temperature. The aqueous was extracted with EtOAc (3×) and the combined organics were washed with brine, dried over Na$_2$SO$_4$, filtered, and concentrated. The crude residue was purified via Biotage (EtOAc/hex) to afford (4-chlorophenyl)(2-(3-(((4-methoxybenzyloxy)methyl)-5-methylisoxazol-4-yl)phenyl)methanol. LC/MS m/z 450 [M+H]$^+$.

Example 11

Synthesis of (4-chlorophenyl)(2-(3-(((4-methoxybenzyl)oxy)methyl)-5-methylisoxazol-4-yl)phenyl)methanone

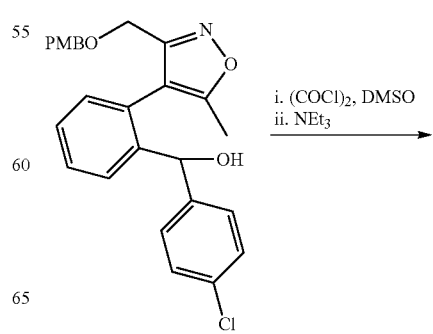

-continued

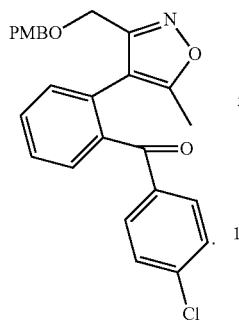

To a round bottomed flask was added DCM (4 mL) and oxalyl chloride (28.0 µl, 0.320 mmol) before the solution was cooled to −78° C. To this solution was added DMSO (37.9 µl, 0.533 mmol) and the reaction stirred at −78° C. for 15 min before addition of (4-chlorophenyl)(2-(3-(((4-methoxybenzyloxy)methyl)-5-methylisoxazol-4-yl)phenyl)methanol (120 mg, 0.267 mmol) dissolved in DCM. The solution was stirred for an additional 15 min before addition of Et$_3$N (112 µl, 0.800 mmol) and the reaction warmed to room temperature. Water was added and the layers separated. The aqueous was extracted with DCM and the combined organics were dried over Na$_2$SO$_4$, filtered, and concentrated. The crude residue was purified via Biotage (EtOAc/hex) to afford (4-chlorophenyl)(2-(3-((4-methoxybenzyloxy)methyl)-5-methylisoxazol-4-yl)phenyl)methanone. LC/MS m/z 448 [M+H]$^+$.

Example 12

Synthesis of (4-chlorophenyl)(2-(3-(hydroxymethyl)-5-methylisoxazol-4-yl)phenyl)methanone

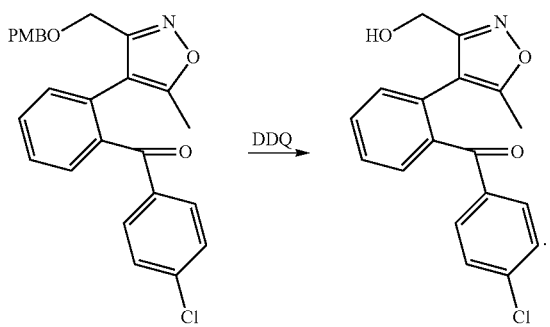

To a round bottomed flask was added (4-chlorophenyl)(2-(3-((4-methoxybenzyloxy)methyl)-5-methylisoxazol-4-yl)phenyl)methan one (69 mg, 0.154 mmol), DCM, and water. This solution was cooled to 0° C. before addition of DDQ (69.9 mg, 0.308 mmol) and the reaction stirred at 0° C. for 4 h before addition of NaHCO$_3$ solution. The layers were separated and the aqueous extracted with DCM. The combined organics were dried over Na$_2$SO$_4$, filtered, and concentrated. The crude residue was purified via Biotage (EtOAc/hex) to afford (4-chlorophenyl)(2-(3-(hydroxymethyl)-5-methylisoxazol-4-yl)phenyl)methanone. LC/MS m/z 328 [M+H]$^+$.

Example 13

Synthesis of 6-(4-chlorophenyl)-1-methyl-4H-benzo[c]isoxazolo[4,3-e]azepine (Compound 191)

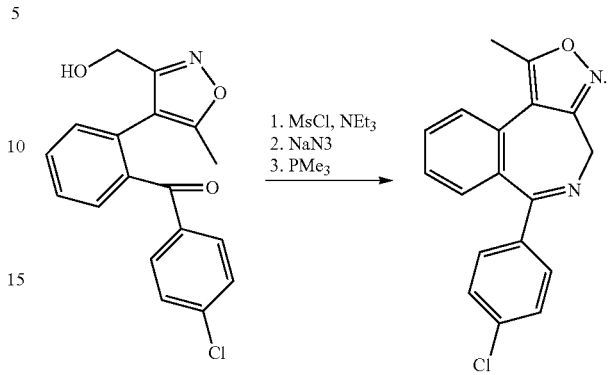

To a round bottomed flask was added (4-chlorophenyl)(2-(3-(hydroxymethyl)-5-methylisoxazol-4-yl)phenyl)methanone (47.2 mg, 0.144 mmol), DCM, and Et$_3$N (40.1 µl, 0.288 mmol). The solution was cooled to 0° C. before addition of Ms-Cl (13.47 µl, 0.173 mmol). The reaction was stirred at 0° C. for 30 min before addition of water. The layers were separated and the aqueous was extracted with DCM. The combined organics were dried over Na$_2$SO$_4$, filtered, and concentrated to afford crude (4-(2-(4-chlorobenzoyl)phenyl)-5-methylisoxazol-3-yl)methyl methanesulfonate. To a round bottomed flask was added (4-(2-(4-chlorobenzoyl)phenyl)-5-methylisoxazol-3-yl)methyl methanesulfonate (58.4 mg, 0.144 mmol), DMF, and sodium azide (28.1 mg, 0.432 mmol). The reaction was stirred at room temperature for 2 h before diluting with water and extracting the aqueous with EtOAc. The combined organics were washed with brine, dried over Na$_2$SO$_4$, filtered, and concentrated to afford crude (2-(3-(azidomethyl)-5-methylisoxazol-4-yl)phenyl) (4-chlorophenyl)methanone. To a round bottomed flask was added (2-(3-(azidomethyl)-5-methylisoxazol-4-yl)phenyl)(4-chlorophenyl)methanone (50.8 mg, 0.144 mmol), toluene (3 mL), and trimethylphosphine solution (216 µl, 1M in toluene, 0.216 mmol). The reaction was stirred at room temperature over 2 days before purifying via Biotage (EtOAc/hex) to afford 6-(4-chlorophenyl)-1-methyl-4H-benzo[c]isoxazolo[4,3-e]azepine. LC/MS m/z 309 [M+H]$^+$; $^1$H NMR (400 MHz, Acetone) δ 7.70-7.76 (m, 1H), 7.63-7.70 (m, 1H), 7.32-7.49 (m, 6H), 5.10 (br. s, 1H), 4.10 (br. s, 1H), 2.68 (s, 3H).

Example 14

General Synthetic Approach to Compounds of Formula I, Wherein R$_2$ is Hydrogen and R$_3$ is —CH$_2$—C(O)—N(R')(R")

Scheme 1 sets forth a general method for making certain compounds of the invention.

Scheme 1.

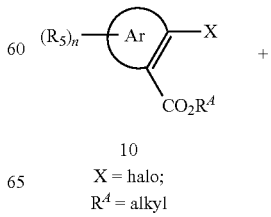

10
X = halo;
R$^A$ = alkyl

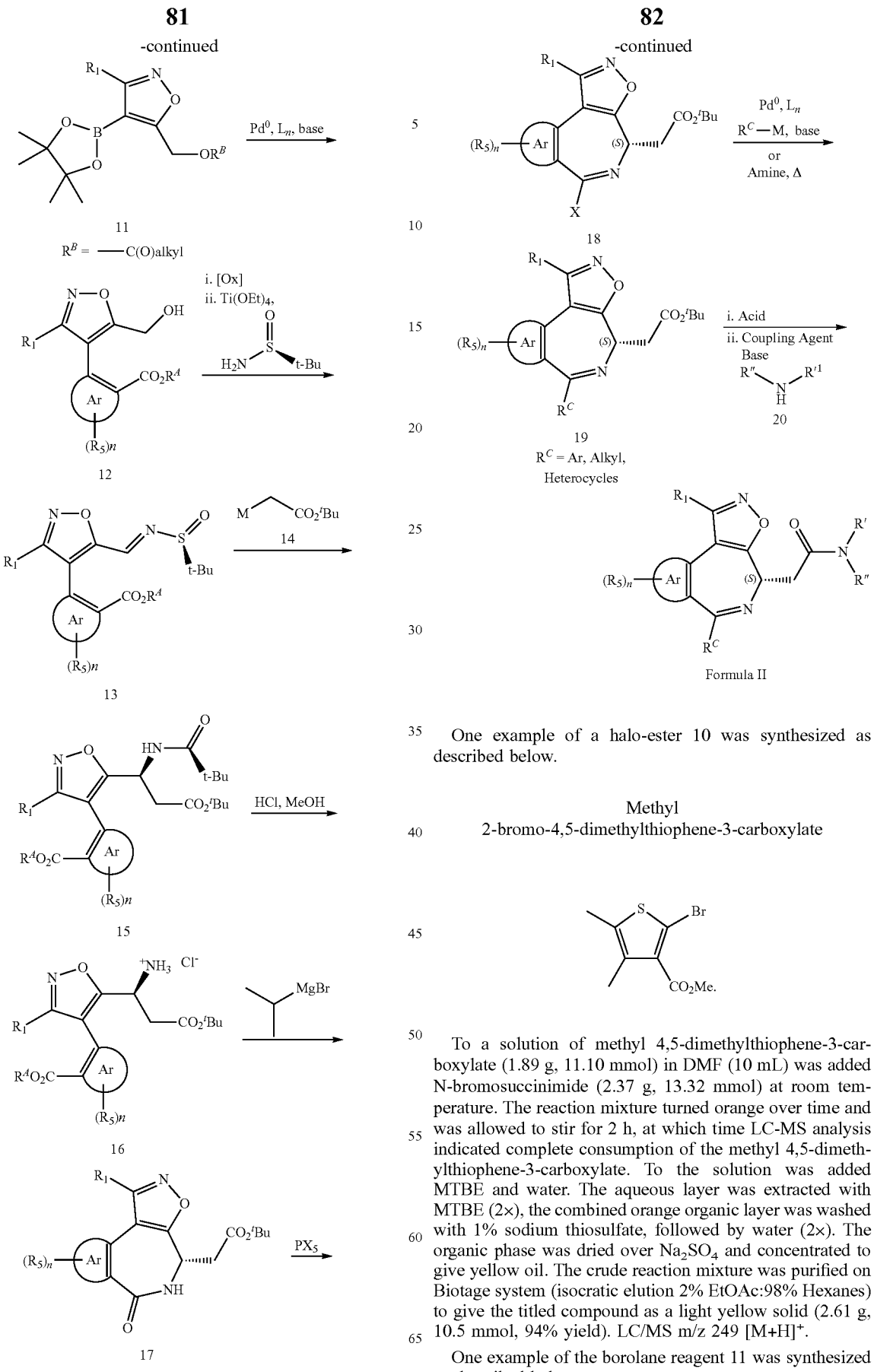

One example of a halo-ester 10 was synthesized as described below.

Methyl 2-bromo-4,5-dimethylthiophene-3-carboxylate

To a solution of methyl 4,5-dimethylthiophene-3-carboxylate (1.89 g, 11.10 mmol) in DMF (10 mL) was added N-bromosuccinimide (2.37 g, 13.32 mmol) at room temperature. The reaction mixture turned orange over time and was allowed to stir for 2 h, at which time LC-MS analysis indicated complete consumption of the methyl 4,5-dimethylthiophene-3-carboxylate. To the solution was added MTBE and water. The aqueous layer was extracted with MTBE (2×), the combined orange organic layer was washed with 1% sodium thiosulfate, followed by water (2×). The organic phase was dried over $Na_2SO_4$ and concentrated to give yellow oil. The crude reaction mixture was purified on Biotage system (isocratic elution 2% EtOAc:98% Hexanes) to give the titled compound as a light yellow solid (2.61 g, 10.5 mmol, 94% yield). LC/MS m/z 249 [M+H]+.

One example of the borolane reagent 11 was synthesized as described below.

(3-Methylisoxazol-5-yl)methyl acetate

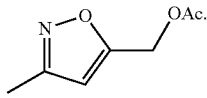

To a suspension of N-chlorosuccimide (71.5 g, 535 mmol) in CHCl$_3$ (360 mL) and pyridine (1.61 g, 20.3 mmol) was added a solution of (E)-acetaldehyde oxime (31.6 g, 535 mmol). After a period of 1 h, propargylacetate (35.0 g, 357 mmol) in a minimum of CHCl$_3$ was added to the previous mixture. Triethylamine (114 g, 1124 mmol) was then added dropwise and the reaction mixture was cooled in a water bath in order to maintain the internal temperature below the boiling point. After a period of 1 h, the reaction mixture was concentrated in vacuo followed by the addition of EtOAc. The mixture was filtered on a glass filter and the solid washed with EtOAc, the combined filtrates were evaporated. After evaporation, additional EtOAc was added and the previous process repeated. The EtOAc was evaporated and the crude product was purified on a on Biotage system (isocratic elution 40% EtOAc:60% Hexanes) and the fractions followed by LC/MS to provide the titled compound as a clear oil. LC/MS m/z 156 [M+H]$^+$.

(4-Bromo-3-methylisoxazol-5-yl)methyl acetate

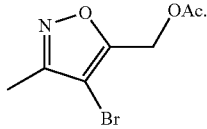

To a solution of (3-methylisoxazol-5-yl)methyl acetate (0.979 g, 6.31 mmol) in AcOH (10 mL, 175 mmol) was added N-bromosuccinimide (1.30 g, 7.30 mmol) and H$_2$SO$_4$ (0.65 mL, 12.19 mmol). The reaction was heated to 110° C. After 1 h, the reaction mixture was cooled to room temperature and carefully poured into a beaker containing ice and saturated NaHCO$_3$. The bi-phasic was vigorously stirred and basic solution (pH ~8-9) was extracted with EtOAc (2×15 mL). The organic layer was washed with 2% sodium thiosulfate, washed with brine (20 mL), dried over Na$_2$SO$_4$, and concentrated to give a light yellow oil. The oil was purified on Biotage system (isocratic elution 10% EtOAc: 90% Hexanes) to give the titled compound (1.30 g, 5.55 mmol, 88% Yield) as a colorless yellow oil. LC/MS m/z 234 [M+H]$^+$.

(3-Methyl-4-(4,4,5,5-tetramethyl-1,3,2-dioxaborolan-2-yl)isoxazol-5-yl)methyl acetate

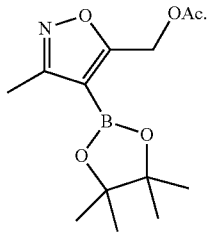

To a 500 mL flask (under N$_2$ (g)) was added dichlorobis(acetonitrile)palladium(II) (0.551 g, 2.12 mmol) and dicyclohexyl(2',6'-dimethoxybiphenyl-2-yl)phosphine (3.50 g, 8.53 mmol). To the solids were sequentially added a solution of (4-bromo-3-methylisoxazol-5-yl)methyl acetate (24.8 g, 106 mmol) in 1,4-dioxane (65 mL), Et$_3$N (44.3 mL, 318 mmol), and 4,4,5,5-tetramethyl-1,3,2-dioxaborolane (24 mL, 160 mmol). The flask was sequentially evacuated and purged under N$_2$, and this process was repeated three times. The reaction mixture was heated to 110° C. (under a constant stream of N$_2$ (g)) and allowed to stir for ~4 h. LC-MS analysis at this point showed complete conversion of the starting bromo-isoxazole. The reaction mixture was cooled to room temperature and EtOAc (100 mL) was added. After 15 min of stirring, the suspension was filtered over a pad of Celite. The filter cake was washed with EtOAc (3×100 mL), concentrated in vacuo, and the solvent was switched using 1,4-Dioxane (2×50 mL). The borate ester with used without further purification.

Suzuki Couplings to Produce Intermediate 12

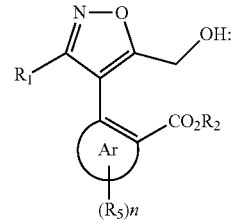

Protocol I: Coupling Under Anhydrous Conditions

A solution of the borolane reagent (11; 1.6 equivalents) in 1,4-dioxane (1.6 M) was added to Pd$_2$(dba)$_3$ (~2 mol %), anhydrous K$_3$PO$_4$ (tribasic) (2.0 equivalents), and dicyclohexyl(2',6'-dimethoxybiphenyl-2-yl)phosphine (~4 mol %) under N$_2$ (g). After stirring the suspension for 2 min., a solution of halo-ester (10; 1.0 equivalents) in MeOH (0.3 M) was introduced in one portion. The suspension was evacuated and purged with N$_2$ (3×), and subsequently heated to 67° C. for 1 h. The reaction mixture was cooled to room temperature and filtered through a plug of Celite. The filter cake was washed with MeOH (3×). The filtrate was concentrated to give a brown oil. The resultant oil was concentrated from MeOH several times (3×) to aid in cleavage of the acetyl ester and produced the alcohol. The crude reaction mixture was purified on Biotage system (generally gradient elution 5% EtOAc:95% Hexanes to 30% EtOAc:70% Hexanes, then isocratic 30% EtOAc:70% Hexanes) to give the titled compound (typically in 80%-93% yield).

Protocol II: Coupling Under Bi-Phasic Conditions

To a round bottomed flask was added PdCl$_2$(dppf)-CH$_2$Cl$_2$ adduct (~5 mol %) and potassium carbonate (2 equivalents) before the flask was evacuated and backfilled with N$_2$ (3×). To this flask was added borolane reagent 11 (such as 3-methyl-4-(4,4,5,5-tetramethyl-1,3,2-dioxaborolan-2-yl)isoxazol-5-yl)methyl acetate (typically 1.5-2 equivalents) dissolved in dioxane (typically ~0.3-0.5 M), the appropriate halo-ester 10 (1 equivalent) and water. The solution was heated to reflux until LC-MS analysis indicated complete consumption of starting material (typically 2-4 h). The reaction was cooled to room temperature and diluted with water and EtOAc. The layers were separated and the aqueous phase was extracted with EtOAc. The combined organics were washed with water and brine, before being dried over Na$_2$SO$_4$, filtered, and concentrated. The crude residue was taken up MeOH (typically ~0.3 M) and sodium methoxide was added (0.2 equivalents). The reaction was stirred at room temperature until LC-MS analysis indicated complete consumption of starting material. The reaction was diluted with water and EtOAc. The layers were separated and the aqueous phase extracted with EtOAc (3×). The combined organics were washed with brine, dried over $Na_2SO_4$, filtered, and concentrated. The crude residue was purified via Biotage (EtOAc/hex) to afford the alcohol (typically 40-80% yield).

General Protocol to Produce Intermediate 13.

a. Oxidation

To a round bottomed flask charged with anhydrous $CH_2Cl_2$ (typically 0.2 M in substrate) was added oxalyl chloride (2 equivalents) and the solution cooled to −78° C. before dropwise addition of DMSO (4 equivalents; caution gas evolution). The solution was stirred at −78° C. for 15 min before dropwise addition of the alcohol dissolved in a minimal amount of $CH_2Cl_2$. This solution was stirred for 15 min at −78° C. before addition of triethylamine (3-5 equivalents) and the solution warmed to room temperature. The reaction was poured into water and the layers separated. The aqueous phase was extracted with $CH_2Cl_2$ and the combined organics were dried over $Na_2SO_4$, filtered, and concentrated. The crude residue was purified via Biotage (EtOAc/Hex) to afford the aldehyde (typically 60-90% yield).

b. (S)-tert-Butylsulfinylimine (Intermediate 13) Formation

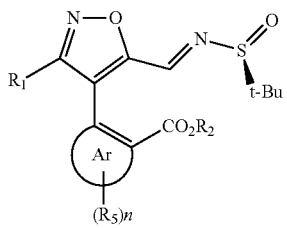

To a round bottomed flask charged with aldehyde, (S)-2-methylpropane-2-sulfinamide (1.2 equivalents), and $CH_2Cl_2$ (typically ~0.2-0.5 M in substrate) was added tetraethoxytitanium (2 equivalents). The solution was stirred overnight at room temperature before addition of brine. This slurry was vigorously stirred for 30 min before filtering. The filter cake was washed with $CH_2Cl_2$. The layers were separated and the aqueous phase was extracted with $CH_2Cl_2$. The combined organics were washed with brine, dried over $Na_2SO_4$, filtered, and concentrated. The crude residue was purified via Biotage (EtOAc/hex) to afford the sulfinamine (typically 60-90% yield).

General Protocol to Produce Intermediate 15

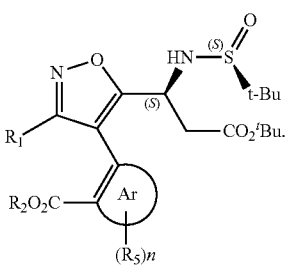

To a cooled (−8.5° C.) solution of the appropriate (S)-tert-butylsulfinylimine (1 equivalent) in N-methylpyrrolidinone (0.16 M) was added in a dropwise fashion a 0.5 M solution of reagent 14, e.g., 2-tert-butoxy-2-oxoethyl)zinc (II) chloride (2 equivalent) in $Et_2O$ over a period of 10 min. The yellow solution turned clear and colorless. The reaction temperature was maintained between −8.5° C. to 5° C. until complete consumption of sulfinylimine was observed by LC-MS and TLC. After 4.5 h, saturated aqueous $NH_4Cl$ and MTBE were introduced. The aqueous layer turned thick and "gel-like", at which point 1 N HCl was added. The aqueous layer was extracted with MTBE (2×). The combined organic layers were washed with saturated $NaHCO_3$, dried over $Na_2SO_4$, and concentrated in vacuo. The mixture was purified on Biotage system (typically gradient elution 17% MTBE:83% Hexanes to 70% MTBE:30% Hexanes) to give the desired (S,S)-diastereomer (typically in 60%-69% yield). Partial separation of diastereomers was achieved during purification and successive chromatographic runs were performed to maximize yield of major pure diastereomer. The undesired (S,R)-diastereomer was obtained is typically obtained in 10% yield.

General Protocol to Produce Intermediate 16

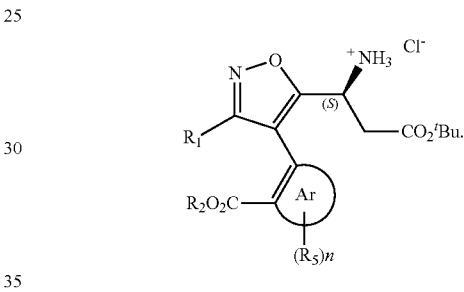

To a solution of methyl N-tert-butylsulfinyl amines (1 equivalent) in MeOH (~0.16 M) was added a solution of 4 M HCl (1.6 equivalent) in 1,4-dioxane. LC-MS analysis after 15 min indicated complete consumption of the starting material. The solvent was evaporated and the excess HCl was azeotropically removed using heptane (2×), followed by THF to give the appropriate chiral ammonium chloride (99% yield) as a white foam that was used without further purification.

General Protocol to Produce Intermediate 17

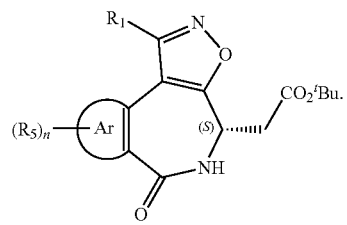

To a cooled solution (−20° C.) of the appropriate chiral ammonium salt (1 equivalent) in THF (0.4 M) was introduced a solution of 2.9 M isopropylmagnesium bromide (4.22 equivalent) in 2-methyl-tetrahydrofuran. After complete addition of the base, LC-MS analysis indicated complete consumption of the ammonium salt. To the reaction mixture was added 1 N HCl and EtOAc. The aqueous layer (the pH ~1) was extracted with EtOAc (3×), washed with saturated $NaHCO_3$, dried over $Na_2SO_4$, and concentrated to give a red oil. The crude product was purified on Biotage system (generally gradient elution 7% EtOAc:93% Hexanes to 60% EtOAc:40% Hexanes) to give the appropriate lactam as an orange foam (typically 74% yield).

General Protocol to Produce Intermediate 18

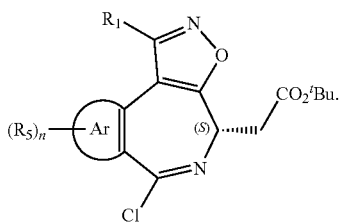

To a solution of lactam (1 equivalent) in CH$_2$Cl$_2$ (typically ~0.1 M in substrate concentration) at room temperature was added PCl$_5$ (1.6 equivalent). The homogeneous reaction mixture was allowed to stir for 1.5 h, at which point LC-MS analysis indicated complete consumption of SM. The reaction was quenched by the addition of 2 M Na$_2$CO$_3$ and the aqueous layer was extracted with EtOAc (3×). The combined organic extracts were washed with water, dried over Na$_2$SO$_4$, and concentrated to give a brown oil. The crude chloro-imine was purified on Biotage system using gradient elution (generally 5% EtOAc:95% Hexanes to 20% EtOAc:80% Hexanes) to give the titled compound as an white foam (typically 50-70% yield).

Chloro-Imine Couplings to Produce Intermediate 19

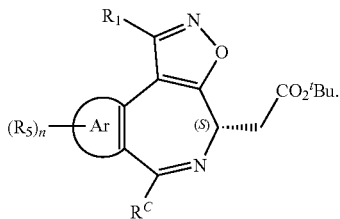

a. Suzuki Reactions on Chloro-Imines (Step H).

To a solution of chloro-imine 18 (1 equivalent) in toluene (~0.2 M in substrate) was added the desired boronic acid or boronic ester (1.2-2 equivalent) and Pd(PPh$_3$)$_4$ (~5 mol %). The reaction was evacuated and purged with N$_2$ (g) (3×), followed by addition of aqueous solution of Na$_2$CO$_3$ (2 equivalent). The heterogeneous reaction mixture was heated to 82° C. for 0.5-1 h. After complete consumption of chloro-imine as detected by LC-MS or TLC, the reaction mixture was cooled to ambient temperatures. The organic layer was removed and the aqueous layer was extracted with EtOAc (3×), the combined organic extracts were washed with water, brine, and concentrated in vacuo. The crude couple product was purified on Biotage system.

b. Stille Reactions on Chloro-Imines (Step I).

To a solution of chloro-imine 18 (1 equivalent) in toluene (~0.1 M in substrate) was added the desired tributyl aryl stannane (1.7-2 equivalent) and Pd(PPh$_3$)$_4$ (~5 mol %). The reaction was evacuated and purged with N$_2$ (g) (3×) and heated to 82° C. for 40 h. After cooling to room temperature, the organic layer was removed and the aqueous layer was extracted with EtOAc (3×), the combined organic extracts were washed with water, brine, and concentrated in vacuo. The crude coupled product was purified on a Biotage system.

c. Negishi Reactions on Chloro-Imines (Step J).

To a solution of chloro-imine 18 (1 equivalent) in toluene (~0.1 M in substrate) was added the desired dialkyl zinc reagent (1.5 equivalent) and PdCl$_2$(dppf)-CH$_2$Cl$_2$ adduct (~5 mol %). The reaction was evacuated and purged with N$_2$ (g) (3×) and heated to 50° C. for 1 h. After cooling to room temperature, the organic layer was removed and the aqueous layer was extracted with EtOAc (3×), the combined organic extracts were washed with water, brine, and concentrated in vacuo. The crude coupled product was purified on a Biotage system.

d. Nucleophilic Additions on Chloro-Imines (Step K).

Chloro-imine (1 equivalent) was dissolved in neat amine in a microwave vial and heated by 300 W microwave at 160° C. for 2 h. Excess amine was evaporated under reduced pressure and the crude mixture purified on a Biotage system.

General Procedure for Production of a Compound of Formula I (Step L

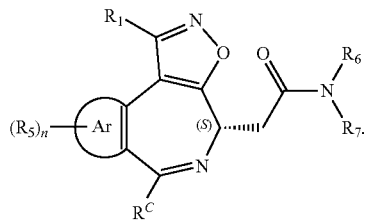

To a solution of imino tert-butyl ester 19 (1 equivalent) in CHCl$_3$ (typically 0.5-0.1 M in substrate) was added TFA (40-60 equivalent). The reaction mixture was heated to 36° C. until LC-MS analysis indicated complete consumption of ester and formation of desired acid. The yellow reaction mixture is cooled to ambient temperatures, concentrated in vacuo, and excess TFA is azeotropically removed using toluene (2×), followed by CHCl$_3$ (2×). The crude carboxylic acid is dried and used without further purification.

To a cooled (0° C.) solution of crude carboxylic acid (1 equivalent) in DMF (typically 0.5-0.1 M in substrate concentration) was sequentially added base (10 equivalent), desired amine 20 (8 equivalent), and coupling reagent (typically HATU or COMU, 1.5 equivalent). After complete addition of reagents the reaction mixture was warmed to room temperature and allowed to stir until complete consumption of carboxylic acid was detected by LC-MS. The reaction mixture was diluted with EtOAc and water. The organic layer was removed and the aqueous layer was extracted with EtOAc (3×), the combined organic extracts were washed with water, brine, and concentrated in vacuo. The crude couple product was purified on Biotage system.

2-((6S)-4-benzyl-2,3,9-trimethyl-6H-isoxazolo[5,4-c]thieno[2,3-e]azepin-6-yl)acetamide (Compound 127)

Compound 127 was also synthesized according to Scheme 1, above, using benzylzinc(II) bromide in a Negishi reaction (Step J) to convert the chloroimine 18 to the corresponding benzylimine intermediate and then to the title product using Step L.

The compounds in Table 5 were made using the general protocol described above.

TABLE 5

| Compound No. | Physical Data | General Protocol for final two steps (Scheme 1)* |
|---|---|---|
| 100 | LRMS m/z 356 [M + H]+; 1H NMR (400 MHz, DMSO-d6) δ 13.08-12.94 (m, 1H), 7.71-7.53 (m, 2H), 7.49-7.31 (m, 1H), 7.02-6.86 (m, 1H), 4.09 (s, 1H), 3.24-2.99 (m, 2H), 2.46-2.34 (m, 6H), 1.87 (s, 3H) | H, L |
| 101 | LRMS m/z 370 [M + H]+; 1H NMR (400 MHz, DMSO-d6) δ 7.69-7.64 (m, 1H), 7.63-7.57 (m, 1H), 7.40-7.34 (m, 1H), 7.00-6.90 (m, 1H), 4.12-4.02 (m, 1H), 3.78 (s, 3H), 3.2-3.01 (m, 2H), 2.43 (s, 3H), 2.41 (s, 3H), 1.91 (d, J = 0.69 Hz, 3H) | H, L |
| 102 | LRMS m/z 382 [M + H]+; 1H NMR (400 MHz, Acetone-d6) δ 7.88 (s, 1H), 7.45 (dd, J = 2.2, 8.6 Hz, 1H), 7.22-7.06 (m, 1H), 6.50 (d, J = 8.5 Hz, 1H), 6.41-6. 29 (m, 1H), 5.81 (br. s, 2H), 4.25 (t, J = 7.2 Hz, 1H), 3.27 (d, J = 7.0 Hz, 2H), 2.49 (s, 6H), 1.81 (s, 3H) | H, L |
| 103 | LRMS m/z 401[M + H]+; 1H NMR (400 MHz, DMSO-d6) δ 8.52 (d, J = 2.5 Hz, 1H), 8.05 (d, J = 2.5 Hz, 1H), 7.81 (d, J = 8.47 Hz, 1H), 7.72-7.60 (m, 1H), 7.09-6.93 (m, 1H), 4.35-4.17 (m, 1H), 3.26-3.11 (m, 2H), 2.44 (s, 3H), 2.38 (s, 3H), 1.54 (s, 3H) | I, L |
| 104 | LRMS m/z 368 [M + H]+; 1H NMR (400 MHz, DMSO-d6) δ 9.27 (s, 1H), 9.16-9.08 (m, 1H), 7.76-7.60 (m, 1H), 7.46-7.36 (m, 1H), 7.13-6.98 (m, 1H), 4.37-4.19 (m, 1H), 3.29-3.13 (m, 2H), 2.45 (s, 3H), 2.43 (s, 3H), 1.63 (s, 3H) | H, L |
| 105 | LRMS m/z 368 [M + H]+; 1H NMR (400 MHz, Acetone-d6) δ 9.16 (s, 1H), 8.69 (s, 2H), 7.17 (br. s, 1H), 6.41 (br. s, 1H), 4.40 (br. s, 1H), 3.37 (d, J = 5.9 Hz, 2H), 2.48 (s, 6H), 1.75 (d, J = 0.88 Hz, 3H) | H, L |
| 106 | LRMS m/z 367 [M + H]+; 1H NMR (400 MHz, Acetone-d6) δ 8.60 (dd, J = 1.76, 4.7 Hz, 1H), 8.53 (d, J = 2.3 Hz, 1H), 7.70 (td, J = 1.9, 7.9 Hz, 1H), 7.36 (ddd, J = 0.73, 4.9, 7.8 Hz, 1H), 7.16 (br. s, 1H), 6.39 (br. s, 1H), 4.37 (br. s, 1H), 3.35 (d, J = 7.0 Hz, 2H), 2.48 (s, 3H), 2.46 (d, J = 0.59 Hz, 3H), 1.69 (s, 3H) | H, L |
| 107 | LRMS m/z 367 [M + H]+; 1H NMR (400 MHz, Acetone-d6) δ 8.62-8.54 (m, 2H), 7.31-7.25 (m, 2H), 7.16 (br. s, 1H), 6.40 (br. s, 1H), 4.40 (br. s, 1H), 3.35 (d, J = 6.1 Hz, 2H), 2.47 (s, 3H), 2.45 (d, J = 0.88 Hz, 3H), 1.70 (d, J = 0.88 Hz, 3H) | H, L |
| 108 | LRMS m/z 366 [M + H]+; 1H NMR (400 MHz, Acetone-d6) δ 7.54-7.24 (m, 5H), 7.20-7.06 (m, 1H), 6.46-6.25 (m, 1H), 4.33 (br. s, 1H), 3.31 (d, J = 6.7 Hz, 2H), 2.46 (s, 3H), 2.43 (d, J = 0.59 Hz, 3H), 1.65 (d, J = 0.59 Hz, 3H) | H, L |
| 109 | LRMS m/z 384 [M + H]+; 1H NMR (400 MHz, CDCl3) δ 7.40 (dd, J = 5.6, 8.8 Hz, 2H), 7.11 (t, J = 8.9 Hz, 3H), 6.39 (br. s, 1H), 4.32 (t, J = 7.0 Hz, 1H), 3.31 (d, J = 6.7 Hz, 2H), 2.46 (s, 3H), 2.41 (s, 3H), 1.69 (d, J = 0.59 Hz, 3H) | H, L |
| 110 | LRMS m/z 400 [M(+H)]+; 1H NMR (400 MHz, Acetone-d6) δ 7.42-7.31 (m, 4H), 7.17 (br. s, 1H), 6.44 (br. s, 1H), 4.34 (t, J = 6.9 Hz, 1H), 3.33 (d, J = 7.0 Hz, 2H), 2.46 (s, 3H), 2.44 (d, J = 0.59 Hz, 3H), 1.69 (d, J = 0.59 Hz, 3H) | H, L |
| 111 | LRMS m/z 400 [M + H]+=,; 1H NMR (400 MHz, Acetone-d6) δ 7.53-7.29 (m, 4H), 7.17 (br. s, 1H), 6.44 (br. s, 1H), 4.50 (br. s, 1H), 3.32 (m, 2H), 2.48 (s, 3H), 2.36 (s, 3H), 1.55 (s, 3H) | H, L |
| 112 | LRMS m/z 414 [M + H]+; 1H NMR (300 MHz, DMSO-d6) δ 7.61 (br, 1H), 7.36 (d, J = 9 Hz, 1H), 7.21 (d, J = 9 Hz, 1H), 7.02 (s, 1H), 6.80 (br, 1H), 4.28-4.26 (m, 1H), 3.17-3.10 (m, 2H), 2.42 (s, 3H), 2.32 (s, 3H), 2.15 (s, 3H), 1.42 (s, 3H) | H, L |
| 113 | LRMS m/z 419 [M + H]+; 1H NMR (400 MHz, Acetone-d6) δ 7.78 (d, J = 8.8 Hz, 2H), 7.53 (d, J = 8.2 Hz, 2H), 7.49-7.40 (m, 1H), 4.44-4.36 (m, 1H), 3.33-3.24 (m, 4H), 2.47 (s, 3H), 2.45 (s, 3H), 1.67 (s, 3H), 1.14 (t, J = 7.17 Hz, 3H) | H, L |
| 114 | LRMS m/z 437 [M + H]+; 1H NMR (400 MHz, Acetone-d6) δ 7.77 (d, J = 8.5 Hz, 2H), 7.75-7.70 (m, 1H), 7.54 (d, J = 8.5 Hz, 2H), 4.59 (t, J = 4.5 Hz, 1H), 4.47 (t, J = 5.0 Hz, 1H), 4.41 (br. s, 1H), 3.70-3. 46 (m, 2H), 3.29-3.40 (m, 2H), 2.47 (s, 3H), 2.45 (s 3H), 1.67 (s, 3H) | H, L |
| 115 | LRMS m/z 391 [M + H]+; 1H NMR (400 MHz, Acetone-d6) δ 7.78 (d, J = 8.8 Hz, 2H), 7.54 (d, J = 8.8 Hz, 2H), 7.16 (br. s, 1H), 6.40 (br. s, 1H), 4.38 (br. s, 1H), 3.35 (d, J = 6.7 Hz, 2H), 2.47 (s, 3H), 2.45 (s, 3H), 1.68 (s, 3H) | H, L |
| 116 | LRMS m/z 409 [M + H]+; 1H NMR (400 MHz, Acetone-d6) δ 7.90 (d, J = 8.8 Hz, 2H), 7.49-7.45 (m, 1H), 7.43 (d, J = 8.8 Hz, 2H), 7.15 (br. s, 1H), 6.65 (br. s, 1H), 6.38 (br. s, 1H), 4.36 (br. s, 1H), 3.34 (br. s, 2H), 2.47 (s, 3H), 2.44 (s, 3H), 1.66 (s, 3H) | H, L |

TABLE 5-continued

| Compound No. | Physical Data | General Protocol for final two steps (Scheme 1)* |
|---|---|---|
| 117 | LRMS m/z 409 [M + H]$^+$; $^1$H NMR (400 MHz, Acetone-d$_6$) δ 8.00-7.87 (m, 2H), 7.52-7.33 (m, 3H), 7.16 (br. s, 1H), 6.64 (br. s, 1H), 6.38 (br. s, 1H), 4.36 (t, J = 6.4 Hz, 1H), 3.33 (d, J = 7.0 Hz, 2H), 2.47 (s, 3H), 2.43 (s, 3H), 1.65 (s, 3H) | H, L |
| 118 | LRMS m/z 423 [M + H]$^+$; $^1$H NMR (400 MHz, Acetone-d$_6$) δ 9.39-9.30 (m, 1H), 7.63 (m, 2H), 7.29 (m, 2H), 7.16 (br. s, 1H), 6.38 (br. s, 1H), 4.35-4.18 (m, 1H), 3.30 (m, 2H), 2.45 (s, 3H), 2.44 (s, 3H), 2.07 (s, 3H), 1.65 (s, 3H) | H, L |
| 119 | LRMS m/z 397 [M + H]$^+$; $^1$H NMR (400 MHz, Acetone-d$_6$) δ 7.57 (d, J = 7.0 Hz, 1H), 7.14 (br. s, 1H), 6.38 (br. s, 1H), 6.25 (dd, J = 1.8, 7.0 Hz, 1H), 6.12 (d, J = 1.8 Hz, 1H), 4.34 (br. s, 1H), 3.46 (s, 3H), 3.32 (d, J = 6.4 Hz, 2H), 2.47 (s, 3H), 2.46 (d, J = 0.59 Hz, 3H), 1.91 (s, 3H) | H, L |
| 120 | LRMS m/z 397 [M + H]$^+$; $^1$H NMR (400 MHz, Acetone-d$_6$) δ 7.56 (d, J = 2.3 Hz, 1H), 7.49 (dd, J = 2.6, 9.4 Hz, 1H), 7.25-7.12 (m, 1H), 6.48-6.36 (m, 1H), 6.36-6.30 (m, 1H), 4.25 (t, J = 7.0 Hz, 1H), 3.48-3.43 (m, 3H), 3.28 (dd, J = 2.3, 7.0 Hz, 2H), 2.47-2.41 (m, 6H), 1.97-1.93 (m, 3H) | H, L |
| 121 | LRMS m/z 388 [M + H]$^+$; $^1$H NMR (400 MHz, CDCl$_3$) δ 7.00 (br. s, 1H), 5.43 (br. s, 1H), 4.10-4.03 (m, 1H), 3.69-3.53 (m, 2H), 3.17-2.92 (m, 6H), 2.79-2.53 (m, 2H), 2.45 (s, 3H), 2.41 (s, 3H), 2.29 (s, 3H), 2.26 (s, 3H) | K, L |
| 122 | LRMS m/z 375 [M + H]$^+$; $^1$H NMR (400 MHz, CDCl$_3$) δ 7.08-6.71 (m, 1H), 5.47 (br. s, 1H), 4.30-4.15 (m, 1H), 3.88 (br. s, 2H), 3.63 (m, 4H), 3.11 (m, 4H), 2.46 (s, 3H), 2.42 (s, 3H), 2.28 (s, 3H) | K, L |
| 123 | LRMS m/z 402 [M + H]$^+$ | K, L |
| 124 | LRMS m/z 332 [M + H]$^+$; $^1$H NMR (400 MHz, Acetone-d$_6$) δ 7.07 (br. s, 1H), 6.30(br. s, 1H), 4.20-4.10 (m, 1H), 3.27-3.04 (m, 2H), 2.65-2.48 (m, 2H), 2.44 (s, 3H), 2.40 (s, 3H), 2.24 (s, 3H), 1.44-1.20 (m, 2H), 0.72-0.52 (m, 3H) | J, L |
| 125 | LRMS m/z 330 [M + H]$^+$; $^1$H NMR (400 MHz, Acetone-d$_6$) δ 7.01 (br. s, 1H), 6.28 (br. s, 1H), 4.20-4.01 (m, 1H), 2.94-3.23 (m, 2H), 2.45 (s, 3H), 2.42-2.38 (m, 6H), 1.79 (m, 1H), 1.12-1.04 (m, 1H), 1.02-0.93 (m, 1H), 0.87 (br. s, 1H), 0.67 (d, J = 7.3 Hz, 1H) | J, L |
| 126 | LRMS m/z 372 [M + H]$^+$; $^1$H NMR (300 MHz, CDCl$_3$) δ 4.04 (t, J = 7.2 Hz, 1H), 3.31-3.21 (m, 2H), 2.69-2.59 (m, 1H), 2.44 (s, 6H), 2.28 (s, 3H), 2.03-1.99 (m, 1H), 1.83-1.79 (m, 1H), 1.69-1.55 (m, 3H), 1.39-1.31 (m, 1H), 1.20-1.14 (m, 4H) | J, L |
| 127 | LRMS m/z 380 [M + H]$^+$; $^1$H NMR (300 MHz, CDCl$_3$) δ 7.17-7.10 (m, 3H), 6.90-6.87 (m, 2H), 6.52 (br, 1H), 5.52 (br, 1H), 4.12 (t, J = 6.0 Hz, 1H), 4.04-3.86 (m, 2H), 3.27-3.09 (m, 2H), 2.39-2.32 (m, 9H) | J, L |
| 128 | LRMS m/z 380 [M + H]$^+$; $^1$H NMR (400 MHz, DMSO-d$_6$) δ 7.73-7.55 (m, 3H), 7.40 (d, J = 8.70 Hz, 2H), 7.24-7.12 (m, 3H), 7.06-6.94 (m, 1H), 4.32-4.20 (m, 1H), 3.20 (s, 2H), 2.52 (s, 3H), 1.91 (s, 3H) | H, L |
| 129 | LRMS m/z 364 [M + H]$^+$; $^1$H NMR (400 MHz, DMSO-d$_6$) δ 7.72-7.64 (m, 2H), 7.63-7.57 (m, 1H), 7.32-7.27 (m, 1H), 7.25-7.20 (m, 2H), 7.19-7.11 (m, 2H), 7.01 (br. s, 1H), 4.25 (t, J = 7.32 Hz, 1H), 3.18 (dd, J = 1.60, 7.32 Hz, 2H), 2.50 (s, 3H), 1.91 (s, 3H) | H, L |
| 130 | LRMS m/z 371 [M + H]$^+$; $^1$H NMR (400 MHz, DMSO-d$_6$) δ 7.81 (d, J = 8.70 Hz, 2H), 7.73-7.57 (m, 3H), 7.38-7.26 (m, 3H), 7.02 (br. s, 1H), 4.31 (t, J = 7.32 Hz, 1H), 3.26-3.13 (m, 2H), 2.51 (s, 3H), 1.88 (s, 3H) | H, L |
| 131 | LRMS m/z 347 [M + H]$^+$; $^1$H NMR (400 MHz, DMSO-d$_6$) δ 8.55 (d, J = 6.14 Hz, 2H), 7.70-7.61 (m, 3H), 7.32 (s, 1H), 7.12 (d, J = 6.14 Hz, 2H), 7.02 (bs, 1H), 4.32 (t, J = 7.31 Hz, 1H), 3.25-3.08 (m, 2H), 2.51 (s. 3H), 1.91 (s, 3H) | H, L |
| 132 | LRMS m/z 414 [M + H]$^+$; $^1$H NMR (400 MHz, DMSO-d$_6$) δ 7.74-7.60 (m, 5H), 7.38 (d, J = 8.24 Hz, 2H), 7.31 (d, J = 7.10 Hz, 1H), 7.03 (br. s, 1H), 4.32 (t, J = 7.32 Hz, 1H), 3.22 (dd, J = 1.49, 7.44 Hz, 2H), 2.52 (s, 3H), 1.89 (s, 3H) | H, L |
| 133 | LRMS m/z 381 [M + H]$^+$; $^1$H NMR (400 MHz, DMSO-d$_6$) δ 8.44 (dd, J = 0.69, 2.52 Hz, 1H), 8.02 (dd, J = 2.52, 8.47 Hz, 1H), 7.90 (dd, J = 0.80, 8.58 Hz, 1H), 7.67 (br. s, 1H), 7.62 (d, J = 7.55 Hz, 1H), 7.56 (d, J = 7.32 Hz, 1H), 7.25 (s, 1H), 7.03 (br. s, 1H), 4.33 (t, J = 7.32 Hz, 1H), 3.24-3.15 (m, 2H), 2.50 (s, 3H) 1.98-1.67 (m, 3H) | I, L |

TABLE 5-continued

| Compound No. | Physical Data | General Protocol for final two steps (Scheme 1)* |
|---|---|---|
| 134 | LRMS m/z 389 [M + H]+; 1H NMR (400 MHz, DMSO-d6) δ 7.97 (br. s, 1H), 7.80 (d, J = 8.47 Hz, 2H), 7.69 (s, 2H), 7.62 (d, J = 7.78 Hz, 1H), 7.41 (s, 1H), 7.30 (s, 1H), 7.23 (s, 2H), 7.02 (br. s, 1H), 4.28 (t, J = 7.44 Hz, 1H), 3.24-3.15 (m, 2H), 2.52 (s, 3H), 1.89 (s, 3H) | H, L |
| 135 | LRMS m/z 376 [M + H]+; 1H NMR (400 MHz, DMSO-d6) δ 7.65 (d, J = 6.64 Hz, 2H), 7.61-7.54 (m, 1H), 7.28 (d, J = 7.32 Hz, 1H), 7.12 (d, J = 8.24 Hz, 2H), 6.99 (br. s, 1H), 6.86 (d, J = 9.16 Hz, 2H), 4.21 (t, J = 7.32 Hz, 1H), 3.73 (s, 3H), 3.24-3.02 (m, 2H), 2.50 (s, 3H), 1.90 (s, 3H) | H, L |
| 136 | LRMS m/z 430 [M + H]+; 1H NMR (400 MHz, DMSO-d6) δ 7.72-7.65 (m, 3H), 7.64-7.57 (m, 1H), 7.36-7.25 (m, 4H), 7.01 (br. s, 1H), 4.28 (t, J = 7.44 Hz, 1H), 3.23-3.12 (m, 2H), 2.50 (s, 3H), 1.91 (s, 3H) | H, L |
| 137 | LRMS m/z 367 [M + H]+; 1H NMR (400 MHz, DMSO-d6) δ 8.55 (d, J = 6.18 Hz, 2H), 7.93-7.85 (m, 1H), 7.79-7.74 (m, 1H), 7.71-7.67 (m, 1H), 7.62-7.58 (m, 1H), 7.16-7.12 (m, 2H), 7.08-7.03 (m, 1H), 4.46-4.27 (m, 1H), 3.26-3.08 (m, 2H), 2.53 (s, 3H) | H, L |
| 138 | LRMS m/z 384 [M + H]+; 1H NMR (400 MHz, DMSO-d6) δ 7.90-7.82 (m, 1H), 7.73 (s, 1H), 7.69-7.64 (m, 1H), 7.61-7.52 (m, 1H), 7.29-7.20 (m, 2H), 7.15 (s, 2H), 7.05-7.01 (m, 1H), 4.33-4.27 (m, 1H), 3.20 (d, J = 7.55 Hz, 2H), 2.53 (s, 3H) | H, L |
| 139 | LRMS m/z 400 [M + H]+; 1H NMR (400 MHz, DMSO-d6) δ 7.90-7.83 (m, 1H), 7.78-7.69 (m, 1H), 7.70-7.65 (m, 1H), 7.61-7.54 (m, 1H), 7.38 (s, 2H), 7.25-7.16 (m, 2H), 7.06-6.97 (m, 1H), 4.36-4.25 (m, 1H), 3.25-3.14 (m, 2H), 2.53 (s, 3H) | H, L |
| 140 | LRMS m/z 391 [M + H]+; 1H NMR (400 MHz, DMSO-d6) δ 7.88 (dd, J = 1.14, 8.01 Hz, 1H), 7.81 (d, J = 8.70 Hz, 2H), 7.76 (t, J = 7.90 Hz, 1H), 7.69 (br. s, 1H), 7.59 (dd, J = 1.14, 8.01 Hz, 1H), 7.36 (d, J = 8.24 Hz, 2H), 7.05 (br. s, 1H), 4.37 (t, J = 7.32 Hz, 1H), 3.23 (dd, J = 3.32, 7.21 Hz, 2H), 2.53 (s, 3H) | H, L |
| 141 | LRMS m/z 400 [M + H]+; 1H NMR (400 MHz, DMSO-d6) δ 7.90-7.82 (m, 1H), 7.78 (dd, J = 2.29, 8.47 Hz, 1H), 7.64 (br. s, 1H), 7.49-7.44 (m, 2H), 7.41 (d, J = 2.06 Hz, 1H), 7.36-7.29 (m, 2H), 7.04 (br. s, 1H), 4.48-4.17 (m, 1H), 3.15 (br. s, 2H), 2.55 (s, 3H) | H, L |
| 142 | LRMS m/z 391 [M + H]+; 1H NMR (400 MHz, DMSO-d6) δ 7.94 (s, 1H), 7.87 (d, J = 8.01 Hz, 2H), 7.82-7.74 (m, 1H), 7.65 (br. s, 1H), 7.49 (d, J = 8.47 Hz, 2H), 7.40 (d, J = 2.06 Hz, 1H), 7.05 (br. s, 1H), 4.40 (br. s, 1H), 3.17 (br. s, 2H), 2.50 (s, 3H) | H, L |
| 143 | LRMS m/z 419 [M + H]+; 1H NMR (400 MHz, DMSO-d6) δ 8.26-8.14 (m, 1H), 7.87 (d, J = 8.01 Hz, 3H), 7.82-7.76 (m, 1H), 7.48 (s, 2H), 7.42-7.37 (m, 1H), 4.65-4.21 (m, 1H), 3.24-2.92 (m, 4H), 2.50 (s, 3H), 1.06 (s, 3H) | H, L |
| 144 | LRMS m/z 366 [M + H]+; 1H NMR (400 MHz, Acetone-d6) δ 7.87-7.80 (m, 1H), 7.71 (ddd, J = 1.90, 6.58, 8.19 Hz, 1H), 7.51-7.34 (m, 6H), 7.13 (br. s, 1H), 6.38 (br. s, 1H), 4.48 (br. s, 1H), 3.40-3.19 (m, 2H), 2.53 (s, 3H) | H, L |
| 145 | LRMS m/z 424 [M + H]+; 1H NMR (400 MHz, Acetone-d6) δ 7.86-7.80 (m, 1H), 7.75-7.67 (m, 1H), 7.49 (br. s, 1H), 7.46-7.35 (m, 6H), 4.48 (br. s, 1H), 3.50-3.35 (m, 4H), 3.33-3.30 (m, 3H), 3.30-3.22 (m, 2H), 2.53 (s, 3H) | H, L |
| 146 | LRMS m/z 362 [M + H]+; 1H NMR (300 MHz, CDCl3) δ 7.59-7.58 (m, 2H), 7.46-7.43 (m, 4H), 6.84-6.81 (m, 1H), 6.43-6.42 (br, 1H), 5.59-5.58 (br, 1H), 4.41 (t, J = 2.1 Hz, 1H), 3.80 (s, 3H), 3.35-3.26 (m, 2H), 2.55 (s, 3H) | H, L |
| 147 | LRMS m/z 362 [M + H]+; 1H NMR (300 MHz, Acetone-d6) δ 7.87 (d, J = 0.6, 1H), 7.84-7.71 (m, 1H), 7.51-7.42 (m, 2H), 7.31-7.20 (m, 2H), 7.17-7.01 (m, 2H), 6.91 ( d, J = 7.5, 1H), 6.47 (s, 1H), 4.52 (s, 1H), 3.80 (d, J = 5.1, 3H), 3.33 (t, J = 6.9, 2H), 2.59 (s, 3H) | H, L |
| 148 | LRMS m/z 357 [M + H]+; 1H NMR (300 MHz, Acetone-d6) δ 7.92-7.88 (m, 1H), 7.83-7.78 (m, 3H), 7.64-7.61 (m, 2H), 7.51-7.49 (m, 2H), 7.19 (s, 1H), 6.45 (s, 1H), 4.57 (d, J = 7.2, 1H), 3.38-3.34 (m, 2H), 2.58 (s, 3H) | H, L |
| 149 | LRMS m/z 385 [M + H]+; 1H NMR (300 MHz, DMSO-d6) δ 7.62-7.59 (m, 4H), 7.50-7.47 (m, 2H), 7.30 (m, 2H), 6.08 (br, 1H), 4.58 (t, J = 6.9 Hz, 1H), 3.42-3.36 (m, 2H), 3.28-3.26 (m, 2H), 2.60 (s, 3H), 1.22 (t, J = 7.2 Hz, 3H) | H, L |

TABLE 5-continued

| Compound No. | Physical Data | General Protocol for final two steps (Scheme 1)* |
|---|---|---|
| 150 | LRMS m/z 415 [M + H]$^+$; $^1$H NMR (300 MHz, CDCl$_3$) δ 7.62-7.59 (m, 4H), 7.53-7.50 (m, 2H), 7.31-7.28 (m, 2H), 6.50-6.49 (br, 1H), 4.55 (t, J = 1.8 Hz, 1H), 3.53 (br, 4H), 3.4 (s, 3H), 3.30-3.27 (s, 2H), 2.55 (s, 3H) | H, L |
| 151 | LRMS m/z 380 [M + H]$^+$; $^1$H NMR (300 MHz, Acetone-d$_6$) δ 7.86 (d, J = 7.5, 1H), 7.73-7.68 (m, 1H), 7.43-7.37 (m, 1H), 7.30-7.23 (m, 3H), 7.12 (d, J = 7.5, 2H), 6.43-6.41 (m, 1H), 4.6 (m, 1H), 3.32-3.27 (m, 2H), 2.59 (s, 3H), 1.98 (s, 3H) | H, L |
| 152 | LRMS m/z 341 [M + H]$^+$; $^1$H NMR (300 MHz, Acetone-d$_6$) δ 7.92 (d, J = 7.5, 1H), 7.77-7.70 (m, 2H), 7.50 (d, J = 7.5, 1H), 7.1 (s, 1H)), 6.26 (s, 1H), 4.31 (s, 1H), 3.76-3.58 (m, 4H), 3.12-2.88 (m, 6H), 2.52 (s, 3H) | K, L |

*All compounds were prepared using general procedures A-G, and the final two steps were as indicated in the table. Either version of general procedure A could be used.

Example 15

Synthesis of Compounds of Formula III, wherein R$^C$ is 4-Chlorophenyl, R$_2$ is Hydrogen and R$_3$ is OH or N(R')(R")

Certain compounds of Formula III may be synthesized according to Scheme 2, below.

Scheme 2:

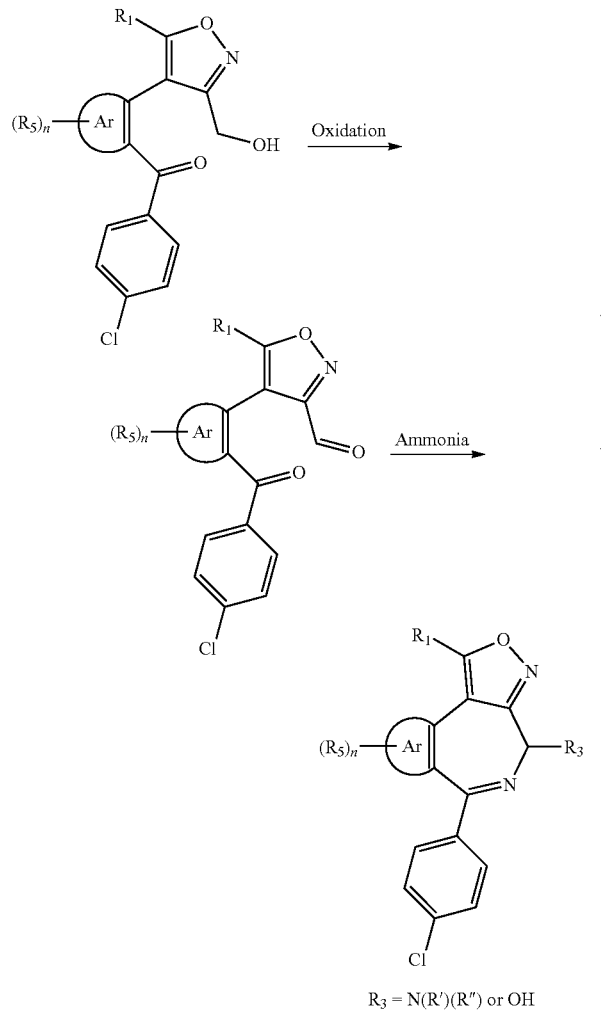

R$_3$ = N(R')(R") or OH

Specific examples of intermediates and compounds made and/or used in this scheme are as follows.

(4-(2-formylphenyl)-5-methylisoxazol-3-yl)methyl acetate

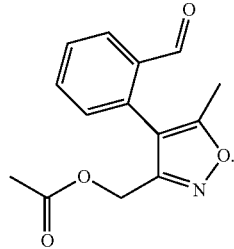 [SMILES: CC(=O)OCc1noc(C)c1-c1ccccc1C=O]

To a resealable vial was added palladium(II) chloride (4.49 mg, 0.025 mmol), potassium acetate (1.24 g, 12.7 mmol), and 2-bromobenzaldehyde (0.59 mL, 5.07 mmol). The vial was sealed and evacuated/backfilled with N$_2$ (3×) before addition of 3-(chloromethyl)-5-methylisoxazole (1.00 g, 7.60 mmol) as a solution in DMA (25 mL). The vial was then heated to 130° C. overnight. The reaction was cooled to room temperature and diluted with water. The solution was extracted with ether and the combined organics were washed with brine, dried over Na$_2$SO$_4$, filtered, and concentrated. The crude residue was purified via Biotage (EtOAc/hex) to afford (4-(2-formylphenyl)-5-methylisoxazol-3-yl)methyl acetate (1.01 g, 3.90 mmol). LC/MS m/z 260 [M+H]$^+$.

(4-chlorophenyl)(2-(3-(hydroxymethyl)-5-methyl-isoxazol-4-yl)phenyl)methanol

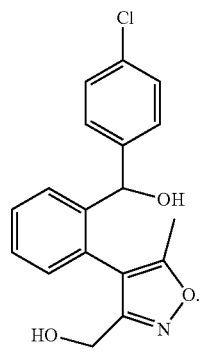 [SMILES: Cc1onc(CO)c1-c1ccccc1C(O)c1ccc(Cl)cc1]

To a round bottomed flask was added (4-(2-formylphenyl)-5-methylisoxazol-3-yl)methyl acetate (1.01 g, 3.90 mmol) and THF (20 mL) before the reaction was cooled to −78° C. To this solution was added 1.0 M (4-chlorophenyl)magnesium bromide (4.68 mL, 4.68 mmol) and the reaction stirred at −78° C. for 30 min before addition of ammonium chloride solution. The reaction was warmed to room temperature and diluted with EtOAc. The layers were separated and the aqueous was extracted with EtOAc. The combined organics were washed with brine, dried over Na$_2$SO$_4$, filtered, and concentrated. The crude residue was taken up in THF:MeOH:Water (2:2:1, 20 mL) before addition of lithium hydroxide hydrate (0.491 g, 11.70 mmol). The reaction was stirred at room temperature for 1 h before diluting with water and EtOAc. The layers were separated and the aqueous was extracted with EtOAc. The combined organics were washed with brine, dried over Na$_2$SO$_4$, filtered, and concentrated. The crude diol was purified via Biotage (EtOAc/hex) to afford (4-chlorophenyl)(2-(3-(hydroxymethyl)-5-methylisoxazol-4-yl)phenyl)methanol (1.14 g, 3.44 mmol). LC/MS m/z 330 [M+H]$^+$.

4-(2-(4-chlorobenzoyl)phenyl)-5-methylisoxazole-3-carbaldehyde

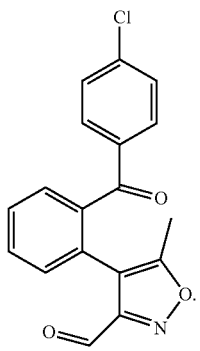 [SMILES: Cc1onc(C=O)c1-c1ccccc1C(=O)c1ccc(Cl)cc1]

To a round bottomed flask was added CH$_2$Cl$_2$ and oxalyl chloride (1.21 mL, 13.8 mmol) before the solution was cooled to −78° C. To this solution was added DMSO (1.47 mL, 20.65 mmol) and the solution stirred for 15 min before addition of (4-chlorophenyl)(2-(3-(hydroxymethyl)-5-methylisoxazol-4-yl)phenyl)methanol (1.14 g, 3.44 mmol) dissolved in CH$_2$Cl$_2$. The reaction was stirred for 15 min at −78° C. before addition of Et$_3$N (3.84 mL, 27.5 mmol) and warming the reaction to room temperature overnight. This reaction was diluted with water and the layers separated. The aqueous was extracted with CH$_2$Cl$_2$ and the combined organics were dried over Na$_2$SO$_4$, filtered, and concentrated. The crude residue was purified via Biotage (EtOAc/hex) to afford 4-(2-(4-chlorobenzoyl)phenyl)-5-methylisoxazole-3-carbaldehyde (1.10 g, 3.38 mmol). LC/MS m/z 326 [M+H]$^+$.

6-(4-chlorophenyl)-1-methyl-4H-benzo[c]isoxazolo[4,3-e]azepin-4-ol

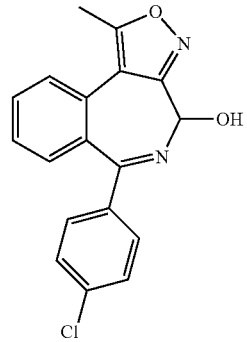 [SMILES: Cc1onc2c1-c1ccccc1C(c1ccc(Cl)cc1)=NC2O]

(Compound 153) and 6-(4-chlorophenyl)-1-methyl-4H-benzo[c]isoxazolo[4,3-e]azepin-4-amine

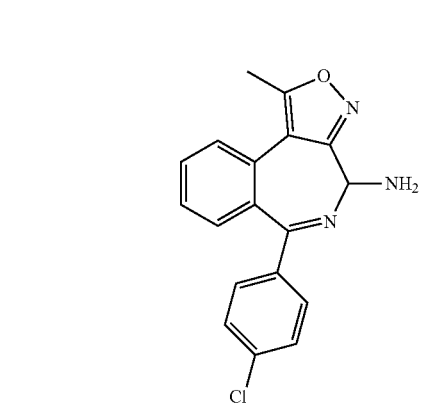 [SMILES: Cc1onc2c1-c1ccccc1C(c1ccc(Cl)cc1)=NC2N]

Compound 154

To a resealable vial was added 4-(2-(4-chlorobenzoyl)phenyl)-5-methylisoxazole-3-carbaldehyde (0.052 g, 0.160 mmol) and ammonia (1.85 mL, 12.93 mmol, 7M in MeOH). The vial was sealed and the reaction stirred at room temperature for two days. The solution was concentrated and the crude residue was purified via Biotage (EtOAc/hex) to afford two products. Minor: 6-(4-chlorophenyl)-1-methyl-4H-benzo[c]isoxazolo[4,3-e]azepin-4-amine (0.0026 g, 0.008 mmol). $^1$H NMR (400 MHz, DMSO-d$_6$) δ 7.75-7.64 (m, 2H), 7.49-7.43 (m, 3H), 7.42-7.37 (m, 2H), 7.31 (d, J=7.32 Hz, 1H), 4.88 (s, 1H), 2.86-2.71 (m, 2H), 2.65 (s, 3H). LC/MS m/z 324 [M+H]$^+$. Major: 6-(4-chlorophenyl)-1-methyl-4H-benzo[c]isoxazolo[4,3-e]azepin-4-ol (27 mg, 0.083 mmol). $^1$H NMR (400 MHz, DMSO-d$_6$) δ 7.75-7.64 (m, 2H), 7.51-7.38 (m, 6H), 7.32 (d, J=7.78 Hz, 1H), 6.84 (br. s, 1H), 5.51 (s, 1H), 2.65 (s, 3H); LC/MS m/z 325 [M+H]$^+$.

Ethyl (6-(4-chlorophenyl)-1-methyl-4H-benzo[c]isoxazolo[4,3-e]azepin-4-yl)carbamate

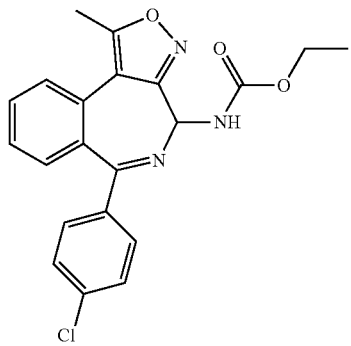 [SMILES: CCOC(=O)NC1N=C(c2ccc(Cl)cc2)c2ccccc2-c2c1noc2C]

Compound 155

To a microwave vial was added 4-(2-(4-chlorobenzoyl)phenyl)-5-methylisoxazole-3-carbaldehyde (0.055 g, 0.169 mmol) and ammonia (1.95 mL, 7M in MeOH, 13.7 mmol). The vial was sealed and the reaction heated to 120° C. for 20 min. The solution was cooled to room temperature and concentrated. The crude residue was purified via Biotage to afford 6-(4-chlorophenyl)-1-methyl-4H-benzo[c]isoxazolo[4,3-e]azepin-4-amine which was taken up in $CH_2Cl_2$ before addition of pyridine (0.013 mL, 0.169 mmol) and ethyl chloroformate (0.016 mL, 0.169 mmol). The reaction was stirred at room temperature for 1 h before addition of sat. aqueous $NaHCO_3$. The layers were separated and aqueous extracted with $CH_2Cl_2$. The combined organics were dried over $Na_2SO_4$, filtered, and concentrated. The crude residue was purified via Biotage (EtOAc/hex) afford ethyl 6-(4-chlorophenyl)-1-methyl-4H-benzo[c]isoxazolo[4,3-e]azepin-4-ylcarbamate (0.0057 g, 0.014 mmol). $^1$H NMR (500 MHz, Acetone-$d_6$) δ 7.81-7.76 (m, 1H), 7.75-7.70 (m, 1H), 7.53-7.46 (m, 3H), 7.45-7.40 (m, 3H), 7.38 (d, J=9.27 Hz, 1H), 5.85 (d, J=8.79 Hz, 1H), 4.13 (q, J=7.32 Hz, 2H), 2.70 (s, 3H), 1.25 (t, J=7.08 Hz, 3H); LC/MS m/z 396 [M+H]$^+$.

Example 16

Synthesis of Compounds of Formula I, Wherein $R_3$ is Methyl

Certain compounds of Formula II or III may be synthesized according to Scheme 3, below.

Scheme 3.

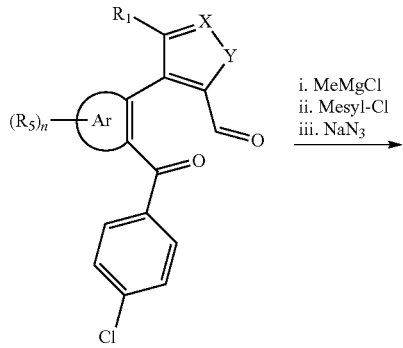

X, Y = N, O or O, N

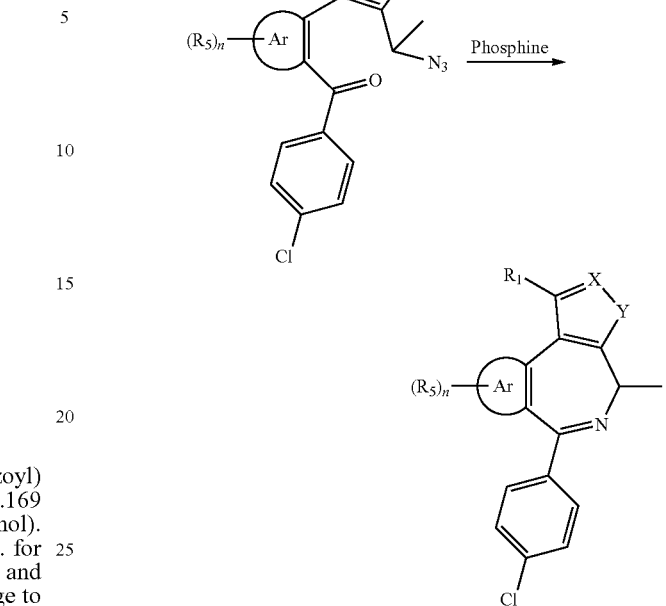

Specific examples of intermediates and compounds made and/or used in this scheme are as follows.

(2-(3-(1-azidoethyl)-5-methylisoxazol-4-yl)phenyl)(4-chlorophenyl)methanone

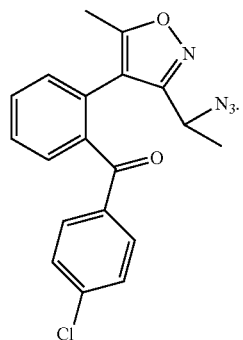 [SMILES: Cc1onc(C(C)N=[N+]=[N-])c1-c1ccccc1C(=O)c1ccc(Cl)cc1]

To a resealable vial was added 4-(2-(4-chlorobenzoyl)phenyl)-5-methylisoxazole-3-carbaldehyde from Example 15 (0.100 g, 0.307 mmol) and THF (2.0 mL). The vial was sealed and cooled to −78° C. before addition of methylmagnesium chloride (0.107 mL, 0.322 mmol). The reaction was stirred at −78° C. for 30 min before addition of ammonium chloride solution and water. The aqueous was extracted with EtOAc and the combined layers washed with brine, dried over $Na_2SO_4$, filtered, and concentrated to afford crude (4-chlorophenyl)(2-(3-(1-hydroxyethyl)-5-methylisoxazol-4-yl)phenyl)methanone (0.092 g, 0.269 mmol).

To a round bottomed flask was added (4-chlorophenyl)(2-(3-(1-hydroxyethyl)-5-methylisoxazol-4-yl)phenyl)methanone (0.092 g, 0.269 mmol), $CH_2Cl_2$ (3.0 mL), and $Et_3N$ (0.075 mL, 0.538 mmol). The vial was cooled to 0° C. before addition of methanesulfonyl chloride (0.025 mL, 0.323 mmol) and the reaction stirred for 45 min at 0° C. before quenching with water. The layers were separated and the aqueous extracted with CH$_2$Cl$_2$. The combined organics were dried over Na$_2$SO$_4$, filtered, and concentrated. The crude residue was taken up in DMF (2 mL) and sodium azide (0.053 g, 0.808 mmol) was added. The reaction was stirred at room temperature overnight before being diluted with water and EtOAc. The layers were separated and the aqueous was extracted with EtOAc. The combined organics were washed with brine, dried over Na$_2$SO$_4$, filtered, and concentrated. The crude residue was purified via Biotage (EtOAc/hex) to afford (2-(3-(1-azidoethyl)-5-methylisoxazol-4-yl)phenyl)(4-chlorophenyl)methanone (0.073 g, 0.199 mmol). LC/MS m/z 389 [M+Na]$^+$.

6-(4-chlorophenyl)-1,4-dimethyl-4H-benzo[c]isoxazolo[4,3-e]azepine

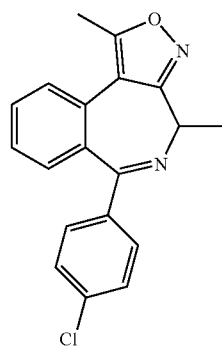 [SMILES: Cc1onc2c1-c1ccccc1C(c1ccc(Cl)cc1)=NC2C]

Compound 156

To a round bottomed flask was added (2-(3-(1-azidoethyl)-5-methylisoxazol-4-yl)phenyl)(4-chlorophenyl)methanone (0.073 g, 0.199 mmol), toluene, and trimethylphosphine (0.239 mL, 1M in toluene, 0.239 mmol). The reaction was stirred at room temperature overnight before concentrating. The crude residue was purified via Biotage (EtOAc/hex) to afford impure 6-(4-chlorophenyl)-1,4-dimethyl-4H-benzo[c]isoxazolo[4,3-e]azepine. This material was purified via preparatory HPLC and the fractions neutralized before being extracted with EtOAc. The organics were washed with brine, dried over Na$_2$SO$_4$, filtered, and concentrated. The crude residue was purified via Biotage (EtOAc/hex) to afford 6-(4-chlorophenyl)-1,4-dimethyl-4H-benzo[c]isoxazolo[4,3-e]azepine (0.0011 g, 0.003 mmol). $^1$H NMR (400 MHz, Acetone-d$_6$) δ 7.74-7.70 (m, 1H), 7.69-7.63 (m, 1H), 7.49-7.41 (m, 3H), 7.41-7.33 (m, 3H), 4.24-4.16 (m, 1H), 2.66 (s, 3H), 1.86 (d, J=6.35 Hz, 3H); LC/MS m/z 323 [M+H]$^+$.

Example 17

Synthesis of Compounds of Formula I, Wherein R$_2$ is Hydrogen and R$_3$ is (S)—CH$_2$—C(O)—N(R')(R")

Certain compounds of Formula II or III may be synthesized according to Scheme 4, below.

Scheme 4:

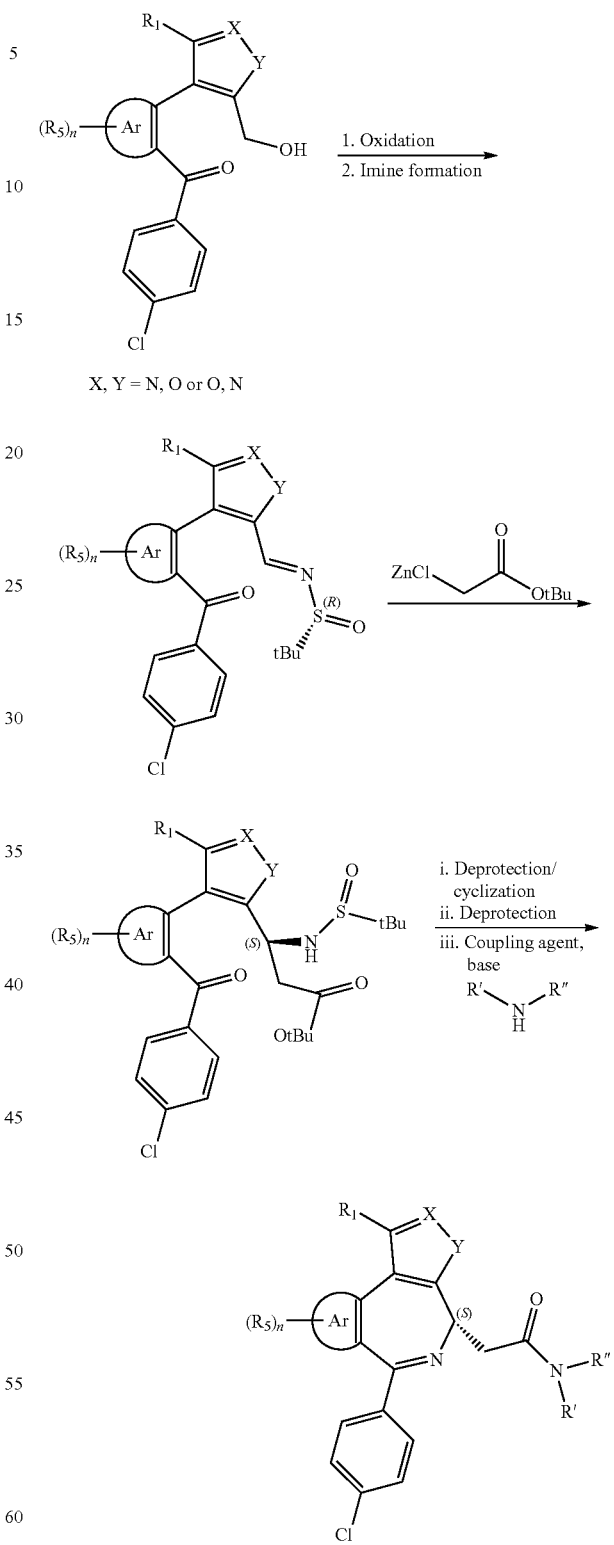

X, Y = N, O or O, N

Specific examples of intermediates and compounds made and/or used in this scheme are as follows.

103

(4-chlorophenyl)(2-(5-(hydroxymethyl)-3-methyl-isoxazol-4-yl)phenyl)methanone

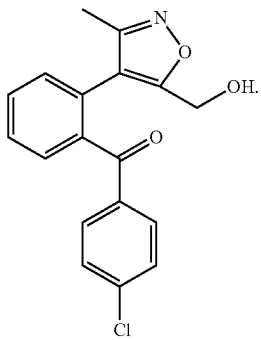 [SMILES: Cc1noc(CO)c1-c1ccccc1C(=O)c1ccc(Cl)cc1]

To a round bottomed flask was added (4-(2-(4-chlorobenzoyl)phenyl)-3-methylisoxazol-5-yl)methyl benzoate from Example 12 (0.780 g, 1.806 mmol), THF (4 mL), MeOH (4 mL), and water (2 mL). The solution was cooled to 0° C. before addition of lithium hydroxide monohydrate (0.227 g, 5.42 mmol). The reaction was stirred at 0° C. for 45 min before diluting with water and extracting with EtOAc. The combined organics were washed with brine, dried over $Na_2SO_4$, filtered and concentrated. The crude residue was purified via Biotage (EtOAc/hex) to afford (4-chlorophenyl)(2-(5-(hydroxymethyl)-3-methylisoxazol-4-yl)phenyl)methanone (0.451 g, 1.376 mmol). LC/MS m/z 328 [M+H]$^+$.

4-(2-(4-chlorobenzoyl)phenyl)-3-methylisoxazole-5-carbaldehyde

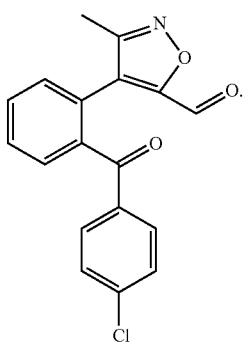 [SMILES: Cc1noc(C=O)c1-c1ccccc1C(=O)c1ccc(Cl)cc1]

To a round bottomed flask was added $CH_2Cl_2$ (15 mL) and oxalyl chloride (0.24 mL, 2.75 mmol). The solution was cooled to −78° C. before addition of DMSO (0.29 mL, 4.13 mmol) and the reaction stirred at −78° C. for 15 minutes before addition of (4-chlorophenyl)(2-(5-(hydroxymethyl)-3-methylisoxazol-4-yl)phenyl)methanone (0.451 mg, 1.38 mmol) dissolved in $CH_2Cl_2$ (5 mL). The reaction was stirred an additional 15 min at −78° C. before addition of $Et_3N$ (0.959 mL, 6.88 mmol) and removal of the cold bath. After warming to room temperature water was added and the layers separated. The aqueous was extracted with $CH_2Cl_2$ and the combined organics were dried over $Na_2SO_4$, filtered, and concentrated. The crude residue was purified via Biotage (EtOAc/hex) to afford 4-(2-(4-chlorobenzoyl)phenyl)-3-methylisoxazole-5-carbaldehyde (0.448 g, 1.38 mmol). LC/MS m/z 326 [M+H]$^+$.

104

(R,E)-N-((4-(2-(4-chlorobenzoyl)phenyl)-3-methyl-isoxazol-5-yl)methylene)-2-methylpropane-2-sulfinamide

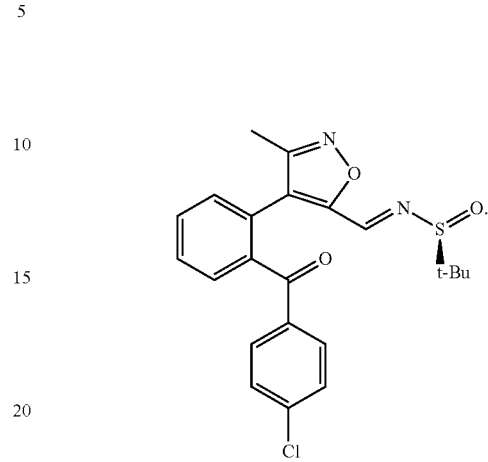

To a round bottomed flask was added 4-(2-(4-chlorobenzoyl)phenyl)-3-methylisoxazole-5-carbaldehyde (0.224 g, 0.688 mmol) and THF (3 mL). To this solution were added tetraethoxytitanium (0.29 mL, 1.38 mmol) and (R)-2-methylpropane-2-sulfinamide (0.092 g, 0.756 mmol) and the reaction stirred at room temperature overnight. The reaction was diluted with brine (3 mL) and EtOAc and this mixture was stirred vigorously for 1.5 h. This solution was filtered though Celite and the layers separated. The aqueous was extracted with EtOAc and the combined organics were dried over $Na_2SO_4$, filtered, and concentrated. The crude residue was purified via Biotage (EtOAc/hex) to afford (R,E)-N4(4-(2-(4-chlorobenzoyl)phenyl)-3-methylisoxazol-5-yl)methylene)-2-methylpropane-2-sulfinamide (0.233 g, 0.543 mmol). LC/MS m/z 429 [M+H]$^+$.

(3S)-tert-butyl 3-(4-(2-(4-chlorobenzoyl)phenyl)-3-methylisoxazol-5-yl)-3-((R)-1,1-dimethylethylsulfinamido)propanoate

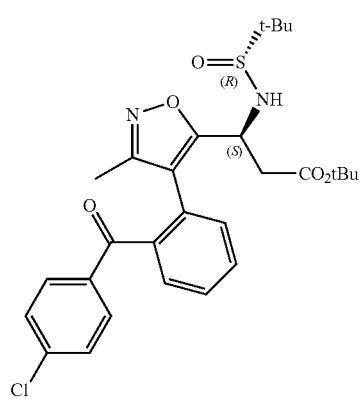

(3R)-tert-butyl 3-(4-(2-(4-chlorobenzoyl)phenyl)-3-methylisoxazol-5-yl)-3-((R)-1,1-dimethylethylsulfinamido)propanoate

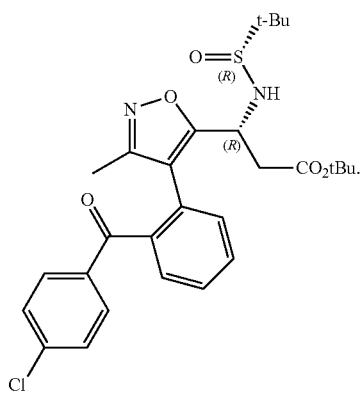

To a round bottomed flask was added (R,E)-N-((4-(2-(4-chlorobenzoyl)phenyl)-3-methylisoxazol-5-yl)methylene)-2-methylpropane-2-sulfinamide (0.083 g, 0.194 mmol) in THF (0.5 mL). This solution was cooled to 0° C. before addition of (2-tert-butoxy-2-oxoethyl)zinc(II) chloride (0.464 mL, 0.232 mmol) and stirring at 0° C. for 1 h before addition of another more zinc reagent (0.388 mL, 0.194 mmol). After stirring 3 h at 0° C. the solution was quenched with aqueous ammonium chloride solution and EtOAc added. The layers were separated and the aqueous extracted with EtOAc. The combined organics were washed with brine, dried over $Na_2SO_4$, filtered and concentrated. The crude residue was purified via Biotage (EtOAc/hex) to afford (3S)-tert-butyl 3-(4-(2-(4-chlorobenzoyl)phenyl)-3-methylisoxazol-5-yl)-3-((R)-1,1-dimethylethylsulfinamido)propanoate ($R_f$(1:1 EtOAc:hex)=~0.3, Mass: 0.043 g, LC/MS m/z 545 [M+H]$^+$) and (3R)-tert-butyl 3-(4-(2-(4-chlorobenzoyl)phenyl)-3-methylisoxazol-5-yl)-3-((R)-1,1-dimethylethylsulfinamido)propanoate ($R_f$(1:1 EtOAc:hex)=~0.15, Mass: 0.045 g, LC/MS m/z 545 [M+H]$^+$).

2-((4S)-6-(4-chlorophenyl)-1-methyl-4H-benzo[c]isoxazolo[4,5-e]azepin-4-yl)acetate

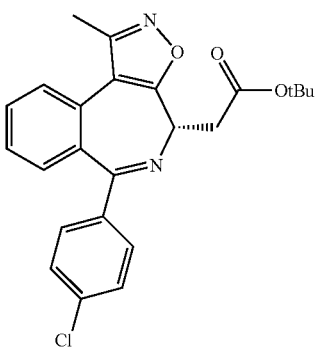 [SMILES: Cc1noc2c1-c1ccccc1C(c1ccc(Cl)cc1)=N[C@H]2CC(=O)OC(C)(C)C]

Compound 157

To a resealable vial was added (3S)-tert-butyl 3-(4-(2-(4-chlorobenzoyl)phenyl)-3-methylisoxazol-5-yl)-3-((R)-1,1-dimethylethylsulfinamido)propanoate (0.043 g, 0.079 mmol), EtOH (3 mL), and acetyl chloride (0.017 mL, 0.237 mmol). The vial was sealed and heated to 60° C. for 1.75 h before being cooled to room temperature and diluting with saturated $NaHCO_3$ and EtOAc. The layers were separated and the aqueous was extracted with EtOAc. The combined organics were washed with brine, dried over $Na_2SO_4$, filtered, and concentrated. The crude residue was purified via Biotage (EtOAc/hex) to afford tert-butyl 2-((4S)-6-(4-chlorophenyl)-1-methyl-4H-benzo[c]isoxazolo[4,5-e]azepin-4-yl)acetate (0.026 g, 0.061 mmol). $^1$H NMR (400 MHz, Acetone-$d_6$) δ 7.87-7.83 (m, 1H), 7.76-7.70 (m, 1H), 7.51-7.41 (m, 2H), 7.40 (s, 4H), 4.40 (br. s, 1H), 3.32 (d, J=7.19 Hz, 2H), 2.54 (s, 3H), 1.48 (s, 9H); LC/MS m/z 423 [M+H]$^+$.

Tert-butyl 2-((4R)-6-(4-chlorophenyl)-1-methyl-4H-benzo[c]isoxazolo[4,5-e]azepin-4-yl)acetate

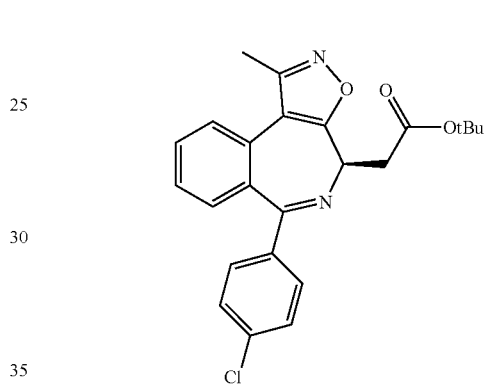

Compound 158

The title compound was made in a similar manner as above starting from (3R)-tert-butyl 3-(4-(2-(4-chlorobenzoyl)phenyl)-3-methylisoxazol-5-yl)-3-((R)-1,1-dimethylethylsulfinamido)propanoate. $^1$H NMR (400 MHz, Acetone-$d_6$) δ 7.85 (dd, J=0.83, 7.66 Hz, 1H), 7.76-7.70 (m, 1H), 7.50-7.41 (m, 2H), 7.40 (s, 4H), 4.40 (br. s, 1H), 3.32 (d, J=7.4 Hz, 2H), 2.54 (s, 3H), 1.48 (s, 9H); LC/MS m/z 423 [M+H]$^+$.

2-((4S)-6-(4-chlorophenyl)-1-methyl-4H-benzo[c]isoxazolo[4,5-e]azepin-4-yl)-N-ethylacetamide

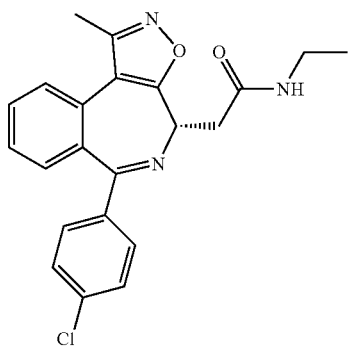 [SMILES: CCNC(=O)C[C@@H]1N=C(c2ccc(Cl)cc2)c2ccccc2-c2c(C)noc21]

Compound 159

To a round bottomed flask was added tert-butyl 2-((4S)-6-(4-chlorophenyl)-1-methyl-4H-benzo[c]isoxazolo[4,5-e]azepin-4-yl)acetate (0.019 g, 0.046 mmol), CH$_2$Cl$_2$ (2 mL), and TFA (0.400 mL, 5.19 mmol). The reaction was stirred for 1 h before being concentrated. The crude residue was dissolved in DMF (1 mL) and ethylamine (0.032 mL, 0.064 mmol), HATU (0.026 g, 0.068 mmol), and Hunig's base (0.024 mL, 0.137 mmol) were added. The reaction was stirred at room temperature for 1 h before diluting with water and methanol and purification via preparatory HPLC. The fractions were neutralized and the aqueous extracted with CH$_2$Cl$_2$. The combined organics were dried over Na$_2$SO$_4$, filtered, and concentrated. The crude residue was purified via Biotage (EtOAc/hex) to afford 2-((4S)-6-(4-chlorophenyl)-1-methyl-4H-benzo[c]isoxazolo[4,5-e]azepin-4-yl)-N-ethylacetamide (0.0068 g, 0.017 mmol). $^1$H NMR (400 MHz, DMSO-d$_6$) δ 8.27-8.13 (m, 1H), 7.83 (d, J=7.3 Hz, 1H), 7.72 (d, J=1.6 Hz, 1H), 7.49-7.36 (m, 4H), 7.34-7.25 (m, 2H), 4.42-4.23 (m, 1H), 3.14 (dd, J=6.98, 12.7 Hz, 4H), 2.51 (s, 3H), 1.07 (t, J=7.2 Hz, 3H); LC/MS m/z 394 [M+H]$^+$.

2-bromo-N,5-dimethoxy-N-methylbenzamide

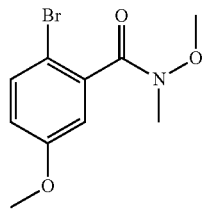

was prepared according to the procedure described in *Tetrahedron*, 2001, 57, 7765-7770.

(2-bromo-5-methoxyphenyl)(4-chlorophenyl)methanone

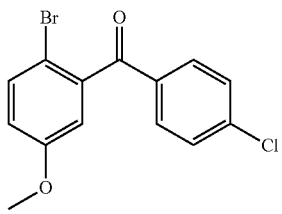 [SMILES: COc1ccc(Br)c(C(=O)c2ccc(Cl)cc2)c1]

and (4-chlorophenyl)(3-methoxyphenyl)methanone

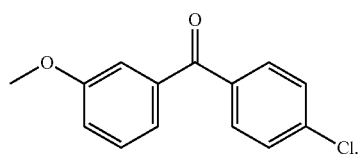 [SMILES: COc1cccc(C(=O)c2ccc(Cl)cc2)c1]

To a round bottomed flask was added 2-bromo-N,5-dimethoxy-N-methylbenzamide (6.23 g, 22.73 mmol) and THF (75 mL). To this solution was added (4-chlorophenyl)magnesium bromide (42 mL, 42.0 mmol) and the reaction stirred at room temperature overnight. The solution was diluted with water and EtOAc. The layers were separated and the aqueous was extracted with EtOAc. The combined organics were washed with brine, dried over Na$_2$SO$_4$, filtered, and concentrated. The crude residue was purified via Biotage (EtOAc/hex) to afford a mixture of (2-bromo-5-methoxyphenyl)(4-chlorophenyl)methanone and (4-chlorophenyl)(3-methoxyphenyl)methanone. LC/MS m/z 325 [M+H]$^+$.

2-((4S)-6-(4-chlorophenyl)-8-methoxy-1-methyl-4H-benzo[c]isoxazolo[4,5-e]azepin-4-yl)-N-ethylacetamide

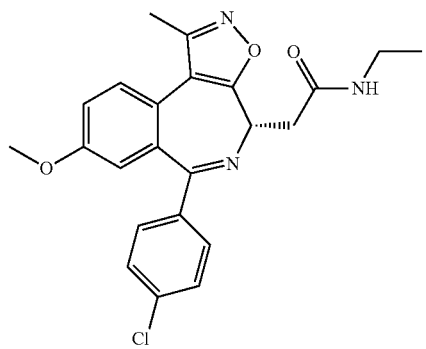 [SMILES: CCNC(=O)C[C@@H]1N=C(c2ccc(Cl)cc2)c2cc(OC)ccc2-c2c(C)noc21]

(Compound 160)

The title compound was made in a similar manner to 2-((4S)-6-(4-chlorophenyl)-1-methyl-4H-benzo[c]isoxazolo[4,5-e]azepin-4-yl)-N-ethylacetamide, starting from (4-(2-(4-chlorobenzoyl)-4-methylphenyl)-3-methylisoxazol-5-yl)methyl benzoate, which is synthesized according to Example 5. $^1$H NMR (400 MHz, Acetone-d$_6$) δ 7.76 (d, J=8.78 Hz, 1H), 7.46-7.41 (m, 2H), 7.41-7.36 (m, 2H), 7.31 (dd, J=2.6, 8.8 Hz, 1H), 6.96 (d, J=2.6 Hz, 1H), 4.53-4.43 (m, 1H), 3.82-3.76 (m, 3H), 3.36-3.13 (m, 4H), 2.50 (s, 3H), 1.14 (t, J=7.31 Hz, 3H); LC/MS m/z 424 [M+H]$^+$.

(R,E)-N-((4-(2-(4-chlorobenzoyl)phenyl)-5-methylisoxazol-3-yl)methylene)-2-methylpropane-2-sulfinamide

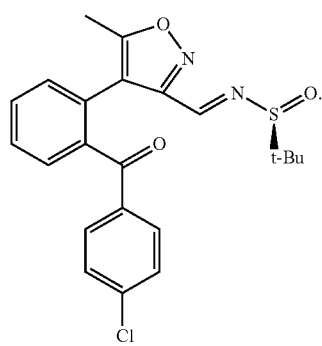 [SMILES: Cc1onc(/C=N/[S@@](=O)C(C)(C)C)c1-c1ccccc1C(=O)c1ccc(Cl)cc1]

This material can be made in a similar manner as (R,E)-N-((4-(2-(4-chlorobenzoyl)phenyl)-3-methylisoxazol-5-yl)methylene)-2-methylpropane-2-sulfinamide starting from 4-(2-(4-chlorobenzoyl)phenyl)-5-methylisoxazole-3-carbaldehyde (1.10 g, 3.38 mmol). LC/MS m/z 429 [M+H]+.

(3S)-tert-butyl 3-(4-(2-(4-chlorobenzoyl)phenyl)-5-methylisoxazol-3-yl)-3-((R)-1,1 dimethylethylsulfinamido)propanoate

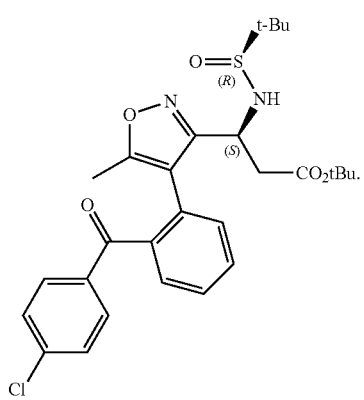

To a round bottomed flask was added (R,E)-N-((4-(2-(4-chlorobenzoyl)phenyl)-5-methylisoxazol-3-yl)methylene)-2-methylpropane-2-sulfinamide (0.480 g, 1.12 mmol) and THF (6 mL). This solution was cooled to 0° C. before addition of (2-tert-butoxy-2-oxoethyl)zinc(II) chloride (4.48 mL, 2.24 mmol). The solution was stirred at 0° C. before for 3.5 h before addition of more of (2-tert-butoxy-2-oxoethyl) zinc(II) chloride (1.12 mL, 0.560 mmol). The reaction was stirred for an additional 2.5 h before being diluted with aqueous NH4Cl and EtOAc. The layers were separated and the aqueous was extracted with EtOAc. The combined organics were washed with brine, dried over Na2SO4, filtered, and concentrated. The crude residue was purified via Biotage (EtOAc/hex) to afford (3S)-tert-butyl 3-(4-(2-(4-chlorobenzoyl)phenyl)-5-methylisoxazol-3-yl)-3-((R)-1,1-dimethylethylsulfinamido)propanoate (0.118 g, 0.216 mmol) and (3R)-tert-butyl 3-(4-(2-(4-chlorobenzoyl)phenyl)-5-methylisoxazol-3-yl)-3-((R)-1,1-dimethylethylsulfinamido)propanoate (0.094 g, 0.172 mmol). LC/MS m/z 545 [M+H]+.

Tert-butyl 2-((4S)-6-(4-chlorophenyl)-1-methyl-4H-benzo[c]isoxazolo[4,3-e]azepin-4-yl)acetate

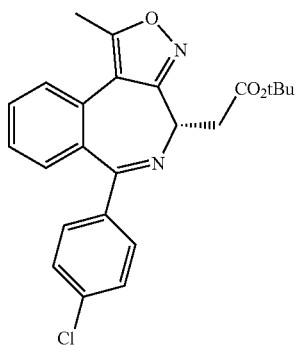 [SMILES: Cc1onc2c1-c1ccccc1C(c1ccc(Cl)cc1)=N[C@H]2CC(=O)OC(C)(C)C]

(Compound 161) and Ethyl 2-((4S)-6-(4-chlorophenyl)-1-methyl-4H-benzo[c]isoxazolo[4,3-e]azepin-4-yl)acetate

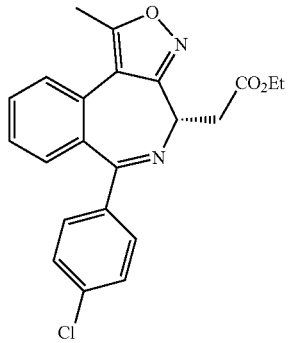 [SMILES: CCOC(=O)C[C@@H]1N=C(c2ccc(Cl)cc2)c2ccccc2-c2c1noc2C]

Compound 162

To a resealable vial was added (3S)-tert-butyl 3-(4-(2-(4-chlorobenzoyl)phenyl)-5-methylisoxazol-3-yl)-3-((R)-1,1-dimethylethylsulfinamido)propanoate (0.118 g, 0.216 mmol), EtOH, and acetyl chloride (0.046 mL, 0.647 mmol). The vial was sealed and heated to 60° C. for 2 h. The reaction was cooled to room temperature and diluted with a solution of NaHCO3 and EtOAc. The layers were separated and the aqueous was extracted with EtOAc (3×). The combined organics were washed with brine, dried over Na2SO4, filtered, and concentrated. The crude residue was purified via Biotage (EtOAc/hex) to afford two products. Major: tert-butyl 2-((4S)-6-(4-chlorophenyl)-1-methyl-4H-benzo[c]isoxazolo[4,3-e]azepin-4-yl)acetate (0.062 g, 0.147 mmol), 423 [M+H]+. Minor: ethyl 2-((4S)-6-(4-chlorophenyl)-1-methyl-4H-benzo[c]isoxazolo[4,3-e]azepin-4-yl)acetate (0.0036 g, 0.0091 mmol). $^1$H NMR (500 MHz, acetone-$d_6$) δ 7.78-7.74 (m, 1H), 7.70 (dt, J=1.5, 7.6 Hz, 1H), 7.50-7.46 (m, 1H), 7.45-7.42 (m, 2H), 7.41-7.36 (m, 3H), 4.57 (t, J=7.08 Hz, 1H), 4.20-4.14 (m, 2H), 3.36 (d, J=7.3 Hz, 2H), 2.68 (s, 3H), 1.26 (t, J=7.1 Hz, 3H); LC/MS m/z 395 [M+H]+.

2-((4S)-6-(4-chlorophenyl)-1-methyl-4H-benzo[c]isoxazolo[4,3-e]azepin-4-yl)-N-ethylacetamide

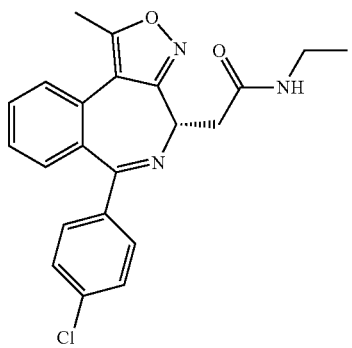 [SMILES: CCNC(=O)C[C@@H]1N=C(c2ccc(Cl)cc2)c2ccccc2-c2c1noc2C]

Compound 163

To a round bottomed flask was added tert-butyl 2-((4S)-6-(4-chlorophenyl)-1-methyl-4H-benzo[c]isoxazolo[4,3-e]azepin-4-yl)acetate (0.059 g, 0.140 mmol), CH$_2$Cl$_2$ (2 mL), and TFA (0.400 mL, 5.19 mmol). The reaction was stirred at room temperature for 2 h before concentrating. The crude residue was dried for 30 min before addition of DMF (2 mL), ethylamine (0.098 mL, 0.195 mmol, 2M in THF), HATU (0.080 g, 0.209 mmol), and Hunig's Base (0.073 mL, 0.419 mmol). The reaction was stirred at room temperature for 1 h before diluting with water and extracting with EtOAc. The combined organics were washed with brine, dried over Na$_2$SO$_4$, filtered, and concentrated. The crude residue was purified via Biotage (EtOAc/hex) to afford 2-((4S)-6-(4-chlorophenyl)-1-methyl-4H-benzo[c]isoxazolo[4,3-e]azepin-4-yl)-N-ethylacetamide (0.022 g, 0.056 mmol). $^1$H NMR (500 MHz, Acetone-d$_6$) δ 7.76-7.72 (m, 1H), 7.71-7.66 (m, 1H), 7.49-7.42 (m, 3H), 7.41-7.36 (m, 3H), 7.32 (br. s, 1H), 4.62 (dd, J=5.4, 8.3 Hz, 1H), 3.35-3.21 (m, 2H), 3.20-3.09 (m, 2H), 2.67 (s, 3H), 1.14 (t, J=7.3 Hz, 3H); LC/MS m/z 394.

2-((4R)-6-(4-chlorophenyl)-1-methyl-4H-benzo[c]isoxazolo[4,3-e]azepin-4-yl)-N-ethylacetamide

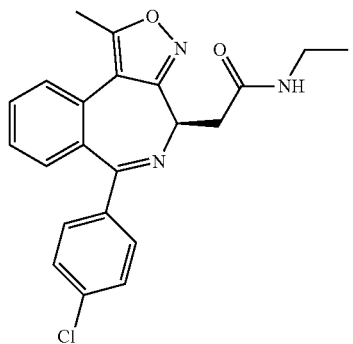 [SMILES: CCNC(=O)C[C@H]1N=C(c2ccc(Cl)cc2)c2ccccc2-c2c1noc2C]

Compound 189

This material was made in a similar manner as 2-((4S)-6-(4-chlorophenyl)-1-methyl-4H-benzo[c]isoxazolo[4,3-e]azepin-4-yl)-N-ethylacetamide, starting from (3R)-tert-butyl 3-(4-(2-(4-chlorobenzoyl)phenyl)-5-methylisoxazol-3-yl)-3-((R)-1,1-dimethylethylsulfinamido)propanoate. $^1$H NMR (500 MHz, Acetone-d$_6$) δ 7.76-7.72 (m, 1H), 7.71-7.66 (m, 1H), 7.49-7.42 (m, 3H), 7.41-7.36 (m, 3H), 7.32 (br. s, 1H), 4.62 (dd, J=5.4, 8.3 Hz, 1H), 3.35-3.21 (m, 2H), 3.20-3.09 (m, 2H), 2.67 (s, 3H), 1.14 (t, J=7.3 Hz, 3H); LC/MS m/z 394.

Example 18

Synthesis of Compounds of Formula I wherein Ar is Thiophene

The compounds of this example were prepared in the manner set forth in Scheme 4, above. Exemplary synthesis of compounds of Formula I wherein Ar is thiophene, and intermediates useful in such compound are set forth below.

Methyl 4,5-dimethylthiophene-3-carboxylate

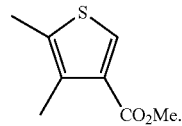

This intermediate was prepared according to the procedure described in *Organic Process Research & Development*, 2002, 6, 357-366.

N-Methoxy-N,4,5-trimethylthiophene-3-carboxamide

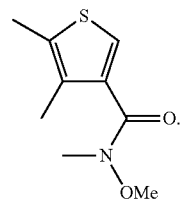

To a cooled (−30° C. to −20° C.) slurry of methyl 4,5-dimethylthiophene-3-carboxylate (5.44 g, 32.0 mmol) and N,O-dimethylhydroxylamine hydrochloride (4.80 g, 49.2 mmol) in THF (45 mL) at was added slowly (over 15 min) a solution of isopropylmagnesium bromide (3.85 mL, 11.16 mmol, 2.9 M) in 2-methyl-tetrahydrofuran. After complete addition of the base, the reaction mixture was warmed to 0° C. and partitioned between 1 N HCl (55 mL) and MTBE (50 mL). The aqueous phase was extracted with MTBE (2×) and the combined organic layer was washed with water (until the pH of the aqueous was ~5). The organic layer was dried over Na$_2$SO$_4$ and concentrated to give a light yellow oil. The crude product was purified on Biotage system (gradient elution 7% EtOAc:93% Hexanes to 60% EtOAc:40% Hexanes) to give the titled compound as a yellow oil (5.17 g, 25.9 mmol, 81% yield). LC/MS m/z 200 [M+H]$^+$.

(4-Chlorophenyl)(4,5-dimethylthiophen-3-yl)methanone

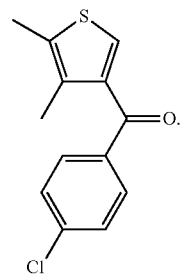 [SMILES: Cc1scc(C(=O)c2ccc(Cl)cc2)c1C]

To a cooled (−40° C.) solution of N-methoxy-N,4,5-trimethylthiophene-3-carboxamide (1.77 g, 8.88 mmol) in THF (10 mL) was slowly added (over 10 min) a solution of 4-chlorophenylmagnesium bromide (17 mL, 17.00 mmol, 1 M) in diethyl ether. The reaction mixture was allowed to gradually warm to room temperature and age for several hours. To the mixture was added 1 N HCl and the aqueous layer was extracted with EtOAc (2x). The combined organic layer was washed with saturated NaHCO₃, water, dried over Na₂SO₄, and concentrated to give an oil. The resultant oil was purified on Biotage system (gradient elution 1% EtOAc: 99% Hexanes to 4% EtOAc:96% Hexanes) to give the titled compound as white solids (2.00 g, 7.96 mmol, 90% yield). LC/MS m/z 251 [M+H]⁺.

(2-Bromo-4,5-dimethylthiophen-3-yl)(4-chlorophenyl)methanone

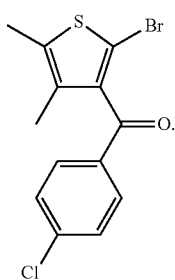 [SMILES: Cc1sc(Br)c(C(=O)c2ccc(Cl)cc2)c1C]

To a solution of (4-chlorophenyl)(4,5-dimethylthiophen-3-yl)methanone (1.99 g, 7.94 mmol) in DMF (15 mL) was added N-bromosuccinimide (1.55 g, 8.71 mmol) in one portion. After 2 h, the reaction mixture was partitioned between water and MTBE. The aqueous layer was extracted with MTBE and the combined organic layer was washed with 1% sodium thiosulfate, water, dried over Na₂SO₄ and concentrated to give light yellow solids. The resultant solids was purified on Biotage system (gradient elution 1% EtOAc: 99% Hexanes to 4% EtOAc:96% Hexanes) to give the titled compound as yellow solids (2.40 g, 7.28 mmol, 92% yield). LC/MS m/z 329 [(M (³⁵Cl, ⁷⁹Br)+H]⁺ and m/z 331 [M+H]⁺.

(4-Chlorophenyl)(2-(5-(hydroxymethyl)-3-methylisoxazol-4-yl)-4,5-dimethylthiophen-3-yl)methanone

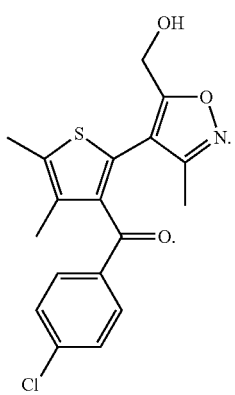 [SMILES: Cc1noc(CO)c1-c1sc(C)c(C)c1C(=O)c1ccc(Cl)cc1]

To a solution of (3-methyl-4-(4,4,5,5-tetramethyl-1,3,2-dioxaborolan-2-yl)isoxazol-5-yl)methyl acetate (0.865 g, 3.08 mmol) and (2-bromo-4,5-dimethylthiophen-3-yl)(4-chlorophenyl)methanone (0.534 g, 1.619 mmol) in 1,4-dioxane (7 mL) and water (2 mL) was added PdCl₂(dppf)-CH₂Cl₂ adduct (0.090 g, 0.110 mmol) and K₂CO₃ (0.560 g, 4.05 mmol). The bi-phasic mixture was heated to 95° C. under a constant stream of N₂ (g). After 5 h, the mixture was cooled to 45° C. and aqueous 1 N NaOH (4.0 mL, 4.00 mmol) was introduced. After an additional 1 h, LC-MS analysis shows complete conversion of acetate to alcohol. The mixture was cooled to room temperature, 1 N HCl was added to acidify the aqueous layer (pH ~1) and the aqueous layer extracted MTBE (2x). The combined organic layer was washed with saturated NaHCO₃, brine, dried over Na₂SO₄, and concentrated to give a dark brown oil. The oil was diluted with MTBE and stirred over activated charcoal for 15 min, then filtered over a plug of silica and Celite. The filter cake was washed with MTBE (2x) and subsequently concentration gave a brown oil. The resultant oil was purified on Biotage system (gradient elution 5% EtOAc:95% Hexanes to 40% EtOAc:60% Hexanes) to give the titled compound as a yellow oil (0.463 g, 1.28 mmol, 79% yield). LC/MS m/z 362 [M+H]⁺.

(R,E)-N-((4-(3-(4-chlorobenzoyl)-4,5-dimethylthiophen-2-yl)-3-methylisoxazol-5-yl)methylene)-2-methylpropane-2-sulfinamide

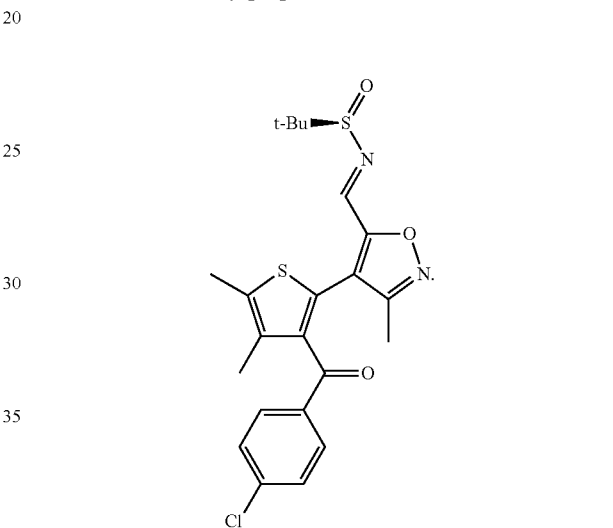

To a cooled (−78° C.) solution of oxalyl chloride (0.15 mL, 1.714 mmol) in CH₂Cl₂ (1 mL) was slowly added a solution of DMSO (0.17 mL, 2.396 mmol) in CH₂Cl₂ (0.30 mL). After 15 min, a solution of (4-chlorophenyl)(2-(5-(hydroxymethyl)-3-methylisoxazol-4-yl)-4,5-dimethylthiophen-3-yl)methanone (0.399 g, 1.10 mmol) in CH₂Cl₂ (2 mL) was slowly added. After 30 min, Et₃N (0.40 mL, 2.87 mmol) was added and the mixture was warmed to room temperature. After stirring for an additional 15 min, the reaction mixture was diluted with 1 N HCl and the aqueous layer was extracted with CH₂Cl₂ (2x). The combined organic layer was washed with saturated NaHCO₃, water, dried over Na₂SO₄, and concentrated to provide the aldehyde as a light brown oil, which was used directly without further purification.

To a solution of unpurified aldehyde in CH₂Cl₂ (22 mL) was sequentially added (R)-2-methylpropane-2-sulfinamide (0.150 g, 1.24 mmol) and titanium(IV) ethoxide (0.46 mL, 2.19 mmol). After 24 h, water (15 mL) was slowly introduced to the vigorously stirred reaction. The heterogeneous mixture was filtered over Celite, the filter cake was washed with CH₂Cl₂. The organic layer was washed with water, dried over Na₂SO₄, and concentrated to give an orange oil. The resultant oil was purified on Biotage system (gradient elution, 5% EtOAc:95% Hexanes to 40% EtOAc:60% Hexanes) to deliver the titled product (0.450 g, 0.972 mmol, 88% yield over 2-steps) as a light yellow oil. LC/MS m/z 463 [M+H]⁺.

(3R)-tert-butyl 3-(4-(3-(4-chlorobenzoyl)-4,5-dimethylthiophen-2-yl)-3-methylisoxazol-5-yl)-3-((R)-1,1-dimethylethylsulfinamido)propanoate

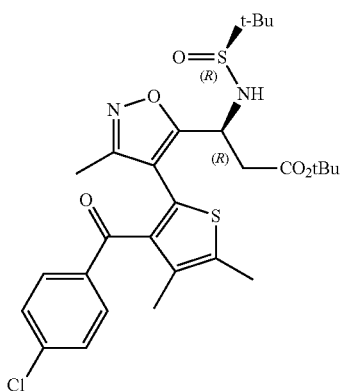

and

(3S)-tert-butyl 3-(4-(3-(4-chlorobenzoyl)-4,5-dimethylthiophen-2-yl)-3-methylisoxazol-5-yl)-3-((R)-1,1-dimethylethylsulfinamido)propanoate

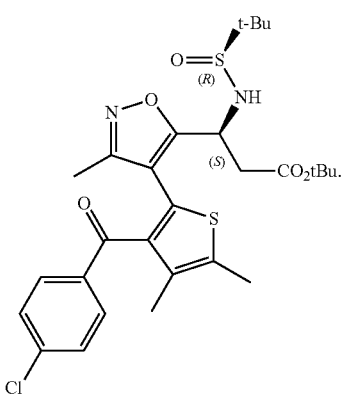

To a cooled (0° C.) solution of (2-tert-butoxy-2-oxoethyl)zinc(II) chloride (0.200 mL, 0.100 mmol) was added a solution of (R,E)-N-((4-(3-(4-chlorobenzoyl)-4,5-dimethylthiophen-2-yl)-3-methylisoxazol-5-yl)-methylene)-2-methylpropane-2-sulfinamide (0.039 g, 0.084 mmol) in THF (0.5 mL). Additional THF (2×0.5 mL) was used to aid in complete transfer of the sulfinamide. After 1.5 h, additional (2-tert-butoxy-2-oxoethyl)zinc(II) chloride (1.00 mL, 0.500 mmol) was added and the reaction temperature was allowed to reach to ambient temperatures. After several hours, the reaction mixture was diluted aqueous saturated NH$_4$Cl and EtOAc. The aqueous layer was extracted with EtOAc (2×), the combined organic phase was washed with water (2×), dried over Na$_2$SO$_4$ and concentrated in vacuo to give a thick oil. The resultant oil was purified on Biotage system (gradient elution, 12% MTBE:95% Hexanes to 100% MTBE) to deliver the (3R)-tert-butyl 3-(4-(3-(4-chlorobenzoyl)-4,5-dimethylthiophen-2-yl)-3-methylisoxazol-5-yl)-3-((R)-1,1-dimethylethylsulfinamido)propanoate (0.016 g, 0.027 mmol, 31% yield) as a light white foam and (3S)-tert-butyl 3-(4-(3-(4-chlorobenzoyl)-4,5-dimethylthiophen-2-yl)-3-methylisoxazol-5-yl)-3-((R)-1,1-dimethylethylsulfinamido)propanoate (0.021 g, 0.036 mmol, 43% yield) as a light white foam. (3R)-tert-butyl 3-(4-(3-(4-chlorobenzoyl)-4,5-dimethylthiophen-2-yl)-3-methylisoxazol-5-yl)-3-((R)-1,1-dimethylethylsulfinamido)propanoate: LC/MS m/z 579 [(M ($^{35}$Cl)+H]$^+$ and m/z 581 [(M ($^{37}$Cl)+H]$^+$ and (3S)-tert-butyl 3-(4-(3-(4-chlorobenzoyl)-4,5-dimethylthiophen-2-yl)-3-methylisoxazol-5-yl)-3-((R)-1,1-dimethylethylsulfinamido)propanoate: LC/MS m/z 579 [M+H]$^+$.

2-((6S)-4-(4-Chlorophenyl)-2,3,9-trimethyl-6H-isoxazolo[5,4-c]thieno[2,3-e]azepin-6-yl)acetic acid

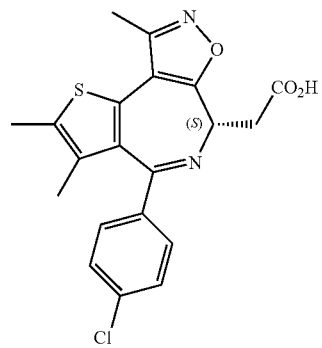

Compound 164

To a solution of (3S)-tert-butyl 3-(4-(3-(4-chlorobenzoyl)-4,5-dimethylthiophen-2-yl)-3-methylisoxazol-5-yl)-3-((R)-1,1-dimethylethylsulfinamido)propanoate (0.310 g, 0.535 mmol) in MeOH (1.5 mL) was added a solution of HCl in Dioxane (0.25 mL, 1.00 mmol, 4 M). After 30 min, the mixture was concentrated in vacuo and excess HCl was azeotropically removed using CH$_2$Cl$_2$ (3×) to give the amino-ester as an oil.

The resultant amino-ester was diluted with CHCl$_3$ (3 mL) and TFA (0.20 mL, 2.60 mmol) and the mixture was heated at reflux. After 24 h, the solution was cooled to room temperature and concentrated to give yellow-green oil. The titled imino-acid (0.344 g) was obtained as an oil that was processed to the amide bond formation without further purification. LC/MS m/z 401 [M+H]$^+$.

2-((6S)-4-(4-chlorophenyl)-2,3,9-trimethyl-6H-isoxazolo[4,5-e]thieno[3,2-c]azepin-6-yl)-N-ethylacetamide

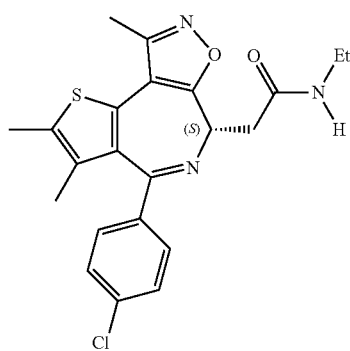

Compound 165

To a cooled (−10° C.) solution of unpurified 2-((6S)-4-(4-Chlorophenyl)-2,3,9-trimethyl-6H-isoxazolo[5,4-c]thieno[2,3-e]azepin-6-yl)acetic acid (Compound 164; 0.344 g, 0.858 mmol) in $CH_2Cl_2$ (2 mL) was added $Et_3N$ (1.5 mL, 10.8 mmol) and 2 M $EtNH_2$ (in THF) (2.60 mL, 5.20 mmol), followed by 2-(3H-[1,2,3]triazolo[4,5-b]pyridin-3-yl)-1,1,3,3-tetramethylisouronium hexafluorophosphate(V) (1.00 g, 2.63 mmol). After complete addition of the reagents, the reaction mixture was warmed to ambient temperatures and stirred for 1 h. The mixture was concentrated and the resultant paste was partitioned between MTBE and 1 N HCl. The aqueous layer was extracted with MTBE (2×) and the combined organic layer were washed with saturated $NaHCO_3$, water (2×), dried over $Na_2SO_4$, concentration gave a light yellow solids. The resultant solids were purified on Biotage system (gradient elution, 12% EtOAc:95% Hexanes to 75% EtOAc:25% Hexanes) to give off-white solids. The solids were diluted in $CH_3CN$ (2.0 mL) and water (0.50 mL), the solution was frozen and lyophilized to give the titled compound as off-white amorphous solids (0.047 g, 0.110 mmol, 13% yield). $^1H$ NMR (400 MHz, D6-Acetone) δ 7.50-7.30 (m, 5H), 4.35 (t, J=6.8 Hz, 1H), 3.42-3.16 (m, 4H), 2.46 (s, 3H), 2.44 (s, 3H), 1.70 (s, 3H), 1.14 (t, J=7.3 Hz, 3H); LC/MS m/z 428 [M+H]$^+$.

2-((6R)-4-(4-Chlorophenyl)-2,3,9-trimethyl-6H-isoxazolo[5,4-c]thieno[2,3-e]azepin-6-yl)acetic acid

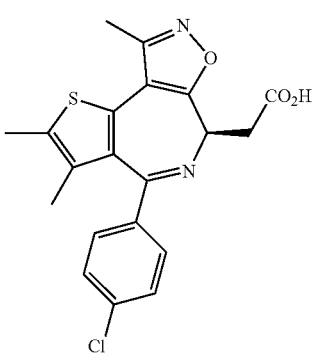 [SMILES: Cc1noc2c1-c1sc(C)c(C)c1C(c1ccc(Cl)cc1)=N[C@@H]2CC(=O)O]

Compound 166

The titled compound was synthesized according to the protocol outlined above for intermediate 2-((6S)-4-(4-Chlorophenyl)-2,3,9-trimethyl-6H-isoxazolo[5,4-c]thieno[2,3-e]azepin-6-yl)acetic acid starting from intermediate (3R)-tert-butyl 3-(4-(3-(4-chlorobenzoyl)-4,5-dimethylthiophen-2-yl)-3-methylisoxazol-5-yl)-3-((R)-1,1-dimethylethylsulfinamido)propanoate. LC/MS m/z 401 [M+H]$^+$.

2-((6R)-4-(4-chlorophenyl)-2,3,9-trimethyl-6H-isoxazolo[4,5-e]thieno[3,2-c]azepin-6-yl)-N-ethylacetamide

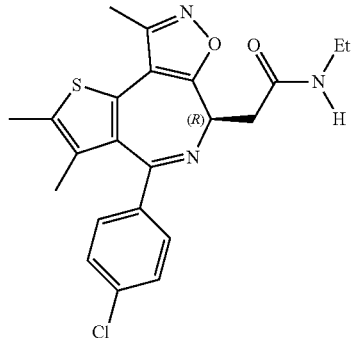

Compound 167

The titled example was synthesized according to the protocol outlined above for 2-((6S)-4-(4-chlorophenyl)-2,3,9-trimethyl-6H-isoxazolo[4,5-e]thieno[3,2-c]azepin-6-yl)-N-ethylacetamide starting from intermediate 2-((6R)-4-(4-Chlorophenyl)-2,3,9-trimethyl-6H-isoxazolo[5,4-c]thieno[2,3-e]azepin-6-yl)acetic acid. $^1H$ NMR (400 MHz, D6-Acetone) δ 7.50-7.30 (m, 5H), 4.35 (t, J=6.8 Hz, 1H), 3.42-3.16 (m, 4H), 2.46 (s, 3H), 2.44 (s, 3H), 1.70 (s, 3H), 1.14 (t, J=7.3 Hz, 3H); LC/MS m/z 428 [M+H]$^+$.

(Tetrahydro-2H-pyran-4-yl)magnesium chloride

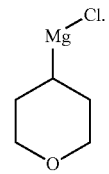

To a vigorously stirred suspension of Mg (0.500 g, 20.57 mmol) turnings and iodine (0.019 g, 0.075 mmol) in THF (5 mL) under $N_2$ (g) was added 1,2-dibromoethane (0.10 mL, 1.160 mmol) and 10% of a solution of 4-chlorotetrahydro-2H-pyran (1.00 mL, 9.24 mmol) in THF (5 mL). The mixture was heated to 60° C. and as the reaction mixture turned clear and Grignard initiation took place, the remainder of the solution of 4-chlorotetrahydro-2H-pyran (1.00 mL, 9.24 mmol) in THF was added slowly over 30 min. The reaction mixture was stirred at 65° C. for 2 h to deliver a solution of (tetrahydro-2H-pyran-4-yl)magnesium chloride in THF. The Grignard solution was used without any further purification.

119

(6S)-tert-butyl 6-(2-(tert-butoxy)-2-oxoethyl)-2,3,9-trimethyl-4-oxo-4H-isoxazolo[5,4-c]thieno[2,3-e]azepine-5(6H)-carboxylate

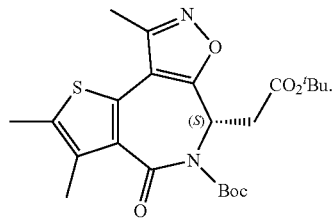

To a murky yellow solution of tert-butyl 2-((6S)-2,3,9-trimethyl-4-oxo-5,6-dihydro-4H-isoxazolo[4,5-e]thieno[3,2-c]azepin-6-yl)acetate a form of intermediate 17, prepared according to Example 14 (0.209 g, 0.577 mmol) and DMAP (0.007 g, 0.058 mmol) in THF (2.0 mL) was added Boc$_2$O (0.166 mL, 0.715 mmol). After 30 min, the reaction mixture was concentrated in vacuo to give brown solids. The crude product was purified on Biotage system (gradient elution 5% EtOAc:95% Hexanes to 10% EtOAc:90% Hexanes, then isocratic 10% EtOAc:90% Hexanes) to deliver the titled product (8.61 g, 20.1 mmol, 88% yield) as white solids. LC/MS m/z 563 [M+H]$^+$.

(3S)-tert-Butyl 3-((tert-butoxycarbonyl)amino)-3-(4-(4,5-dimethyl-2-(tetrahydro-2H-pyran-4-carbonyl)thiophen-3-yl)-3-methylisoxazol-5-yl)propanoate

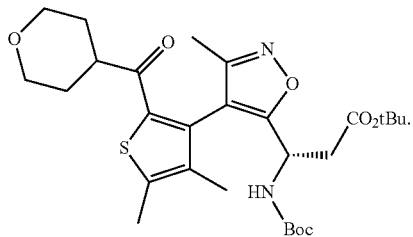 [SMILES: Cc1noc([C@H](CC(=O)OC(C)(C)C)NC(=O)OC(C)(C)C)c1-c1c(C(=O)C2CCOCC2)sc(C)c1C]

To a cooled (−40° C.) solution of (6S)-tert-butyl 6-(2-tert-butoxy-2-oxoethyl)-2,3,9-trimethyl-4-oxo-4H-isoxazolo[4,5-e]thieno[3,2-c]azepine-5(6H)-carboxylate (136 mg, 0.294 mmol) in THF (0.5 mL) was added (tetrahydro-2H-pyran-4-yl)magnesium chloride (1.05 mL, 0.882 mmol) in one-portion. After 5 min, the purple mixture was allowed to warm to rt. The pink reaction was quenched with 1 N HCl and the aqueous layer was extracted with EtOAc (2×), washed with saturated NaHCO$_3$, dried over Na$_2$SO$_4$, and concentrated to give a yellow oil. The oil was purified on Biotage system (gradient elution 5% EtOAc:95% Hexanes to 30% EtOAc:70% Hexanes, then isocratic 30% EtOAc:70% Hexanes) to yield the titled compound (0.148 g, 0.270 mmol, 92% yield) as a white foam. LC/MS m/z 571 [M+Na]$^+$

120

2-((6S)-2,3,9-trimethyl-4-(tetrahydro-2H-pyran-4-yl)-6H-isoxazolo[5,4-c]thieno[2,3-e]azepin-6-yl)acetamide

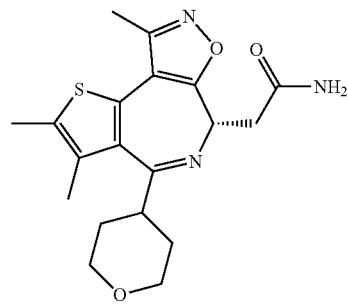 [SMILES: Cc1noc2c1-c1sc(C)c(C)c1C(C1CCOCC1)=N[C@H]2CC(N)=O]

Compound 168

To a solution of (3S)-tert-butyl 3-(tert-butoxycarbonylamino)-3-(4-(4,5-dimethyl-3-(tetrahydro-2H-pyran-4-carbonyl)thiophen-2-yl)-3-methylisoxazol-5-yl)propanoate (68 mg, 0.124 mmol) in CHCl$_3$ (1.0 mL) was added TFA (0.477 mL, 6.20 mmol) and the reaction mixture was heated at reflux for 3 h. The yellow reaction mixture is cooled to ambient temperatures, concentrated in vacuo, and excess TFA is azeotropically removed using CHCl$_3$ (2×2 mL), followed by toluene (2×10 mL). The crude carboxylic acid is dried and used without further purification.

To a cooled (0° C.) solution of the carboxylic acid in DMF (1.0 mL) was sequentially added N,N-diisopropylethyl amine (0.100 mL, 0.573 mmol), NH$_4$Cl (0.024 g, 0.449 mmol), and COMU (0.080 g, 0.186 mmol). After complete addition the reaction mixture turned light orange and was allowed to warm to room temperature. After complete consumption of the acid (as detected by LC-MS analysis), the reaction mixture was diluted with H$_2$O and MTBE. The aqueous phase was extracted with MTBE (3×) and the combined organic phase was washed with H$_2$O (2×), brine, dried over Na$_2$SO$_4$, and concentrated to give a white foam. The foam was purified on Biotage system (gradient elution 15% EtOAc:85% Hexanes to 100% EtOAc), the volatile organics were removed, and the purified compound was subsequently diluted with CH$_3$CN (10 mL) and H$_2$O (1 mL), and lyophilized to give the titled compound (0.031 g, 0.084 mmol, 68% yield) as off white-amorphous solids. $^1$H NMR (400 MHz, Acetone-d$_6$) δ 7.08 (br. s, 1H), 6.28 (br. s, 1H), 4.12 (t, J=6.73 Hz, 1H), 3.90 (d, J=11.12 Hz, 1H), 3.66 (d, J=10.82 Hz, 1H), 3.40 (dt, J=3.66, 11.19 Hz, 1H), 3.14-3.31 (m, 3H), 2.89-3.00 (m, 1H), 2.45 (s, 3H), 2.41 (s, 3H), 2.31 (d, J=0.59 Hz, 3H), 1.79-1.91 (m, 2H), 1.11 (d, J=12.29 Hz, 1H), 1.00 (dt, J=4.10, 12.14 Hz, 1H); LC/MS m/z 374 [M+H]$^+$.

Example 19

Synthesis of Compounds of Formula I Wherein Ar is Pyridine

The compounds of this example were prepared in the manner set forth in Scheme 5, below. Appropriate modification of this scheme to produce other compounds of the invention will be readily apparent to those of skill in the art.

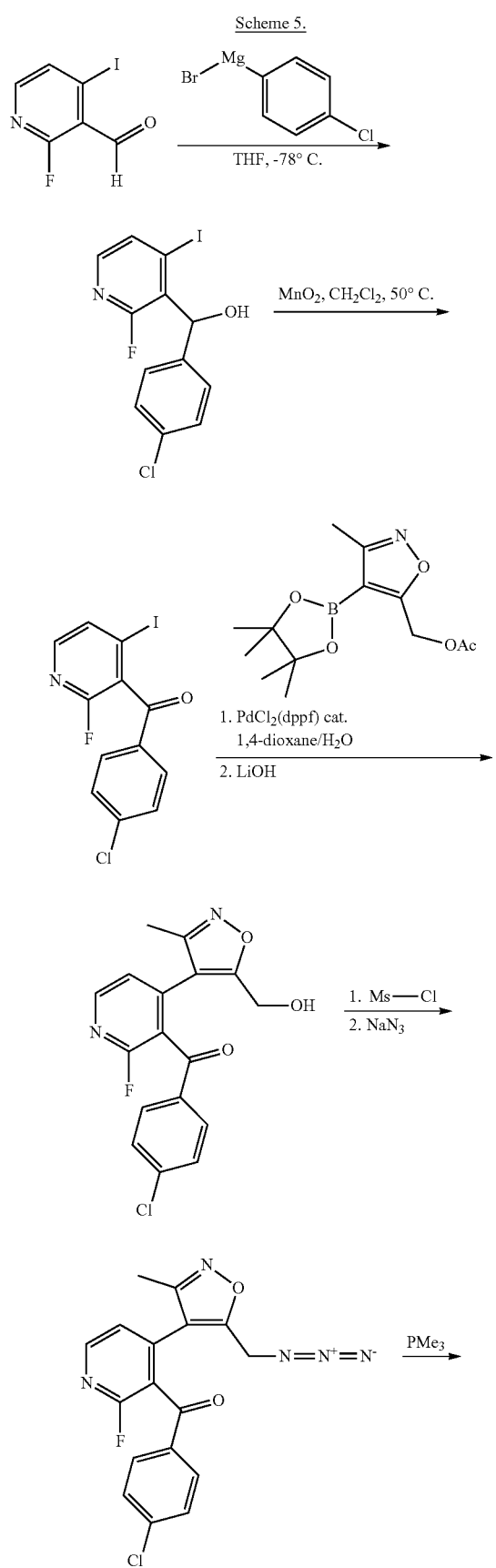

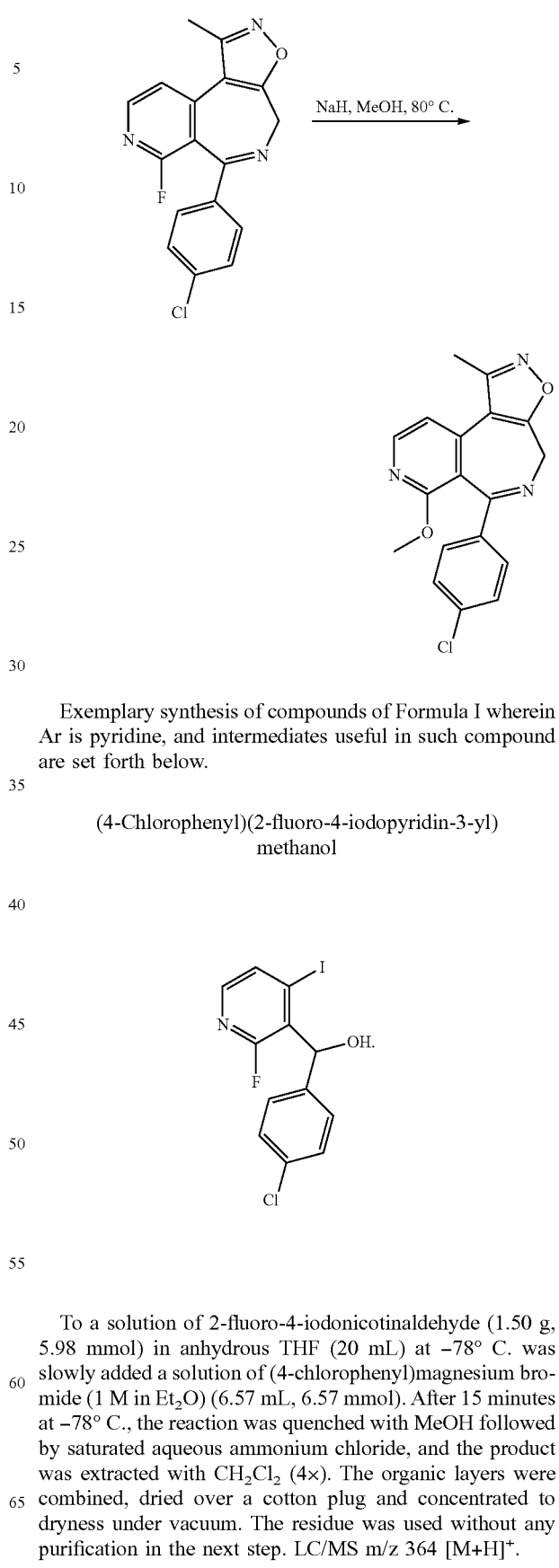

Exemplary synthesis of compounds of Formula I wherein Ar is pyridine, and intermediates useful in such compound are set forth below.

(4-Chlorophenyl)(2-fluoro-4-iodopyridin-3-yl)methanol

To a solution of 2-fluoro-4-iodonicotinaldehyde (1.50 g, 5.98 mmol) in anhydrous THF (20 mL) at −78° C. was slowly added a solution of (4-chlorophenyl)magnesium bromide (1 M in $Et_2O$) (6.57 mL, 6.57 mmol). After 15 minutes at −78° C., the reaction was quenched with MeOH followed by saturated aqueous ammonium chloride, and the product was extracted with $CH_2Cl_2$ (4×). The organic layers were combined, dried over a cotton plug and concentrated to dryness under vacuum. The residue was used without any purification in the next step. LC/MS m/z 364 [M+H]$^+$.

(4-Chlorophenyl)(2-fluoro-4-iodopyridin-3-yl)methanone

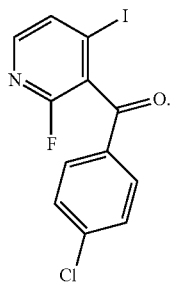 [SMILES: O=C(c1ccc(Cl)cc1)c1c(I)ccnc1F]

To a solution of (4-chlorophenyl)(2-fluoro-4-iodopyridin-3-yl)methanol (2.17 g, 5.98 mmol) in CH$_2$Cl$_2$ (100 mL) was added manganese dioxide (10.40 g, 120 mmol) at room temperature. The reaction was heated to 45° C. for 3 h before the heterogeneous mixture was filtered through a pad of silica gel. The cake was rinsed with EtOAc, and the filtrate was concentrated to dryness under vacuum. The residue was used in the next step without any additional purification. LC/MS m/z 362 [M+H]$^+$.

(4-Chlorophenyl)(2-fluoro-4-(5-(hydroxymethyl)-3-methylisoxazol-4-yl)pyridin-3-yl)methanone

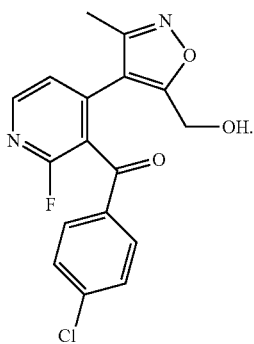 [SMILES: Cc1noc(CO)c1-c1ccnc(F)c1C(=O)c1ccc(Cl)cc1]

A procedure analogous to the synthesis of (4-Chlorophenyl)(2-(5-(hydroxymethyl)-3-methylisoxazol-4-yl)-4,5-dimethylthiophen-3-yl)methanone in Example 18 was followed. Haloaryl (4-chlorophenyl)(2-fluoro-4-iodopyridin-3-yl)methanone was used as starting material. LC/MS m/z 347 [M+H]$^+$.

(4-(5-(Azidomethyl)-3-methylisoxazol-4-yl)-2-fluoropyridin-3-yl)(4-chlorophenyl)methanone

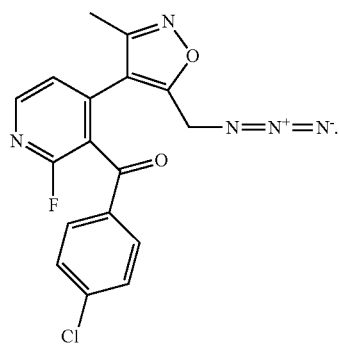

A procedure similar to the synthesis of (2-(3-(1-azidoethyl)-5-methylisoxazol-4-yl)phenyl)(4-chlorophenyl)methanone in Example 16 was followed, except that DMF was substituted by a mixture of acetonitrile and water; and that (4-Chlorophenyl)(2-fluoro-4-(5-(hydroxymethyl)-3-methylisoxazol-4-yl)pyridin-3-yl)methanone was used as starting material. LC/MS m/z 372 [M+H]$^+$.

6-(4-Chlorophenyl)-7-fluoro-1-methyl-4H-isoxazolo[5,4-c]pyrido[4,3-e]azepine

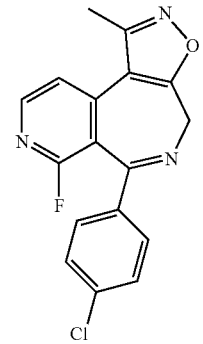 [SMILES: Cc1noc2c1-c1ccnc(F)c1C(c1ccc(Cl)cc1)=NC2]

Compound 169

A procedure similar to that used to produce 6-(4-chlorophenyl)-1,4-dimethyl-4H-benzo[c]isoxazolo[4,3-e]azepine in Example 16 was followed. Crude (4-(5-(azidomethyl)-3-methylisoxazol-4-yl)-2-fluoropyridin-3-yl)(4-chlorophenyl)methanone was used as starting material. $^1$H NMR (400 MHz, DMSO-d$_6$) δ 8.49 (d, J=5.26 Hz, 1H), 7.80 (dd, J=1.14, 5.26 Hz, 1H), 7.45 (td, J=2.30, 8.70 Hz, 2H), 7.38 (td, J=2.10, 8.70 Hz, 2H), 5.32 (d, J=13.50 Hz, 1H), 4.30 (d, J=13.50 Hz, 1H), 2.57 (s, 3H); LC/MS m/z 328 [M+H]$^+$.

The side product (4-(5-(aminomethyl)-3-methylisoxazol-4-yl)-2-fluoropyridin-3-yl)(4-chlorophenyl)methanone was be converted to 6-(4-chlorophenyl)-7-fluoro-1-methyl-4H-isoxazolo[5,4-c]pyrido[4,3-e]azepine in a mixture of absolute EtOH and acetic acid (2:1 v/v) at 110° C. for more than 1 h.

6-(4-Chlorophenyl)-7-methoxy-1-methyl-4H-isoxazolo[5,4-c]pyrido[4,3-e]azepine

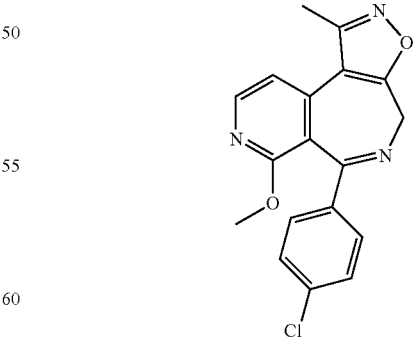

Compound 170

To a solution of 6-(4-chlorophenyl)-7-fluoro-1-methyl-4H-isoxazolo[4,5-e]pyrido[3,4-c]azepine (0.030 g, 0.092 mmol) in MeOH (2 mL) was added sodium hydride (60% dispersed in mineral oil) (0.037 g, 0.915 mmol) at room temperature. The reaction was stirred at room temperature for 15 min (or until the gas evolution stopped) before it was heated to 80° C. for 75 min in a sealed vial. The reaction was then concentrated to dryness under vacuum, and the residue was purified by flash chromatography (hexane/EtOAc 19:1 to 5:5) to give 6-(4-chlorophenyl)-7-methoxy-1-methyl-4H-isoxazolo[5,4-c]pyrido[4,3-e]azepine as a white solid (0.031 g). $^1$H NMR (400 MHz, DMSO-$d_6$) δ 8.42 (d, J=5.49 Hz, 1H), 7.43 (d, J=5.26 Hz, 1H), 7.39 (td, J=2.10, 8.70 Hz, 2H), 7.26 (td, J=2.10, 8.47 Hz, 2H), 5.24 (d, J=13.28 Hz, 1H), 4.11 (d, J=13.50 Hz, 1H), 3.61 (s, 3H), 2.55 (s, 3H); LC/MS m/z 340 [M+H]$^+$.

6-(4-Chlorophenyl)-7-isopropoxy-1-methyl-4H-isoxazolo[5,4-c]pyrido[4,3-e]azepine

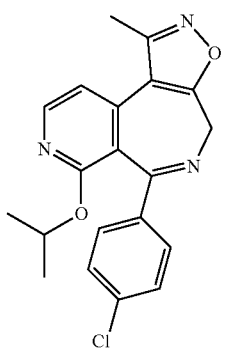 [SMILES: Cc1noc2c1-c1ccnc(OC(C)C)c1C(c1ccc(Cl)cc1)=NC2]

Compound 171

A procedure similar to 6-(4-chlorophenyl)-7-methoxy-1-methyl-4H-isoxazolo[5,4-c]pyrido[4,3-e]azepine was followed, except that 2-propanol was used instead of MeOH. $^1$H NMR (400 MHz, DMSO-$d_6$) δ 8.38 (d, J=5.49 Hz, 1H), 7.36-7.41 (m, 3H), 7.22 (td, J=2.10, 8.47 Hz, 2H), 5.22 (d, J=13.28 Hz, 1H), 5.06 (spt, J=6.20 Hz, 1H), 4.10 (d, J=13.28 Hz, 1H), 2.55 (s, 3H), 1.08 (d, J=5.95 Hz, 3H), 0.62 (d, J=6.18 Hz, 3H); LC/MS m/z 368 [M+H]$^+$.

6-(4-Chlorophenyl)-1-methyl-4H-isoxazolo[5,4-c]pyrido[4,3-e]azepin-7-amine

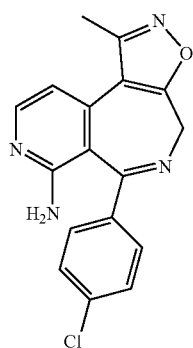 [SMILES: Cc1noc2c1-c1ccnc(N)c1C(c1ccc(Cl)cc1)=NC2]

Compound 172

To a solution of 6-(4-chlorophenyl)-7-fluoro-1-methyl-4H-isoxazolo[4,5-e]pyrido[3,4-c]azepine (0.025 g, 0.076 mmol) in 1,4-dioxane (1 mL) was added concentrated ammonium hydroxide (2.00 mL, 51.4 mmol) at room temperature. The reaction was heated to 80° C. for 17 h before silica gel was added. The solvent was removed under vacuum, the dry silica gel was packed and the adsorbed product was purified by flash chromatography (hexane/EtOAc 6:4 to 0:10) to give 6-(4-chlorophenyl)-1-methyl-4H-isoxazolo[5,4-c]pyrido[4,3-e]azepin-7-amine as an off-white solid (0.006 g). $^1$H NMR (400 MHz, DMSO-$d_6$) δ 8.19 (d, J=5.26 Hz, 1H), 7.38 (td, J=2.20, 8.93 Hz, 2H), 7.34 (td, J=2.20, 8.47 Hz, 2H), 6.94 (d, J=5.26 Hz, 1H), 5.91 (s, 2H), 5.21 (d, J=12.82 Hz, 1H), 4.04 (d, J=13.05 Hz, 1H), 2.50 (s, 3H); LC/MS m/z 325 [M+H]$^+$.

6-(4-Chlorophenyl)-N,1-dimethyl-4H-isoxazolo[5,4-c]pyrido[4,3-e]azepin-7-amine

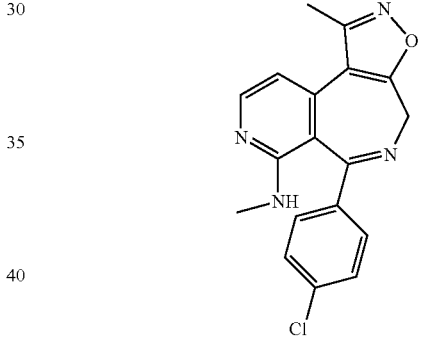

Compound 173

To 6-(4-chlorophenyl)-7-fluoro-1-methyl-4H-isoxazolo[4,5-e]pyrido[3,4-c]azepine (0.020 g, 0.061 mmol) was added a solution of methylamine (33% in EtOH) (4 mL) at room temperature. The reaction was heated to 80° C. for 22 h before silica gel was added. The solvent was removed under vacuum, the dry silica gel was packed and the adsorbed product was purified by flash chromatography (hexane/EtOAc 8:2 to 2:8) to give 6-(4-chlorophenyl)-N,1-dimethyl-4H-isoxazolo[5,4-c]pyrido[4,3-e]azepin-7-amine as a white solid (0.014 g). $^1$H NMR (400 MHz, DMSO-$d_6$) δ 8.27 (d, J=5.26 Hz, 1H), 7.35 (td, J=2.30, 8.93 Hz, 2H), 7.30 (td, J=2.30, 8.93 Hz, 2H), 6.93 (d, J=5.26 Hz, 1H), 5.87 (q, J=4.35 Hz, 1H), 5.22 (d, J=12.82 Hz, 1H), 4.03 (s, 1H), 2.61 (d, J=4.58 Hz, 3H), 2.50 (s, 3H); LC/MS m/z 339 [M+H]$^+$.

6-(4-Chlorophenyl)-N-ethyl-1-methyl-4H-isoxazolo[5,4-c]pyrido[4,3-e]azepin-7-amine

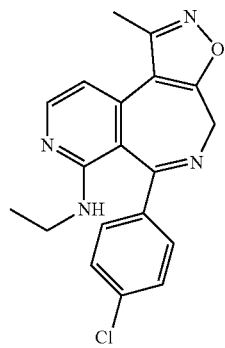 [SMILES: CCNc1nccc2c1C(c1ccc(Cl)cc1)=NCc1onc(C)c1-2]

Compound 174

A procedure similar to 6-(4-chlorophenyl)-N,1-dimethyl-4H-isoxazolo[5,4-c]pyrido[4,3-e]azepin-7-amine was followed, except that ethylamine was used instead of methylamine. $^1$H NMR (400 MHz, DMSO-$d_6$) δ 8.24 (d, J=5.26 Hz, 1H), 7.35 (td, J=2.10, 8.93 Hz, 2H), 7.30 (td, J=1.80, 8.20 Hz, 2H), 6.91 (d, J=5.26 Hz, 1H), 5.80 (t, J=5.49 Hz, 1H), 5.22 (d, J=12.82 Hz, 1H), 4.01 (d, J=12.82 Hz, 1H), 3.20-3.29 (m, 1H), 2.98-3.09 (m, 1H), 2.50 (s, 3H), 0.72 (s, 3H); LC/MS m/z 353 [M+H]$^+$.

6-(4-Chlorophenyl)-N,N,1-trimethyl-4H-isoxazolo[5,4-c]pyrido[4,3-e]azepin-7-amine

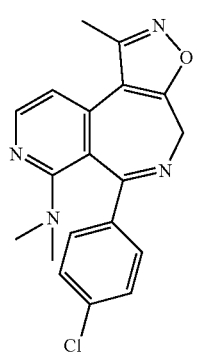 [SMILES: Cc1noc2c1-c1ccnc(N(C)C)c1C(c1ccc(Cl)cc1)=NC2]

Compound 175

A procedure similar to 6-(4-chlorophenyl)-N,1-dimethyl-4H-isoxazolo[5,4-c]pyrido[4,3-e]azepin-7-amine was followed, except that a solution of dimethylamine (2 M in MeOH) was used instead of methylamine (33% in EtOH). $^1$H NMR (400 MHz, DMSO-$d_6$) δ 8.35 (d, J=5.04 Hz, 1H), 7.37 (d, J=8.70 Hz, 2H), 7.20 (d, J=8.70 Hz, 2H), 7.14 (d, J=5.04 Hz, 1H), 5.28 (s, 1H), 4.25 (d, J=12.82 Hz, 1H), 2.70 (s, 6H), 2.54 (s, 3H); LC/MS m/z 353 [M+H]$^+$.

Example 20

Synthesis of Compounds of Formula I, Wherein Ar is Pyridone

Compounds of Formula I wherein Ar is pyridone are synthesized according to Scheme 6, below. Appropriate modification of this scheme to produce other compounds of the invention will be readily apparent to those of skill in the art.

Scheme 6:

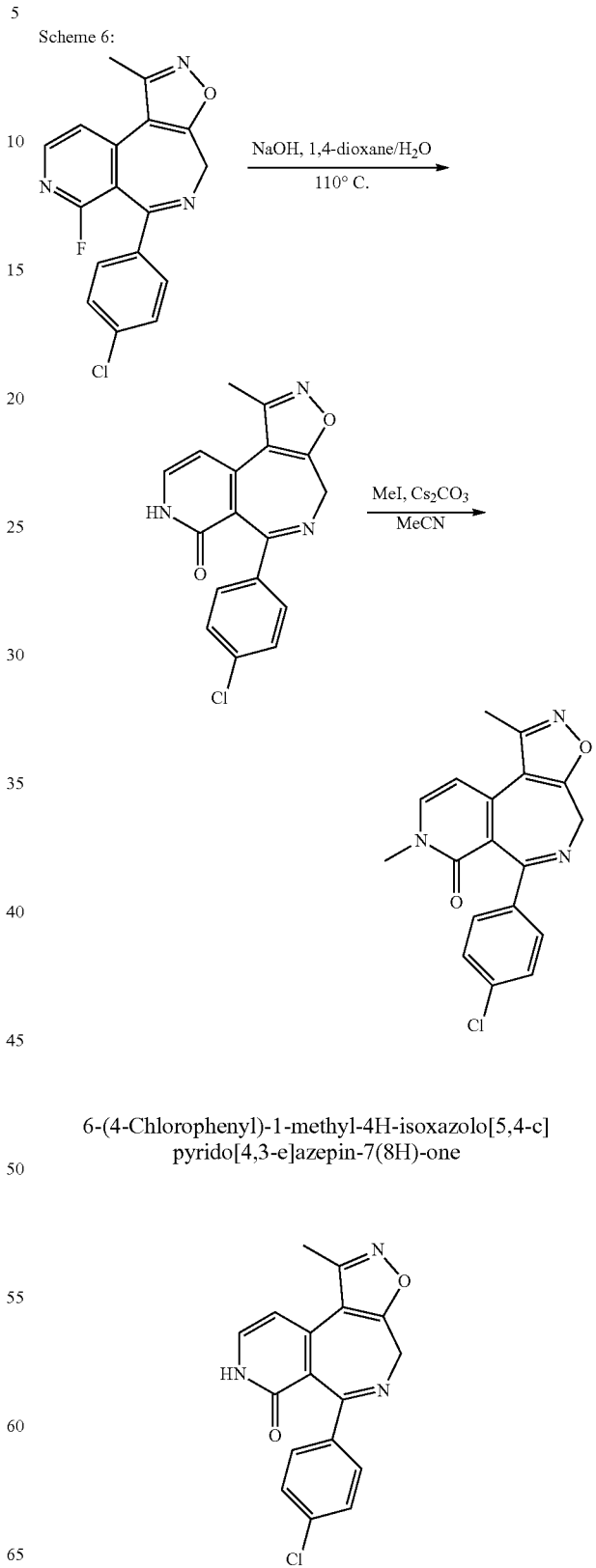

6-(4-Chlorophenyl)-1-methyl-4H-isoxazolo[5,4-c]pyrido[4,3-e]azepin-7(8H)-one

Compound 176

To a solution of 6-(4-chlorophenyl)-7-fluoro-1-methyl-4H-isoxazolo[4,5-e]pyrido[3,4-c]azepine from Example 19 (0.244 g, 0.744 mmol) in 1,4-dioxane (5 mL) was added an aqueous solution of sodium hydroxide (1M) (5.00 mL, 5.00 mmol) at room temperature. The reaction was heated to 110° C. for 90 min, then cooled to room temperature before a saturated solution of ammonium chloride was added. The product was extracted with $CH_2Cl_2$ (repeated 4 times), and the organic layers were combined, dried over sodium sulfate, filtered and concentrated to dryness under vacuum. The product was purified twice by flash chromatography (hexane/EtOAc 8:2 to 1:9) to give 6-(4-chlorophenyl)-1-methyl-4H-isoxazolo[5,4-c]pyrido[4,3-e]azepin-7(8H)-one as a white solid (0.211 g). $^1$H NMR (400 MHz, DMSO-d$_6$) δ 11.92 (br.s., 1H), 7.66 (d, J=6.64 Hz, 1H), 7.38 (d, J=8.00 Hz, 2H), 7.33 (d, J=8.47 Hz, 2H), 6.60 (d, J=6.87 Hz, 1H), 5.19 (d, J=13.05 Hz, 1H), 4.07 (d, J=13.05 Hz, 1H), 2.50 (s, 3H); LC/MS m/z 326 [M+H]$^+$.

6-(4-Chlorophenyl)-1,8-dimethyl-4H-isoxazolo[5,4-c]pyrido[4,3-e]azepin-7(8H)-one

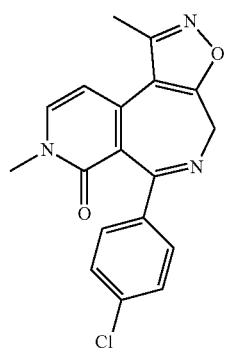 [SMILES: Cc1noc2c1-c1ccn(C)c(=O)c1C(c1ccc(Cl)cc1)=NC2]

Compound 177

To a solution of 6-(4-chlorophenyl)-1-methyl-4H-isoxazolo[4,5-e]pyrido[3,4-c]azepin-7(8H)-one (0.070 g, 0.215 mmol) in acetonitrile (2 mL) were added cesium carbonate (0.210 g, 0.645 mmol) and iodomethane (16.09 μl, 0.258 mmol) at room temperature. The reaction was stirred at room temperature for 2 h before it was diluted with $CH_2Cl_2$ and filtered. The filtrate was concentrated to dryness under vacuum, and the residue was purified by flash chromatography (hexane/EtOAc 9:1 to 3:7) to give 6-(4-chlorophenyl)-1,8-dimethyl-4H-isoxazolo[5,4-c]pyrido[4,3-e]azepin-7 (8H)-one as an off-white solid (0.064 g) and 6-(4-chlorophenyl)-7-methoxy-1-methyl-4H-isoxazolo[5,4-c]pyrido[4,3-e]azepine as side product. $^1$H NMR (400 MHz, DMSO-d$_6$) δ 8.00 (d, J=7.10 Hz, 1H), 7.34 (d, J=2.06 Hz, 4H), 6.67 (d, J=7.10 Hz, 1H), 5.20 (d, J=13.05 Hz, 1H), 4.06 (d, J=13.05 Hz, 1H), 3.43 (s, 3H), 2.51 (s, 3H); LC/MS m/z 340 [M+H]$^+$.

Substitutions on the pyridone ring were achieved following the general step set forth in Scheme 7, below.

Scheme 7:

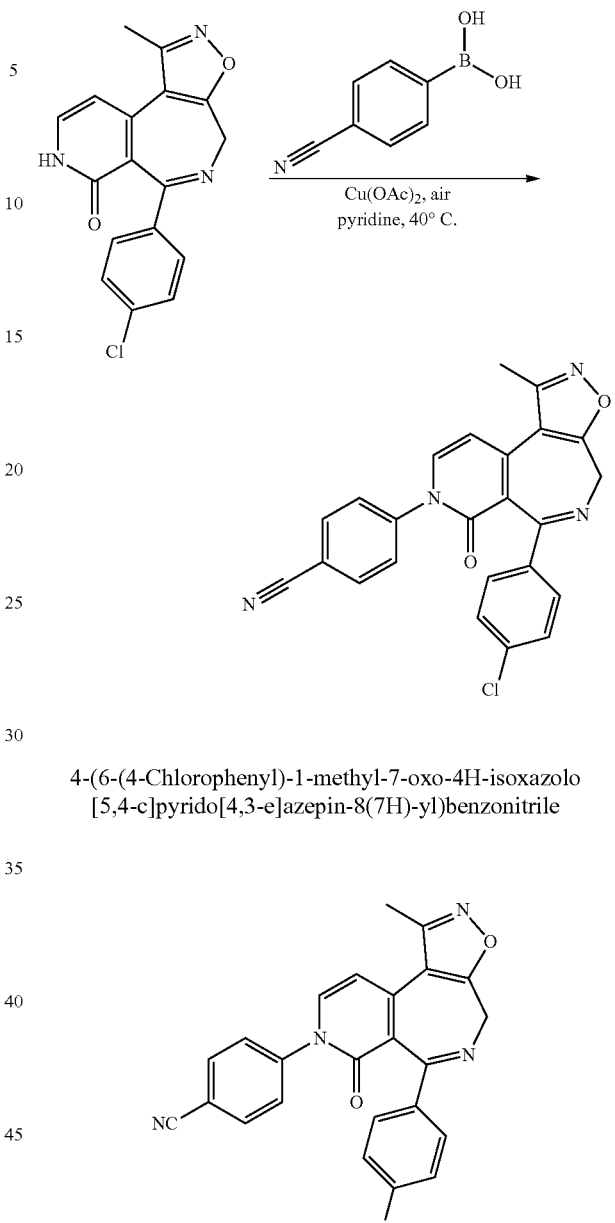

4-(6-(4-Chlorophenyl)-1-methyl-7-oxo-4H-isoxazolo[5,4-c]pyrido[4,3-e]azepin-8(7H)-yl)benzonitrile Compound 178

6-(4-Chlorophenyl)-1-methyl-4H-isoxazolo[4,5-e]pyrido [3,4-c]azepin-7(8H)-one (0.025 g, 0.077 mmol), 4-cyanophenylboronic acid (0.023 g, 0.153 mmol), copper(II) acetate (0.035 g, 0.192 mmol) and pyridine (1 mL) were charged into a vial equipped with a stir bar. The reaction was heated to 40° C. for 3 h in an open vial (to allow contact with air) before silica gel was added. Then the pyridine was removed under vacuum. The dry silica gel was packed and the adsorbed product was purified by flash chromatography (hexane/EtOAc 19:1 to 4:6) to give 4-(6-(4-chlorophenyl)-1-methyl-7-oxo-4H-isoxazolo[5,4-c]pyrido[4,3-e]azepin-8 (7H)-yl)benzonitrile as an off-white solid (0.027 g). $^1$H NMR (400 MHz, DMSO-d$_6$) δ 8.04 (d, J=6.87 Hz, 1H), 8.02 (td, J=2.10, 8.24 Hz, 2H), 7.66 (td, J=2.10, 8.70 Hz, 2H), 7.49 (td, J=2.10, 8.47 Hz, 2H), 7.35 (td, J=2.30, 8.70 Hz, 2H), 6.84 (d, J=7.32 Hz, 1H), 5.26 (d, J=13.28 Hz, 1H), 4.18 (d, J=13.05 Hz, 1H), 2.56 (s, 3H); LC/MS m/z 427 [M+H]⁺.

6-(4-Chlorophenyl)-1-methyl-8-phenyl-4H-isoxazolo[5,4-c]pyrido[4,3-e]azepin-7(8H)-one

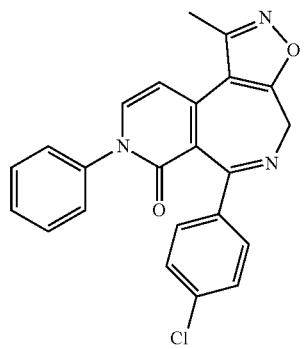 [SMILES: Cc1noc2c1-c1ccn(-c3ccccc3)c(=O)c1C(c1ccc(Cl)cc1)=NC2]

Compound 179

A procedure similar to 4-(6-(4-chlorophenyl)-1-methyl-7-oxo-4H-isoxazolo[5,4-c]pyrido[4,3-e]azepin-8(7H)-yl)benzonitrile was followed, except that phenylboronic acid was used instead of 4-cyanophenylboronic acid. ¹H NMR (400 MHz, DMSO-d₆) δ 8.00 (d, J=7.10 Hz, 1H), 7.31-7.55 (m, 9H), 6.78 (d, J=7.10 Hz, 1H), 5.25 (d, J=13.05 Hz, 1H), 4.18 (d, J=13.28 Hz, 1H), 2.55 (s, 3H); LC/MS m/z 402 [M+H]⁺.

Example 21

Synthesis of Compounds of Formula I Wherein Ar is Substituted Pyridine

Compounds of Formula I wherein Ar is substituted pyridine were synthesized according to Scheme 8. Appropriate modification of this scheme to produce other compounds of the invention will be readily apparent to those of skill in the art.

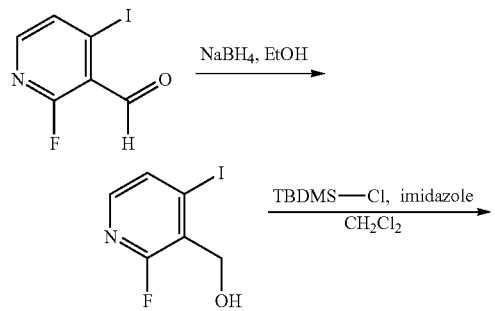

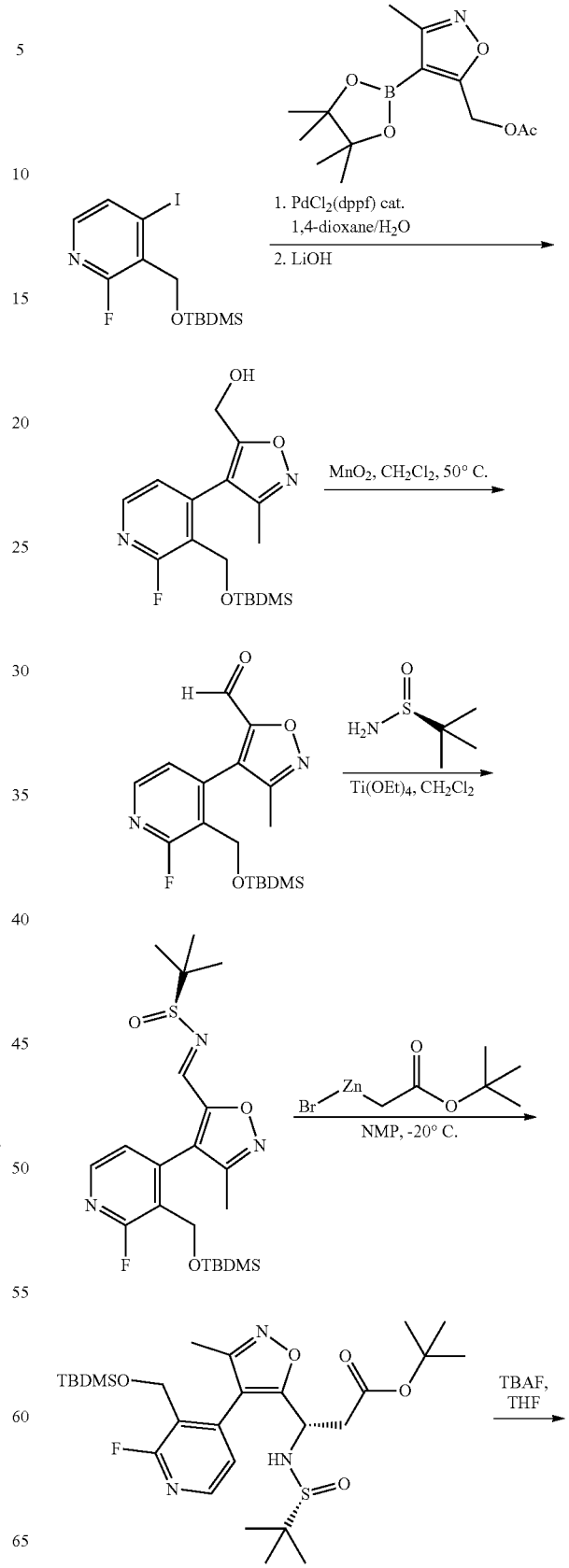

133
-continued
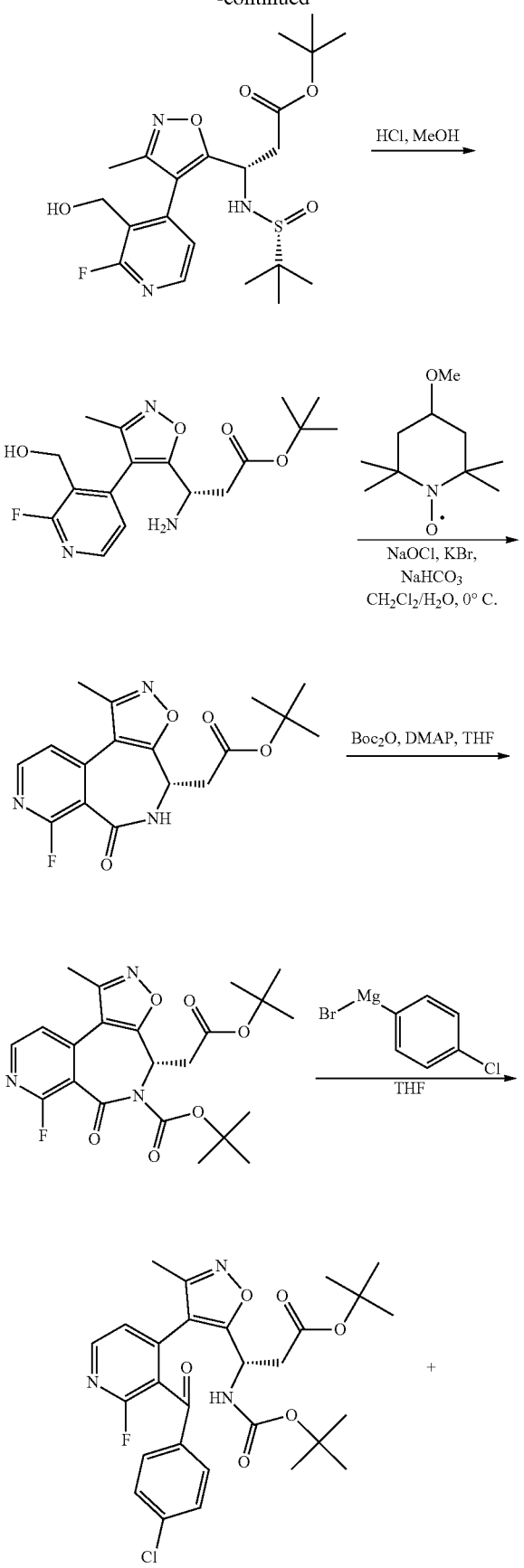
134
-continued
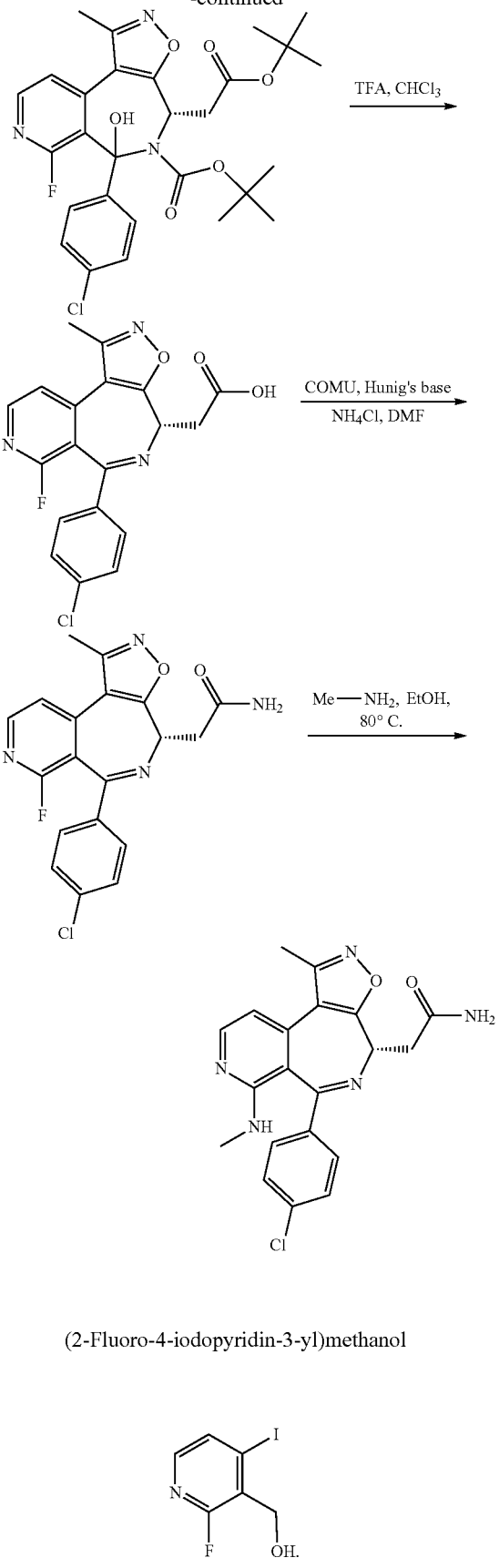
(2-Fluoro-4-iodopyridin-3-yl)methanol To a solution of 2-fluoro-4-iodonicotinaldehyde (3.50 g, 13.94 mmol) in absolute EtOH (56 mL) was added sodium borohydride (0.264 g, 6.97 mmol) at room temperature. The reaction was stirred at room temperature for 1 h, followed by the slow addition of 1 M aqueous hydrochloric acid. The product was extracted with CH$_2$Cl$_2$ (repeated four times), and the organic layers were combined, dried over sodium sulfate, filtered and concentrated to dryness. The aqueous phase was basified to pH 8-10 with 2 M aqueous sodium hydroxide and extracted with diethylether (repeated four times). Then the organic layers were combined, dried over sodium sulfate, filtered, combined with the previously obtained residue and concentrated to dryness under vacuum. The residue was used without any purification in the next step. LC/MS m/z 254 [M+H]$^+$.

3-(((tert-Butyldimethylsilyl)oxy)methyl)-2-fluoro-4-iodopyridine

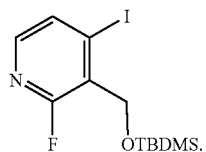 [SMILES: CC(C)(C)[Si](C)(C)OCc1c(I)ccnc1F]

To a solution of (2-fluoro-4-iodopyridin-3-yl)methanol (3.52 g, 13.91 mmol) in CH$_2$Cl$_2$ (80 mL) at room temperature was sequentially added imidazole (1.894 g, 27.8 mmol) and TBDMS-Cl (2.52 g, 16.69 mmol). The reaction was stirred at room temperature for 1 h before diethylether was added and the insoluble salts were filtered. Silica gel was added to the filtrate prior to the solvent removal under vacuum. The dry silica gel was packed, and the adsorbed product was purified by flash chromatography (hexane/EtOAc 10:0 to 7:3) to give 3-(((tert-butyldimethylsilyl)oxy)methyl)-2-fluoro-4-iodopyridine as a white solid (4.5 g). LC/MS m/z 368 [M+H]$^+$.

(4-(3-(((tert-butyldimethylsilyl)oxy)methyl)-2-fluoropyridin-4-yl)-3-methylisoxazol-5-yl)methanol

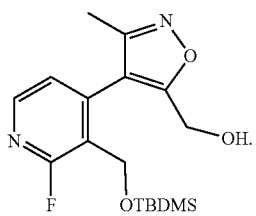 [SMILES: Cc1noc(CO)c1-c1ccnc(F)c1CO[Si](C)(C)C(C)(C)C]

A procedure similar to that used to synthesize (4-Chlorophenyl) (2-(5-(hydroxymethyl)-3-methylisoxazol-4-yl)-4,5-dimethylthiophen-3-yl)methanone in Example 18 was followed. LC/MS m/z 353 [M+H]$^+$.

4-(3-(((tert-Butyldimethylsilyl)oxy)methyl)-2-fluoropyridin-4-yl)-3-methylisoxazole-5-carbaldehyde

To a solution of (4-(3-(((tert-butyldimethylsilyloxy)methyl)-2-fluoropyridin-4-yl)-3-methylisoxazol-5-yl)methanol (1.35 mg, 8.83 mmol) in CH$_2$Cl$_2$ (38 mL) at room temperature was added manganese dioxide (6.66 g, 77 mmol). The heterogeneous reaction was heated to 50° C. in a sealed tube for 2 h. The reaction was then cooled to room temperature and filtered. Then the solid was rinsed with EtOAc and the filtrate was concentrated to dryness under vacuum. The residue was used without any purification in the next step. LC/MS m/z 351 [M+H]$^+$.

(S,E)-N-((4-(3-(((tert-Butyldimethylsilyloxy)methyl)-2-fluoropyridin-4-yl)-3-methylisoxazol-5-yl)methylene)-2-methylpropane-2-sulfinamide

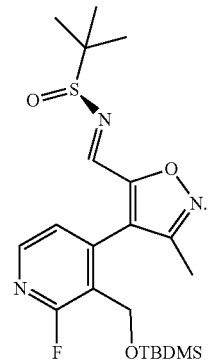 [SMILES: Cc1noc(/C=N/[S@@](=O)C(C)(C)C)c1-c1ccnc(F)c1CO[Si](C)(C)C(C)(C)C]

A procedure analogous to general protocol for (S)-tert-Butylsulfinylimine formation in Example 14 was followed. LC/MS m/z 454 [M+H]$^+$.

(3S)-tert-Butyl 3-(4-(3-(((tert-butyldimethylsilyloxy)methyl)-2-fluoropyridin-4-yl)-3-methylisoxazol-5-yl)-3-((S)-1,1-dimethylethylsulfinamido)propanoate

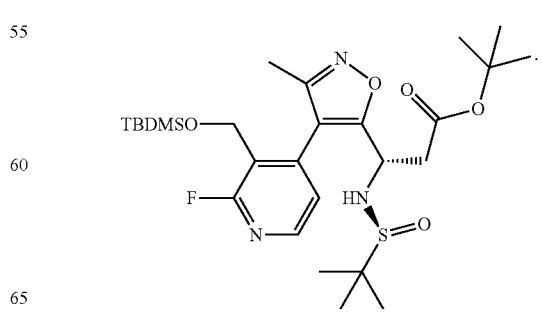

A procedure analogous to general protocol for Addition of (2-tert-Butoxy-2-oxoethyl)zinc(II) Chloride to (S)-tert-Butylsulfinylimine in Example 14 was followed. LC/MS m/z 570 [M+H]+.

(3S)-tert-Butyl 3-((S)-1,1-dimethylethylsulfinamido)-3-(4-(2-fluoro-3-(hydroxymethyl)pyridin-4-yl)-3-methylisoxazol-5-yl)propanoate

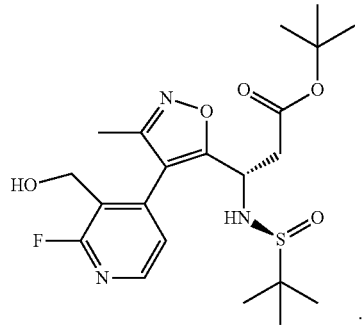 [SMILES: Cc1noc([C@H](CC(=O)OC(C)(C)C)N[S@@](=O)C(C)(C)C)c1-c1ccnc(F)c1CO]

To a solution of (3S)-tert-butyl 3-(4-(3-((tert-butyldimethylsilyloxy)methyl)-2-fluoropyridin-4-yl)-3-methylisoxazol-5-yl)-3-((S)-1,1-dimethylethylsulfinamido)propanoate (1.01 g, 1.76 mmol) in anhydrous THF (20 mL) at room temperature was added a solution of tetrabutylammonium fluoride (1M in wet THF) (2.21 mL, 2.205 mmol). The reaction was stirred at room temperature for 1 h before MeOH and silica gel were added. The solvent was removed, the dry silica gel was packed and the adsorbed product was purified by flash chromatography (hexane/EtOAc 7:3 to 5:5) to give (3S)-tert-butyl 3-((S)-1,1-dimethylethylsulfinamido)-3-(4-(2-fluoro-3-(hydroxymethyl)pyridin-4-yl)-3-methylisoxazol-5-yl)propanoate as a gummy solid (0.694 g). LC/MS m/z 456 [M+H]+.

(3S)-tert-Butyl 3-amino-3-(4-(2-fluoro-3-(hydroxymethyl)pyridin-4-yl)-3-methylisoxazol-5-yl)propanoate

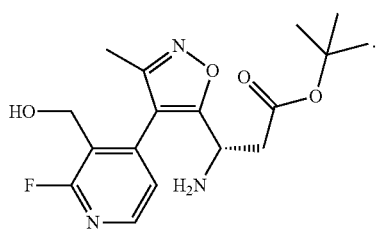 [SMILES: Cc1noc([C@@H](N)CC(=O)OC(C)(C)C)c1-c1ccnc(F)c1CO]

A procedure similar to the general protocol for HCl-mediated cleavage of the sulfinyl group in Example 14 was followed. LC/MS m/z 352 [M+H]+.

tert-Butyl 2-((4S)-7-fluoro-1-methyl-6-oxo-5,6-dihydro-4H-isoxazolo[5,4-c]pyrido[4,3-e]azepin-4-yl)acetate

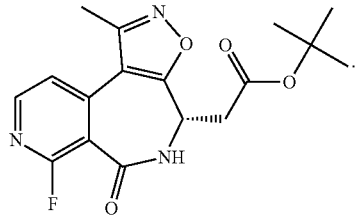 [SMILES: Cc1noc2c1-c1ccnc(F)c1C(=O)N[C@H]2CC(=O)OC(C)(C)C]

To a solution of (3S)-tert-butyl 3-amino-3-(4-(2-fluoro-3-(hydroxymethyl)pyridin-4-yl)-3-methylisoxazol-5-yl)propanoate (200 mg, 0.569 mmol) and TEMPO (4.45 mg, 0.028 mmol) in CH$_2$Cl$_2$ (5 mL) at 0° C. was sequentially added potassium bromide (33.9 mg, 0.285 mmol) and an aqueous solution of sodium hypochlorite (~0.35M buffered to pH ~8.6 with sodium bicarbonate) (4.879 mL, 1.708 mmol). The reaction was vigorously stirred (to produce an emulsion) at 0° C. for 45 min before diluting with CH$_2$Cl$_2$. The product was extracted with CH$_2$Cl$_2$ (repeated once), with CH$_2$Cl$_2$/MeOH (95:5) (repeated once) and CH$_2$Cl$_2$/TFE (95:5) (repeated once). The organic layers were combined, dried over a cotton plug and concentrated to dryness under vacuum. The residue was purified by flash chromatography (Hexane/EtOAc 8:2 to 5:5) to give tert-butyl 2-((4S)-7-fluoro-1-methyl-6-oxo-5,6-dihydro-4H-isoxazolo[5,4-c]pyrido[4,3-e]azepin-4-yl)acetate as a solid (45 mg). LC/MS m/z 348 [M+H]+.

(4S)-tert-Butyl 4-(2-(tert-butoxy)-2-oxoethyl)-7-fluoro-1-methyl-6-oxo-4H-isoxazolo[5,4-c]pyrido[4,3-e]azepine-5(6H)-carboxylate

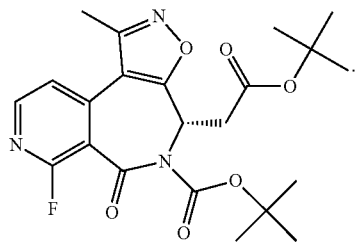 [SMILES: Cc1noc2c1-c1ccnc(F)c1C(=O)N(C(=O)OC(C)(C)C)[C@H]2CC(=O)OC(C)(C)C]

A procedure analogous to that used to synthesize (6S)-tert-butyl 6-(2-tert-butoxy-2-oxoethyl)-2,3,9-trimethyl-4-oxo-4H-isoxazolo[4,5-e]thieno[3,2-c]azepine-5(6H)-carboxylate in Example 18 was followed. LC/MS m/z 448 [M+H]+.

139

Mixture of (3S)-tert-butyl 3-((tert-butoxycarbonyl)amino)-3-(4-(3-(4-chlorobenzoyl)-2-fluoropyridin-4-yl)-3-methylisoxazol-5-yl)propanoate

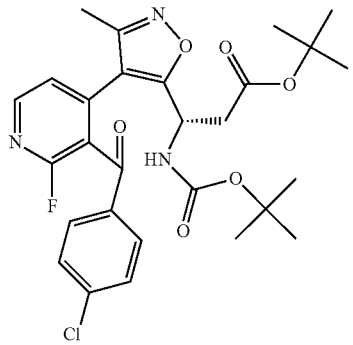 [SMILES: Cc1noc([C@H](CC(=O)OC(C)(C)C)NC(=O)OC(C)(C)C)c1-c1ccnc(F)c1C(=O)c1ccc(Cl)cc1]

and (4S)-tert-butyl 4-(2-(tert-butoxy)-2-oxoethyl)-6-(4-chlorophenyl)-7-fluoro-6-hydroxy-1-methyl-4H-isoxazolo[5,4-c]pyrido[4,3-e]azepine-5(6H)-carboxylate

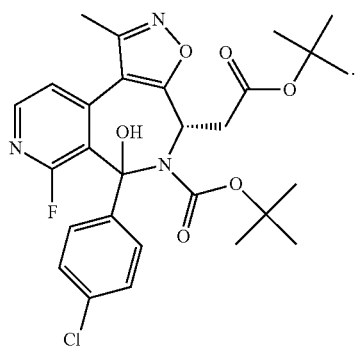

A procedure analogous to that used to synthesize (3S)-tert-Butyl 3-((tert-butoxycarbonyl)amino)-3-(4-(4,5-dimethyl-2-(tetrahydro-2H-pyran-4-carbonyl)thiophen-3-yl)-3-methylisoxazol-5-yl)propanoate in Example 18 was followed. LC/MS m/z 560 [M+H]⁺.

2-((4S)-6-(4-Chlorophenyl)-7-fluoro-1-methyl-4H-isoxazolo[5,4-c]pyrido[4,3-e]azepin-4-yl)acetamide

140

Compound 180

A procedure similar to that used to synthesize 2-((6S)-2,3,9-trimethyl-4-(tetrahydro-2H-pyran-4-yl)-6H-isoxazolo[5,4-c]thieno[2,3-e]azepin-6-yl)acetamide in Example 18 was followed. LC/MS m/z 385 [M+H]⁺.

2-((4S)-6-(4-chlorophenyl)-1-methyl-7-(methylamino)-4H-isoxazolo[5,4-c]pyrido[4,3-e]azepin-4-yl)acetamide

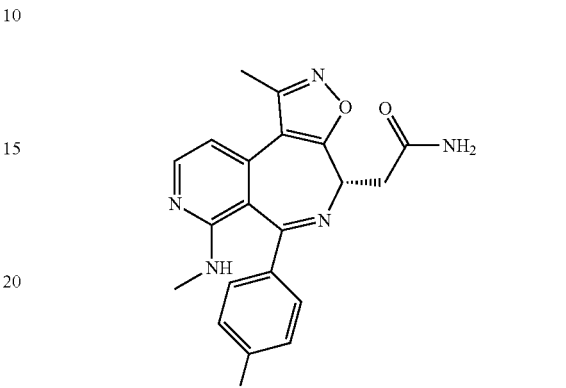

Compound 181

A procedure analogous to that used to synthesize 6-(4-chlorophenyl)-N,1-dimethyl-4H-isoxazolo[5,4-c]pyrido[4,3-e]azepin-7-amine in Example 20 was followed. $^1$H NMR (400 MHz, DMSO-d$_6$) δ 8.30 (d, J=5.26 Hz, 1H), 7.67 (br. s, 1H), 7.36 (d, J=8.70 Hz, 2H), 7.30 (d, J=8.70 Hz, 2H), 7.04 (br. s, 1H), 6.95 (d, J=5.26 Hz, 1H), 5.76-5.91 (q, J=4.38 Hz, 1H), 4.38 (t, J=7.30 Hz, 1H), 3.28 (dd, J=7.80, 15.50 Hz, 1H), 3.12 (dd, J=6.75, 15.68 Hz, 1H), 2.63 (d, J=4.58 Hz, 3H), 2.50 (s, 3H); LC/MS m/z 396 [M+H]⁺.

Example 22

Synthesis of Compounds of Formula I Wherein R² is Hydrogen and R³ is —CH₂—NR'—C(O)—R The synthesis of compounds of Formula I wherein R² is hydrogen and R³ is —CH₂—NR'—C(O)—R are exemplified below. Appropriate modification of this scheme to produce other compounds of the invention will be readily apparent to those of skill in the art.

N-(((6S)-4-(4-Chlorophenyl)-2,3,9-trimethyl-6H-isoxazolo[5,4-c]thieno[2,3-e]azepin-6-yl)methyl)acetamide

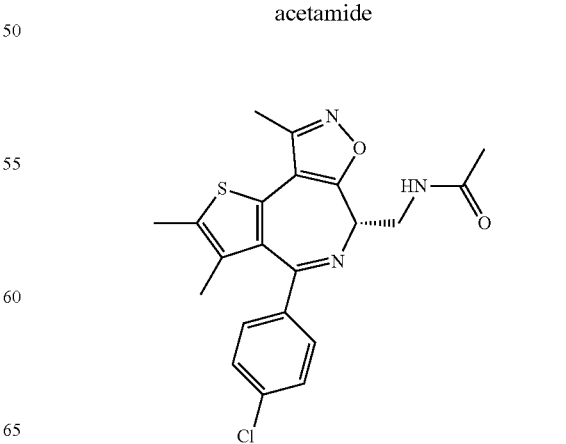

Compound 182

To a solution of 2-((6S)-4-(4-Chlorophenyl)-2,3,9-trimethyl-6H-isoxazolo[5,4-c]thieno[2,3-e]azepin-6-yl)acetic acid (Compound 164; 0.044 g, 0.110 mmol) in toluene (1.5 mL) was added Et$_3$N (0.050 mL, 0.359 mmol) and diphenylphosphoryl azide (0.060 mL, 0.278 mmol). The reaction mixture was heated to 80-90° C. After 30 min, LC-MS analysis indicated complete consumption of the acid. The reaction mixture was cooled to ambient temperatures and concentrated in vacuo to give the isocyanate as a thick paste.

To the crude isocyanate was introduced 1,4-dioxane (1 mL) and aqueous 1 N NaOH (1.00 mL, 1.000 mmol) and subsequently heated to 90° C. After 60 min, LC-MS analysis indicated complete consumption of starting material. The bi-phasic mixture was cooled to room temperature and the aqueous layer was extracted with EtOAc (3×). The combined organic phase was washed with water, dried over Na$_2$SO$_4$, and concentrated to give the free amine as an orange oil.

The resultant amine was diluted with 1,4-dioxane (1 mL) followed by sequential addition of Et$_3$N (0.1 mL, 0.717 mmol) and acetic anhydride (0.05 mL, 0.530 mmol). After 1 h, the solution was concentrated in vacuo and the resultant oil was purified on Biotage system (gradient elution 10% EtOAc:90% Hexanes to 80% EtOAc:20% Hexanes, then isocratic 80% EtOAc:20% Hexanes) to give the titled compound as product as white solids. The solids were diluted in CH$_3$CN (2.0 mL) and water (1.0 mL), the solution was frozen and lyophilized to yield the titled product (0.030 g, 0.072 mmol, 66% yield) as off-white amorphous solids. $^1$H NMR (400 MHz, Acetone) δ 7.60 (br. s, 1H), 7.35-7.46 (m, 4H), 4.15 (br. s, 2H), 4.04 (br. s, 1H), 2.47 (s, 3H), 2.43 (s, 3H), 1.91 (s, 3H), 1.69 (s, 3H); LC/MS m/z 414 [M+H]$^+$.

Methyl (((6S)-4-(4-chlorophenyl)-2,3,9-trimethyl-6H-isoxazolo[5,4-c]thieno[2,3-e]azepin-6-yl)methyl)carbamate

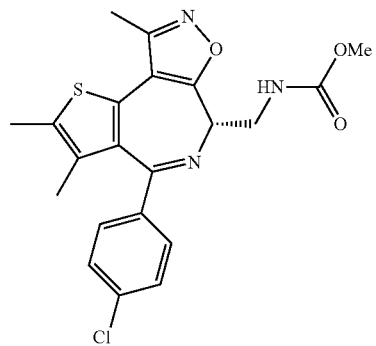 [SMILES: COC(=O)NC[C@@H]1N=C(c2ccc(Cl)cc2)c2c(sc(C)c2C)-c2c(C)noc21]

Compound 183

To a solution of 2-((6S)-4-(4-Chlorophenyl)-2,3,9-trimethyl-6H-isoxazolo[5,4-c]thieno[2,3-e]azepin-6-yl)acetic acid (Compound 164; 0.047 g, 0.117 mmol) in toluene (1.5 mL) was added Et$_3$N (0.100 mL, 0.717 mmol) and diphenylphosphoryl azide (0.080 mL, 0.370 mmol). The reaction mixture was heated to 80° C. After 1 h, LC-MS analysis indicated complete consumption of the carboxylic acid. The reaction mixture was cooled to ambient temperatures and concentrated in vacuo to give a thick paste.

To the paste was introduced 1,4-dioxane (5 mL), MeOH (5 mL) and aqueous 1 N NaOH (5 mL) and the bi-phasic mixture was subsequently heated to 90° C. After 24 h, LC-MS analysis indicated complete consumption of acyl-azide. The bi-phasic mixture was cooled to room temperature and the aqueous layer extracted with EtOAc (3×). The combined organic phase was washed with water, dried over Na$_2$SO$_4$, and concentrated to give the free amine as white solids. The solids were purified on Biotage system (gradient elution 10% EtOAc:90% Hexanes to 20% EtOAc:80% Hexanes) to give the titled product (0.005 g, 0.012 mmol, 10% yield) as white solids; $^1$H NMR (400 MHz, D6-Acetone) δ 7.43 (s, 2H), 7.40 (s, 2H), 6.70 (br. s, 1H), 4.00-4.22 (m, 3H), 3.58 (s, 3H), 2.47 (s, 3H), 2.44 (s, 3H), 1.70 (s, 3H); LC/MS m/z 430 [M+H]$^+$.

Example 23

Synthesis of Other Compounds of Formula I

The synthesis of other exemplary compounds of Formula I are set forth below.

2-((6S)-4-((4-Chlorophenyl)amino)-2,3,9-trimethyl-6H-isoxazolo[5,4-c]thieno[2,3-e]azepin-6-yl)acetic acid

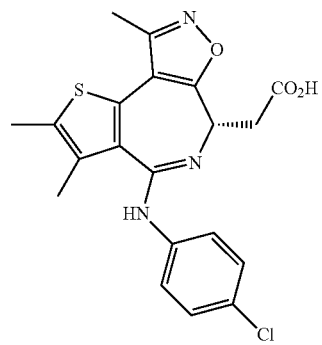 [SMILES: Cc1noc2c1-c1sc(C)c(C)c1C(Nc1ccc(Cl)cc1)=N[C@H]2CC(=O)O]

Compound 184

To a vial was added tert-butyl 2-((6S)-4-chloro-2,3,9-trimethyl-6H-isoxazolo[4,5-e]thieno[3,2-c]azepin-6-yl)acetate, a form of intermediate 18, prepared according to Example 14 (0.056 g, 0.147 mmol), 4-chloroaniline (0.042 g, 0.333 mmol), ((1S,4R)-7,7-dimethyl-2-oxobicyclo[2.2.1]heptan-1-yl)methanesulfonic acid (0.039 g, 0.168 mmol) and DMSO (0.5 mL). The vial was sealed and initially heated to 125° C. for 3 h in the microwave reactor. LC-MS analysis shows complete consumption of starting material and formation of the desired coupled product as a mixture of acid and ester. The reaction mixture was subsequently heated at 145° C. for an additional 2 h, at which time LC-MS analysis show conversion of all intermediates to desired acid. The solution was partitioned between MTBE and 1 N NaOH. The organic layer was washed with additional 1 N NaOH (2×) and the combined aqueous layer was acidified to with concentrated HCl. The acidic aqueous layer (pH ~3-4) was extracted with EtOAc (4×). The combined organic phase was washed with water (2×), brine (1×), dried over Na$_2$SO$_4$, and concentrated to yield the titled product (0.056 g, 0.135 mmol, 92% yield) as a brown foam that was used without further purification. LC/MS m/z 416 [M+H]$^+$.

2-((6S)-4-((4-Chlorophenyl)amino)-2,3,9-trimethyl-6H-isoxazolo[5,4-c]thieno[2,3-e]azepin-6-yl)acetamide

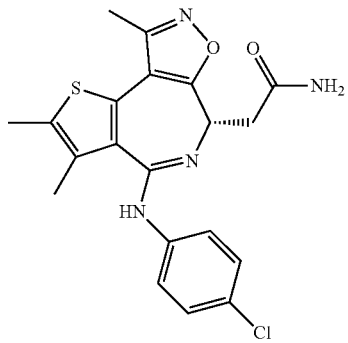 [SMILES: Cc1noc2c1-c1sc(C)c(C)c1C(Nc1ccc(Cl)cc1)=N[C@H]2CC(N)=O]

Compound 185

To a solution of crude carboxylic acid in DMF (1.0 mL) was sequentially added N,N-diisopropylethyl amine (0.100 mL, 0.573 mmol), NH$_4$Cl (0.028 g, 0.523 mmol), and 1-Cyano-2-ethoxy-2-oxoethylidenaminooxy)dimethyl-amino-morpholino-carbenium hexafluorophosphate (("COMU"), Sigma-Aldrich) (0.038 g, 0.089 mmol). After complete addition of reagents the reaction mixture was allowed to age until complete consumption of the carboxylic acid was detected by LC-MS. The reaction mixture was dilute with EtOAc and brine. The aqueous layer was extracted with EtOAc (3×) and the combined organic extract was washed with water (2×), dried over Na$_2$SO$_4$ and concentrated to give a pink oil. The oil was purified on Biotage system (gradient elution 10% EtOAc:90% Hexanes to 80% EtOAc:20% Hexanes, then isocratic 80% EtOAc:20% Hexanes), the volatile organics were removed, and the purified compound was subsequently diluted with CH$_3$CN (10 mL) and H$_2$O (1 mL), and lyophilized to give the titled compound (0.023 g, 0.055 mmol, 41.2% yield) as off white-amorphous solids. $^1$H NMR (400 MHz, Acetone-d$_6$) δ 7.80 (d, J=8.78 Hz, 2H), 7.21 (d, J=8.78 Hz, 2H), 7.12 (br. s, 1H), 6.35 (br. s, 1H), 4.40 (br. s, 1H), 3.03-3.19 (m, J=8.50 Hz, 2H), 2.44 (s, 3H), 2.40 (s, 3H), 2.31 (s, 3H); LC/MS m/z 415 [M+H]$^+$.

2-((6S)-2,3,9-trimethyl-4-phenoxy-6H-isoxazolo[5,4-c]thieno[2,3-e]azepin-6-yl)acetamide

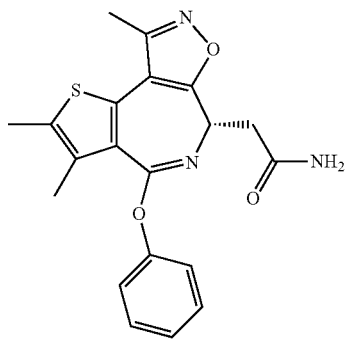 [SMILES: Cc1noc2c1-c1sc(C)c(C)c1C(Oc1ccccc1)=N[C@H]2CC(N)=O]

Compound 186

A mixture of tert-butyl 2-((6S)-4-chloro-2,3,9-trimethyl-6H-isoxazolo[5,4-c]thieno[2,3-e]azepin-6-yl)acetate, a form of intermediate 18, prepared according to Example 14 (0.220 g, 0.58 mmol) and phenol (0.276 g, 2.90 mmol) in pyridine (1 mL) was heated at 130° C. for 1 h by MW. After the solvent was removed in vacuo, the residue was washed with 1 N NaOH, dried by anhydrous Na$_2$SO$_4$. The product was purified by Prep-TLC (PE:EA=4:1) to give tert-butyl 2-((6S)-2,3,9-trimethyl-4-phenoxy-6H-isoxazolo[5,4-c]thieno[2,3-e]azepin-6-yl)acetate (0.020 g, 7.9% yield) as a white solid. tert-butyl 2-((6S)-2,3,9-trimethyl-4-phenoxy-6H-isoxazolo[5,4-c]thieno[2,3-e]azepin-6-yl)acetate was converted to target compound 2-((6S)-2,3,9-trimethyl-4-phenoxy-6H-isoxazolo[5,4-c]thieno[2,3-e]azepin-6-yl)acetamide using Step L in Example 14. $^1$H NMR (300 MHz, CDCl$_3$) δ 7.39-7.34 (m, 2H), 7.22-7.07 (m, 3H), 6.07 (s, 1H), 5.18 (s, 1H), 4.46 (q, J=4.5 Hz, 1H), 2.99-2.84 (m, 2H), 2.48 (s, 3H), 2.45 (s, 3H), 2.42 (s, 3H); LC/MS m/z 382 [M+H]$^+$.

(6S)-6-((1H-imidazol-2-yl)methyl)-4-(4-chlorophenyl)-2,3,9-trimethyl-6H-isoxazolo[5,4-c]thieno[2,3-e]azepine

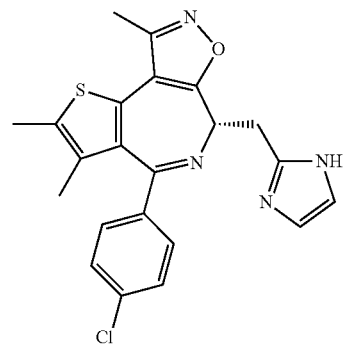 [SMILES: Cc1noc2c1-c1sc(C)c(C)c1C(c1ccc(Cl)cc1)=N[C@H]2Cc1ncc[nH]1]

Compound 187

To a solution of 2-((6S)-4-(4-chlorophenyl)-2,3,9-trimethyl-6H-isoxazolo[5,4-c]thieno[2,3-e]azepin-6-yl)acetamide (Compound 110, 0.120 g, 0.30 mmol) in THF (5 mL) was added Lawesson reagent (0.248 g, 0.60 mmol). The mixture was refluxed overnight. The reaction mixture was concentrated in vacuo and the residue was recrystallized by petroleum and ethyl acetate to give 2-((6S)-4-(4-chlorophenyl)-2,3,9-trimethyl-6H-isoxazolo[5,4-c]thieno[2,3-e]azepin-6-yl)ethanethioamide (0.080 g, 64% yield).

To a solution of 2-((6S)-4-(4-chlorophenyl)-2,3,9-trimethyl-6H-isoxazolo[5,4-c]thieno[2,3-e]azepin-6-yl)ethanethioamide (0.080 g, 0.19 mmol) and 2,2-dimethoxyethanamine (0.200 g, 1.90 mmol) in CH$_3$CN (5 mL) was added HgCl$_2$ (0.515 g, 1.90 mmol). The mixture was refluxed overnight. The reaction mixture was filtered, concentrated in vacuo and the residue was purified by column chromatography (silica-gel, petroleum:ethyl acetate=2:1) to give (6S)-6-((1H-imidazol-2-yl)methyl)-4-(4-chlorophenyl)-2,3,9-trimethyl-6H-isoxazolo[5,4-c]thieno[2,3-e]azepine as a yellow solid (0.005 g, 6.2% yield): $^1$H NMR (300 MHz, DMSO-d$_6$) δ 8.26 (br, 1H), 7.42 (d, J=4.8 Hz, 2H), 7.24 (d, J=4.8 Hz, 2H), 6.82 (d, J=1.2 Hz, 2H), 4.40-4.30 (m, 1H), 3.84-3.74 (m, 2H), 2.50 (s, 3H), 2.42 (s, 3H), 1.64 (s, 3H); LC/MS m/z 423 [M+H]+.

(6S)-4-(4-chlorophenyl)-2,3,9-trimethyl-6-(thiazol-2-ylmethyl)-6H-isoxazolo[5,4-c]thieno[2,3-e]azepine

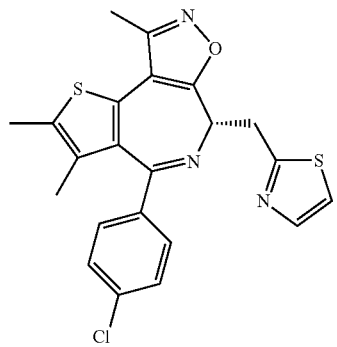 [SMILES: Cc1noc2c1-c1sc(C)c(C)c1C(c1ccc(Cl)cc1)=N[C@H]2Cc1nccs1]

Compound 188

To a solution of 2-((6S)-4-(4-Chlorophenyl)-2,3,9-trimethyl-6H-isoxazolo[5,4-c]thieno[2,3-e]azepin-6-yl)acetic acid (Compound 164; 0.160 g, 0.40 mmol) and DMF (1 drop) in dichloromethane (2 mL) was added oxalyl chloride (0.070 g, 0.55 mmol) drop-wise at 0° C. The mixture was stirred for 0.5 hour at room temperature. The solution was cooled to 0° C. and 2,2-dimethoxyethanamine (0.210 g, 5.00 mmol) was added. The mixture was stirred for 0.5 hour at room temperature. Then the solution was diluted with water (5 mL) and extracted with ethyl acetate (10 mL×3). The combined organic layers were washed with 1 N HCl and NaHCO$_3$, dried over Na$_2$SO$_4$, concentrated in vacuo to give 2-((6S)-4-(4-chlorophenyl)-2,3,9-trimethyl-6H-isoxazolo[5,4-c]thieno[2,3-e]azepin-6-yl)-N-(dimethoxymethyl)acetamide as a light yellow solid (0.120 g, yield 63.4%) which was used directly in the next step without further purification.

To a solution of 2-((6S)-4-(4-chlorophenyl)-2,3,9-trimethyl-6H-isoxazolo[5,4-c]thieno[2,3-e]azepin-6-yl)-N-(dimethoxymethyl)acetamide (0.120 g, 0.25 mmol) in dichloromethane (3 mL) was added trifluoroacetic acid (2 mL, 26 mmol). The reaction mixture was stirred for 5 h. The mixture was concentrated and THF (5 mL) and Lawesson reagent (0.248 g, 0.60 mmol) were added. The mixture was refluxed overnight. The reaction mixture was concentrated in vacuo and the residue was purified by column chromatography (silica-gel, petroleum:ethyl acetate=10:1) to give (6S)-4-(4-chlorophenyl)-2,3,9-trimethyl-6-(thiazol-2-ylmethyl)-6H-isoxazolo[5,4-c]thieno[2,3-e]azepine as a yellow solid (0.030 g, 17% yield). $^1$H NMR (300 MHz, CDCl$_3$) δ 7.73 (d, J=3.3 Hz, 1H); 7.35-7.29 (m, 5H), 4.31-4.20 (m, 3H), 2.51 (s, 3H), 2.40 (s, 3H), 1.64 (s, 3H); LC/MS m/z 440 [M+H]+.

Example 24

IC50 Measurements for Inhibitors Using BRD4 AlphaLisa Binding Assay

His/Flag epitope tagged BRD4 BD1$_{42-168}$ was cloned, expressed and purified to homogeneity. BRD4 binding and inhibition was assessed by monitoring the engagement of biotinylated H4-tetraacetyl peptide (Millipore #12-379) with the target using the AlphaLisa technology (Perkin-Elmer). Specifically, in a 384 well ProxiPlate BRD4(BD1) (30 nM final) was combined with peptide (200 nM final) in 40 mM HEPES (pH 7.0), 40 mM NaCl, 1 mM DTT, 0.01% (w/v) BSA, and 0.008% (w/v) Brij-35 either in the presence of DMSO (final 1.2% DMSO) or compound dilution series in DMSO. After 20 minute incubation at room temperature Alpha streptavidin donor beads and AlphaLisa anti-Flag acceptor beads were added to a final concentration of 10 ug/mL each. After three hours equilibration plates were read on an Envision instrument and IC$_{50}$s calculated using a four parameter non-linear curve fit. The results of this assay are set forth in Table 6, below.

TABLE 6

Activity of Exemplary Compounds of the Invention

| Compound No. | BRD4 Alphascreen IC$_{50}$ |
|---|---|
| 100 | + |
| 101 | + |
| 102 | + |
| 103 | + |
| 104 | ++ |
| 105 | +++ |
| 106 | + |
| 107 | + |
| 108 | + |
| 109 | + |
| 110 | + |
| 111 | + |
| 112 | + |
| 113 | + |
| 114 | + |
| 115 | + |
| 116 | + |
| 117 | + |
| 118 | + |
| 119 | + |
| 120 | + |
| 121 | +++ |
| 122 | +++ |
| 123 | +++ |
| 124 | + |
| 125 | +++ |
| 126 | + |
| 127 | +++ |
| 128 | + |
| 129 | + |
| 130 | + |
| 131 | + |
| 132 | + |
| 133 | + |
| 134 | + |
| 135 | + |
| 136 | + |
| 137 | + |
| 138 | + |
| 139 | + |
| 140 | + |
| 141 | + |
| 142 | + |
| 143 | + |
| 144 | + |
| 145 | + |
| 146 | + |
| 147 | + |
| 148 | + |
| 149 | + |
| 150 | + |
| 151 | + |
| 152 | +++ |
| 153 | +++ |
| 154 | +++ |
| 155 | + |
| 156 | + |

TABLE 6-continued

Activity of Exemplary Compounds of the Invention

| Compound No. | BRD4 Alphascreen IC$_{50}$ |
|---|---|
| 159 | + |
| 160 | + |
| 162 | + |
| 163 | + |
| 165 | + |
| 167 | +++ |
| 168 | +++ |
| 169 | +++ |
| 170 | + |
| 171 | +++ |
| 172 | + |
| 173 | + |
| 174 | + |
| 175 | + |
| 176 | +++ |
| 177 | +++ |
| 178 | +++ |
| 179 | +++ |
| 181 | + |
| 182 | + |
| 183 | + |
| 185 | +++ |
| 186 | ++ |
| 187 | + |
| 188 | + |
| 189 | +++ |
| 190 | + |
| 191 | +++ |

In Table 6, "+" represents a value under 0.50 µM; "++" a value between 0.50 µM and 1 µM; and "+++" a value greater than 1 µM.

Example 25

Cell-Based Assays cMyc RNA Quantification Assay (QuantiGene® Assay):

MV4:11 (AML) or Raji (Burkitt's lymphoma) cells were seeded in a 96-well plate and incubated in the presence of various concentrations of compounds for 4 h. Relative mRNA levels were quantitated by using QuantiGene 2.0 assay (Affymetrix) according to the manufacturer's recommendation. Signals were detected by using an Envision plate reader (Perkin-Elmer). Biological duplicates were averaged and normalized to vehicle (DMSO) control to calculate percent MYC mRNA levels.

Cell-Based IL-6 Quantification Assay (ELISA, Mesoscale Assay):

100,000 THP-1 cells were seeded in RPMI1640-10% FBS in 96-well plates. LPS (*E. Coli* Invitrogen) in RPMI-10% FBS at a final concentration of 4 µg/mL was added to the wells and the cells are then incubated in the presence of various concentrations of compounds for 16 h. Plates are spun (2 rpm, 5 min), an aliquot of 25 uL supernatant is transferred in to an ELISA plate (Mesoscale technology, MSD) and the detection of IL-6 is performed using manufacturer's instructions. The amount of cells in each well is assessed using CellTiter-Glo® (Promega). The ratio of ELISA value/CellTiter-Glo value is used to calculate the percent of inhibition of IL-6 secretion. The result of these assays for certain compounds of the invention are set forth in Table 7 below.

| Cmpd No. | IL6 | MYC-Raji | MYC-MV411 |
|---|---|---|---|
| 100 | ++ | n.t. | n.t. |
| 101 | ++ | n.t. | n.t. |
| 102 | + | + | n.t. |
| 103 | + | + | n.t. |
| 104 | ++ | n.t. | n.t. |
| 105 | +++ | n.t. | n.t. |
| 106 | + | n.t. | n.t. |
| 107 | + | n.t. | n.t. |
| 108 | + | + | n.t. |
| 109 | + | + | n.t. |
| 110 | + | + | + |
| 111 | + | n.t. | n.t. |
| 112 | + | + | n.t. |
| 113 | + | + | n.t. |
| 114 | + | + | n.t. |
| 115 | + | + | n.t. |
| 116 | + | + | n.t. |
| 117 | + | n.t. | n.t. |
| 118 | + | + | n.t. |
| 119 | ++ | n.t. | n.t. |
| 120 | + | ++ | n.t. |
| 121 | +++ | n.t. | n.t. |
| 122 | +++ | n.t. | n.t. |
| 123 | +++ | n.t. | n.t. |
| 124 | ++ | +++ | n.t. |
| 125 | +++ | n.t. | n.t. |
| 126 | + | +++ | n.t. |
| 127 | +++ | n.t. | n.t. |
| 128 | + | + | n.t. |
| 129 | + | + | n.t. |
| 130 | + | + | + |
| 131 | + | + | n.t. |
| 132 | + | + | + |
| 133 | + | ++ | n.t. |
| 134 | + | ++ | n.t. |
| 135 | + | + | n.t. |
| 136 | + | + | + |
| 137 | + | ++ | n.t. |
| 138 | + | + | n.t. |
| 139 | + | + | + |
| 140 | + | + | n.t. |
| 141 | + | +++ | n.t. |
| 142 | + | ++ | n.t. |
| 143 | + | ++ | n.t. |
| 144 | + | + | + |
| 145 | + | + | + |
| 146 | + | + | n.t. |
| 147 | + | ++ | n.t. |
| 148 | + | + | + |
| 149 | + | + | n.t. |
| 150 | + | + | n.t. |
| 151 | + | n.t. | n.t. |
| 152 | +++ | +++ | n.t. |
| 153 | +++ | n.t. | n.t. |
| 154 | +++ | n.t. | n.t. |
| 155 | ++ | + | n.t. |
| 156 | +++ | n.t. | n.t. |
| 159 | + | + | n.t. |
| 160 | + | + | n.t. |
| 162 | +++ | n.t. | n.t. |
| 163 | + | +++ | n.t. |
| 165 | + | + | n.t. |
| 168 | +++ | n.t. | n.t. |
| 169 | +++ | n.t. | n.t. |
| 170 | +++ | n.t. | n.t. |
| 171 | +++ | n.t. | n.t. |
| 172 | + | ++ | n.t. |
| 173 | + | + | n.t. |
| 174 | + | ++ | n.t. |
| 175 | ++ | +++ | n.t. |
| 176 | +++ | n.t. | n.t. |
| 177 | +++ | n.t. | n.t. |
| 178 | +++ | n.t. | n.t. |
| 179 | +++ | n.t. | n.t. |
| 180 | + | ++ | ++ |
| 181 | + | + | + |
| 182 | ++ | n.t. | n.t. |
| 183 | ++ | n.t. | n.t. |
| 185 | +++ | n.t. | n.t. |
| 186 | ++ | +++ | n.t. |

-continued

| Cmpd No. | IL6 | MYC-Raji | MYC-MV411 |
|---|---|---|---|
| 187 | +++ | +++ | n.t. |
| 188 | + | +++ | n.t. |

In Table 7, "n.t." = not tested, "+" represents a value under 0.50 μM; "++" a value between 0.50 μM and 1 μM; and "+++" a value greater than 1 μM.

Example 26

Preparation of Compounds of Formula II, Where $R^5$ is Aryl or Heteroaryl

Scheme 9, below sets forth a general method for making certain compounds of the invention.

Scheme 9:

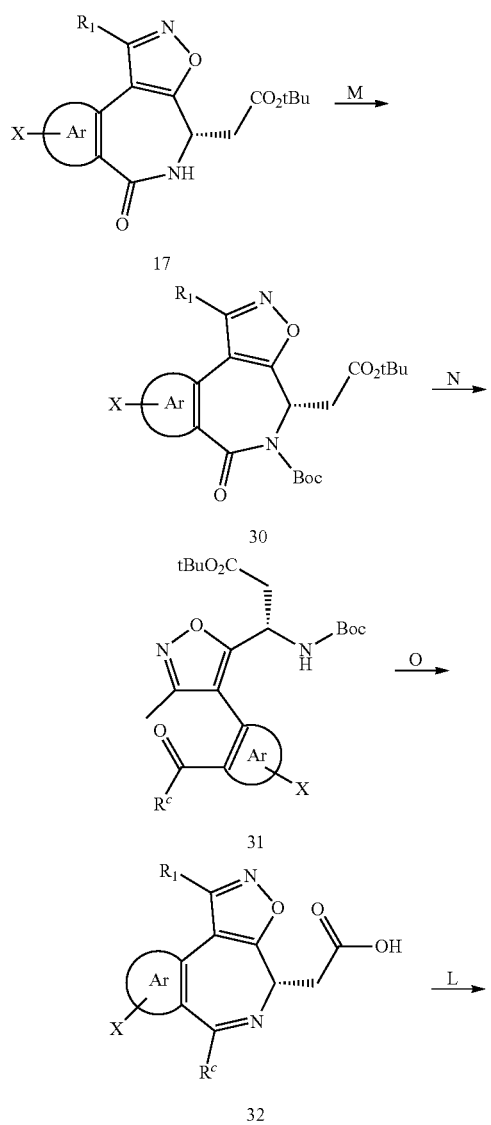

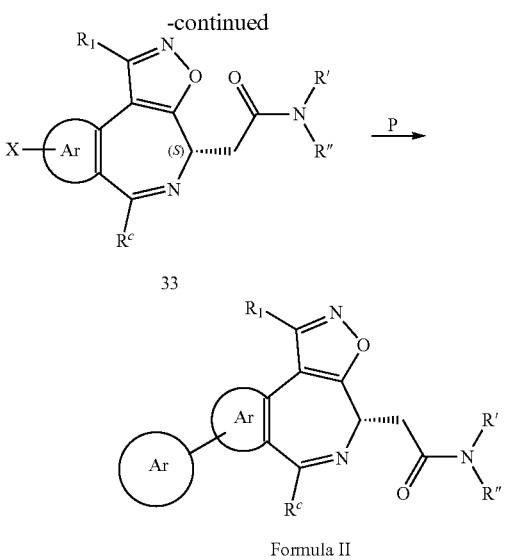

Formula II

General Procedure for Imide 30 Formation (Step M).

To a solution of lactam starting material (intermediate 17 wherein ring A is aryl or heteroaryl and $(R^5)_n$ is a single halo substituent; 1 equivalent) and DMAP (0.10 equivalent or 10 mol %) in THF (0.5 M in substrate concentration) was added $Boc_2O$ (1.2-1.3 equivalent). After 30 min, the reaction mixture was concentrated in vacuo to yield brown solids. The crude product may either be purified on Biotage system (gradient elution 5% EtOAc: 95% Hexanes to 10% EtOAc: 90% Hexanes, then isocratic 10% EtOAc:90% Hexanes) or crystallized from EtOAc:Hexanes mixtures to deliver the titled N-Boc imide product 30 (generally in the range of 88% to 97% yield) as white solids.

General Procedure for Addition of Nucleophiles to N-Boc-Imide 30 (Step N).

To a cooled (−40° C.) solution of N-Boc-Imide 30 (1 equivalent) in THF (0.5 M in substrate concentration) was added the appropriate Grignard reagent (typically 1.1-1.5 equivalent) in one-portion. After 5 min, the mixture was allowed to warm to room temperature and quenched with 1 N HCl. The aqueous layer was extracted with EtOAc (2×). The combined organic extracts were washed with aqueous saturated $NaHCO_3$, dried over $Na_2SO_4$, and concentrated in vacuo. The crude product was purified on Biotage system (typically gradient elution 5% EtOAc:95% Hexanes to 30% EtOAc:70% Hexanes) to yield the desired N-Boc ketone compound 31 (generally >90% yield) generally as a either a white foam or solids.

General Procedure for TFA-Deprotection and Azepine 32 Formation (Step O).

To a solution of N-Boc ketone 31 in $CHCl_3$ (0.2 M in substrate concentration) was added TFA (10-30 equivalent) and the reaction mixture was heated at reflux for ~24 h. The yellow reaction mixture is cooled to ambient temperatures, concentrated in vacuo, and excess TFA was azeotropically removed using excess $CHCl_3$, followed by toluene. The crude carboxylic acid 32 was dried and used without further purification. The carboxylic acid 32 was converted to the corresponding carboxamide 33 using a coupling reagent and an appropriate base as described in Step L.

An alternative method to the coupling step described in Step L utilized for converting carboxylic acid 32 to the corresponding carboxamide 33 (designated Step S) as follows. To a solution of carboxylic acid 32 (1 equivalent) in anhydrous dichloromethane was added oxalyl chloride (25 equivalents) in a dropwise manner. After stirring for 1 h, the mixture was concentrated. The resulting residue was dissolved in dichloromethane and 0.5 N ammonia in 1.4-dioxane (5 equivalents) was introduced. After aging for 2 h, the reaction mixture was concentrated in vacuo and the resulting residue was purified by flash column chromatography (silica-gel, dichloromethane:methanol=20:1) to give the desired carboxamide 33 product as a solid.

General Procedure for Suzuki Cross-Coupling to Arylhalide (Step P).

To a re-sealable vial the carboxamide 33 from above (1.0 equivalent) was added $Pd_2(dba)_3$ (0.10 equivalent), tri-tert-butylphosphonium tetrafluoroborate (0.22 equivalent), potassium phosphate tribasic, monohydrate (2.0 equivalent), and the appropriate aryl boronic acid or hetero-aryl boronic acid (1.5 equivalents). The flask was evacuated and purged (3×), followed by sequential addition of 1,4-dioxane and water (typical ratio 20:1), and the flask was once again evacuated and purged with $N_2$ (g) (3×) and the reaction mixture was heated to 100° C. until the consumption of the aryl chloride was detected by LC-MS. The reaction mixture was subsequently cooled to room temperature and filtered over a plug of Celite. The filter cake was washed with EtOAc (3×) and the filtrate was concentrated in vacuo. The cross-coupled product of Formula II was purified via Biotage system (generally gradient elution using mixtures of EtOAc-Hexanes) to yield the desired coupled product (in 50-90% yield).

The compounds in Tables 8 and 9 were made using the general protocol described above in Example 26 and/or the protocols described in Example 14. The final steps employed from those Examples are indicated for each compound. Steps Q and R employed in the synthesis of Compounds 239, 248 and 249 are described in the next example.

TABLE 8

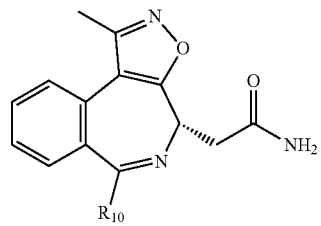

| Compound No. | $R_{10}$ | Physical Data | Final steps |
|---|---|---|---|
| 196 |  | LC/MS m/z 351 [M + H]$^+$; $^1$H NMR (300 MHz, CDCl$_3$) δ 8.45 (s, 1H), 7.99-7.94 (m, 1H), 7.62-7.59 (m, 2H), 7.50-7.33(m, 3H), 6.25 (br. s, 1H), 5.62 (br. s, 1H), 4.62-4.58 (m, 1H), 3.43-3.30 (m, 2H), 2.55 (s, 3H). | H, L |

TABLE 9

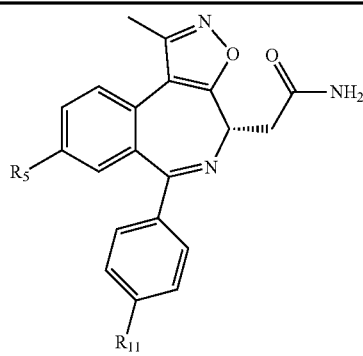

| Compound No. | $R_5$ | $R_{11}$ | Physical Data | Final Steps |
|---|---|---|---|---|
| 192 | Cl | CN | LC/MS m/z 437 [M + H]$^+$; $^1$H NMR (400 MHz, DMSO-d$_6$) δ 8.55-8.46 (m, 1H), 7.91-7.83 (m, 3H), 7.82-7.75 (m, 1H), 7.50-7.43 (m, 2H), 7.42-7.37 (m, 1H), 4.55-4.50 (m, 1H), 4.44-4.38 (m, 1H), 3.26-3.12 (m, 2H), 2.50 (br. s, 3H). | H, L |
| 197 | OCF$_3$ | Cl | LC/MS m/z 450 [M + H]$^+$; $^1$H NMR (400 MHz, DMSO-d$_6$) δ 7.97 (d, J = 8.70 Hz, 1H), 7.77-7.71 (m, 1H), 7.65 (br. s, 1H), 7.48-7.43 (m, 2H), 7.36-7.30 (m, 3H), 7.05 (br. s, 1H), 4.40-4.29 (m, 1H), 3.23-3.12 (m, 2H), 2.51 (s, 3H). | H, L |
| 201 | Cl | CF$_3$ | LC/MS m/z 434 [M + H]$^+$; $^1$H NMR (400 MHz, DMSO-d$_6$) δ 7.90-7.85 (m, 1H), 7.81-7.74 (m, 3H), 7.67-7.62 (m, 1H), 7.52 (d, J = 8.0 Hz, 2H), 7.42 (d, J = 2.3 Hz, 1H), 7.07-7.02 (m, 1H), 4.43-4.35 (m, 1H), 3.22-3.11 (m, 2H), 2.50 (s, 3H). | H, L |

TABLE 9-continued

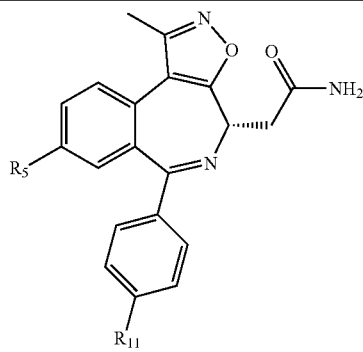

| Compound No. | $R_5$ | $R_{11}$ | Physical Data | Final Steps |
|---|---|---|---|---|
| 203 | H | $CF_3$ | LC/MS m/z 399 [M + H]$^+$; $^1$H NMR (300 MHz, Acetone-d$_6$) δ 7.86 (d, J = 7.8 Hz, 1H), 7.75-7.69 (m, 3H), 7.60 (d, J = 8.4 Hz, 2H), 7.44 (d, J = 8.1 Hz, 2H), 7.16 (m, 1H), 6.42-6.41 (m, 1H), 4.54-4.52 (m, 1H), 3.35-3.31 (m, 2H), 2.58 (s, 3H). | H, L |
| 206 | 6-aminopyridin-3-yl | $CF_3$ | LC/MS m/z 492 [M + H]$^+$; $^1$H NMR (400 MHz, DMSO-d$_6$) δ 8.24 (d, J = 2.5 Hz, 1H), 7.99-7.93 (m, 1H), 7.92-7.84 (m, 2H), 7.74 (d, J = 8.1 Hz, 2H), 7.68 (br. s, 1H), 7.58-7.51 (m, 3H), 7.06 (br. s, 1H), 6.82 (br. s, 2H), 6.67 (d, J = 8.9 Hz, 1H), 4.46-4.34 (m, 1H), 3.20 (br. s, 2H), 2.56 (s, 3H). | H, L, P |
| 210 | F | Cl | LC/MS m/z 384 [M + H]$^+$; $^1$H NMR (400 MHz, Acetone-d$_6$) δ 7.90 (dd, J = 5.56, 8.78 Hz, 1H), 7.57-7.48 (m, 1H), 7.48-7.34 (m, 4H), 7.23 (dd, J = 2.93, 9.65 Hz, 1H), 7.14 (br. s, 1H), 6.41 (br. s, 1H), 4.50 (br. s, 1H), 3.31 (d, J = 7.02 Hz, 2H), 2.53 (s, 3H). | M, N, O |
| 211 | Cl | F | LC/MS m/z 384 [M + H]$^+$; $^1$H NMR (400 MHz, DMSO-d$_6$) δ 7.87-7.84 (m, 1H), 7.79-7.76 (m, 1H), 7.64 (br. s, 1H), 7.37-7.32 (m, 3H), 7.24-7.21 (m, 2H), 7.02 (br. s, 1H), 4.39-4.12 (m, 1H), 3.18 (m, 2H), 2.47 (s, 3H). | H, L |
| 212 | F | CN | LC/MS m/z 375 [M + H]$^+$; $^1$H NMR (400 MHz, DMSO-d$_6$) δ 7.93-7.84 (m, 3H), 7.68-7.59 (m, 2H), 7.52-7.47 (m, 2H), 7.22 (dd, J = 2.75, 9.61 Hz, 1H), 7.05 (br. s, 1H), 4.31-4.44 (m, 1H), 3.18 (br. s, 2H), 2.50 (s, 3H). | H, L |
| 213 | 6-aminopyridin-3-yl | Cl | LC/MS m/z 458 [M + H]$^+$; $^1$H NMR (400 MHz, DMSO-d$_6$) δ 8.23 (d, J = 2.29 Hz, 1H), 7.97-7.90 (m, 1H), 7.88-7.83 (m, 1H), 7.81-7.75 (m, 1H), 7.70-7.62 (br. s, 1H), 7.53 (d, J = 1.83 Hz, 1H), 7.47-7.30 (m, 4H), 7.04 (br. s, 1H), 6.49 (d, J = 8.93 Hz, 1H), 6.15 (br. s, 2H), 4.39-4.31 (m, 1H), 3.23-3.13 (m, 2H), 2.53 (s, 3H). | M, P, N, O, L |

TABLE 9-continued

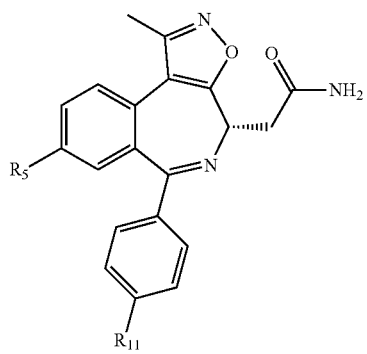

| Compound No. | R₅ | R₁₁ | Physical Data | Final Steps |
|---|---|---|---|---|
| 216 | H₂N-pyridin-5-yl | F | LC/MS m/z 442 [M + H]⁺; ¹H NMR (400 MHz, DMSO-d₆) δ 8.25 (s, 1H), 8.07 (br. s, 1H), 7.95 (m, 1H), 7.93 (m, 1H), 7.69 (br. s, 1H), 7.58 (s, 1H), 7.40 (dd, J = 5.49, 8.70 Hz, 2H), 7.19 (t, J = 8.81 Hz, 2H), 7.05 (br. s, 1H), 6.85 (br. s, 1H), 4.41-4.26 (m, 1H), 3.20-3.15 (m, 2H), 2.53 (s, 3H). | H, L, P |
| 217 | OCH₃ | Cl | LC/MS m/z 396 [M + H]⁺; ¹H NMR (400 MHz, DMSO-d₆) δ 7.79-7.73 (m, 1H), 7.64 (br. s, 1H), 7.45-7.42 (m, 2H), 7.37-7.32 (m, 2H), 7.31 (d, 1H), 7.02 (br. s, 1H), 6.86 (d, J = 2.75 Hz, 1H), 4.39-4.12 (m, 1H), 3.74 (s, 3H), 3.15 (br. s, 2H), 2.47 (s, 3H). | H, L |
| 224 | CN | Cl | LC/MS m/z 391 [M + H]⁺; ¹H NMR (400 MHz, DMSO-d₆) δ 8.13 (dd, J = 1.66, 8.31 Hz, 1H), 8.00 (d, J = 8.31 Hz, 1H), 7.89 (d, J = 1.25 Hz, 1H), 7.65 (br. s, 1H), 7.49-7.43 (m, 2H), 7.35-7.30 (m, 2H), 7.05 (br. s, 1H), 4.36 (br. s, 1H), 3.17 (br. s, 2H), 2.53 (s, 3H). | P (Zn(CN)₂ was used as the nucleophile), H, L |
| 226 | H | 1-hydroxycyclopropyl | LC/MS m/z 388 [M + H]⁺; ¹H NMR (400 MHz, DMSO-d₆) δ 7.80 (s, 1H), 7.72-7.67 (m, 1H), 7.66-7.62 (m, 1H), 7.44-7.35 (m, 2H), 7.21 (d, J = 3.32 Hz, 4H), 7.04-7.00 (m, 1H), 5.97 (s, 1H), 4.30-4.22 (m, 1H), 3.20-3.11 (m, 2H), 2.51 (s, 3H), 1.12 (d, J = 2.49 Hz, 2H), 0.95 (d, J = 2.49 Hz, 2H). | H, L |
| 233 | H | 2-amino-2-methylpropan-2-yl | LC/MS m/z 389 [M + H]⁺; ¹H NMR (400 MHz, DMSO-d₆) δ 7.81 (d, J = 7.69 Hz, 1H), 7.72-7.67 (m, 1H), 7.64 (br. s, 1H), 7.50 (d, J = 8.52 Hz, 2H), 7.45-7.36 (m, 2H), 7.23 (d, J = 8.31 Hz, 2H), 7.02 (br. s, 1H), 4.31-4.24 (m, 1H), 3.16 (br. s, 2H), 2.51 (s, 3H), 1.35 (s, 6H). | H, L |

TABLE 9-continued

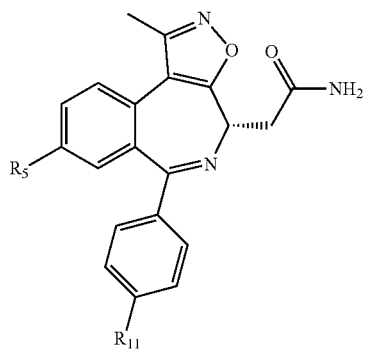

| Compound No. | R$_5$ | R$_{11}$ | Physical Data | Final Steps |
|---|---|---|---|---|
| 234 | 4-(HOOC)-C$_6$H$_4$- | F | LC/MS m/z 470 [M + H]$^+$; $^1$H NMR (400 MHz, DMSO-d$_6$) δ 12.99-12.84 (m, 1H), 8.08 (dd, J = 1.97, 8.21 Hz, 1H), 8.02-7.92 (m, 3H), 7.79 (d, J = 8.52 Hz, 2H), 7.68 (s, 2H), 7.42 (dd, J = 5.51, 8.83 Hz, 2H), 7.20 (t, J = 8.72 Hz, 2H), 7.05 (br. s, 1H), 4.40-4.33 (m, 1H), 3.16 (s, 2H), 2.55 (s, 3H). | H, L, P |
| 235 | H | -C(CH$_3$)$_2$OH | LC/MS m/z 390 [M + H]$^+$; $^1$H NMR (400 MHz, DMSO-d$_6$) δ 7.81 (d, J = 7.69 Hz, 1H), 7.70 (dt, J = 1.66, 7.37 Hz, 1H), 7.64 (br. s, 1H), 7.46-7.36 (m, 4H), 7.23 (d, J = 8.52 Hz, 2H), 7.02 (br. s, 1H), 5.05 (br. s, 1H), 4.27 (br. s, 1H), 3.16 (br. s, 2H), 2.51 (s, 3H), 1.39 (s, 6H). | H, L |
| 239 | OH | Cl | LC/MS m/z 382 [M + H]$^+$; $^1$H NMR (400 MHz, DMSO-d$_6$) δ 9.95-9.83 (m, 1H), 7.64 (d, J = 8.5 Hz, 2H), 7.45 (d, J = 8.5 Hz, 2H), 7.38-7.26 (m, 2H), 7.17-7.08 (m, 1H), 7.05-6.96 (m, 1H), 6.72 (d, J = 2.5 Hz, 1H), 4.34-4.18 (m, 1H), 3.21-3.01 (m, 2H), 2.45 (s, 3H). | H, L, Q |
| 248 | OEt | Cl | LC/MS m/z 410 [M + H]$^+$; $^1$H NMR (400 MHz, Acetone-d$_6$) δ 7.74 (d, J = 9.07 Hz, 1H), 7.47-7.35 (m, 4H), 7.28 (dd, J = 2.78, 8.63 Hz, 1H), 7.15-7.09 (br. s, 1H), 6.93 (d, J = 2.63 Hz, 1H), 6.38 (br. s, 1H), 4.54-4.36 (m, 1H), 4.2-3.9 (m, 2H), 3.27 (br. s, 2H), 2.49 (s, 3H), 1.33 (t, J = 6.87 Hz, 3H). | H, L, Q, R |
| 249 | O$^i$Pr | Cl | LC/MS m/z 424 [M + H]$^+$; $^1$H NMR (400 MHz, Acetone-d$_6$) δ 7.73 (d, J = 8.78 Hz, 1H), 7.50-7.34 (m, 4H), 7.27 (dd, J = 2.63, 8.78 Hz, 1H), 7.17-7.07 (br. s, 1H), 6.91 (d, J = 2.63 Hz, 1H), 6.36 (br. s, 1H), 4.68-4.55 (m, 1H), 4.52-4.38 (m, 1H), 3.37-3.17 (m, 2H), 2.49 (s, 3H), 1.28 (d J = 6.00 Hz, 3H), 1.24 (d, J = 6 Hx, 3H). | H, L, Q, R |

Example 27

Preparation of Compounds of Formula II, where Ring A is Phenyl and $R^5$ is Hydroxy or Alkoxy This general preparation scheme is exemplified by using 2-((4S)-6-(4-chlorophenyl)-8-methoxy-1-methyl-4H-benzo[c]isoxazolo[4,5-e]azepin-4-yl)acetamide as starting material.

General Procedure for Synthesis of Compounds where Ring A is Phenol (Step Q)

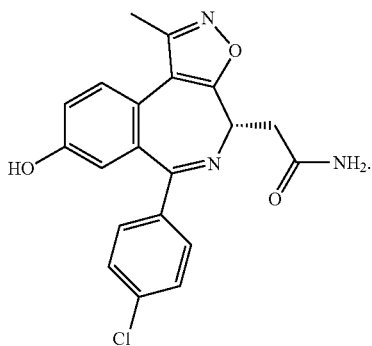

A round bottom flask was charged with 2-((4S)-6-(4-chlorophenyl)-8-methoxy-1-methyl-4H-benzo[c]isoxazolo[4,5-e]azepin-4-yl)acetamide (1 equivalent), a stirbar and dichloromethane (volume to make concentration 0.1M). The flask was cooled to 0° C. and BBr$_3$ (50 equivalents) was added dropwise. The resulting suspension was allowed to stir and warm to room temperature over 16 h, then re-cooled to 0° C. for the dropwise addition of methanol (20 mL). The solution was concentrated, then redissolved in EtOAc and washed with 1 M HCl. The aqueous phase was extracted with EtOAc (2×); the combined organics were washed with brine, dried (Na$_2$SO$_4$), filtered and concentrated. The product phenol could be purified on silica gel or used directly in the next reaction.

General Procedure for Synthesis of Compounds where Ring A is Alkoxy-Substituted Phenyl (Step R)

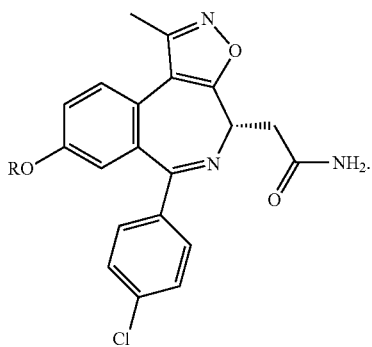

A re-sealable reaction vial was charged with 2-((4S)-6-(4-chlorophenyl)-8-hydroxy-1-methyl-4H-benzo[c]isoxazolo[4,5-e]azepin-4-yl)acetamide (1 equivalent), a stirbar and 4-methylpentan-2-one (volume to make concentration 0.1M). Potassium carbonate (3 equivalents) was added, followed by the appropriate alkyl iodide (2 equivalents). The tube was heated at 75° C. for 4 h, then poured into water and washed with EtOAc (3×). The combined organics were washed with brine, dried (Na$_2$SO$_4$), filtered and concentrated. The product ether was purified on silica gel or by reverse phase HPLC.

Example 28

Synthesis of (4S)-8-chloro-1,4-dimethyl-4H-benzo[c]isoxazolo[4,5-e]azepin-6(5H)-one The title compound was used as an alternative for intermediate 17 in Scheme 9 and can be used with Steps M, N, O and P (but does not require step L).

Methyl 5-chloro-2-iodobenzoate

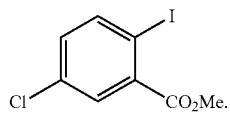

To a round bottomed flask was added NaHCO$_3$ (22.31 g, 266 mmol), 5-chloro-2-iodobenzoic acid (25 g, 89 mmol), DMF, and MeI (11.07 mL, 177 mmol). The reaction was stirred at room temperature overnight. The reaction was diluted with water and EtOAc. The layers were separated and the aqueous layer was extracted with EtOAc. The combined organic layers were washed with water (3×) and brine before being dried over Na$_2$SO$_4$, filtered, and concentrated. The crude residue was purified via Biotage to afford the titled compound (25.81 g, 87 mmol). LC/MS m/z 297 [M+H]$^+$.

Methyl 2-(5-((E)-(((S)-tert-butylsulfinyl)imino)methyl)-3-methylisoxazol-4-yl)-5-chlorobenzoate

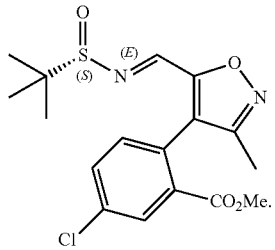

This intermediate was prepared using the protocol outlined for the synthesis of intermediate 13 in Scheme 1, starting from methyl 5-chloro-2-iodobenzoate. LC/MS m/z 383 [M+H]$^+$.

5-chloro-2-(5-((S)-1-((S)-1,1-dimethylethylsulfinamido)ethyl)-3-methylisoxazol-4-yl)benzoate

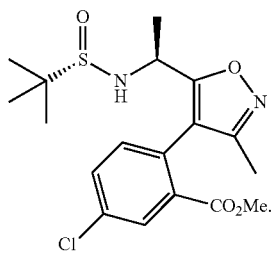 [SMILES: COC(=O)c1cc(Cl)ccc1-c1c(C)noc1[C@H](C)N[S@@](=O)C(C)(C)C]

To a round bottomed flask was added methyl 2-(5-((E)-((S)-tert-butylsulfinylimino)methyl)-3-methylisoxazol-4-yl)-5-chlorobenzoate (4.18 g, 10.92 mmol) and toluene (50 mL) before the solution was cooled to −78° C. To this solution was added methylmagnesium bromide (8.58 mL, 12.01 mmol) and the solution stirred at −78° C. for 1 h. To this solution was added an additional amount of methylmagnesium bromide (4.9 mL, 6.86 mmol) and the reaction stirred at −78° C. for 1.25 h. The reaction was quenched with saturated aqueous NH₄Cl and the layers separated. The aqueous phase was extracted with EtOAc. The combined organic phase was washed with brine, dried over Na₂SO₄, filtered, and concentrated. The crude residue was purified via Biotage (EtOAc/hex) to afford the titled compound as the major component of a mixture of diastereomers (3.37 g, 8.45 mmol); LC/MS m/z 399 [M+H]⁺.

(4S)-8-chloro-1,4-dimethyl-4H-benzo[c]isoxazolo[4,5-e]azepin-6(5H)-one

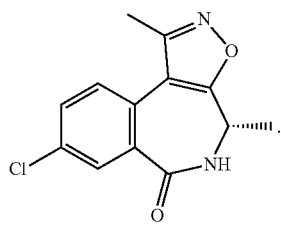 [SMILES: Cc1noc2c1-c1ccc(Cl)cc1C(=O)N[C@H]2C]

To a round bottomed flask was added methyl 5-chloro-2-(5-((S)-1-((S)-1,1-dimethylethylsulfinamido)ethyl)-3-methylisoxazol-4-yl)benzoate (3.37 g, 8.45 mmol), MeOH (48 mL), and HCl [2M in ether] (8.45 mL, 16.90 mmol). The reaction was stirred at room temperature for 30 min before concentrating. The crude residue was concentrated from toluene (2×) and hexane (1×) before being placed on a high vacuum line overnight. The crude residue (as an off-white foam) was dissolved in THF (100 mL) before cooling to −78° C. and addition of isopropylmagnesium chloride (15 mL, 30.0 mmol). The solution was stirred at −78° C. for 5 min before removal of the cold bath and warming the reaction to room temperature. The solution was quenched with saturated aqueous NH₄Cl and diluted with EtOAc. The layers were separated and the aqueous layer was extracted with EtOAc. The combined organic layers were washed with brine, dried over Na₂SO₄, filtered, and concentrated to afford a white solid. This material was purified via chiral SFC to afford the titled compound (1.9 g, 7.23 mmol); LC/MS m/z 263 [M+H]⁺.

Example 29

Synthesis of Compound 223

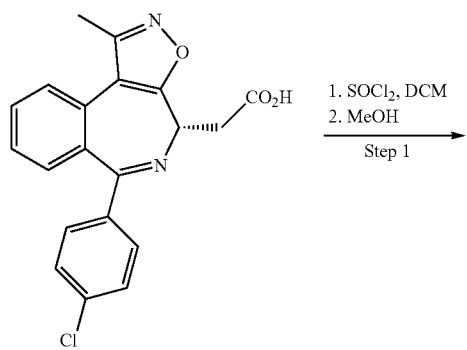

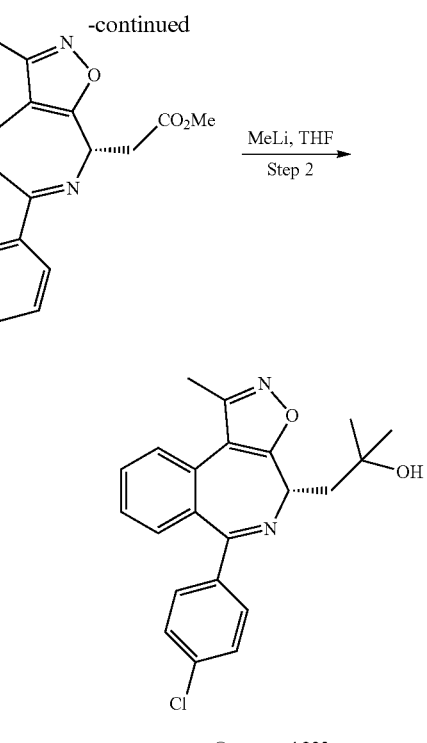

Compound 223

Synthesis of methyl 2-((4S)-6-(4-chlorophenyl)-1-methyl-4H-benzo[c]isoxazolo[4,5-e]azepin-4-yl)acetate To a solution of 2-((4S)-6-(4-chlorophenyl)-1-methyl-4H-benzo[c]isoxazolo[4,5-e]azepin-4-yl)acetic acid (100 mg, 0.27 mmol) and N,N-dimethylformamide (1 drop) in dichloromethane (10 mL) was added oxalyl chloride (56 mg, 0.40 mmol) dropwise at 0° C. The mixture was stirred for 0.5 hour at room temperature. The solution was cooled to 0° C. and methanol (100 mL) was added. The mixture was stirred for 0.5 hour at room temperature. The mixture was concentrated in vacuo, and the residue was diluted with water (5 mL), and extracted with ethyl acetate (10 mL×3). The combined organic layers were dried by sodium sulfate, concentrated in vacuo and the residue was purified by column chromatography (silica-gel, petroleum:ethyl acetate=2:1) to give methyl 2-((4S)-6-(4-chlorophenyl)-1-methyl-4H-benzo[c]isoxazolo[4,5-e]azepin-4-yl)acetate (80 mg, 77%) as a light yellow solid. LC/MS m/z 380 [M+H]⁺.

Synthesis of 1-((4S)-6-(4-chlorophenyl)-1-methyl-4H-benzo[c]isoxazolo[4,5-e]azepin-4-yl)-2-methylpropan-2-ol (Compound 223)

To the solution of methyl 2-((4S)-6-(4-chlorophenyl)-1-methyl-4H-benzo[c]isoxazolo[4,5-e]azepin-4-yl)acetate (76.2 mg, 0.20 mmol) in tetrahydrofuran (10 mL) was slowly added methyllithium (3N) (0.40 mL, 1.20 mmol) at 0° C. The mixture was stirred for 0.5 h at 0° C., quenched with saturated ammonium chloride and extracted with ethyl acetate (3×10 mL). The combined organic phase was washed with brine, dried over sodium sulfate and concentrated. The residue was purified by preparative-HPLC (isocratic acetonitrile:0.01% acetic acid water=65:35) to give 1-((4S)-6-(4-chlorophenyl)-1-methyl-4H-benzo[c]isoxazolo[4,5-e]azepin-4-yl)-2-methylpropan-2-ol (30 mg, 39%) as a white solid. LC/MS m/z 380 [M+H]⁺; ¹H NMR (300 MHz, CD₃Cl) δ 7.59-7.63 (m, 2H), 7.40-7.28 (m, 7H), 4.36-4.31 (m, 1H), 2.91-2.82 (m, 1H), 2.55 (s, 3H), 2.30-2.35 (m, 1H), 1.29 (s, 3H), 1.24 (s, 3H).

Other compounds of the invention were made following the general procedures in Examples 14 and 28 and are set forth in Table 10. The final steps employed from those Examples are indicated for each compound.

TABLE 10

| Compound No. | $R_5$ | $R_{11}$ | $R_3$ | Physical Data | Final steps |
|---|---|---|---|---|---|
| 199 | H | Cl | -CH₂-C(O)-NH-CH₂-CH₂-F | LC/MS m/z 412 [M + H]⁺; ¹H NMR (300 MHz, CDCl₃) δ 7.64-7.62 (m, 2H), 7.43-7.21 (m, 6H), 6.70 (br. s, 1H), 4.67-4.63 (m, 1H), 4.50-4.40 (m, 2H), 3.76-3.59 (m, 2H), 3.42-3.20 (m, 2H), 2.60 (s, 3H). | H, L |
| 204 | H | Cl | -CH₂-C(O)-NH-iPr | LC/MS m/z 407 [M + H]⁺; ¹H NMR (300 MHz, CDCl₃) δ 7.61-7.60 (m, 2H), 7.40-7.26 (m, 6H), 6.02 (br. s, 1H), 4.65-4.50 (m, 1H), 4.20-4.13 (m, 1H), 3.27-3.21 (m, 2H), 2.55 (s, 3H), 1.27-1.20 (m, 6H). | H, L |
| 205 | H | Cl | -CH₂-C(O)-NH-tBu | LC/MS m/z 422 [M + H]⁺. ¹H NMR (300 MHz, CDCl₃) δ 7.66-7.61 (m, 2H), 7.41-7.25 (m, 6H), 6.38 (br. s, 1H), 4.57-4.52 (m, 1H), 3.36-3.14 (m, 2H), 2.56 (s, 3H), 1.47 (s, 9H). | H, L |
| 214 | H | Cl | -CH₂-C(O)-NH-CH₂-CH₂-OH | LC/MS m/z 410 [M + H]⁺; ¹H NMR (300 MHz, CDCl₃) δ 7.63-7.59 (m, 2H), 7.40-7.32 (m, 6H), 6.88-6.82 (br. s,1H), 4.67-4.62 (m, 1H), 3.78-3.68 (m, 2H), 3.52-3.41 (m, 2H), 3.31-3.20 (m, 2H), 2.81-2.78 (m, 1H), 2.56 (s, 3H). | H, L |
| 230 | Cl | F | CH₃ | LC/MS m/z 341 [M + H]⁺; ¹H NMR (400 MHz, Acetone-d₆) δ 7.85 (d, J = 8.5 Hz, 1H), 7.71 (dd, J = 2.3, 8.5 Hz, 1H), 7.51-7.46 (m, 2H), 7.44 (d, J = 2.3 Hz, 1H), 7.17-7.10 (m, 2H), 4.16 (br. s, 1H), 2.53 (s, 3H), 1.89 (d, J = 6.7 Hz, 3H). | H |

TABLE 10-continued

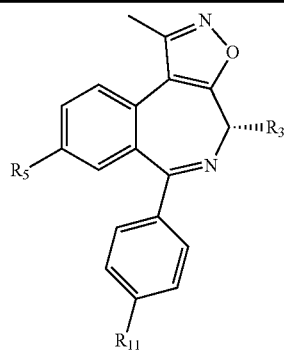

| Compound No. | $R_5$ | $R_{11}$ | $R_3$ | Physical Data | Final steps |
|---|---|---|---|---|---|
| 231 | 5-(2-aminopyridyl) | F | CH$_3$ | LC/MS m/z 399 [M + H]$^+$; $^1$H NMR (400 MHz, DMSO-d$_6$) δ 8.20 (d, J = 2.5 Hz, 1H), 7.90 (dd, J = 1.7, 8.3 Hz, 1H), 7.82 (d, J = 8.3 Hz, 1H), 7.64 (dd, J = 2.5, 8.7 Hz, 1H), 7.49 (d, J = 1.7 Hz, 1H), 7.47-7.39 (m, 2H), 7.19 (t, J = 8.9 Hz, 2H), 6.49 (d, J = 8.3 Hz, 1H), 6.14 (s, 2H), 4.16 (br. s, 1H), 2.54 (s, 3H), 1.84 (d, J = 6.2 Hz, 3H). | H, P |
| 237 | 4-carboxyphenyl | F | CH$_3$ | LC/MS m/z 427 [M + H]$^+$; $^1$H NMR (400 MHz, Methanol-d$_4$) δ 8.05 (d, J = 8.1 Hz, 2H), 8.01 (dd, J = 2.0, 8.1 Hz, 1H), 7.90 (d, J = 8.3 Hz, 1H), 7.64 (d, J = 2.0 Hz, 1H), 7.62 (d, J = 8.3 Hz, 2H), 7.48-7.43 (m, 2H), 7.11 (t, J = 8.8 Hz, 2H), 4.19 (br. s, 1H), 2.61 (s, 3H), 1.93 (d, J = 6.8 Hz, 3H). | H, P |

Example 30

Preparation of 6-(4-chlorophenyl)-1-methyl-4H-benzo[c]isoxazolo[4,5-e]azepine-4-carbonitrile (Compound 215)

(E)-(2-(5-((benzhydrylimino)methyl)-3-methylisoxazol-4-yl)phenyl)(4-chlorophenyl)methanone

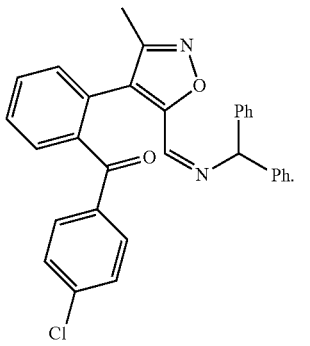 [SMILES: Cc1noc(/C=N\C(c2ccccc2)c2ccccc2)c1-c1ccccc1C(=O)c1ccc(Cl)cc1]

To a round bottomed flask was added 4-(2-(4-chlorobenzoyl)phenyl)-3-methylisoxazole-5-carbaldehyde (3.86 g, 11.85 mmol), DCM (50 mL), diphenylmethanamine (2.143 mL, 12.44 mmol), and Na$_2$SO$_4$ (5.05 g, 35.5 mmol). The reaction was stirred at room temperature overnight before being filtered and concentrated. The crude residue was purified via Biotage (EtOAc/hex) to afford the titled compound (5.61 g, 11.43 mmol) as pale yellow foam. LC/MS m/z 491 [M+H]$^+$.

2-(benzhydrylamino)-2-(4-(2-(4-chlorobenzoyl)phenyl)-3-methylisoxazol-5-yl)acetonitrile

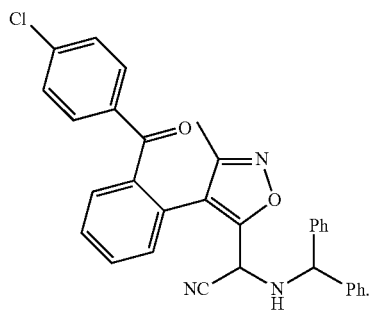 [SMILES: Cc1noc(C(C#N)NC(c2ccccc2)c2ccccc2)c1-c1ccccc1C(=O)c1ccc(Cl)cc1]

To a round bottomed flask was added (E)-(2-(5-((benzhydrylimino)methyl)-3-methylisoxazol-4-yl)phenyl)(4-chlorophenyl)methanone (320 mg, 0.652 mmol), DCM (4.5 mL), and Yt(OTf)$_3$ (40.4 mg, 0.065 mmol). To this solution was added TMS-CN (175 µl, 1.304 mmol) and the reaction was stirred overnight at room temperature. This solution was diluted with saturated aqueous NaHCO$_3$. The layers were separated and the aqueous phase was extracted with DCM. The combined organic layers were dried over Na$_2$SO$_4$, filtered, and concentrated. The crude residue was purified via Biotage (EtOAc/hex) to afford the titled compound (300 mg, 0.579 mmol). LC/MS m/z 518 [M+H]$^+$.

6-(4-chlorophenyl)-1-methyl-4H-benzo[c]isoxazolo[4,5-e]azepine-4-carbonitrile (Compound 215)

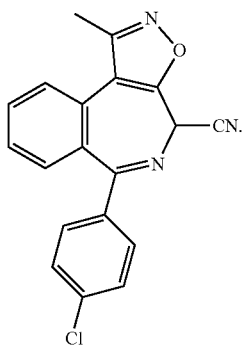 [SMILES: Cc1noc2c1-c1ccccc1C(c1ccc(Cl)cc1)=NC2C#N]

To a re-sealable vial was added 2-(benzhydrylamino)-2-(4-(2-(4-chlorobenzoyl)phenyl)-3-methylisoxazol-5-yl)acetonitrile (16 mg, 0.031 mmol), DCE (0.5 mL), and TFA (0.5 mL, 6.49 mmol). The vial was sealed and heated to 80° C. for 3.5 h before cooling to room temperature and concentrating. The crude residue was purified via Biotage (EtOAc/hex) to afford the titled compound (9 mg, 0.027 mmol).

LC/MS m/z 334 [M+H]$^+$; $^1$H NMR (400 MHz, CHLOROFORM-d) δ 7.77-7.63 (m, 2H), 7.51-7.40 (m, 4H), 7.38-7.32 (m, 2H), 5.21-4.84 (m, 1H), 2.62 (s, 3H).

Example 31

Preparation of 6-(4-chlorophenyl)-1-methyl-4H-benzo[c]isoxazolo[4,5-e]azepine-4-carboxamide (Compound 218)

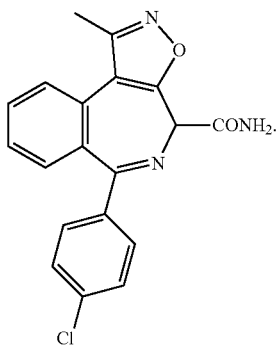 [SMILES: Cc1noc2c1-c1ccccc1C(c1ccc(Cl)cc1)=NC2C(N)=O]

To a round bottomed flask was added 6-(4-chlorophenyl)-1-methyl-4H-benzo[c]isoxazolo[4,5-e]azepine-4-carbonitrile (32 mg, 0.096 mmol) and conc. HCl (1 mL, 32.9 mmol). The reaction was stirred at room temperature for 1 h and during this time a precipitate formed. This solution was diluted with water and the precipitate was collected via filtration. Upon washing with water the precipitate dissolved. The layers were separated and the aqueous was extracted with ether (3×). The combined organic layers were washed with brine, dried over Na$_2$SO$_4$, filtered, and concentrated. This crude mixture was taken up in DCE (1 mL) and TFA (1 mL, 12.98 mmol). The vial was sealed and the reaction heated to 80° C. for 1 h before cooling to room temperature and stirring for an additional 2 h. The solution was concentrated and the crude residue was purified via Biotage (EtOAc/hex) to afford the titled compound (16.2 mg, 0.046 mmol) as a white solid. LC/MS m/z 352 [M+H]$^+$; $^1$H NMR (400 MHz, DMSO-d$_6$) δ 8.07-7.86 (m, 2H), 7.82 (d, J=7.8 Hz, 1H), 7.71 (t, J=7.2 Hz, 1H), 7.52-7.47 (m, 2H), 7.46-7.36 (m, 4H), 4.73-4.42 (m, 1H), 2.50 (s, 3H)

Example 32

Preparation of 6-(4-fluorophenyl)-1-methyl-4-(trifluoromethyl)-4H-benzo[c]isoxazolo[4,5-e]azepine (Compound 238)

Ethyl 2-(5-((S)-1-((S)-1,1-dimethylethylsulfinamido)-2,2,2-trifluoroethyl)-3-methylisoxazol-4-yl)benzoate

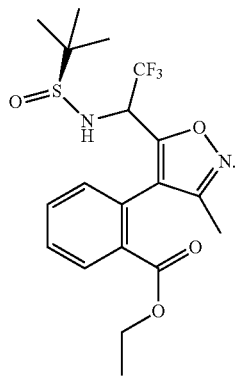 [SMILES: CCOC(=O)c1ccccc1-c1c(C)noc1C(N[S@@](=O)C(C)(C)C)C(F)(F)F]

To a round bottomed flask was added ethyl 2-(5-((E)-((S)-tert-butylsulfinylimino)methyl)-3-methylisoxazol-4-yl)benzoate (200 mg, 0.552 mmol), THF, and TBAT (tetrabutylammonium difluorotriphenylsilicate) (357 mg, 0.662 mmol). The solution was cooled to −42° C. in an acetonitrile/dry-ice bath before addition of trimethyl(trifluoromethyl)silane (131 µl, 0.883 mmol). The solution was stirred at −42° C. before warming to −10° C. The solution was diluted with water and EtOAc before the layers were separated. The aqueous phase was extracted with EtOAc and the combined organic phase was washed with brine, dried over Na$_2$SO$_4$, filtered, and concentrated. The crude residue was purified via Biotage (EtOAc/hex) to afford the titled compound (182.4 mg, 0.422 mmol). LC/MS m/z 433 [M+H]$^+$.

1-methyl-4-(trifluoromethyl)-4H-benzo[c]isoxazolo[4,5-e]azepin-6(5H)-one

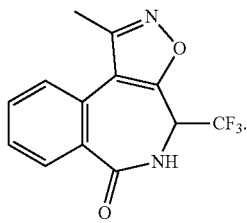 [SMILES: Cc1noc2c1-c1ccccc1C(=O)NC2C(F)(F)F]

To a round bottomed flask was added ethyl 2-(5-((S)-1-amino-2,2,2-trifluoroethyl)-3-methylisoxazol-4-yl)benzoate (124.2 mg, 0.378 mmol) and THF (2 mL) before the solution was cooled to −40° C. To this solution was added isopropylmagnesium chloride (473 µl, 0.946 mmol) and the reaction warmed to room temperature. The solution was diluted with NH$_4$Cl solution and EtOAc. The layers were separated and the aqueous phase was extracted with EtOAc. The combined organics were washed with brine, dried over Na$_2$SO$_4$, filtered, and concentrated. The crude residue was purified via Biotage (EtOAc/hex) to afford the titled compound (86 mg, 0.305 mmol). LC/MS m/z 283 [M+H]$^+$.

6-chloro-1-methyl-4-(trifluoromethyl)-4H-benzo[c]isoxazolo[4,5-e]azepine

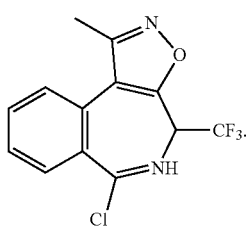 [SMILES: Cc1noc2c1-c1ccccc1C(Cl)=NC2C(F)(F)F]

To a round bottomed flask was added 1-methyl-4-(trifluoromethyl)-4H-benzo[c]isoxazolo[4,5-e]azepin-6(5H)-one (86 mg, 0.305 mmol), DCM (2 mL), and PCl$_5$ (102 mg, 0.488 mmol). The solution was stirred at room temperature for 30 min before addition of more PCl$_5$ (~0.5 eq). The solution was stirred at room temperature for 4 h before pouring onto an ice-saturated aqueous NaHCO$_3$ mixture. The layers were separated and the aqueous phase was extracted with DCM. The combined organic phase was dried over Na$_2$SO$_4$, filtered, and concentrated. The crude residue was purified via Biotage (EtOAc/hex) to afford the titled compound (52.9 mg, 0.176 mmol). LC/MS m/z 301 [M+H]$^+$.

6-(4-fluorophenyl)-1-methyl-4-(trifluoromethyl)-4H-benzo[c]isoxazolo[4,5-e]azepine (Compound 238)

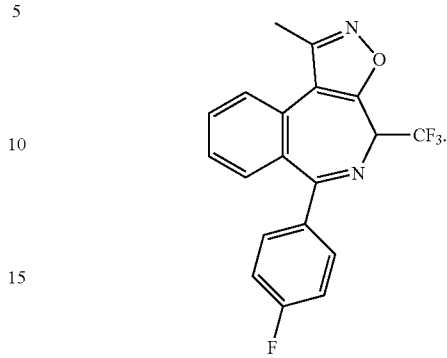

To a resealable vial was added Pd(Ph$_3$P)$_4$ (20.33 mg, 0.018 mmol) and 4-fluorophenylboronic acid (49.2 mg, 0.352 mmol) before the vial was sealed and evacuated/backfilled with N$_2$ (3×). To the vial was added 6-chloro-1-methyl-4-(trifluoromethyl)-4H-benzo[c]isoxazolo[4,5-e]azepine (52.9 mg, 0.176 mmol) dissolved in toluene (500 µL) and Na$_2$CO$_3$ (2M, 176 µl, 0.352 mmol). The solution was heated to 100° C. for 2 h before cooling to room temperature and diluting with water and EtOAc. The layers were separated and the aqueous phase was extracted with EtOAc. The combined organic layers were washed with brine, dried over Na$_2$SO$_4$, filtered, and concentrated. The crude residue was purified via Biotage (EtOAc/hex) to afford the titled compound (31.2 mg, 0.087 mmol). LC/MS m/z 361 [M+H]$^+$; $^1$H NMR (400 MHz, DMSO-d$_6$) δ 7.88 (d, J=7.1 Hz, 1H), 7.77 (dt, J=1.7, 7.5 Hz, 1H), 7.52-7.41 (m, 4H), 7.29-7.21 (m, 2H), 5.38 (q, J=7.6 Hz, 1H), 2.56 (s, 3H).

Example 33

Synthesis of Compounds of the General Formula

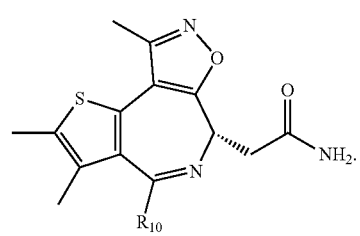

Tert-butyl 2-((6S)-2,3,9-trimethyl-4-(thiazol-4-yl)-6H-isoxazolo[5,4-c]thieno[2,3-e]azepin-6-yl)acetate (Step T)

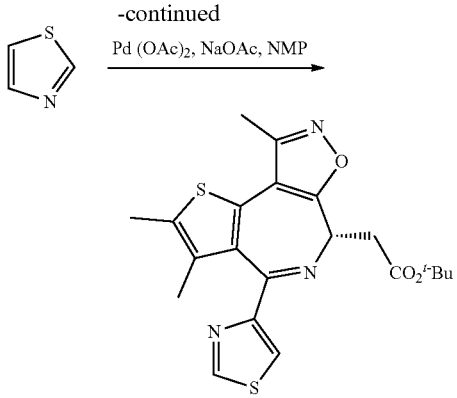

A disposable reaction tube was charged with intermediate 18 from Scheme 1, wherein ring A is thiophene (1 equivalent), thiazole (2 equivalents), palladium acetate (10 mol %), sodium acetate (2 equivalents) and N-methylpyrrolidone (volume to make concentration 0.1 M). The tube was heated to 90° C. for 16 hours. The mixture was diluted with water and extracted with ethyl acetate (3×10 mL). The organic phase was washed with brine, dried over sodium sulfate, and concentrated. The residue was purified by column chromatography (silica-gel, petroleum:ethyl acetate=5:1) to give tert-butyl 2-((6S)-2,3,9-trimethyl-4-(thiazol-4-yl)-6H-isoxazolo[5,4-c]thieno[2,3-e]azepin-6-yl)acetate (40 mg, 17.8% yield) as an off-white solid.

Synthesis of Compound 198

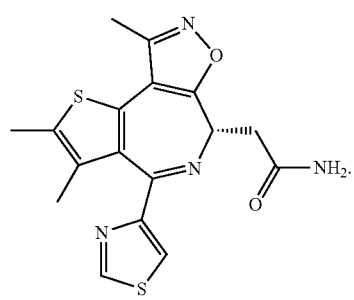 [SMILES: Cc1noc2c1-c1sc(C)c(C)c1C(c1cscn1)=N[C@H]2CC(N)=O]

The resulting tert-butyl 2-((6S)-2,3,9-trimethyl-4-(thiazol-4-yl)-6H-isoxazolo[5,4-c]thieno[2,3-e]azepin-6-yl)acetate is then subjected to step L from Scheme 1 to form Compound 198.

Tert-butyl 2-((6S)-4-isopropoxy-2,3,9-trimethyl-6H-isoxazolo[5,4-c]thieno[2,3-d]azepin-6-yl)acetate

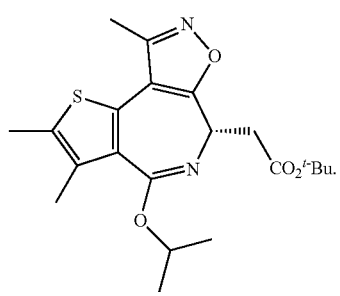 [SMILES: Cc1noc2c1-c1sc(C)c(C)c1C(OC(C)C)=N[C@H]2CC(=O)OC(C)(C)C]

A mixture of tert-butyl 2-((6S)-2,3,9-trimethyl-4-oxo-5,6-dihydro-4H-isoxazolo[5,4-c]thieno[2,3-e]azepin-6-yl)acetate (17 wherein ring A is thiophene; 100 mg, 0.276 mmol), silver oxide (70 mg, 0.304 mmol) and 2-iodopropane (61 mg, 0.359 mmol) in toluene (5 mL) was heated to 90° C., and stirred overnight. After cooling to room temperature, the reaction mixture was evaporated to dryness and the residue was purified by flash chromatography eluting with petroleum ether/ethyl acetate=5:1 to give tert-butyl 2-((6S)-4-isopropoxy-2,3,9-trimethyl-6H-isoxazolo[5,4-c]thieno[2,3-e]azepin-6-yl)acetate as a yellow solid (80 mg, 72% yield). LC/MS m/z 404 [M+H]$^+$; $^1$H NMR (300 MHz, CDCl$_3$) δ 5.30-5.03 (m, 1H), 4.51 (t, J=6 Hz, 1H), 3.11-3.08 (m, 2H), 2.43 (s, 3H), 2.39 (s, 3H), 2.26 (s, 3H), 1.46 (s, 9H), 1.30 (d, J=6 Hz, 3H), 1.20 (d, J=6 Hz, 3H).

Synthesis of Compound 193

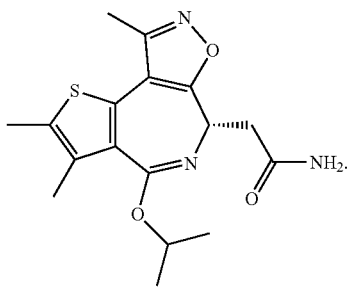 [SMILES: Cc1noc2c1-c1sc(C)c(C)c1C(OC(C)C)=N[C@H]2CC(N)=O]

Tert-butyl 2-((6S)-4-isopropoxy-2,3,9-trimethyl-6H-isoxazolo[5,4-c]thieno[2,3-e]azepin-6-yl)acetate is subjected to step L or deprotection followed by Step S to produce Compound 193.

Table 11, below, lists a number of compounds of the formula:

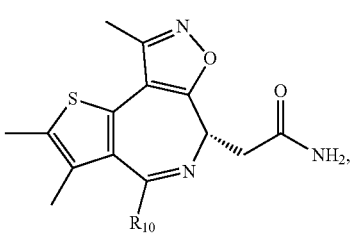

produced by the indicated steps.

TABLE 11

| Compound No. | R$_{10}$ | Physical Data | Final Steps |
|---|---|---|---|
| 208 | 4-CF$_3$-phenyl | LC/MS m/z 434 [M + H]$^+$; $^1$H NMR (400 MHz, DMSO-d$_6$) δ 7.75 (d, J = 8.24 Hz, 2H), 7.63-7.68 (m, 1H), 7.46 (d, J = 8.01 Hz, 2H), 7.01-7.06 (m, 1H), 4.25 (t, J = 7.40 Hz, 1H), 3.22 (d, J = 7.32 Hz, 2H), 2.45 (s, 3H), 2.40 (s, 3H), 1.58 (s, 3H). | H, L |

TABLE 11-continued

| Compound No. | R10 | Physical Data | Final Steps |
|---|---|---|---|
| 236 | *4-(2-hydroxypropan-2-yl)phenyl with CMe2OH* | LC/MS m/z 424 [M + H]+; 1H NMR (400 MHz, DMSO-d6) δ 7.65 (br. s, 1H), 7.44 (d, J = 8.52 Hz, 2H), 7.19 (d, J = 8.10 Hz, 2H), 7.02 (br. s, 1H), 5.11-4.99 (m, 1H), 4.18 (t, J = 7.17 Hz, 1H), 3.19 (dd, J = 3.84, 7.17 Hz, 2H), 2.45 (s, 3H), 2.40 (s, 3H), 1.61 (s, 3H), 1.39 (d, J = 1.66 Hz, 6H). | H, L |
| 195 | *1-phenylethyl* | LC/MS m/z 393 [M + H]+; 1H NMR (300 MHz, CDCl3) δ 6.96-6.94 (m, 3H), 6.63-6.60 (m, 2H), 4.93 (s, 1H), 4.58 (s, 1H), 4.24 (q, J = 6.9 Hz, 1H), 4.17-4.11 (m, 1H), 3.41-3.35 (m, 1H), 3.27-3.22 (m, 1H), 2.39 (s, 3H), 2.36 (s, 3H), 2.21 (s, 3H), 1.46 (d, J = 6.9 Hz, 3H). | J, L |
| 198 | *thiazol-4-yl* | LRMS m/z 373 [M + H]+; 1H NMR (300 MHz, DMSO-d6) δ 9.11 (s, 1H), 7.62 (s, 7.57 (s, 1H), 7.02 (s, 1H), 4.23-4.18 (m, 1H), 3.14-3.19 (m, 2H), 2.46 (s, 3H), 2.44 (s, 3H), 1.92 (s, 3H). | T, L |
| 193 | *isopropoxy* | LC/MS m/z 347 [M + H]+. 1H NMR (300 MHz, CDCl3) δ 6.46 (s, 1H), 5.86 (s, 1H), 5.09-5.01 (m, 1H), 4.45 (t, J = Hz, 1H), 3.06 (d, J = 6 Hz, 2H), 2.43 (s, 3H), 2.38 (s, 3H), 2.25 (s, 3H), 1.33 (d, J = 6 Hz, 3H), 1.20 (d, J = 6 Hz, 3H). | L |
| 194 | *1-methylpiperidin-4-yl* | LC/MS m/z 386 [M + H]+; 1H NMR (300 MHz, CD3OD) δ 4.80-4.85 (m, 1H), 4.09-4.10 (m, 1H), 3.16-3.20 (m, 4H), 2.70-2.95 (m, 2H), 2.40-2.47 (m, 9H), 2.31 (s, 3H), 2.07-2.08 (m, 2H), 1.33-1.42 (m, 1H), 1.21-1.29 (m, 1H). | M, N, L |

Example 34

Synthesis of ethyl (6-(4-chlorophenyl)-1-methyl-4H-benzo[c]isoxazolo[4,5-e]azepin-4-yl)carbamate (Compound 225) and its Enantiomers (Compounds 253 and 254)

Compound 225 was synthesized by the scheme set forth below:

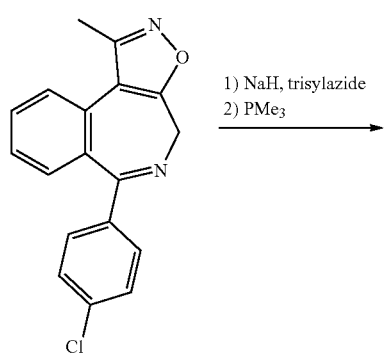

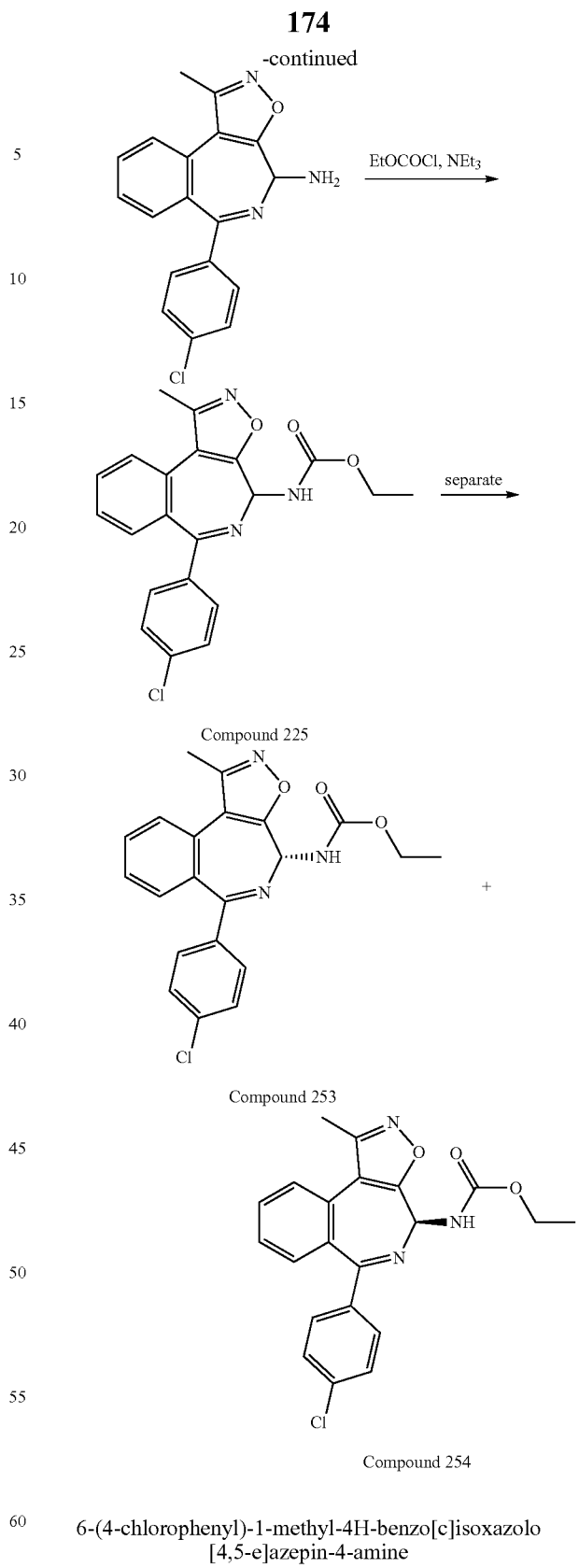

Compound 225

Compound 253

Compound 254

6-(4-chlorophenyl)-1-methyl-4H-benzo[c]isoxazolo[4,5-e]azepin-4-amine

To a round bottom flask was added sodium hydride (0.13 g, 3.3 mmol, 60% in mineral oil). The flask was then purged with nitrogen, DMF (10 mL) was then added and the flask was cooled to 0° C. 6-(4-chlorophenyl)-1-methyl-4H-benzo[c]isoxazolo[4,5-e]azepine (930 mg, 3.0 mmol) in DMF (5 mL) was added and the reaction was allowed to stir for 45 min. Trisyl azide (1.40 g, 4.5 mmol) in DMF (5 mL) was added and the reaction was mixed at 0° C. for 1 h. The reaction poured into ether (100 mL) and washed with brine (3×). The organic layer was dried over Na₂SO₄, filtered, concentrated to afford crude 4-azido-6-(4-chlorophenyl)-1-methyl-4H-benzo[c]isoxazolo[4,5-e]azepine, which was used directly in the following reaction. LC/MS m/z 350 [M+H]⁺.

A round bottomed flask containing crude 4-azido-6-(4-chlorophenyl)-1-methyl-4H-benzo[c]isoxazolo[4,5-e]azepine (1.05 g, 3.0 mmol), was purged with nitrogen and diluted with THF (30 mL) and water (6 mL). Trimethylphosphine (6.03 mL, 6.0 mmol, 1M in toluene) was added dropwise. The solution was stirred at ambient temperature for 2 h. The reaction was poured into half-saturated brine (100 mL), extracted with EtOAc (3×), dried over Na₂SO₄, filtered, concentrated and purified on a Biotage system (isocratic elution 65% EtOAc: 35% Hexanes) to provide the title compound as an oil (0.44 g). LC/MS m/z 324 [M+H]⁺.

Ethyl (6-(4-chlorophenyl)-1-methyl-4H-benzo[c] isoxazolo[4,5-e]azepin-4-yl)carbamate (Compounds 225, 253 and 254)

To a round bottomed flask was added 6-(4-chlorophenyl)-1-methyl-4H-benzo[c]isoxazolo[4,5-e]azepin-4-amine (218 mg, 0.67 mmol). The flask was purged with nitrogen, MeCN was added (7 mL), and the solution was cooled to 0° C. Ethyl chloroformate (78 μL, 0.81 mmol) and triethylamine (122 μL, 0.88 mmol) were added and the reaction was allowed to warm to ambient temperature and stirred for 2 h. The reaction was quenched with a 1:1 mixture of sat. aq. NaHCO₃:brine and extracted with EtOAc. The organic layer was dried over Na₂SO₄, filtered, concentrated and purified on a Biotage (isocratic elution 25% EtOAc: 75% Hexanes) to provide the title compound as white solid (120 mg).

The enantiomers were separated by chrial SFC using a 3.0×25.0 cm RegisPack column, with 35% cosolvent (1:1 MeOH:i-PrOH), 80 mL/min at 100 bar. Rention time peak 1 (compound 253): 1.48 min, 100% ee. Retention time peak 2 (compound 254): 2.96 min, 98.1% ee.

The absolute configuration was not unambiguously determined but was assigned based on the activity data in Table 14. LC/MS m/z 396 [M+H]⁺.

Example 35

1-(6-(4-chlorophenyl)-1-methyl-4H-benzo[c]isoxazolo[4,5-e]azepin-4-yl)-3-ethylurea (Compound 245)

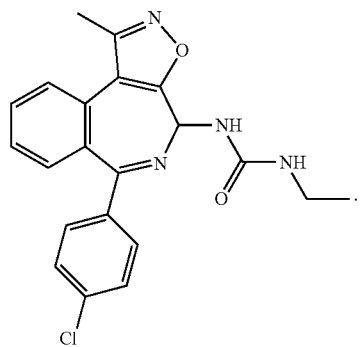 [SMILES: CCNC(=O)NC1N=C(c2ccc(Cl)cc2)c2ccccc2-c2c(C)noc21]

To a round bottomed flask was added 6-(4-chlorophenyl)-1-methyl-4H-benzo[c]isoxazolo[4,5-e]azepin-4-amine (218 mg, 0.67 mmol). The flask was purged with nitrogen, MeCN was added (7 mL), and the solution was cooled to 0° C. Ethyl isocyanate (128 μL, 1.62 mmol) and triethylamine (244 μL, 1.75 mmol) were added and the reaction was allowed to warm to ambient temperature and stirred for 2 h. The reaction was quenched with a 1:1 mixture of sat. aq. NaHCO₃:brine and extracted with EtOAc. The organic layer was dried over Na₂SO₄, filtered, concentrated and purified on a Biotage (isocratic elution 40% EtOAc: 60% Hexanes) to provide the title compound as white solid (220 mg). LC/MS m/z 395 [M+H]⁺.

Example 36

N-(6-(4-cyanophenyl)-1-methyl-4,1-benzo[c]isoxazolo[4,5-e]azepin-4-yl)acetamide (Compound 263)

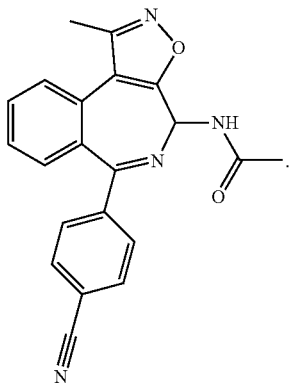 [SMILES: CC(=O)NC1N=C(c2ccc(C#N)cc2)c2ccccc2-c2c(C)noc21]

To a round bottomed flask was added 4-(4-amino-1-methyl-4H-benzo[c]isoxazolo[4,5-e]azepin-6-yl)benzonitrile (69 mg, 0.22 mmol) and DMAP (2.7 mg, 0.022 mmol). The flask was purged with nitrogen, MeCN was added (5 mL), and the solution was cooled to 0° C. Acetic anhydride (49.5 μL, 0.53 mmol) and triethylamine (79 μL, 0.57 mmol) were added and the reaction was allowed to warm to ambient temperature and stirred for 2 h. The reaction was quenched with a 1:1 mixture of sat. aq. NaHCO₃:brine and extracted with EtOAc. The organic layer was dried over Na₂SO₄, filtered, concentrated, and purified on a Biotage (isocratic elution 50% EtOAc: 50% Hexanes) to provide the title compound as white solid (64 mg). LC/MS m/z 357 [M+H]⁺.

Example 37

N-(6-(4-cyanophenyl)-1-methyl-4H-benzo[c]isoxazolo[4,5-e]azepin-4-yl)isobutyramide (Compound 262)

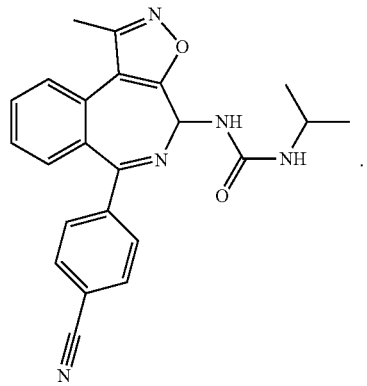 [SMILES: Cc1noc2c1-c1ccccc1C(c1ccc(C#N)cc1)=NC2NC(=O)NC(C)C]

To a round bottomed flask was added 4-(4-amino-1-methyl-4H-benzo[c]isoxazolo[4,5-e]azepin-6-yl)benzonitrile (69 mg, 0.22 mmol) and DMAP (2.7 mg, 0.022 mmol). The flask was purged with nitrogen, acetonitrile (5 mL) was added (5 mL), and the solution was cooled to 0° C. Isobutyryl chloride (55 μL, 0.53 mmol) and triethylamine (79 μL, 0.57 mmol) were added and the reaction was allowed to warm to ambient temperature and stirred for 2 h. The reaction was quenched with a 1:1 mixture of sat. aq. NaHCO$_3$:brine and extracted with EtOAc. The organic layer was dried over Na$_2$SO$_4$, filtered, concentrated, and purified on a Biotage (isocratic elution 30% EtOAc: 70% Hexanes) to provide the title compound as white solid (66 mg). LC/MS m/z 385 [M+H]$^+$.

Data for each of the above compounds having the formula:

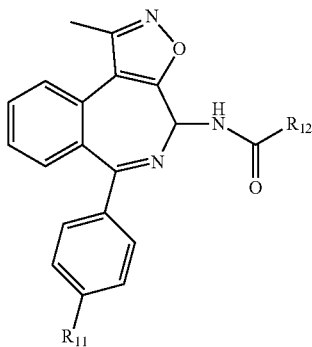

is set forth in Table 12, below.

TABLE 12

| Compound No. | R$_{11}$ | R$_{12}$ | Physical Data |
|---|---|---|---|
| 225 | Cl | OEt | LC/MS m/z 396 [M + H]$^+$; $^1$H NMR (400 MHz, DMSO-d$_6$) δ 9.07-9.01 (m, 1H), 7.84 (d, J = 7.89 Hz, 1H), 7.74 (d, J = 1.45 Hz, 1H), 7.49-7.33 (m, 6H), 5.55-5.50 (m, 1H), 4.07 (d, J = 7.06 Hz, 2H), 2.52 (s, 3H), 1.21 (t, J = 7.06 Hz, 3H). |
| 245 | Cl | NHEt | LC/MS m/z 395 [M + H]$^+$; $^1$H NMR (400 MHz, DMSO-d$_6$) δ 7.84 (d, J = 7.69 Hz, 1H), 7.76-7.70 (m, 1H), 7.55 (d, J = 8.10 Hz, 1H), 7.48-7.39 (m, 4H), 7.36-7.31 (m, 2H), 6.25 (t, J = 5.61 Hz, 1H), 5.61 (d, J = 9.14 Hz, 1H), 3.13-3.04 (m, 2H), 2.52 (s, 3H), 1.03 (t, J = 7.17 Hz, 3H). |
| 259 | OCF$_3$ | NHEt | LC/MS m/z 445 [M + H]$^+$; $^1$H NMR (400 MHz, DMSO-d$_6$) δ 7.85 (d, J = 7.69 Hz, 1H), 7.74 (dt, J = 1.66, 7.48 Hz, 1H), 7.55 (d, J = 8.93 Hz, 1H), 7.49-7.41 (m, 3H), 7.39-7.34 (m, 2H), 6.26 (t, J = 5.61 Hz, 1H), 5.63 (d, J = 8.93 Hz, 1H), 3.13-3.04 (m, 2H), 2.52 (s, 3H), 1.03 (t, J = 7.17 Hz, 3H). |
| 260 | F | NHEt | LC/MS m/z 379 [M + H]$^+$; $^1$H NMR (400 MHz, DMSO-d$_6$) δ 7.84 (dd, J = 0.62, 7.89 Hz, 1H), 7.73 (dt, J = 1.66, 7.48 Hz, 1H), 7.53 (d, J = 8.72 Hz, 1H), 7.48-7.33 (m, 4H), 7.24-7.16 (m, 2H), 6.25 (t, J = 5.61 Hz, 1H), 5.60 (d, J = 8.93 Hz, 1H), 3.13-3.04 (m, 2H), 2.52 (s, 3H), 1.03 (t, J = 7.17 Hz, 3H) |
| 263 | CN | CH$_3$ | LC/MS m/z 357 [M + H]$^+$; $^1$H NMR (400 MHz, DMSO-d$_6$) δ 9.70 (d, J = 7.89 Hz, 1H), 7.90-7.84 (m, 3H), 7.75 (dt, J = 1.35, 7.63 Hz, 1H), 7.55-7.50 (m, 2H), 7.46 (dt, J = 1.25, 7.58 Hz, 1H), 7.40-7.35 (m, 1H), 5.78 (d, J = 7.89 Hz, 1H), 2.53 (s, 3H), 2.06-2.02 (m, 3H). |
| 264 | CN | $^i$Pr | LC/MS m/z 385 [M + H]$^+$; $^1$H NMR (400 MHz, DMSO-d$_6$) δ 9.60 (d, J = 8.10 Hz, 1H), 7.90-7.84 (m, 3H), 7.79-7.73 (m, 1H), 7.55-7.50 (m, 2H), 7.49-7.43 (m, 1H), 7.40-7.35 (m, 1H), 5.78 (d, J = 8.10 Hz, 1H), 2.71 (quin, J = 6.80 Hz, 1H), 2.53 (s, 3H), 1.13-1.05 (m, 6H). |
| 261 | CN | NHEt | LC/MS m/z 386 [M + H]$^+$; $^1$H NMR (400 MHz, DMSO-d$_6$) δ 7.88-7.83 (m, 3H), 7.77-7.72 (m, 1H), 7.59 (d, J = 9.14 Hz, 1H), 7.51-7.43 (m, 3H), 7.40-7.36 (m, 1H), 6.26 (t, J = 5.61 Hz, 1H), 5.67 (d, J = 8.93 Hz, 1H), 3.13-3.04 (m, 2H), 2.52 (s, 3H), 1.03 (t, J = 7.17 Hz, 3H). |
| 262 | CN | NH$^i$Pr | LC/MS m/z 400 [M + H]$^+$; $^1$H NMR (400 MHz, DMSO-d$_6$) δ 7.88-7.83 (m, 3H), 7.77-7.72 (m, 1H), 7.51-7.42 (m, 4H), 7.40-7.35 (m, 1H), 6.18 (d, J = 7.48 Hz, 1H), 5.67 (d, J = 8.93 Hz, 1H), 3.71 (dd, J = 6.65, 13.92 Hz, 1H), 2.52 (s, 3H), 1.08 (t, J = 6.65 Hz, 6H). |

Example 38

6-(4-Chlorophenyl)-1-methyl-7-phenoxy-4H-isoxazolo[5,4-c]pyrido[4,3-e]azepine (Compound 229)

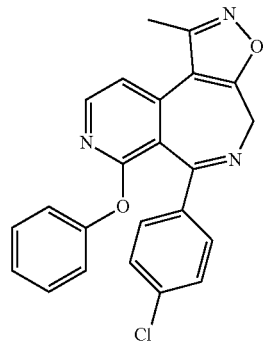

A procedure similar to 6-(4-chlorophenyl)-7-methoxy-1-methyl-4H-isoxazolo[5,4-c]pyrido[4,3-e]azepine (Compound 170) was followed, except that phenol was used instead of methanol. LC/MS m/z 402 [M+H]$^+$; $^1$H NMR (400 MHz, DMSO-d$_6$) δ 8.33 (d, J=5.40 Hz, 1H), 7.56 (d, J=5.40 Hz, 1H), 7.41 (s, 4H), 7.31 (tt, J=2.20, 8.00 Hz, 2H), 7.14 (tt, J=1.40, 7.50 Hz, 1H), 6.79 (d, J=8.00 Hz, 2H), 5.31 (d, J=13.3 Hz, 1H), 4.25 (d, J=13.29 Hz, 1H), 2.58 (s, 3H).

Example 39

Synthesis of 5-(4-Chlorophenyl)-2-methoxy-10-methyl-7H-isoxazolo[5,4-c]pyrido[2,3-e]azepine (Compound 219) and Related Compounds Methyl 2-(5-(hydroxymethyl)-3-methylisoxazol-4-yl)-6-methoxynicotinate

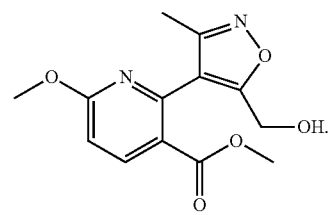 [SMILES: COC(=O)c1ccc(OC)nc1-c1c(C)noc1CO]

General procedures set forth in Scheme 1 were used to prepare this intermediate from commercially available methyl 2-chloro-6-methoxynicotinate. LC/MS m/z 279 [M+H]$^+$.

2-Methoxy-10-methyl-6,7-dihydro-5H-isoxazolo[5,4-c]pyrido[2,3-e]azepin-5-one

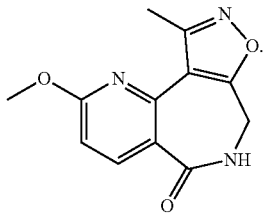 [SMILES: COc1ccc2c(n1)-c1c(C)noc1CNC2=O]

A reaction sequence similar to that used to prepare Compound 191 was followed, except that methyl 2-(5-(hydroxymethyl)-3-methylisoxazol-4-yl)-6-methoxynicotinate was used as starting material instead of (4-chlorophenyl)(2-(3-(hydroxymethyl)-5-methylisoxazol-4-yl)phenyl)methanone and methanol was used as the cosolvent for the conversion of the azide to the lactam. LC/MS m/z 246 [M+H]+.

5-(4-Chlorophenyl)-2-methoxy-10-methyl-7H-isoxazolo[5,4-c]pyrido[2,3-e]azepine (Compound 219)

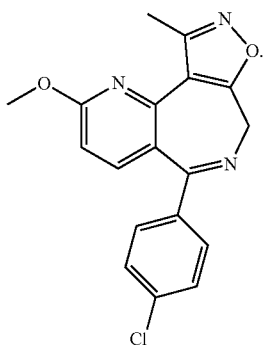 [SMILES: COc1ccc2c(n1)-c1c(C)noc1CN=C2c1ccc(Cl)cc1]

General procedures set forth in Scheme 1 were used to prepare the title compound from 2-methoxy-10-methyl-6,7-dihydro-5H-isoxazolo[5,4-c]pyrido[2,3-e]azepin-5-one. More precisely, the protocol Step H (Suzuki coupling reaction) was followed. LC/MS m/z 340 [M+H]+; 1H NMR (400 MHz, DMSO-d6) δ 7.63 (d, J=8.70 Hz, 1H), 7.45 (td, J=2.30, 8.80 Hz, 2H), 7.37 (td, J=2.30, 8.80 Hz, 2H), 6.81 (d, J=8.70 Hz, 1H), 4.71 (br. s, 2H), 4.02 (s, 3H), 2.62 (s, 3H).

2-Chloro-5-(4-chlorophenyl)-10-methyl-7H-isoxazolo[5,4-c]pyrido[2,3-e]azepine (Compound 227)

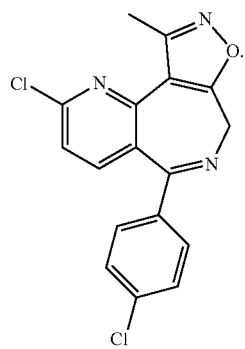 [SMILES: Cc1noc2c1-c1nc(Cl)ccc1C(c1ccc(Cl)cc1)=NC2]

To 5-(4-chlorophenyl)-2-methoxy-10-methyl-7H-isoxazolo[5,4-c]pyrido[2,3-e]azepine (0.050 g, 0.147 mmol) were added phosphoryl chloride (1 mL, 11 mmol) and DMF (0.1 mL) at room temperature. The reaction was heated to 140° C. for 4 h using microwave irradiation before 2M aq. NaOH and 2M aq. Na2CO3 were added to quench the excess of reagent. The desired product was extracted using EtOAc (repeated 4 times). The organic layers were combined, dried over Na2SO4 and concentrated to dryness. A fraction of the residue was purified by reverse phase chromatography to give the title product as a white solid. LC/MS m/z 344 [M+H]+; 1H NMR (400 MHz, DMSO-d6) δ 7.80 (d, J=8.52 Hz, 1H), 7.49 (d, J=8.31 Hz, 1H), 7.46 (td, J=2.10, 8.70 Hz, 2H), 7.41 (td, J=2.10, 8.70 Hz, 2H), 4.80 (s, 2H), 2.56 (s, 3H).

5-(4-Chlorophenyl)-N,10-dimethyl-7H-isoxazolo[5,4-c]pyrido[2,3-e]azepin-2-amine (Compound 221)

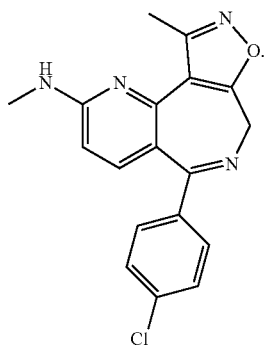 [SMILES: CNc1ccc2c(n1)-c1c(C)noc1CN=C2c1ccc(Cl)cc1]

A procedure similar to 6-(4-chlorophenyl)-N,1-dimethyl-4H-isoxazolo[5,4-c]pyrido[4,3-e]azepin-7-amine was followed, except that 2-chloro-5-(4-chlorophenyl)-10-methyl-7H-isoxazolo[5,4-c]pyrido[2,3-e]azepine was used as starting material instead of 6-(4-chlorophenyl)-7-fluoro-1-methyl-4H-isoxazolo[4,5-e]pyrido[3,4-c]azepine. LC/MS m/z 339 [M+H]+; 1H NMR (400 MHz, DMSO-d6) δ 7.42 (td, J=2.30, 8.70 Hz, 2H), 7.39-7.35 (m, 3H), 7.22 (d, J=8.72 Hz, 1H), 6.41 (d, J=8.93 Hz, 1H), 4.63 (br. s, 2H), 2.91 (d, J=4.57 Hz, 3H), 2.58 (s, 3H).

5-(4-Chlorophenyl)-10-methyl-7H-isoxazolo[5,4-c]pyrido[2,3-e]azepin-2-amine (Compound 228)

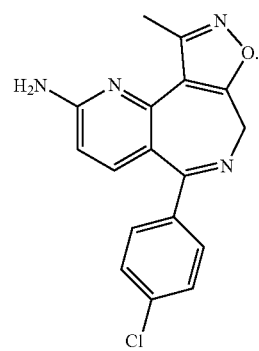 [SMILES: Cc1noc2c1-c1nc(N)ccc1C(c1ccc(Cl)cc1)=NC2]

To a solution of 2-chloro-5-(4-chlorophenyl)-10-methyl-7H-isoxazolo[5,4-c]pyrido[2,3-e]azepine (0.050 g, 0.145 mmol) in EtOH (1 mL) was added concentrated ammonium hydroxide (4.00 mL) and ammonium chloride (just enough to saturate the reaction) at room temperature. The reaction was heated to 100° C. overnight before the desired product was extracted using CH$_2$Cl$_2$ (repeated 4 times). The organic layers were combined, dried over Na$_2$SO$_4$ and concentrated to dryness. The residue was purified by flash chromatography (hexane/EtOAc 6:4 to 0:10) to give the title compound as a tan solid (0.008 g). LC/MS m/z 325 [M+H]$^+$; $^1$H NMR (400 MHz, DMSO-d$_6$) δ 7.43 (td, J=2.10, 8.70 Hz, 2H), 7.37 (td, J=2.10, 8.70 Hz, 2H), 7.24 (d, J=8.72 Hz, 1H), 6.77 (br. s, 2H), 6.38 (d, J=8.72 Hz, 1H), 4.61 (s, 2H), 2.56 (s, 3H).

5-(4-Chlorophenyl)-10-methyl-1H-isoxazolo[5,4-c]pyrido[2,3-e]azepin-2(7H)-one (Compound 220)

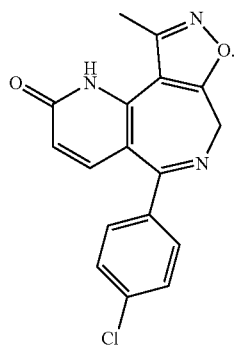 [SMILES: Cc1noc2c1-c1[nH]c(=O)ccc1C(c1ccc(Cl)cc1)=NC2]

To a solution of 5-(4-chlorophenyl)-2-methoxy-10-methyl-7H-isoxazolo[5,4-c]pyrido[2,3-e]azepine (0.050 g, 0.147 mmol) in AcOH (1 mL) was added concentrated 48% hydrobromic acid (1 mL) at room temperature. The reaction was heated to 100° C. for 2 h before it was diluted with water, and the desired product was extracted with a mixture CH$_2$Cl$_2$/trifluoroethanol (19:1) (repeated 4 times). The organic layers were combined, dried over Na$_2$SO$_4$ and concentrated to dryness. The residue was purified by flash chromatography (hexane/EtOAc 7:3 to 0:10) to give the title compound as a white solid (0.019 g). LC/MS m/z 326 [M+H]$^+$; $^1$H NMR (400 MHz, DMSO-d$_6$) δ 11.79 (br. s, 1H), 7.51-7.41 (m, 4H), 7.36 (br. s, 1H), 6.41 (br. s, 1H), 4.53 (br. s, 2H), 2.55 (s, 3H).

Example 40

Synthesis of 8-Chloro-6-(4-chlorophenyl)-1-methyl-4H-isoxazolo[5,4-c]pyrido[3,2-e]azepine (Compound 240) and Related Compounds 3-Bromo-6-chloro-N-methoxy-N-methylpicolinamide

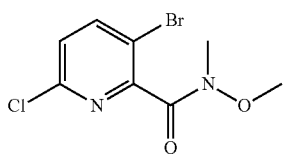

To a solution of 3-bromo-6-chloropicolinic acid (4.516 g, 19.10 mmol), N,O-dimethylhydroxylamine hydrochloride (3.73 g, 38.2 mmol), pyridine (4.63 mL, 57.3 mmol) in CH$_2$Cl$_2$ (40 mL) at 0° C. was added —N$^1$-((ethylimino)methylene)-N$^3$,N$^3$-dimethylpropane-1,3-diamine hydrochloride (4.39 g, 22.92 mmol). After 1 h at 0° C., a saturated aqueous solution of ammonium chloride was added and the product was extracted with MTBE/EtOAc (4:1) (repeated 4 times). The organic layers were combined, dried over Na$_2$SO$_4$ and concentrated to dryness. The product was carried out without purification in the next step. LC/MS m/z 281 [M+H]$^+$.

(3-Bromo-6-chloropyridin-2-yl)(4-chlorophenyl)methanone

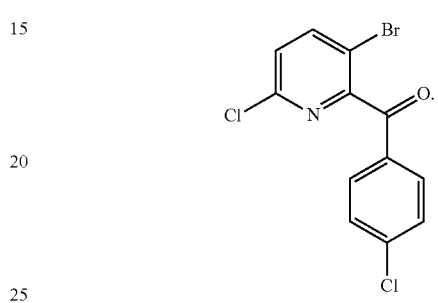

To a solution of 3-bromo-6-chloro-N-methoxy-N-methylpicolinamide (5.34 g, 19.1 mmol) in anhydrous THF (38 mL) at 0° C. was slowly added a solution of (4-chlorophenyl)magnesium bromide (1M in Et$_2$O) (76 mL, 76 mmol). After 3 h at 0° C., a saturated aqueous solution of ammonium chloride was added and the product was extracted with MTBE (repeated 4 times). The organic layers were combined, dried over Na$_2$SO$_4$ and concentrated to dryness. The residue was purified by flash chromatography (hexane/EtOAc 10:0 to 8:2) to give the title compound as a white solid (5.98 g). LC/MS m/z 332 [M+H]$^+$.

8-Chloro-6-(4-chlorophenyl)-1-methyl-4H-isoxazolo[5,4-c]pyrido[3,2-e]azepine

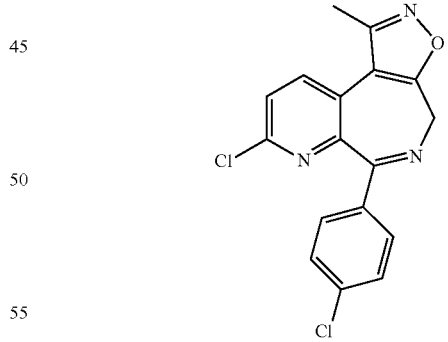

Compound 240

A sequence of reactions similar to the one used to prepare 6-(4-chlorophenyl)-7-fluoro-1-methyl-4H-isoxazolo[5,4-c]pyrido[4,3-e]azepin (Compound 169) was followed, except that (3-bromo-6-chloropyridin-2-yl)(4-chlorophenyl)methanone as starting material instead of the (4-chlorophenyl)(2-fluoro-4-iodopyridin-3-yl)methanone intermediate. For the Suzuki coupling reaction, a trifluoroborate salt was used instead of the boronic ester. LC/MS m/z 344 [M+H]+; 1H NMR (400 MHz, DMSO-d6) δ 8.18 (d, J=8.72 Hz, 1H), 7.40 (s, 4H), 7.17 (d, J=8.72 Hz, 1H), 4.70 (br. s, 2H), 2.50 (s, 3H).

6-(4-Chlorophenyl)-8-methoxy-1-methyl-4H-isoxazolo[5,4-c]pyrido[3,2-e]azepine (Compound 242)

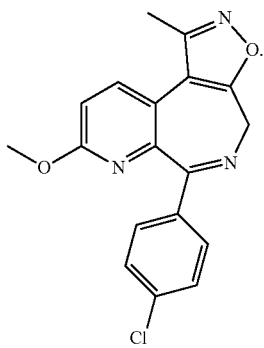 [SMILES: COc1ccc2c(n1)C(c1ccc(Cl)cc1)=NCc1onc(C)c1-2]

A procedure similar to 6-(4-Chlorophenyl)-7-methoxy-1-methyl-4H-isoxazolo[5,4-c]pyrido[4,3-e]azepine (Compound 170) was followed, except that 8-chloro-6-(4-chlorophenyl)-1-methyl-4H-isoxazolo[5,4-c]pyrido[3,2-e]azepine (Compound 240) was used as starting material instead of 6-(4-chlorophenyl)-7-fluoro-1-methyl-4H-isoxazolo[4,5-e]pyrido[3,4-c]azepine. LC/MS m/z 340 [M+H]+; 1H NMR (400 MHz, DMSO-d6) δ 8.31 (d, J=8.31 Hz, 1H), 7.83 (d, J=8.31 Hz, 1H), 7.43 (td, J=2.30, 8.70 Hz, 2H), 7.35 (td, J=2.30, 8.70 Hz, 2H), 4.79 (br. s, 2H), 3.34 (s, 3H), 2.53 (s, 3H).

6-(4-Chlorophenyl)-N,1-dimethyl-4H-isoxazolo[5,4-c]pyrido[3,2-e]azepin-8-amine (Compound 241)

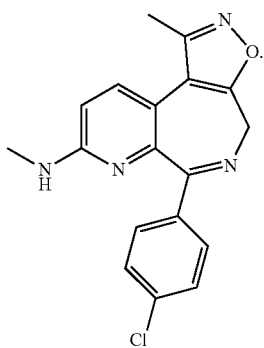 [SMILES: CNc1ccc2c(n1)C(c1ccc(Cl)cc1)=NCc1onc(C)c1-2]

A procedure similar to 6-(4-chlorophenyl)-N,1-dimethyl-4H-isoxazolo[5,4-c]pyrido[4,3-e]azepin-7-amine (Compound 173) was followed, except that 8-chloro-6-(4-chlorophenyl)-1-methyl-4H-isoxazolo[5,4-c]pyrido[3,2-e]azepine (Compound 240) was used as starting material instead of 6-(4-chlorophenyl)-7-fluoro-1-methyl-4H-isoxazolo[4,5-e]pyrido[3,4-c]azepine. LC/MS m/z 339 [M+H]+; 1H NMR (400 MHz, DMSO-d6) δ 7.83 (d, J=8.72 Hz, 1H), 7.41 (td, J=2.10, 8.50 Hz, 2H), 7.36 (td, J=2.10, 8.50 Hz, 2H), 6.96 (q, J=4.50 Hz, 1H), 6.77 (d, J=8.93 Hz, 1H), 4.61 (br. s, 2H), 2.62 (d, J=4.78 Hz, 3H), 2.46 (s, 3H).

6-(4-Chlorophenyl)-1-methyl-4H-isoxazolo[5,4-c]pyrido[3,2-e]azepin-8-amine (Compound 257)

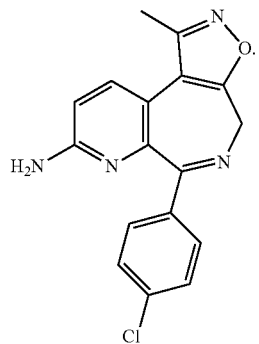 [SMILES: Cc1noc2c1-c1ccc(N)nc1C(c1ccc(Cl)cc1)=NC2]

A procedure similar to 5-(4-chlorophenyl)-10-methyl-7H-isoxazolo[5,4-c]pyrido[2,3-e]azepin-2-amine (Compound 228) was followed, except that 8-chloro-6-(4-chlorophenyl)-1-methyl-4H-isoxazolo[5,4-c]pyrido[3,2-e]azepine (Compound 240) was used as starting material instead of 2-chloro-5-(4-chlorophenyl)-10-methyl-7H-isoxazolo[5,4-c]pyrido[2,3-e]azepine. LC/MS m/z 325 [M+H]+; 1H NMR (400 MHz, DMSO-d6) δ 7.83 (d, J=8.72 Hz, 1H), 7.38 (td, J=2.10, 8.70 Hz, 2H), 7.33 (td, J=1.90, 8.70 Hz, 2H), 6.76 (d, J=8.7 Hz, 1H), 6.39 (s, 2H), 4.60 (br. s, 2H), 2.46 (s, 3H).

6-(4-Chlorophenyl)-1-methyl-8-(pyrrolidin-1-yl)-4H-isoxazolo[5,4-c]pyrido[3,2-e]azepine (Compound 247)

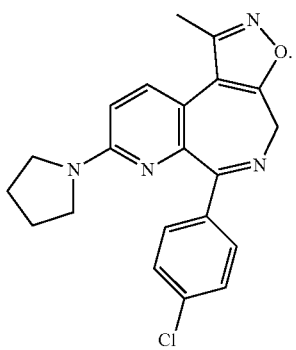 [SMILES: Cc1noc2c1-c1ccc(N3CCCC3)nc1C(c1ccc(Cl)cc1)=NC2]

A procedure similar to 6-(4-chlorophenyl)-N,1-dimethyl-4H-isoxazolo[5,4-c]pyrido[3,2-e]azepin-8-amine (Compound 241) was followed, except that pyrrolidine was used instead of methylamine (33% in EtOH). LC/MS m/z 379 [M+H]+; 1H NMR (400 MHz, DMSO-d6) δ 7.92 (d, J=8.93 Hz, 1H), 7.43 (td, J=2.20, 8.70 Hz, 2H), 7.36 (td, J=2.20, 8.70 Hz, 2H), 6.79 (d, J=8.93 Hz, 1H), 4.62 (br. s, 2H), 3.30-3.25 (m, 4H), 2.47 (s, 3H), 1.96-1.83 (m, 4H).

6-(4-Chlorophenyl)-1-methyl-4H-isoxazolo[5,4-c]pyrido[3,2-e]azepin-8(7H)-one (Compound 243)

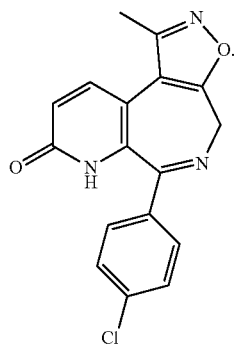 [SMILES: Cc1noc2c1-c1ccc(=O)[nH]c1C(c1ccc(Cl)cc1)=NC2]

A procedure similar to 5-(4-chlorophenyl)-10-methyl-1H-isoxazolo[5,4-c]pyrido[2,3-e]azepin-2(7H)-one was followed, except that 6-(4-chlorophenyl)-8-methoxy-1-methyl-4H-isoxazolo[5,4-c]pyrido[3,2-e]azepine was used as starting material instead of 5-(4-chlorophenyl)-2-methoxy-10-methyl-7H-isoxazolo[5,4-c]pyrido[2,3-e]azepine. LC/MS m/z 326 [M+H]$^+$; $^1$H NMR (400 MHz, DMSO-d$_6$) δ 11.27 (br. s, 1H), 8.01 (br. s, 1H), 7.50-7.31 (m, 4H), 6.85 (br. s, 1H), 4.66 (br. s, 2H), 2.48 (s, 3H).

6-(4-Chlorophenyl)-1,7-dimethyl-4H-isoxazolo[5,4-c]pyrido[3,2-e]azepin-8(7H)-one (Compound 246)

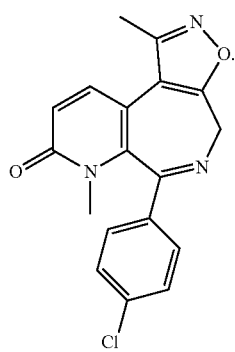 [SMILES: Cc1noc2c1-c1ccc(=O)n(C)c1C(c1ccc(Cl)cc1)=NC2]

A procedure similar to 6-(4-chlorophenyl)-1,8-dimethyl-4H-isoxazolo[5,4-c]pyrido[4,3-e]azepin-7(8H)-one was followed, except that 6-(4-chlorophenyl)-1-methyl-4H-isoxazolo[5,4-c]pyrido[3,2-e]azepin-8(7H)-one was used as starting material instead of 6-(4-chlorophenyl)-1-methyl-4H-isoxazolo[5,4-c]pyrido[4,3-e]azepin-7(8H)-one. LC/MS m/z 340 [M+H]$^+$; $^1$H NMR (400 MHz, DMSO-d$_6$) δ 7.98 (d, J=9.56 Hz, 1H), 7.48 (d, J=8.93 Hz, 2H), 7.35 (d, J=8.52 Hz, 2H), 6.82 (d, J=9.35 Hz, 1H), 5.32 (d, J=12.46 Hz, 1H), 4.15 (d, J=12.7 Hz, 1H), 2.95 (s, 3H), 2.50 (s, 3H).

8-Chloro-6-(4-chlorophenyl)-1-methyl-4H-isoxazolo[5,4-c]pyrido[3,4-e]azepine (Compound 256)

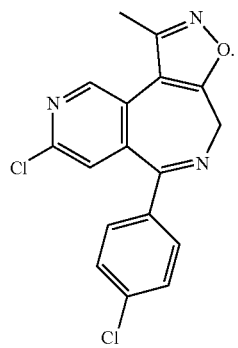 [SMILES: Cc1noc2c1-c1cnc(Cl)cc1C(c1ccc(Cl)cc1)=NC2]

A sequence similar to 8-chloro-6-(4-chlorophenyl)-1-methyl-4H-isoxazolo[5,4-c]pyrido[3,2-e]azepine (Compound 240) was followed, except that 5-bromo-2-chloroisonicotinic acid was used as commercially available starting material instead of 3-bromo-6-chloropicolinic acid. LC/MS m/z 344 [M+H]$^+$; $^1$H NMR (400 MHz, DMSO-d$_6$) δ 8.93 (d, J=0.80 Hz, 1H), 7.49 (td, J=2.10, 8.70 Hz, 2H), 7.46-7.42 (m, 3H), 4.77 (br. s, 2H), 2.57 (s, 3H).

6-(4-Chlorophenyl)-N,1-dimethyl-4H-isoxazolo[5,4-c]pyrido[3,4-e]azepin-8-amine (Compound 258)

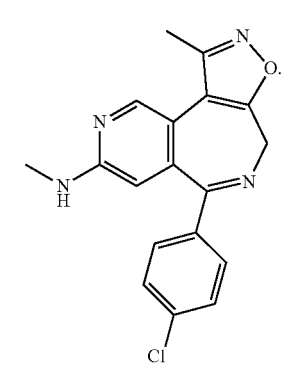 [SMILES: CNc1cc2c(cn1)-c1c(C)noc1CN=C2c1ccc(Cl)cc1]

A procedure similar to 6-(4-chlorophenyl)-N,1-dimethyl-4H-isoxazolo[5,4-c]pyrido[4,3-e]azepin-7-amine was followed, except that 8-chloro-6-(4-chlorophenyl)-1-methyl-4H-isoxazolo[5,4-c]pyrido[3,4-e]azepine was used as starting material instead of 6-(4-chlorophenyl)-7-fluoro-1-methyl-4H-isoxazolo[4,5-e]pyrido[3,4-c]azepine. LC/MS m/z 339 [M+H]$^+$; $^1$H NMR (400 MHz, DMSO-d$_6$) δ 8.46 (s, 1H), 7.49-7.41 (m, 4H), 6.84 (q, J=5.00 Hz, 1H), 6.33 (s, 1H), 4.67 (br. s, 2H), 2.79 (d, J=4.78 Hz, 3H), 2.48 (s, 3H).

6-(4-Chlorophenyl)-1-methyl-8-(pyrrolidin-1-yl)-4H-isoxazolo[5,4-c]pyrido[3,4-e]azepine (Compound 255)

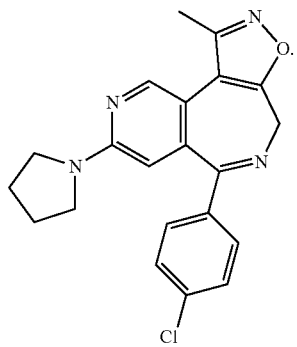 [SMILES: Cc1noc2c1-c1cnc(N3CCCC3)cc1C(c1ccc(Cl)cc1)=NC2]

A procedure similar to 6-(4-chlorophenyl)-N,1-dimethyl-4H-isoxazolo[5,4-c]pyrido[3,4-e]azepin-8-amine was followed, except that pyrrolidine was used instead of methylamine (33% in EtOH). LC/MS m/z 379 [M+H]$^+$; $^1$H NMR (400 MHz, DMSO-d$_6$) δ 8.56 (d, J=0.62 Hz, 1H), 7.48 (ddd, J=1.70, 2.50, 8.20 Hz, 2H), 7.44 (ddd, J=1.70, 2.50, 8.20 Hz, 2H), 6.23 (d, J=0.62 Hz, 1H), 4.66 (br. s, 2H), 3.36-3.32 (m, 4H), 2.49 (s, 3H), 1.98-1.83 (m, 4H).

6-(4-Chlorophenyl)-1-methyl-4H-isoxazolo[5,4-c]pyrido[3,4-e]azepin-8(9H)-one (Compound 266)

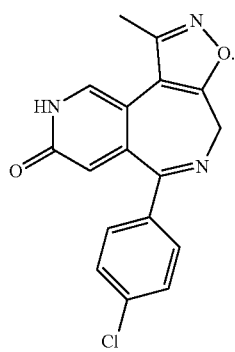 [SMILES: Cc1noc2c1-c1c[nH]c(=O)cc1C(c1ccc(Cl)cc1)=NC2]

A procedure similar to 5-(4-chlorophenyl)-10-methyl-1H-isoxazolo[5,4-c]pyrido[2,3-e]azepin-2(7H)-one was followed, except that 6-(4-chlorophenyl)-8-methoxy-1-methyl-4H-isoxazolo[5,4-c]pyrido[3,4-e]azepine (prepared from 8-chloro-6-(4-chlorophenyl)-1-methyl-4H-isoxazolo[5,4-c]pyrido[3,4-e]azepine in a similar fashion to 6-(4-chlorophenyl)-7-methoxy-1-methyl-4H-isoxazolo[5,4-c]pyrido[4,3-e]azepine) was used as starting material instead of 5-(4-chlorophenyl)-2-methoxy-10-methyl-7H-isoxazolo[5,4-c]pyrido[2,3-e]azepine. LC/MS m/z 326 [M+H]$^+$; $^1$H NMR (400 MHz, DMSO-d$_6$) δ 12.45 (br. s, 1H), 7.92 (br. s, 1H), 7.48 (s, 4H), 6.25 (br. s, 1H), 4.78 (br. s, 2H), 2.43 (s, 3H).

2-((4S)-7-Amino-6-(4-chlorophenyl)-1-methyl-4H-isoxazolo[5,4-c]pyrido[4,3-e]azepin-4-yl)acetamide (Compound 222)

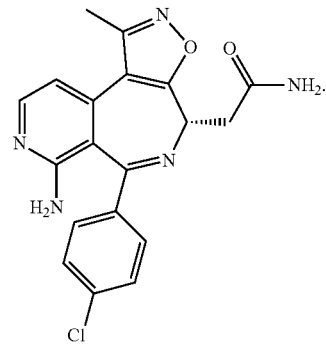 [SMILES: Cc1noc2c1-c1ccnc(N)c1C(c1ccc(Cl)cc1)=N[C@H]2CC(N)=O]

A procedure similar to 5-(4-chlorophenyl)-10-methyl-7H-isoxazolo[5,4-c]pyrido[2,3-e]azepin-2-amine was followed, except that a solution of 2-((4S)-6-(4-chlorophenyl)-7-fluoro-1-methyl-4H-isoxazolo[5,4-c]pyrido[4,3-e]azepin-4-yl)acetamide in DMSO was used instead of a solution of 2-chloro-5-(4-chlorophenyl)-10-methyl-7H-isoxazolo[5,4-c]pyrido[2,3-e]azepine in EtOH. LC/MS m/z 382 [M+H]$^+$; $^1$H NMR (400 MHz, DMSO-d$_6$) δ 8.21 (d, J=5.19 Hz, 1H), 7.67 (br. s, 1H), 7.38 (td, J=2.30, 8.70 Hz, 2H), 7.33 (td, J=2.30, 8.70 Hz, 2H), 7.04 (br. s, 1H), 6.95 (d, J=5.19 Hz, 1H), 5.89 (br. s, 2H), 4.40 (dd, J=6.54, 8.00 Hz, 1H), 3.27 (dd, J=8.00 Hz, 15.60 Hz, 1H), 3.11 (dd, J=6.65, 15.58 Hz, 1H), 2.49 (s, 3H).

Example 41

Synthesis of Compounds 232 and 244

Scheme 10 depicts the synthesis of the title compounds.

Scheme 10

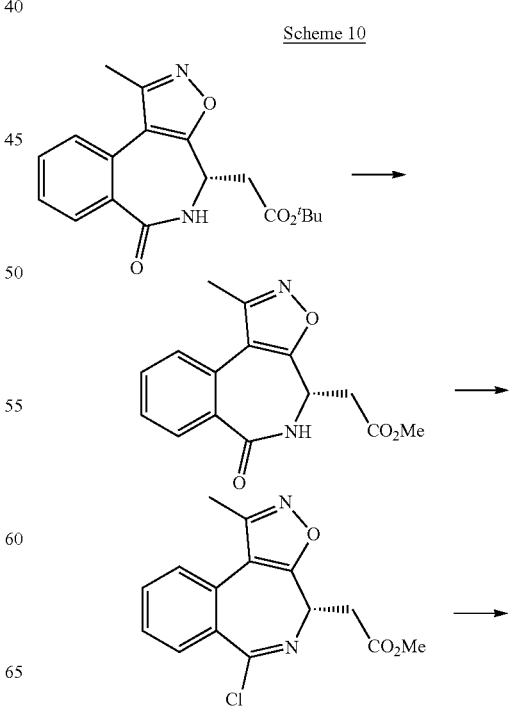

189
-continued

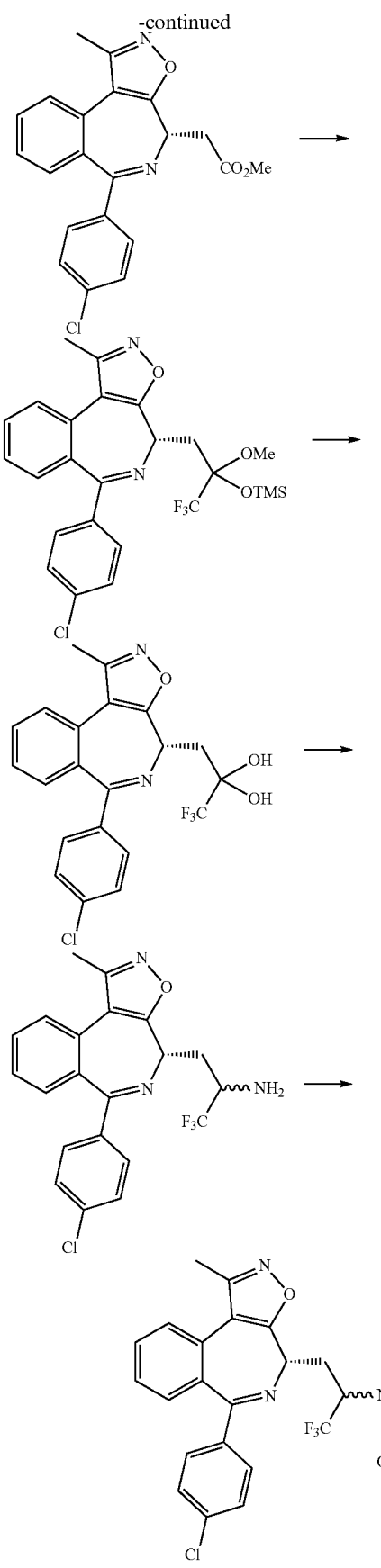

190
Methyl 2-((4S)-1-methyl-6-oxo-5,6-dihydro-4H-benzo[c]isoxazolo[4,5-e]azepin-4-yl)acetate

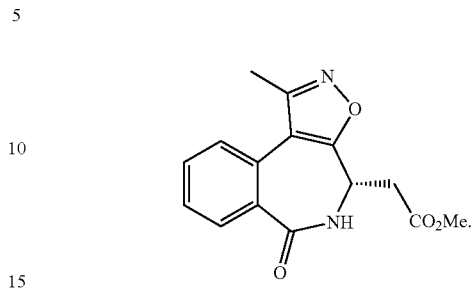

To a re-sealable vial containing a solution of tert-butyl 2-((4S)-1-methyl-6-oxo-5,6-dihydro-4H-benzo[c]isoxazolo[4,5-e]azepin-4-yl)acetate (1.04 g, 3.17 mmol) in MeOH (10 mL) was added hydrochloric acid (0.792 mL, 3.17 mmol, 4 M in 1,4-dioxane). After complete addition of reagents the reaction mixture was allowed to age until complete consumption of the carboxylic acid was detected by LC-MS. After ~24 h, the reaction mixture was cooled to room temperature and concentrated in vacuo to give yellow solids. The solids were purified on Biotage system (gradient elution 5% EtOAc:1% i-PrOH: 94% Hexanes to 80% EtOAc:1% i-PrOH:19% Hexanes) to give the titled product methyl 2-((4S)-1-methyl-6-oxo-5,6-dihydro-4H-benzo[c]isoxazolo[4,5-e]azepin-4-yl)acetate (0.500 g, 1.747 mmol, 55.1% yield) as white crystalline solids. LC/MS m/z 287 [M+H]$^+$.

Methyl 2-((4S)-6-chloro-1-methyl-4H-benzo[c]isoxazolo[4,5-e]azepin-4-yl)acetate

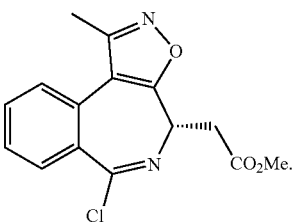 [SMILES: COC(=O)C[C@@H]1N=C(Cl)c2ccccc2-c2c(C)noc21]

To a solution of methyl 2-((4S)-1-methyl-6-oxo-5,6-dihydro-4H-benzo[c]isoxazolo[4,5-e]azepin-4-yl)acetate (0.4754 g, 1.661 mmol) in CH$_2$Cl$_2$ (4 mL) was added phosphorus pentachloride (0.432 g, 2.075 mmol). The reaction mixture was stirred at room temperature for 1 h. To the mixture was added aqueous 10% Na$_2$CO$_3$ and stirred vigorously for 15 min. The aqueous layer was extracted with CH$_2$Cl$_2$ (3×). The combined organic extracts were dried over Na$_2$SO$_4$ and concentrated to give yellow foam after drying. The foam was filtered over a plug of silica and eluted with 20% EtOAc:80% Hexanes. The product methyl 2-((4S)-6-chloro-1-methyl-4H-benzo[c]isoxazolo[4,5-e]azepin-4-yl)acetate (0.4701 g, 1.543 mmol, 93% yield) was obtained as a white foam. LC/MS m/z 305 [M+H]$^+$.

Methyl 2-((4S)-6-(4-chlorophenyl)-1-methyl-4H-benzo[c]isoxazolo[4,5-e]azepin-4-yl)acetate

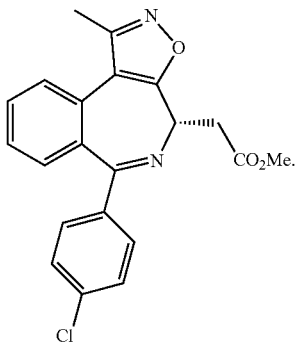 [SMILES: COC(=O)C[C@@H]1N=C(c2ccc(Cl)cc2)c2ccccc2-c2c(C)noc21]

To a 100 mL round bottom flask containing methyl 2-((4S)-6-chloro-1-methyl-4H-benzo[c]isoxazolo[4,5-e]azepin-4-yl)acetate (0.4701 g, 1.543 mmol) was added Pd(PPh$_3$)$_4$ (0.095 g, 0.082 mmol) and 4-chlorophenylboronic acid (0.393 g, 2.51 mmol). The flask was evacuated and purged with N$_2$ (g) (3×), followed by addition of toluene (10 mL) and another cycle of evacuation and purging with N$_2$ (g). To the heterogeneous mixture was added aqueous sodium carbonate (2.4 mL, 4.80 mmol, 2 M) in one portion and the flask was heated to 80° C. After ~30 min, the reaction mixture was cooled to room temperature and diluted with water. The aqueous layer was extracted with EtOAc (3×), dried over Na$_2$SO$_4$, and concentrated to give a dark orange oil. The oil was purified on Biotage system (5% EtOAc:95% Hexanes to 35% EtOAc:65% Hexanes, then isocratic 35% EtOAc:65% Hexanes). The product methyl 2-((4S)-6-(4-chlorophenyl)-1-methyl-4H-benzo[c]isoxazolo[4,5-e]azepin-4-yl)acetate (0.444 g, 1.166 mmol, 76% yield) was obtained as yellow foam after drying. LC/MS m/z 381 [M+H]$^+$.

3-((4S)-6-(4-Chlorophenyl)-1-methyl-4H-benzo[c]isoxazolo[4,5-e]azepin-4-yl)-1,1,1-trifluoropropane-2,2-diol

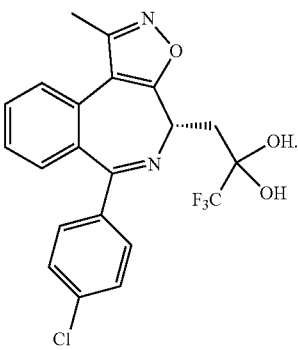 [SMILES: Cc1noc2c1-c1ccccc1C(c1ccc(Cl)cc1)=N[C@H]2CC(O)(O)C(F)(F)F]

A vial containing methyl 2-((4S)-6-(4-chlorophenyl)-1-methyl-4H-benzo[c]isoxazolo[4,5-e]azepin-4-yl)acetate (0.110 g, 0.289 mmol) and CsF (0.028 g, 0.184 mmol, dried under vacuum at 140° C. for 24 h) was evacuated and purged with N$_2$ (g), followed by addition of DME (1 mL). The heterogeneous mixture was cooled to 0° C. and trimethyl(trifluoromethyl)silane (0.085 mL, 0.578 mmol) was added in a dropwise manner. The reaction mixture was carefully monitored by LC-MS and TLC for complete consumption of starting methyl ester. After 30 min, aqueous 1 N HCl (1 mL) was added to the mixture. Vigorous evolution of gas was observed! The biphasic mixture was warmed to room temperature and diluted with MTBE. The aqueous layer was extracted with MTBE (2×), the combined organic extracts were washed with water, and dried over Na$_2$SO$_4$, and concentrated to give the (4S)-6-(4-chlorophenyl)-1-methyl-4-(3,3,3-trifluoro-2-methoxy-2-((trimethylsilyl)oxy)propyl)-4H-benzo[c]isoxazolo[4,5-e]azepinean as an orange-yellow oil. LC/MS m/z 523 [M+H]$^+$.

To a cooled (0° C.) solution of crude (4S)-6-(4-chlorophenyl)-1-methyl-4-(3,3,3-trifluoro-2-methoxy-2-((trimethylsilyl)oxy)propyl)-4H-benzo[c]isoxazolo[4,5-e]azepine in MeOH (3 mL) was added CsF (0.048 g, 0.316 mmol). The reaction was maintained at 0° C. for 30-60 min or until complete conversion of starting material to the desired ketone/di-hydrate was observed. The reaction mixture was diluted with MTBE and aqueous 1 N HCl was added until a phase cut was observed. The aqueous phase was extracted with MTBE (3×), the combined organic phases were washed with water, dried over Na$_2$SO$_4$, and concentrated to give the desired product as an orange oil. The product 3-((4S)-6-(4-chlorophenyl)-1-methyl-4H-benzo[c]isoxazolo[4,5-e]azepin-4-yl)-1,1,1-trifluoropropane-2,2-diol (0.121 g, 0.277 mmol, 96% yield) was used without further purification. LC/MS m/z 437 [M+H]$^+$.

Mixture of (2S)-3-((4S)-6-(4-chlorophenyl)-1-methyl-4H-benzo[c]isoxazolo[4,5-e]azepin-4-yl)-1,1,1-trifluoropropan-2-amine and (2R)-3-((4S)-6-(4-chlorophenyl)-1-methyl-4H-benzo[c]isoxazolo[4,5-e]azepin-4-yl)-1,1,1-trifluoropropan-2-amine
(Compound 232)

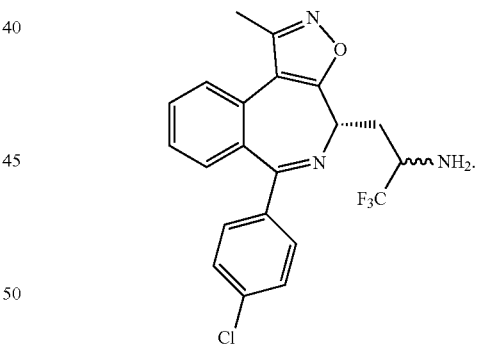

To a re-sealable vial containing a solution of 3-((4S)-6-(4-chlorophenyl)-1-methyl-4H-benzo[c]isoxazolo[4,5-e]azepin-4-yl)-1,1,1-trifluoropropane-2,2-diol (110 mg, 0.252 mmol) in toluene (1 mL) was added p-toluenesulfonic acid monohydrate (25 mg, 0.131 mmol) and benzylamine (50 μl, 0.458 mmol). The vial was sealed and heated to 110° C. for 1-2 h or until TLC (1% TEA:30% EtOAc:69% Hex) analysis indicated complete conversion to imine. The reaction mixture was subsequently cooled to room temperature, triethylamine (110 μl, 0.789 mmol) was introduced, and the reaction was again heated to 110° C. for 24 h. After 24 h, the reaction mixture was cooled to room temperature. The solution was diluted with MTBE and water. The aqueous layer was extracted with MTBE (3×) and the combined organic extracts were washed with additional water (1×). The combined organic layers were concentrated to yield an orange oil. To the oil was subsequently introduced CSA (37.5 mg, 0.161 mmol) and MeOH (5 mL) and the mixture was stirred for 3 h. The hydrolysis of the imine was followed by LC-MS and TLC. After complete hydrolysis (~3 h), the reaction mixture was concentrated to give a yellow oil. The oil was purified on Biotage system (gradient elution 5% EtOAc:95% Hexanes to 40% EtOAc:60% Hexanes) to give a 1:1 inseparable mixture of the titled product(s) (2S)-3-((4S)-6-(4-chlorophenyl)-1-methyl-4H-benzo[c]isoxazolo[4,5-e]azepin-4-yl)-1,1,1-trifluoropropan-2-amine and (2R)-3-((4S)-6-(4-chlorophenyl)-1-methyl-4H-benzo[c]isoxazolo[4,5-e]azepin-4-yl)-1,1,1-trifluoropropan-2-amine (43 mg, 0.102 mmol, 40.7% yield) as white solids. LC/MS m/z 420 [M+H]+; 1H NMR (400 MHz, DMSO-$d_6$) δ 7.86-7.80 (m, 2H), 7.75-7.69 (m, 2H), 7.44 (s, 12H), 4.34-4.18 (m, 2H), 3.82-3.63 (m, 1H), 3.58-3.41 (m, 1H), 2.53 (s, 3H), 2.52 (s, 3H), 2.15-2.08 (m, 2H), 2.06-2.00 (m, 2H).

Mixture of N-((2S)-3-((4S)-6-(4-chlorophenyl)-1-methyl-4H-benzo[c]isoxazolo[4,5-e]azepin-4-yl)-1,1,1-trifluoropropan-2-yl)acetamide and N-((2R)-3-((4S)-6-(4-chlorophenyl)-1-methyl-4H-benzo[c]isoxazolo[4,5-e]azepin-4-yl)-1,1,1-trifluoropropan-2-yl)acetamide (Compound 244)

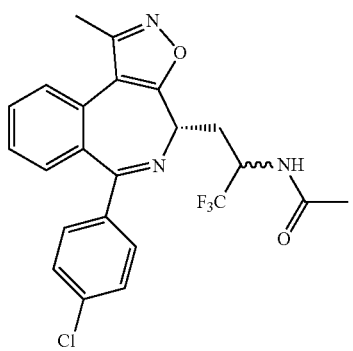

To a solution of 3-((4S)-6-(4-chlorophenyl)-1-methyl-4H-benzo[c]isoxazolo[4,5-e]azepin-4-yl)-1,1,1-trifluoropropan-2-amine (11 mg, 0.026 mmol) in CH$_2$Cl$_2$ (0.5 mL) was added DMAP (3.20 mg, 0.026 mmol), triethylamine (11 μl, 0.079 mmol), and acetic anhydride (2.72 μl, 0.029 mmol). The reaction mixture was stirred until the complete consumption of amine and formation of product was detected by LC-MS and TLC. The reaction mixture was concentrated in vacuo to give a thick paste. The paste was purified on Biotage (5% EtOAc:Hexanes to 40% EtOAc:Hexanes) The product N-(3-((4S)-6-(4-chlorophenyl)-1-methyl-4H-benzo[c]isoxazolo[4,5-e]azepin-4-yl)-1,1,1-trifluoropropan-2-yl)acetamide (10 mg, 0.022 mmol, 83% yield) was isolated as white solids. LC/MS m/z 462 [M+H]+; 1H NMR (400 MHz, Acetone-$d_6$) δ 7.87-7.80 (m, 2H), 7.75-7.68 (m, 2H), 7.51-7.35 (m, 12H), 5.46 (br. s, 1H), 5.16-5.00 (m, 1H), 4.16 (br. s, 1H), 4.05 (br. s, 1H), 3.01-2.83 (m, 2H), 2.68 (ddd, J=7.02, 9.80, 14.19 Hz, 1H), 2.55 (s, 3H), 2.54 (s, 3H), 2.51-2.39 (m, 1H), 1.90 (s, 3H), 1.83 (s, 3H).

Example 42

Synthesis of Compounds 250 and 251

Scheme 11 depicts the steps involved in the synthesis of the title compounds.

Scheme 11

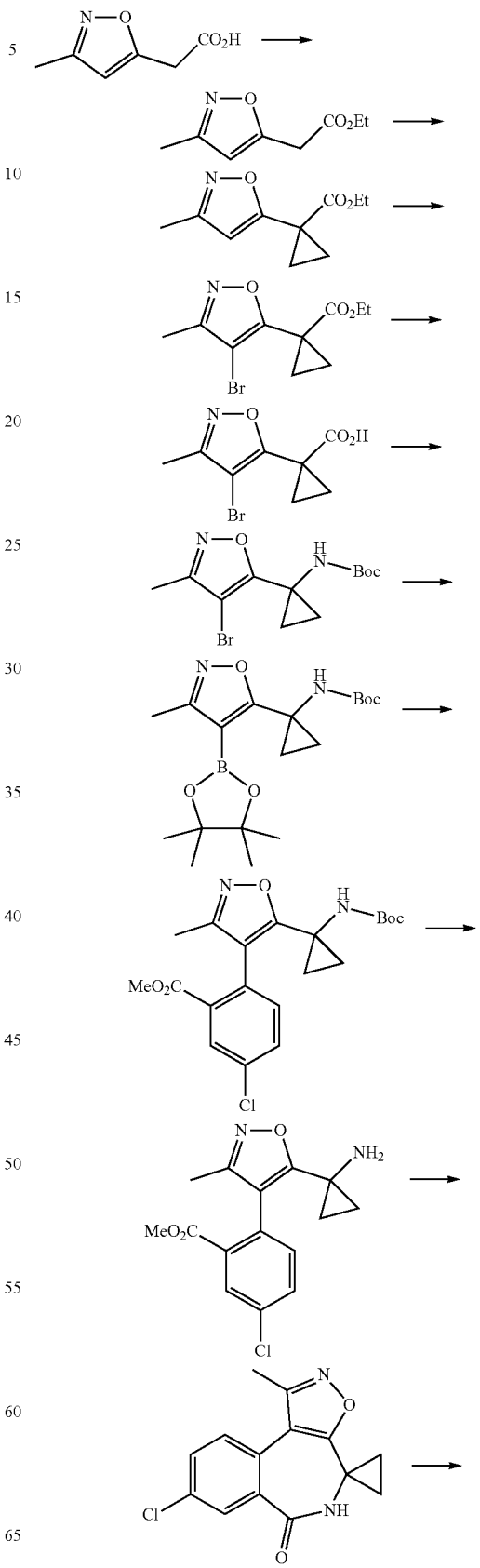

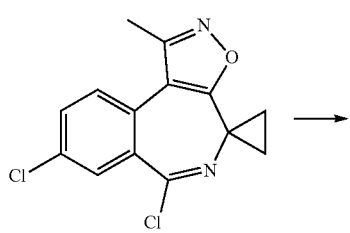

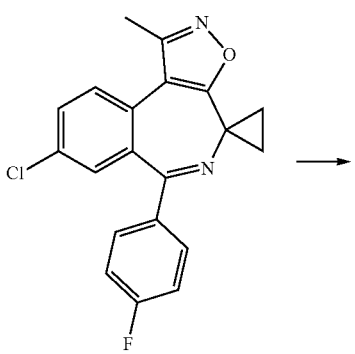

Compound 250

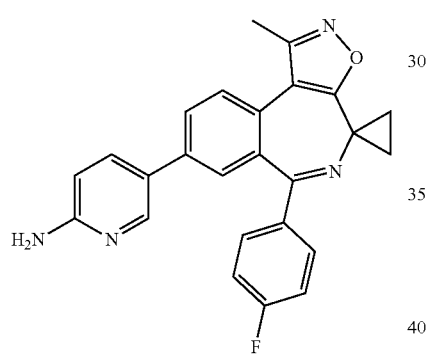

Compound 251

Ethyl 2-(3-methylisoxazol-5-yl)acetate

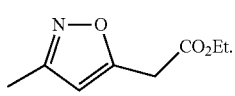

To a solution of 2-(3-methylisoxazol-5-yl)acetic acid (7.28 g, 51.6 mmol) in EtOH (200 mL, 3425 mmol) was added concentrated $H_2SO_4$ (0.30 mL, 5.63 mmol) at room temperature. After 48 h, the reaction mixture was concentrated in vacuo to give a dark brown oil. The crude ester was filtered over a plug of silica (50 g) and the product was eluted with 40% $Et_2O$:60% Hexanes (400 mL). The filtrate was subsequently concentrated to give the product ethyl 2-(3-methylisoxazol-5-yl)acetate (8.50 g, 50.2 mmol, 97% yield) as a clear oil. LC/MS m/z 170 [M+H]$^+$.

Ethyl 1-(3-methylisoxazol-5-yl)cyclopropanecarboxylate

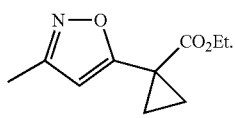

To a solution of ethyl 2-(3-methylisoxazol-5-yl)acetate (8.22 g, 48.6 mmol) in toluene (85 mL) was sequentially added n-tetrabutylammonium bromide (1.67 g, 5.18 mmol), 1,2-dibromoethane (7.0 mL, 81 mmol), and NaOH (30 mL, 582 mmol, ~19.4 M). The reaction mixture was vigorously stirred at room temperature. After 1 h, the reaction mixture was cooled to 0° C. and diluted with water (50 mL). The aqueous phase was extracted with MTBE (3×). The combined organic phases were washed 1 N HCl, water (2×), dried over $Na_2SO_4$, and concentrated to give the product ethyl 1-(3-methylisoxazol-5-yl)cyclopropanecarboxylate (9.49 g, 48.6 mmol, 100% yield) as a clear oil. LC/MS m/z 196 [M+H]$^+$.

Ethyl 1-(4-bromo-3-methylisoxazol-5-yl)cyclopropanecarboxylate

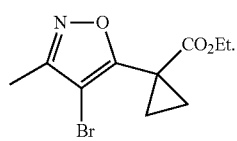

To a solution of ethyl 1-(3-methylisoxazol-5-yl)cyclopropanecarboxylate (9.49 g, 48.6 mmol) in anhydrous DMF (50 mL) was added N-bromosuccinimide (10.31 g, 57.9 mmol). The reaction mixture was stirred at room temperature for 24 h. To the orange mixture was added water and the aqueous layer was extracted with MTBE (3×). The combined organic layers were washed with aqueous 10% sodium thiosulfate, water (2×) and dried to provide the product ethyl 1-(4-bromo-3-methylisoxazol-5-yl)cyclopropanecarboxylate (12.5 g, 45.6 mmol, 94% yield) as a light yellow oil. The product was used directly in the subsequent reaction without further purification. LC/MS m/z 274 [M+H]$^+$.

1-(4-Bromo-3-methylisoxazol-5-yl)cyclopropanecarboxylic acid

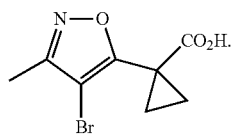

To a solution of ethyl 1-(4-bromo-3-methylisoxazol-5-yl)cyclopropanecarboxylate (11.8 g, 43.0 mmol) in THF (60 mL) was added aqueous NaOH (86 mL, 86 mmol, 1 M). The dark brown bi-phasic reaction mixture was vigorously stirred and heated to 45° C. until consumption of SM (3-4 h) was detected by LC-MS and TLC analysis. After 4 h, the homogeneous mixture was cooled to room temperature and diluted with hexanes. The organic phase was separated and the aqueous phase (pH ~14) was acidified with aqueous 1 N HCl (pH 1) (~100 mL). The product crystallizes upon acidification of the aqueous layer. After vigorously stirring for 30 min, the solids were filtered, washed with cold (0° C.) water (3×50 mL), and dried to give white crystals. The product 1-(4-bromo-3-methylisoxazol-5-yl)cyclopropanecarboxylic acid (10.0 g, 40.6 mmol, 94% yield) was isolated as white crystals. LC/MS m/z 246 [M+H]$^+$.

Tert-Butyl (1-(4-bromo-3-methylisoxazol-5-yl)cyclopropyl)carbamate

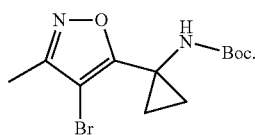 [SMILES: Cc1noc(C2(NC(=O)OC(C)(C)C)CC2)c1Br]

To a suspension of 1-(4-bromo-3-methylisoxazol-5-yl)cyclopropanecarboxylic acid (1.60 g, 6.50 mmol) and powdered 4 Å molecular sieves (pre-dried-0.767 g, 48% wt) in toluene (15 mL) was sequentially added N,N-diisopropylethylamine (1.50 mL, 8.59 mmol), diphenyl phosphorazidate (1.576 mL, 7.05 mmol), and tert-butanol (16.80 mL, 176 mmol). The reaction vessel was fitted with a reflux condenser and the mixture was heated to 100° C. for 1 h. After 1 h, the reaction mixture was cooled to room temperature and filtered over a plug of Celite. The filter cake was washed with EtOAc (3×), and the filtrate was concentrated to give a brown oil. The oil was purified on Biotage system (5% EtOAc:95% Hexanes to 20% EtOAc:80% Hexanes). The product tert-butyl 1-(4-bromo-3-methylisoxazol-5-yl)cyclopropylcarbamate (1.55 g, 4.89 mmol, 75% yield) was isolated as white crystals after concentration. LC/MS m/z 317 [M+H]$^+$.

Tert-Butyl (1-(3-methyl-4-(4,4,5,5-tetramethyl-1,3,2-dioxaborolan-2-yl)isoxazol-5-yl)cyclopropyl)carbamate

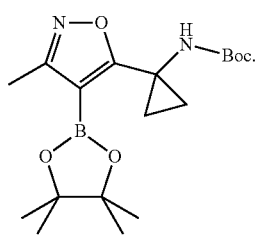 [SMILES: Cc1noc(C2(NC(=O)OC(C)(C)C)CC2)c1B1OC(C)(C)C(C)(C)O1]

To a 50 mL round bottom flask containing tert-butyl 1-(4-bromo-3-methylisoxazol-5-yl)cyclopropylcarbamate (0.219 g, 0.621 mmol) was added dichlorobis(acetonitrile)palladium(II) (0.0025 g, 9.64 μmol), dicyclohexyl(2',6'-dimethoxybiphenyl-2-yl)phosphine (0.0134 g, 0.033 mmol), followed by anhydrous 1,4-dioxane (0.40 mL). The reaction vessel was evacuated and purged with N$_2$ (g) (3×). To the flask was added 4,4,5,5-tetramethyl-1,3,2-dioxaborolane (0.153 mL, 1.056 mmol) and triethylamine (0.294 mL, 2.113 mmol) sequentially. The reaction vessel was evacuated and purged with N$_2$ (g) again, then heated to 100° C. The reaction mixture became heterogeneous and was judged complete within 1 h by LC-MS. The heterogeneous mixture was cooled to room temperature, dilute with EtOAc and the mixture was filtered over a plug of Celite. The filter cake was rinsed with EtOAc (3×) and the filtrate was concentrated to give a yellow oil, that crystallized upon standing under vacuum. The product tert-butyl 1-(3-methyl-4-(4,4,5,5-tetramethyl-1,3,2-dioxaborolan-2-yl)isoxazol-5-yl)cyclopropylcarbamate (0.226 g, 0.620 mmol, 100% yield) was used without further purification. LC/MS m/z 365 [M+H]$^+$.

Methyl 2-(5-(1-(((tert-butoxycarbonyl)amino)cyclopropyl)-3-methylisoxazol-4-yl)-5-chlorobenzoate

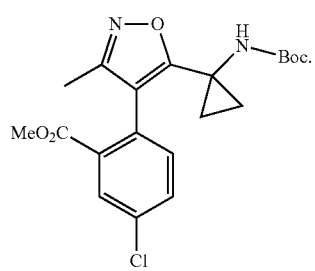 [SMILES: COC(=O)c1cc(Cl)ccc1-c1c(C)noc1C1(NC(=O)OC(C)(C)C)CC1]

A re-sealable vial containing methyl 2-bromo-5-chlorobenzoate (0.205 g, 0.822 mmol), Pd(Ph$_3$P)$_4$ (0.042 g, 0.036 mmol), and anhydrous potassium phosphate, tribasic (0.275 g, 1.296 mmol) was evacuated and purged with N$_2$ (g) (3×). To the solids was added a solution of tert-butyl 1-(3-methyl-4-(4,4,5,5-tetramethyl-1,3,2-dioxaborolan-2-yl)isoxazol-5-yl)cyclopropylcarbamate (0.236 g, 0.648 mmol) in MeOH (2×1 mL, 2 mL total) and 1,4-Dioxane (2×1 mL, 2 mL total). The suspension was evacuated and purged with N$_2$ (g) (3×), the vial was sealed, and the contents heated to 80° C. LC-MS analysis indicated complete conversion to desired product with in 4 h. After 4 h, the reaction mixture was cooled to room temperature and filtered over Celite. The filter cake was washed with MeOH (3×) and the filtrate was concentrated to give a brown oil. The oil was purified on Biotage system (5% EtOAc:95% Hexanes to 30% EtOAc:70% Hexanes, then isocratic 30% EtOAc:70% Hexanes). The product methyl 2-(5-(1-(tert-butoxycarbonylamino)cyclopropyl)-3-methylisoxazol-4-yl)-5-chlorobenzoate (0.226 g, 0.555 mmol, 86% yield) was isolated as a clear oil. LC/MS m/z 407 [M+H]$^+$.

8-Chloro-1-methylspiro[benzo[c]isoxazolo[4,5-e]azepine-4,1'-cyclopropan]-6(5H)-one

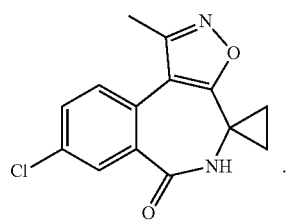 [SMILES: Cc1noc2c1-c1ccc(Cl)cc1C(=O)NC21CC1]

To a solution of methyl 2-(5-(1-(tert-butoxycarbonylamino)cyclopropyl)-3-methylisoxazol-4-yl)-5-chlorobenzoate (131 mg, 0.322 mmol) in MeOH (2 mL) was added anhydrous HCl (1.00 mL, 4.00 mmol, 4 M in 1,4-dioxane). The reaction mixture was stirred at room temperature for 6 h, at which point LC-MS analysis indicated complete consumption of N-Boc carbamate and formation of desired product. The reaction mixture was concentrated in vacuo and excess HCl was azeotropically removed with MeOH (1×1 mL), toluene (1×1 mL), and THF (1×1 mL). The resultant yellow oil was dried for 10 min LC/MS m/z 307 [M+H]⁺.

To a cooled (−40° C.) suspension of crude ammonium hydrochloride salt (~100 mg) in THF (1.5 mL) was added isopropylmagnesium bromide (0.400 mL, 1.160 mmol) in a dropwise manner. After complete addition, the reaction mixture was allowed to warm to room temperature and stirred for an additional 15 min. To the reaction mixture was added aqueous 1 N HCl (until pH ~1 was obtained for the aqueous layer). The aqueous phase was extracted with EtOAc and the combined organic phase was washed with water, dried over Na₂SO₄ and concentrated to give the product 8-chloro-1-methylspiro[benzo[e]isoxazolo[5,4-c]azepine-4,1'-cyclopropan]-6(5H)-one (0.0631 g, 0.230 mmol, 71.3% yield over 2-steps) as light yellow solids. The crude product was sufficiently pure by LC-MS analysis and used without further purification. LC/MS m/z 275 [M+H]⁺.

6,8-Dichloro-1-methylspiro[benzo[c]isoxazolo[4,5-e]azepine-4,1'-cyclopropane]

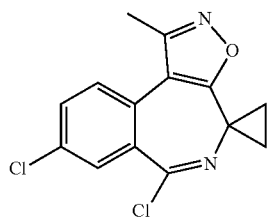

To a vial containing 8-chloro-1-methylspiro[benzo[e]isoxazolo[5,4-c]azepine-4,1'-cyclopropan]-6(5H)-one (0.0631 g, 0.230 mmol) was added CH₂Cl₂ (1 mL). The reaction mixture was heterogeneous and to aid in solubility CHCl₃ (0.5 mL) was added. To the homogeneous mixture was added phosphorous pentachloride (0.092 g, 0.442 mmol) in one portion at room temperature. The reaction mixture eventually turned heterogeneous again (~<10 min) and LC-MS analysis after ~30 min indicated complete consumption of starting material and formation of desired product. The mixture was diluted with EtOAc and aqueous 10% Na₂CO₃ (2.8 mL). After initial effervescence, the mixture was stirred for an additional 5-10 min, and the aqueous layer was extracted with EtOAc (3×). The combine organic extracts were washed with water, brine, dried over Na₂SO₄ and concentrated to give yellow solids. The solids were filtered over a plug of silica and eluted with 30% EtOAc:70% Hexanes. The product 6,8-dichloro-1-methylspiro[benzo[e]isoxazolo[5,4-c]azepine-4,1'-cyclopropane] (61.8 mg, 0.211 mmol, 92% yield) was obtained as off-white solids. LC/MS m/z 293 [M+H]⁺.

8-Chloro-6-(4-fluorophenyl)-1-methylspiro[benzo[c]isoxazolo[4,5-e]azepine-4,1'-cyclopropane] (Compound 250)

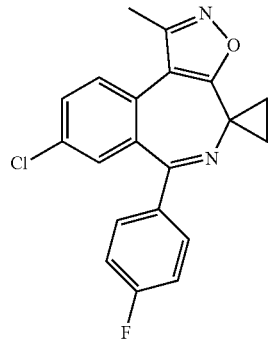

To a solution of 6,8-dichloro-1-methylspiro[benzo[e]isoxazolo[5,4-c]azepine-4,1'-cyclopropane] (61.9 mg, 0.211 mmol) in toluene (22 mL) was added 4-fluorophenylboronic acid (37 mg, 0.264 mmol) and Pd(Ph₃P)₄ (11.22 mg, 9.71 μmol). The reaction was evacuated and purged with N₂ (g) (3×), followed by addition of aqueous Na₂CO₃ (211 μl, 0.422 mmol, 2 M). The reaction was heated to 82° C. for 15 min at which time LC-MS analysis indicated complete conversion to desired product. The reaction mixture was cooled to room temperature and diluted with water. The aqueous layer was extracted with EtOAc (3×) and the combined organic extracts were dried over Na₂SO₄, and concentrated in vacuo. The crude product was purified on Biotage system (5% EtOAc:95% Hexanes to 10% EtOAc:90% Hexanes). The product 8-chloro-6-(4-fluorophenyl)-1-methylspiro[benzo[e]isoxazolo[5,4-c]azepine-4,1'-cyclopropane] (62 mg, 0.176 mmol, 83% yield) was obtained as a white crystals. LC/MS m/z 353 [M+H]⁺; ¹H NMR (400 MHz, DMSO-d₆) δ 7.81-7.77 (m, 1H), 7.75-7.71 (m, 1H), 7.45-7.38 (m, 2H), 7.19-7.26 (m, 3H), 2.52 (s, 3H), 1.29 (s, 4H).

5-(6-(4-Fluorophenyl)-1-methylspiro[benzo[c]isoxazolo[4,5-e]azepine-4,1'-cyclopropan]-8-yl)pyridin-2-amine (Compound 251)

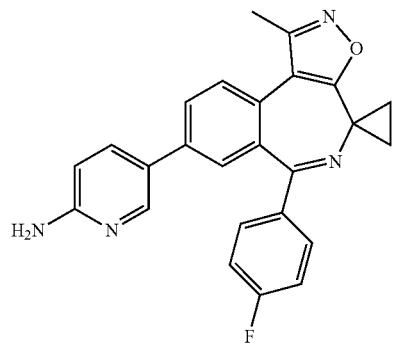

To a 25 mL round bottom flask containing 8-chloro-6-(4-fluorophenyl)-1-methylspiro[benzo[e]isoxazolo[5,4-c]azepine-4,1'-cyclopropane](57 mg, 0.162 mmol) was added Pd₂(dba)₃ (9.1 mg, 9.94 μmol), tri-tert-butylphosphonium tetrafluoroborate (6.5 mg, 0.022 mmol), potassium phosphate (77 mg, 0.363 mmol), and 5-(4,4,5,5-tetramethyl-1,3,2-dioxaborolan-2-yl)pyridin-2-amine (56 mg, 0.254 mmol). The flask was evacuated and purged with $N_2$ (g) (3×), followed by addition of 1,4-dioxane (1 mL) and water (0.05 mL). The flask was evacuated and purged with $N_2$ (g) (3×) and the reaction mixture was heated to 100° C. After 3 h, ~50% conversion of starting material was observed by LC-MS analysis. The reaction mixture was cooled to room temperature and additional $Pd_2(dba)_3$ (9.1 mg, 9.94 μmol), tri-tert-butylphosphonium tetrafluoroborate (6.5 mg, 0.022 mmol), potassium phosphate (77 mg, 0.363 mmol), and 5-(4,4,5,5-tetramethyl-1,3,2-dioxaborolan-2-yl)pyridin-2-amine (56 mg, 0.254 mmol) were introduced. The mixture was subsequently heated again for an additional 24 h. LC-MS analysis after 24 h, indicated ~80% conversion to desired product. The reaction mixture was cooled and filtered over a pad of Celite. The filter cake was washed with EtOAc (3×) and the filtrate was concentrated to give a dark brown oil. The oil was purified on Biotage system (25% EtOAc:75% Hexanes to 70% EtOAc:30% Hexanes, then isocratic 70% EtOAc:30% Hexanes). The product was concentrated to give gummy yellow solid that was contaminated with 2-amino-pyridine. The solid was triturated with IPA (1 mL) and $Et_2O$ (1 mL) and filtered. The solids were washed with ether (1 mL) and filtered. The amino pyridine (yellow color) was cleanly removed in the rinses and the product 5-(6-(4-fluorophenyl)-1-methylspiro[benzo[e]isoxazolo[5,4-c]azepine-4,1'-cyclopropane]-8-yl)pyridin-2-amine (0.032 g, 0.078 mmol, 48.3% yield) was isolated as white-solids. LC/MS m/z 411 [M+H]$^+$; $^1$H NMR (400 MHz, DMSO-$d_6$) δ 8.16 (d, J=2.49 Hz, 1H), 7.86 (dd, J=1.97, 8.21 Hz, 1H), 7.79 (s, 1H), 7.59 (dd, J=2.60, 8.62 Hz, 1H), 7.49-7.42 (m, 2H), 7.37 (d, J=1.87 Hz, 1H), 7.24-7.15 (m, 2H), 6.49 (dd, J=0.62, 8.72 Hz, 1H), 6.14 (s, 2H), 2.54 (s, 3H), 1.28 (d, J=6.02 Hz, 4H).

Example 42A

Synthesis of Compound 265

4-bromo-N-methoxy-N,1-dimethyl-1H-pyrazole-3-carboxamide

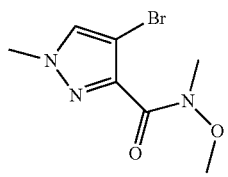

A mixture of 4-bromo-1-methyl-1H-pyrazole-3-carboxylic acid (2.04 g, 10 mmol), 2-(1H-benzotriazole-1-yl)-1,1,3,3-tetramethyluronium tetrafluoroborate (3.21 g, 10 mmol), N,O-dimethylhydroxylamine (1.22 g, 20 mmol) in N,N-Diisopropylethylamine (5 mL) and N,N-Dimethylformamide (20 mL) was stirred for 12 h at room temperature. The mixture was concentrated in vacuum, and the residue was purified by flash chromatography eluting with petroleum ether/ethyl acetate=5:1 to give the titled product as a colorless oil (2.4 g, 97%). LC/MS m/z 247 [M+H]$^+$.

(4-bromo-1-methyl-1H-pyrazol-3-yl)(4-chlorophenyl)methanone

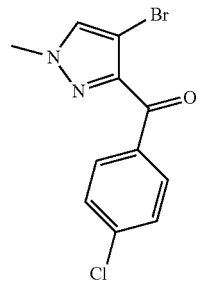

To a solution of compound 4-bromo-N-methoxy-N,1-dimethyl-1H-pyrazole-3-carboxamide (1.0 g, 4 mmol) in anhydrous tetrahydrofuran (20 mL) under nitrogen atmosphere was added (4-chlorophenyl)magnesium bromide (8 mL) in tetrahydrofuran (1 M) at 0° C., The resulting mixture was stirred for 2 h at room temperature. The reaction was quenched by saturated solution of ammonium chloride, and dichloromethane (100 mL) was added, the separated organic layer was dried over anhydrous sodium sulfate and concentrated in vacuum. The residue was purified by flash chromatography eluting with petroleum ether/ethyl acetate=5:1 to give the titled product as a white solid (1.0 g, 84%). LC/MS m/z 298 [M+H]$^+$; $^1$H NMR (300 MHz, CDCl$_3$) δ 8.10 (d, J=9 Hz, 2H), 7.53 (s, 1H), 7.43 (d, J=9 Hz, 2H), 3.99 (s, 3H).

(4-(3-(4-chlorobenzoyl)-1-methyl-1H-pyrazol-4-yl)-3-methylisoxazol-5-yl)methyl acetate

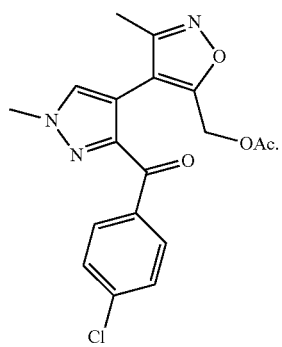 [SMILES: CC(=O)OCc1onc(C)c1-c1cn(C)nc1C(=O)c1ccc(Cl)cc1]

A solution of (4-bromo-1-methyl-1H-pyrazol-3-yl)(4-chlorophenyl)methanone (4-bromo-1-methyl-1H-pyrazol-3-yl)(4-chlorophenyl)methanone (0.5 g, 1.7 mmol), [1,1'-bis(diphenylphosphino)ferrocene]palladium(II) chloride (62 mg, 0.085 mmol), $K_2CO_3$ (0.94 g, 6.8 mmol), (3-methyl-4-(4,4,5,5-tetramethyl-1,3,2-dioxaborolan-2-yl)isoxazol-5-yl) methyl acetate (0.96 g, 3.4 mmol) in water (2 mL) and 1,4-dioxane (10 mL) was heated at 90° C., and stirred for 4 hours. After cooling to room temperature, DCM (100 mL) was added and the layers separated. The separated organic layer was dried over anhydrous sodium sulfate and concentrated. The residue was purified by flash chromatography eluting with petroleum ether/ethyl acetate=5:1 to give the titled product as a yellow oil (0.3 g, 47%). LC/MS m/z 373 [M+H]$^+$.

(4-chlorophenyl)(4-(5-(hydroxymethyl)-3-methyl-isoxazol-4-yl)-1-methyl-1H-pyrazol-3-yl)methanone

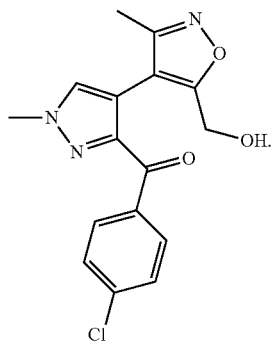 [SMILES: Cc1noc(CO)c1-c1cn(C)nc1C(=O)c1ccc(Cl)cc1]

To a solution of (4-(3-(4-chlorobenzoyl)-1-methyl-1H-pyrazol-4-yl)-3-methylisoxazol-5-yl)methyl acetate (0.3 g, 0.8 mmol) in THF (10 mL), was added NaOH solution (5 mL, 1 N in water). The mixture was stirred for 2 hours at 55° C. After cooling to room temperature, DCM (50 mL) was added and the layers separated. The separated organic layer was dried over anhydrous sodium sulfate and concentrated to afford the titled product as a yellow oil (0.2 g, 75% yield). LC/MS m/z 331 [M+H]$^+$; $^1$H NMR (300 MHz, CDCl$_3$) δ 8.13 (d, J=9 Hz, 2H), 7.45 (d, J=9 Hz, 3H), 4.62 (s, 2H), 4.07 (s, 3H), 2.15 (s, 3H).

(4-(3-(4-chlorobenzoyl)-1-methyl-1H-pyrazol-4-yl)-3-methylisoxazol-5-yl)methyl methanesulfonate

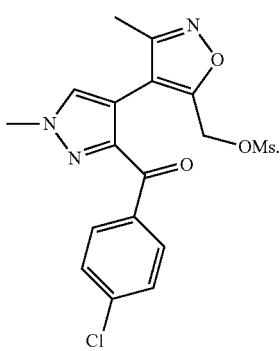 [SMILES: Cc1noc(COS(C)(=O)=O)c1-c1cn(C)nc1C(=O)c1ccc(Cl)cc1]

To a solution of (4-chlorophenyl)(4-(5-(hydroxymethyl)-3-methylisoxazol-4-yl)-1-methyl-1H-pyrazol-3-yl)methanone (0.05 g, 0.15 mmol) in DCM (10 mL), was added triethylamine (0.1 mL) and methane sulfonyl chloride (0.05 mL) at room temperature. The mixture was stirred for 2 h at room temperature. DCM (50 mL) and saturated sodium bicarbonate solution (20 mL) were added. The combined organic layers were dried over anhydrous sodium sulfate and concentrated to afford the titled product as yellow oil (0.035 g, 56%). LC/MS m/z 409 [M+H]$^+$.

(4-(5-(azidomethyl)-3-methylisoxazol-4-yl)-1-methyl-1H-pyrazol-3-yl)(4-chlorophenyl)methanone

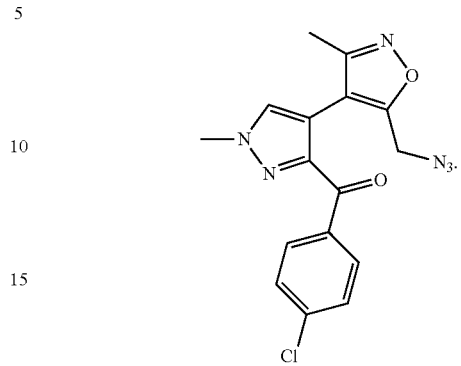

A mixture of (4-(3-(4-chlorobenzoyl)-1-methyl-1H-pyrazol-4-yl)-3-methylisoxazol-5-yl)methyl methanesulfonate (35 mg, 0.09 mmol), sodium azide (12 mg, 0.18 mmol) in N,N-dimethylformamide (10 mL) was heated to 80° C. and stirred for 10 h. After cooling to room temperature, the mixture was concentrated, and the residue was purified by flash chromatography eluting with petroleum ether/ethyl acetate=1:3 to give the titled product as a colorless oil (30 mg, 94%). LC/MS: m/z 356 [M+H]$^+$; $^1$H NMR (300 MHz, CDCl$_3$) δ 8.16 (d, J=9 Hz, 2H), 7.50 (s, 1H), 7.46 (d, J=9 Hz, 2H), 4.37 (s, 2H), 4.09 (s, 3H), 2.19 (s, 3H).

6-(4-chlorophenyl)-1,8-dimethyl-4,8-dihydroisoxazolo[5,4-c]pyrazolo[4,3-e]azepine (Compound 265)

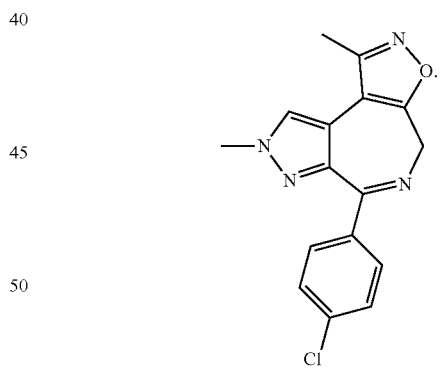

To a solution of (4-(5-(azidomethyl)-3-methylisoxazol-4-yl)-1-methyl-1H-pyrazol-3-yl)(4-chlorophenyl)methanone (0.03 g, 0.08 mmol) in anhydrous THF (10 mL), was added triphenylphosphine (32 mg, 0.12 mmol) at room temperature. The mixture was stirred for 12 h at room temperature. The mixture was concentrated and the residue was purified by flash chromatography eluting with (petroleum ether/ethyl acetate=1:3) to afford the title compound as a white solid (15 mg, 60% yield). LC/MS: m/z 312 [M+H]$^+$; $^1$H NMR (300 MHz, CDCl$_3$) δ 7.62 (d, J=9 Hz, 3H), 7.36 (d, J=9 Hz, 2H), 4.87 (s, 2H), 4.08 (s, 3H), 2.45 (s, 3H).

Example 43

Synthesis of Compound 209

(2R)-tert-butyl 2-((6S)-2,3,9-trimethyl-4-oxo-5,6-dihydro-4H-isoxazolo[4,5-e]thieno[3,2-c]azepin-6-yl)propanoate

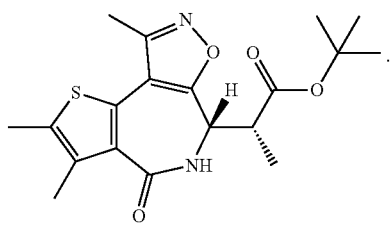 [SMILES: Cc1noc2c1-c1sc(C)c(C)c1C(=O)N[C@H]2[C@@H](C)C(=O)OC(C)(C)C]

To a round bottomed flask was added THF (50 mL) and diisopropylamine (1.29 mL, 9.10 mmol) before the solution was cooled to 0° C. To this solution was added n-BuLi (3.62 mL, 8.69 mmol) and the reaction was stirred at 0° C. for 10 min before cooling to −78° C. and addition of tert-butyl 2-((6S)-2,3,9-trimethyl-4-oxo-5,6-dihydro-4H-isoxazolo[4,5-e]thieno[3,2-c]azepin-6-yl)acetate (1.5 g, 4.14 mmol), a form of intermediate 17, prepared according to Example 14. The solution was stirred at −78° C. for 1 h before addition of iodomethane (0.285 mL, 4.55 mmol) and warming to room temperature overnight. The reaction was quenched with saturated aqueous $NH_4Cl$ solution and then diluted with water and brine. The aqueous layer was extracted with EtOAc and the combined organic layer was dried over $Na_2SO_4$, filtered, and concentrated. The crude residue was purified via Biotage (MTBE/hexanes) to afford the titled product (0.259 g, 0.688 mmol).

(2R)-2-((6S)-4-(4-cyanophenyl)-2,3,9-trimethyl-6H-isoxazolo[5,4-c]thieno[2,3-e]azepin-6-yl)propanamide (Compound 209)

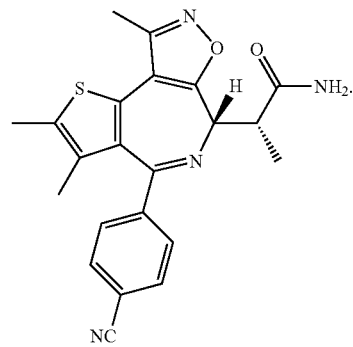 [SMILES: Cc1noc2c1-c1sc(C)c(C)c1C(c1ccc(C#N)cc1)=N[C@H]2[C@@H](C)C(N)=O]

This compound was synthesized from. (2R)-tert-butyl 2-((6S)-2,3,9-trimethyl-4-oxo-5,6-dihydro-4H-isoxazolo[4,5-e]thieno[3,2-c]azepin-6-yl)propanoate following general procedures H, L to afford the titled compound (0.099 g, 0.245 mmol).

Example 44

Additional Compounds of the Invention

Additional compounds of the invention made by the various schemes disclosed above are set forth in Table 13 below, including the identification of the final steps utilized in their syntheses.

TABLE 13

Other Compounds of the Invention

| Compound No. | Structure | Physical Data | Final steps |
|---|---|---|---|
| 200 | 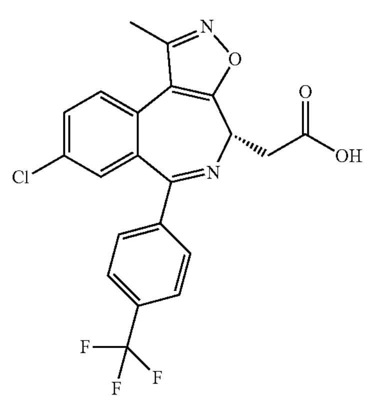 [SMILES: Cc1noc2c1-c1ccc(Cl)cc1C(c1ccc(C(F)(F)F)cc1)=N[C@H]2CC(=O)O] | LC/MS m/z 435 [M + H]$^+$; $^1$H NMR (400 MHz, DMSO-$d_6$) δ 7.94-7.85 (m, 1H), 7.83-7.73 (m, 4H), 7.53 (d, J = 8.2 Hz, 2H), 7.44 (d, J = 2.1 Hz, 1H), 4.38 (br. s, 2H), 3.34 (br. s, 1H), 2.51 (s, 2H). | H, L (amide formation step was eliminated) |

TABLE 13-continued

Other Compounds of the Invention

| Compound No. | Structure | Physical Data | Final steps |
|---|---|---|---|
| 209 | 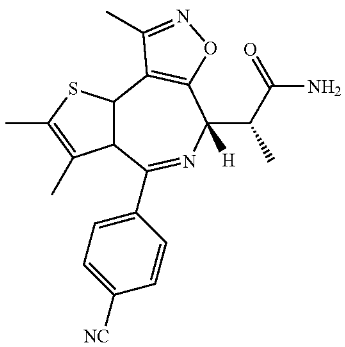 [SMILES: CC1=C(C)C2C(c3ccc(C#N)cc3)=N[C@@H]([C@@H](C)C(N)=O)c3onc(C)c3C2S1] | LC/MS m/z 405 [M + H]$^+$; $^1$H NMR (400 MHz, DMSO-d$_6$) δ 7.86 (d, J = 8.47 Hz, 2H), 7.65 (br. s, 1H), 7.40 (d, J = 8.01 Hz, 2H), 7.02 (br. s, 1H), 3.88 (d, J = 10.30 Hz, 1H), 3.55 (dd, J = 6.98, 10.41 Hz, 1H), 2.45 (s, 3H), 2.41 (s, 3H), 1.58 (s, 3H), 1.27 (d, J = 6.64 Hz, 3H). | H, L |
| 202 | 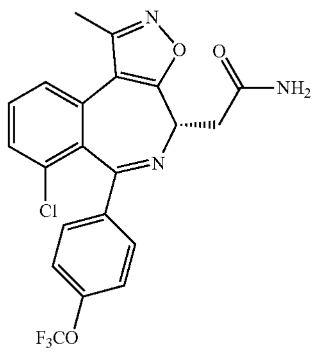 [SMILES: Cc1noc2c1-c1cccc(Cl)c1C(c1ccc(OC(F)(F)F)cc1)=N[C@H]2CC(N)=O] | LC/MS m/z 449 [M + H]$^+$; $^1$H NMR (300 MHz, Acetone-d$_6$) δ 7.85-7.88 (m, 1H), 7.74 (t, J = 9 Hz, 1H), 7.51-7.54 (m, 1H), 7.39-7.44 (m, 2H), 7.24-7.27 (m, 2H), 7.18 (s, 1H), 6.43 (m, 1H), 4.5 (t, J = 6 Hz, 1H), 3.37 (d, J = 3 Hz, 2H), 2.56 (s, 3H). | H, L |

Example 44A

Biological Activity of Compounds 192-266

The activity of Compounds 192-266 in the BRD4 AlphaLisa Binding Assay ("Alphascreen") (see Example 24), cMyc RNA quantification assay and Cell-based IL-6 quantification assay are set forth in Table 14, below. In Table 14, n.t.=not tested, "+" represents a value under 0.50 µM; "++" a value between 0.50 µM and 1 µM; and "+++" a value greater than 1 µM.

TABLE 14

Activity of Compounds 192-266.

| Compound # | Alpha screen | IL6 | MYC-Raji | MYC-MV411 |
|---|---|---|---|---|
| 192 | + | ++ | ++ | n.t. |
| 193 | ++ | +++ | n.t. | n.t. |
| 194 | +++ | +++ | n.t. | n.t. |
| 195 | +++ | +++ | n.t. | n.t. |
| 196 | +++ | ++ | +++ | n.t. |
| 197 | + | + | + | n.t. |
| 198 | + | + | ++ | n.t. |
| 199 | + | + | + | n.t. |
| 200 | +++ | +++ | +++ | n.t. |
| 201 | + | + | ++ | n.t. |
| 202 | + | + | + | + |
| 203 | + | + | + | + |
| 204 | + | + | ++ | n.t. |
| 205 | + | + | +++ | n.t. |
| 206 | + | + | + | + |
| 208 | + | + | + | + |
| 209 | + | + | ++ | + |
| 210 | + | + | ++ | + |
| 211 | + | + | n.t. | ++ |
| 212 | + | + | n.t. | + |
| 213 | + | + | n.t. | + |
| 214 | + | + | n.t. | + |
| 215 | +++ | +++ | n.t. | +++ |
| 216 | + | + | n.t. | + |
| 217 | + | + | n.t. | + |
| 218 | +++ | +++ | n.t. | +++ |
| 219 | +++ | +++ | n.t. | ++ |
| 220 | +++ | +++ | n.t. | +++ |
| 221 | +++ | +++ | n.t. | +++ |
| 222 | + | + | n.t. | + |
| 223 | +++ | +++ | n.t. | +++ |
| 224 | + | + | n.t. | + |
| 225 | + | + | n.t. | + |
| 226 | + | + | n.t. | + |
| 227 | +++ | +++ | n.t. | +++ |
| 228 | +++ | +++ | n.t. | +++ |
| 229 | +++ | +++ | n.t. | +++ |
| 230 | + | + | n.t. | ++ |
| 231 | + | + | n.t. | + |
| 232 | +++ | +++ | n.t. | +++ |
| 233 | + | ++ | n.t. | ++ |
| 234 | + | ++ | n.t. | ++ |
| 235 | + | + | n.t. | + |
| 236 | + | + | n.t. | + |
| 237 | + | + | n.t. | + |
| 238 | +++ | +++ | n.t. | +++ |
| 239 | + | + | n.t. | + |
| 240 | +++ | +++ | n.t. | +++ |
| 241 | + | + | n.t. | + |
| 242 | ++ | +++ | n.t. | +++ |

TABLE 14-continued

Activity of Compounds 192-266.

| Compound # | Alpha screen | IL6 | MYC-Raji | MYC-MV411 |
|---|---|---|---|---|
| 243 | ++ | +++ | n.t. | +++ |
| 244 | +++ | +++ | n.t. | +++ |
| 245 | + | + | n.t. | + |
| 246 | ++ | +++ | n.t. | +++ |
| 247 | + | + | n.t. | ++ |
| 248 | + | + | n.t. | + |
| 249 | + | + | n.t. | + |
| 250 | +++ | +++ | n.t. | +++ |
| 251 | + | + | n.t. | + |
| 252 | +++ | +++ | n.t. | +++ |
| 253 | + | + | n.t. | + |
| 254 | ++ | +++ | n.t. | +++ |
| 255 | + | + | n.t. | ++ |
| 256 | +++ | +++ | n.t. | +++ |
| 257 | + | ++ | n.t. | +++ |
| 258 | + | n.t. | n.t. | n.t. |
| 259 | + | n.t. | n.t. | n.t. |
| 260 | + | n.t. | n.t. | n.t. |
| 261 | + | + | n.t. | n.t. |
| 262 | + | + | n.t. | n.t. |
| 263 | + | + | n.t. | n.t. |
| 264 | +++ | +++ | n.t. | n.t. |
| 265 | +++ | +++ | n.t. | n.t. |
| 266 | + | + | n.t. | n.t. |

Example 44B

In-Vivo Inhibition of LPS-Induced IL-6 Production Protocol

Female Balb/C mice, 6 weeks old upon arrival at animal facility, and weighing 18-20 g/mouse were used for this assay. The mice are acclimated in animal facility for 5-7 days prior experiment initiation. Mice were randomly divided into experimental groups to include several doses of test article, and vehicle and dexamethasone controls. Mice were fasted from 12 hours prior to study initiation (dosing), but allowed free access to water. Mice were dosed following study group design by oral gavage 30 min prior to LPS stimulation. Dosing interval time was 1 min/mouse.

Two hours after LPS challenge animals were anesthetized by $CO_2$ inhalation, and blood was sampled via cardiac puncture into EDTA coated tubes and placed on ice. Plasma was separated by centrifugation at 3000 g at 4° C. for 15 min. The separated plasma was divided into aliquots (50 ul/aliquot) and stored at −80° C. until plasma IL-6 ELISA and drug levels were analyzed. Compound concentrations are also sampled from satellite groups 30 min after dosing (and hence at time of LPS stimulation).

ELISA were run by following standard protocols and $ED_{50}$ was calculated based on 50% inhibition compared to vehicle control. The results are set forth in Table 15. ("++" indicates an $ED_{50}$ of less than 10 mg/kg; "+" indicates and $ED_{50}$ of between 10 and 50 mg/kg.

TABLE 15

| Compound # | $ED_{50}$ (mg/kg) |
|---|---|
| 110 | ++ |
| 128 | ++ |
| 129 | ++ |
| 132 | ++ |
| 144 | ++ |
| 148 | + |
| 165 | + |

Example 45

Myc RNA Quantification in Xenograft Model

Female NOD SCID mice (Harlan) were inoculated s.c. with $3 \times 10^6$ Raji cells per mouse resuspended in 10% Matrigel. Tumors were grown until they reached a size of 200 mm³ to 400 mm³ as measured by caliper. Mice were treated orally (5 mL/kg) with different doses of compounds prepared as a 2 mg/mL suspension of Carboxy-methyl-cellulose. At the indicated time points after treatment, tumors were harvested. RNA was isolated by using TRIzol extraction and processed for QuantiGene® Assay. $ED_{50}$s were calculated based on 50% inhibition compared to vehicle control. The results are set forth in Table 16. ("++" indicates an $ED_{50}$ of less than 20 mg/kg; "+" indicates and $ED_{50}$ of between 20 and 50 mg/kg.

TABLE 16

| Compound # | $ED_{50}$ (mg/kg) |
|---|---|
| 110 | + |
| 129 | + |
| 132 | ++ |
| 144 | ++ |
| 114 | + |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

We claim:

1. A method of treating a cancer selected from adenocarcinoma, adenoid cystic carcinoma, adult T-cell leukemia/lymphoma, bladder cancer, blastoma, bone cancer, breast cancer, brain cancer, carcinoma, myeloid sarcoma, cervical cancer, colorectal cancer, diffuse large B-cell lymphoma, esophageal cancer, follicular lymphoma, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, liver cancer, small cell lung cancer, non-small cell lung cancer, mesothelioma, midline carcinoma, multiple myeloma, neuroblastoma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, soft tissue sarcoma, spinal tumor, small intestine cancer, stomach cancer, T-cell lymphoma, testicular cancer, thyroid cancer, throat cancer, urogenital cancer, urothelial carcinoma, uterine cancer, vaginal cancer, and Wilms' tumor in a patient in need thereof, comprising administering to the patient a compound of formula II-A:

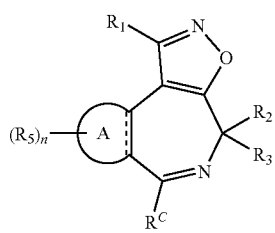

II-A or a pharmaceutically acceptable salt thereof, wherein:
$R_1$ is H, alkyl, aralkyl, aryl, heteroaryl, halo, $OR_A$, $NR_AR_B$, $S(O)_qR_A$, $C(O)R_A$, $C(O)OR_A$, $OC(O)R_A$, or $C(O)NR_AR_B$;
  each $R_A$ is independently optionally substituted alkyl, containing 0, 1, 2, or 3 heteroatoms selected from O, S, or N; optionally substituted aryl; optionally substituted heteroaryl; optionally substituted heterocyclic; optionally substituted carbocyclic; or hydrogen;
  each $R_B$ is independently optionally substituted alkyl, containing 0, 1, 2, or 3 heteroatoms selected from O, S, or N; optionally substituted aryl; optionally substituted heteroaryl; optionally substituted heterocyclic; optionally substituted carbocyclic; or hydrogen;
Ring A is benzo;
$R^C$ is a 3-7 membered saturated, partially unsaturated or completely unsaturated carbocyclic ring; a 3-7 membered aryl ring; or a 3-7 membered saturated, partially unsaturated, or completely unsaturated heterocyclic ring having 1-2 heteroatoms independently selected from nitrogen, oxygen, and sulfur, wherein $R^C$ is optionally substituted with 1-5 independently selected $R_4$;
$R_2$ and $R_3$ are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, C(O)N(R')(R"), —C(O)SR, or —(CH$_2$)$_p$R$_x$; or
$R_2$ and $R_3$ together with the atoms to which each is attached, forms an optionally substituted 3-7 membered saturated or partially unsaturated spiro-fused ring having 0-3 heteroatoms independently selected from nitrogen, oxygen, or sulfur;
each $R_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R");
each R is independently hydrogen, $C_{1-6}$ aliphatic, a 5-6 membered aryl ring, a 3-7 membered saturated, partially unsaturated, or completely unsaturated carbocyclic ring, a 7-12 membered bicyclic saturated, partially unsaturated, or completely unsaturated carbocyclic ring, a 3-7 membered monocyclic heteroaryl ring having 1-3 heteroatoms independently selected from nitrogen, oxygen, and sulfur, a 3-7 membered saturated, partially unsaturated, or completely unsaturated heterocyclic ring having 1-2 heteroatoms independently selected from nitrogen, oxygen, and sulfur, a 7-12 membered bicyclic saturated, partially unsaturated, or completely unsaturated heterocyclic ring having 1-4 heteroatoms independently selected from nitrogen, oxygen, and sulfur, or a 7-12 membered bicyclic heteroaryl ring having 1-4 heteroatoms independently selected from nitrogen, oxygen, and sulfur; each of which is optionally substituted;
each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;
each R" is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted; or
R' and R", together with the atoms to which each is attached, can form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;
each $R_4$ is independently optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl, halogen, —OR, —SR, —N(R')(R"), —CN, —NO$_2$, —C(O)R, —C(S)R, —CO$_2$R, —C(O)N(R')(R"), —C(O)SR, —C(O)C(O)R, —C(O)CH$_2$C(O)R, —C(S)N(R')(R"), —C(S)OR, —S(O)R, —SO$_2$R, —SO$_2$N(R')(R"), —N(R')C(O)R, —N(R')C(O)N(R')(R"), —N(R')C(S)N(R')(R"), —N(R')SO$_2$R, —N(R')SO$_2$N(R')(R"), —N(R')N(R')(R"), —N(R')C(=N(R'))N(R')(R"), —C=NN(R')(R"), —C=NOR, —C(=N(R'))N(R')(R"), —OC(O)R, or —OC(O)N(R')(R");
each $R_5$ is independently —R, halogen, —OR, —SR, —N(R')(R"), —CN, or —NO$_2$;
n is 0-5;
q is 0, 1, or 2; and
p is 1-6.

2. The method according to claim 1, wherein $R^C$ is phenyl or a 4-7 membered saturated or partially unsaturated heterocyclic ring having 1-2 heteroatoms independently selected from nitrogen, oxygen, and sulfur, wherein $R^C$ is optionally substituted with 1-5 independently selected $R_4$.

3. The method according to claim 1, wherein $R_1$ is halo, alkyl, aralkyl, aryl, or heteroaryl.

4. The method according to claim 3, wherein $R_1$ is methyl, ethyl, propyl, i-propyl, butyl, s-butyl, t-butyl, pentyl, hexyl, or heptyl.

5. The method according to claim 1, wherein $R_2$ is H, methyl, ethyl, propyl, i-propyl, butyl, s-butyl, pentyl, hexyl, —OR, —SR, —CN, —N(R')(R''), —C(O)R, —C(S)R, —CO$_2$R, —C(O)N(R')(R''), —C(O)SR, or —(CH$_2$)$_p$R$_x$.

6. The method according to claim 5, wherein $R_2$ is H or —(CH$_2$)$_p$R$_x$.

7. The method according to claim 6, wherein $R_x$ is —N(R')(R''), —C(O)R, —C(S)R, —CO$_2$R, —C(O)N(R')(R''), —C(S)N(R')(R''), —S(O)R, —SO$_2$R, —SO$_2$N(R')(R''), —N(R')C(O)R, —N(R')SO$_2$R, —OC(O)R, —OC(O)N(R')(R''), methyl, ethyl, propyl, i-propyl, butyl, s-butyl, pentyl or hexyl.

8. The method according to claim 1, wherein $R_3$ is H, methyl, ethyl, propyl, i-propyl, butyl, s-butyl, pentyl, hexyl, —OR, —SR, —CN, —N(R')(R''), —C(O)R, —C(S)R, —CO$_2$R, —C(O)N(R')(R''), —C(O)SR, or —(CH$_2$)$_p$R$_x$.

9. The method according to claim 8, wherein $R_3$ is H or —(CH$_2$)$_p$R$_x$.

10. The method according to claim 9, wherein $R_x$ is —N(R')(R''), —C(O)R, —C(S)R, —CO$_2$R, —C(O)N(R')(R''), —C(S)N(R')(R''), —S(O)R, —SO$_2$R, —SO$_2$N(R')(R''), —N(R')C(O)R, —N(R')SO$_2$R, —OC(O)R, —OC(O)N(R')(R''), methyl, ethyl, propyl, i-propyl, butyl, s-butyl, pentyl or hexyl.

11. The method according to claim 1, wherein the compound is selected from

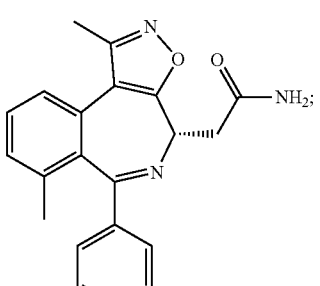

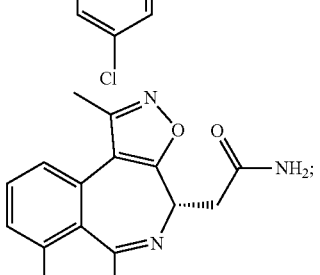

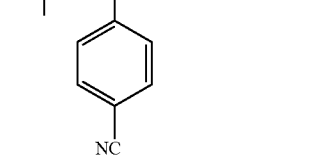

-continued

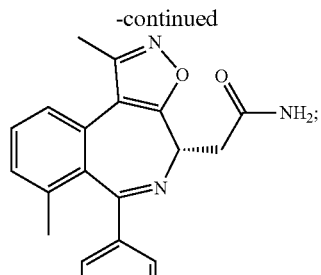

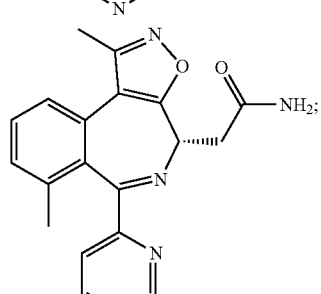

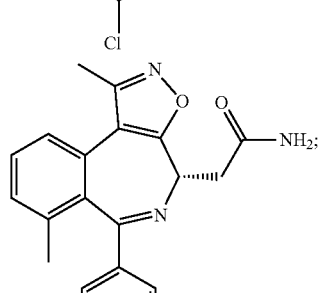

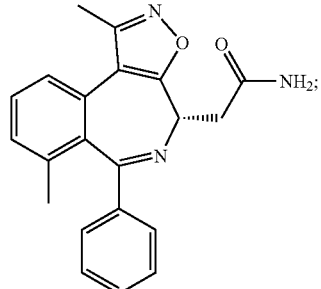

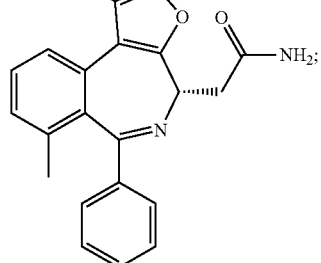

215
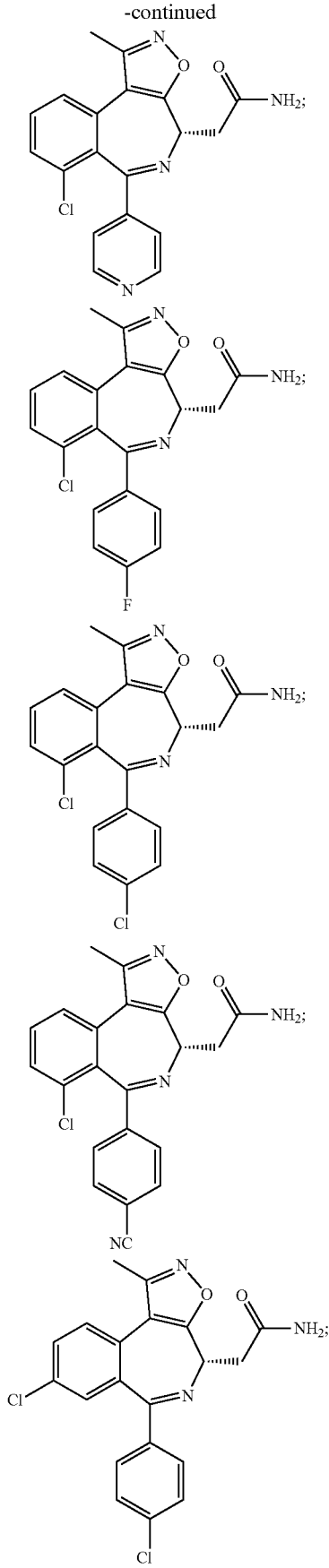
216
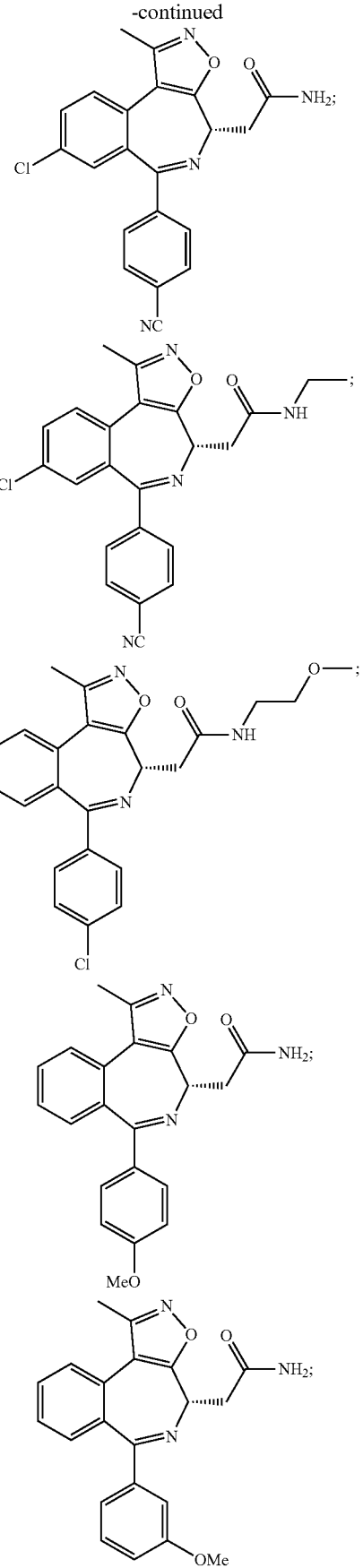

-continued
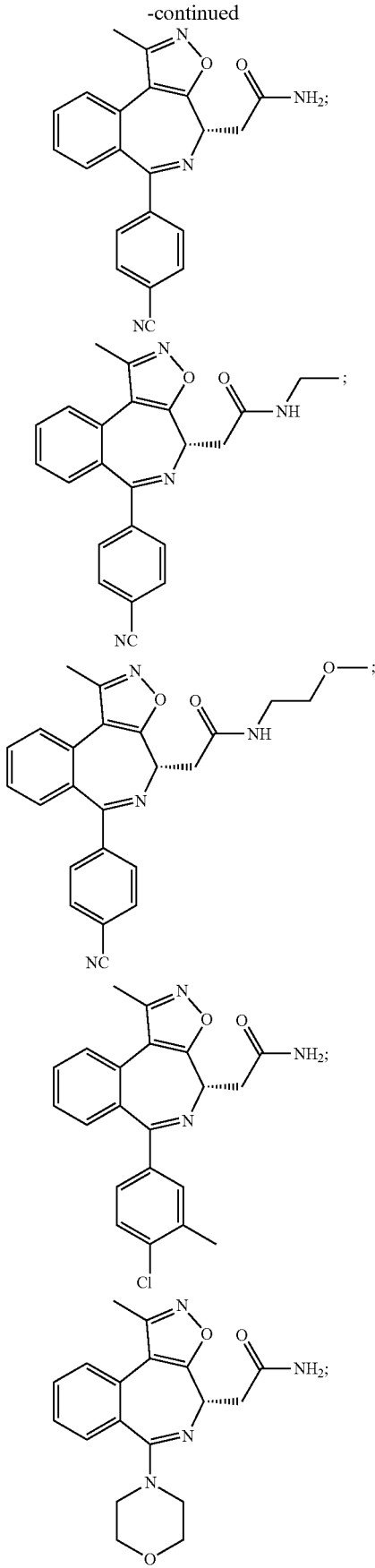
-continued
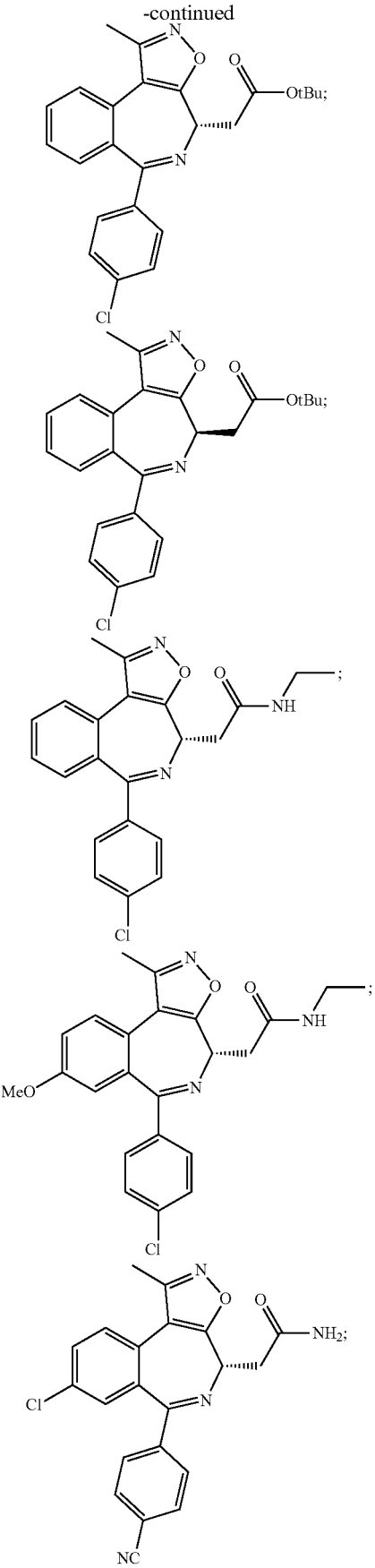

-continued
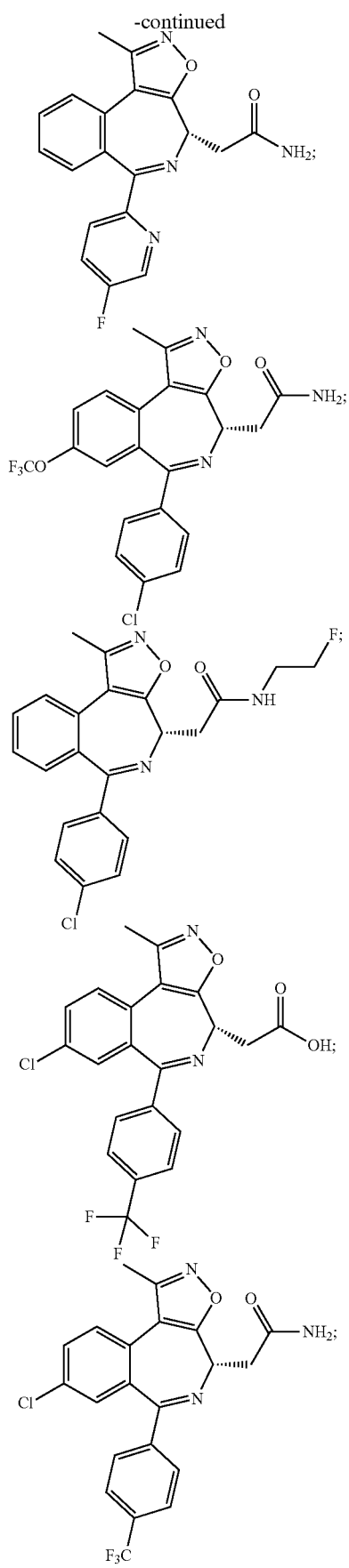
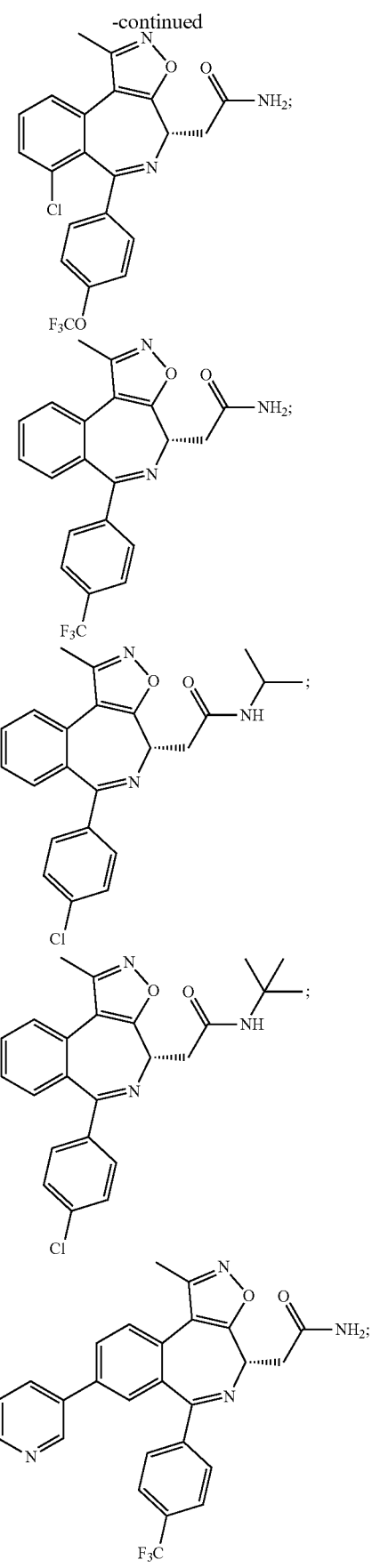

221
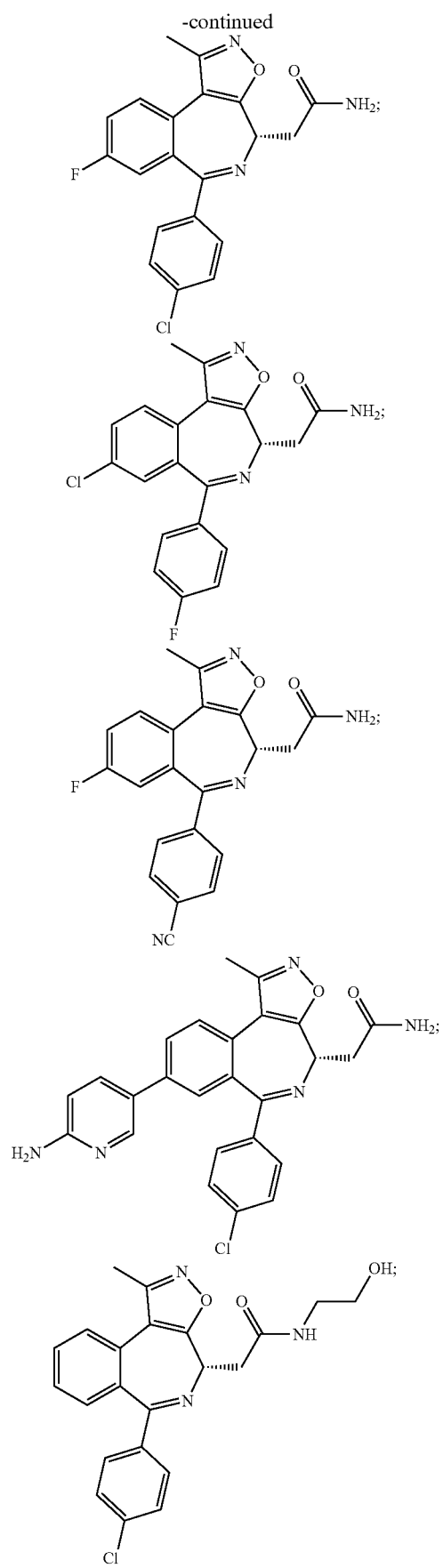
222
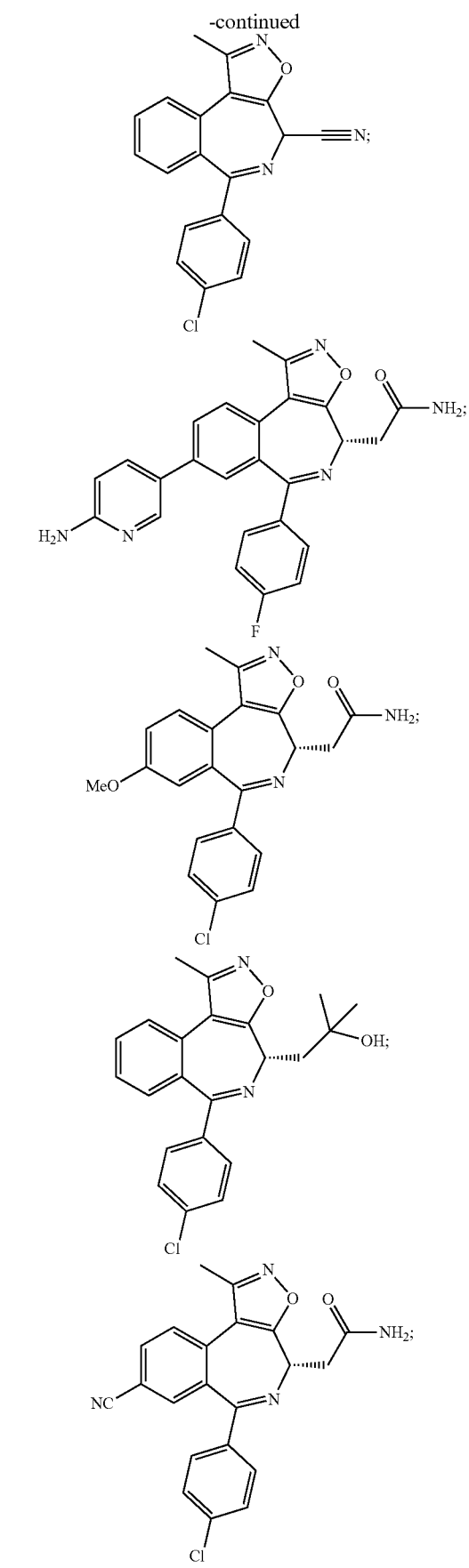

223
-continued
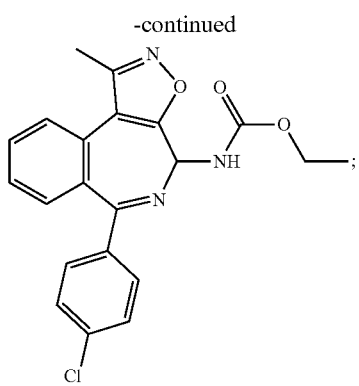
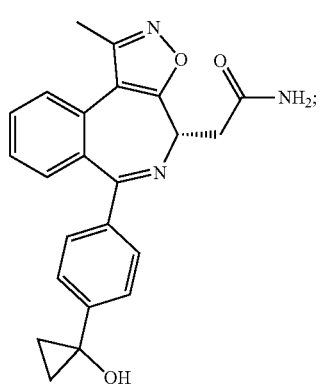
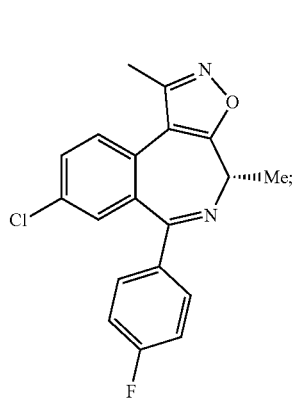
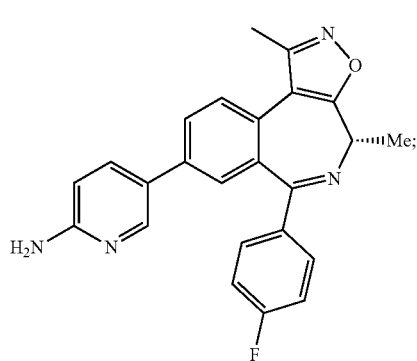
224
-continued
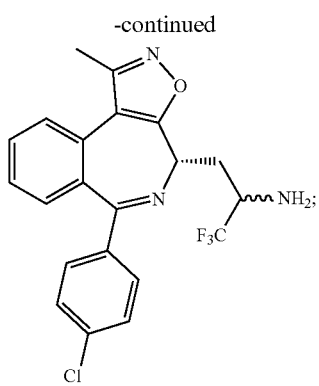
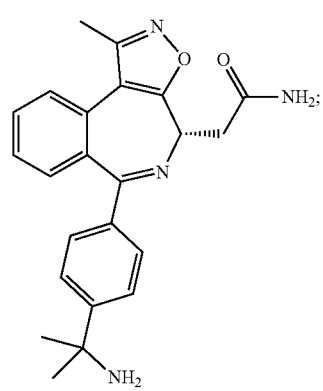
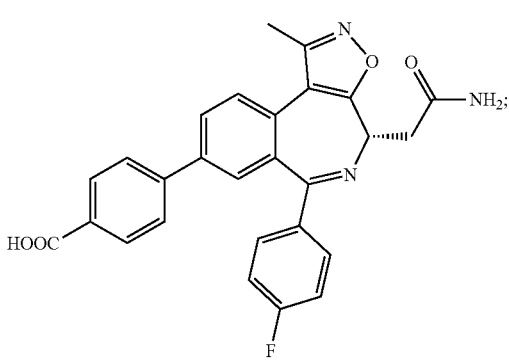
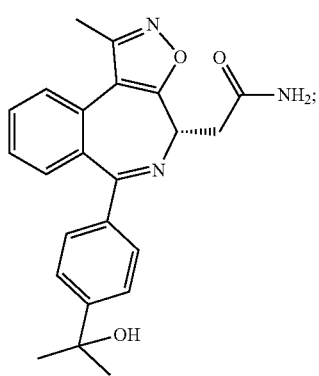

-continued
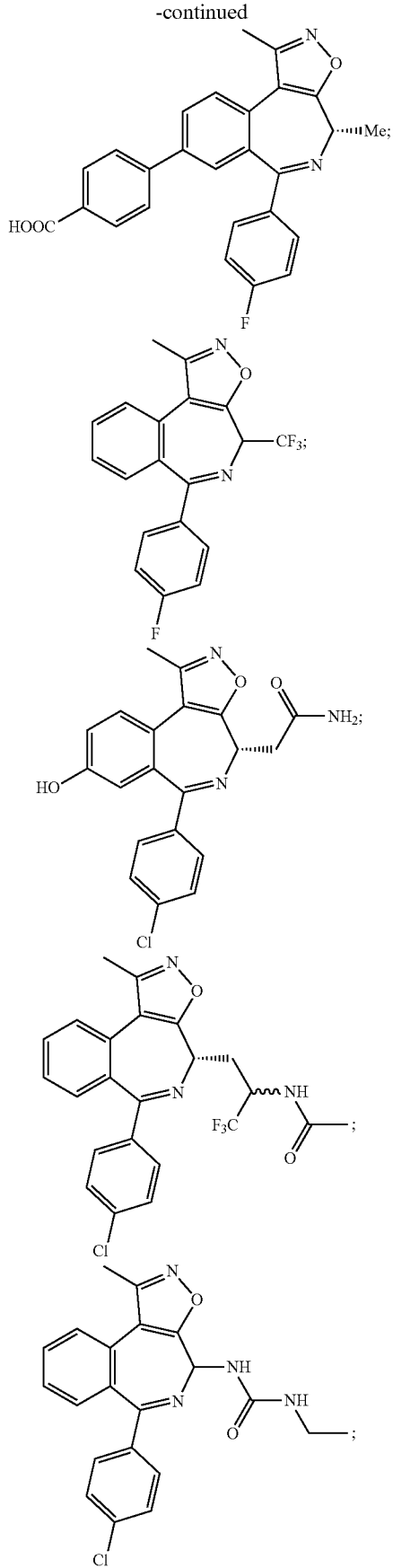
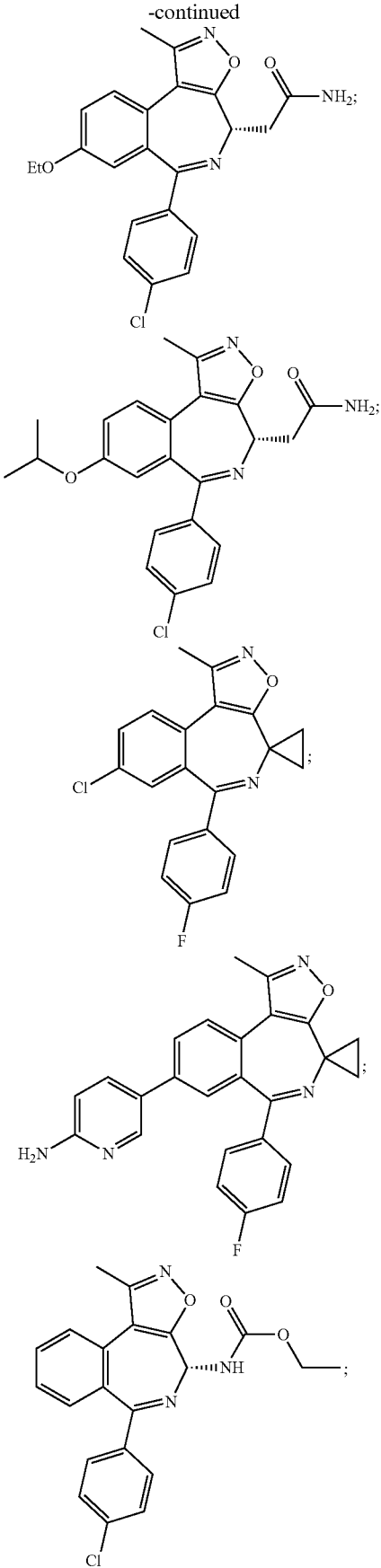

227
-continued

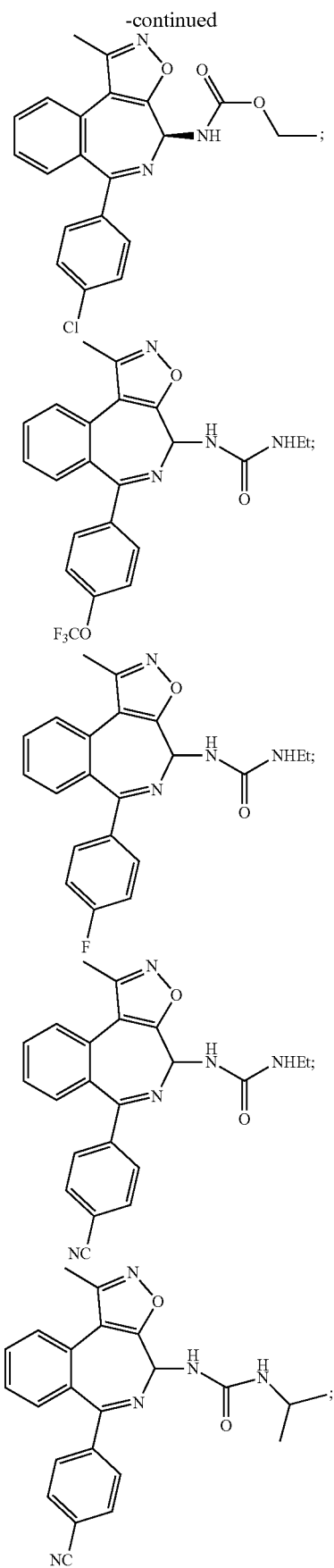

228
-continued

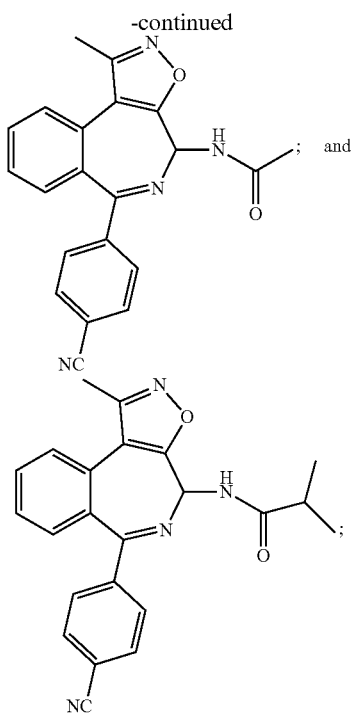

or a pharmaceutically acceptable salt thereof.

12. The method according to claim 1, wherein the cancer is diffuse large B-cell lymphoma, Hodgkin's lymphoma, non-Hodgkin's lymphoma, multiple myeloma, primary central nervous system lymphoma, or T-cell lymphoma.

13. A method of treating a cancer selected from acute myelogenous leukemia, adenocarcinoma, adenoid cystic carcinoma, adult T-cell leukemia/lymphoma, bladder cancer, blastoma, bone cancer, breast cancer, Burkitt's lymphoma, brain cancer, carcinoma, myeloid sarcoma, cervical cancer, colorectal cancer, diffuse large B-cell lymphoma, Hodgkin's lymphoma, non-Hodgkin's lymphoma, T-cell lymphoma, primary central nervous system lymphoma, esophageal cancer, follicular lymphoma, gastrointestinal cancer, glioblastoma multiforme, glioma, gallbladder cancer, gastric cancer, head and neck cancer, intestinal cancer, kidney cancer, laryngeal cancer, leukemia, lung cancer, liver cancer, small cell lung cancer, non-small cell lung cancer, mesothelioma, midline carcinoma, multiple myeloma, neuroblastoma, ocular cancer, optic nerve tumor, oral cancer, ovarian cancer, pituitary tumor, prostate cancer, pancreatic cancer, pharyngeal cancer, renal cell carcinoma, rectal cancer, sarcoma, skin cancer, soft tissue sarcoma, spinal tumor, small intestine cancer, stomach cancer, testicular cancer, thyroid cancer, throat cancer, urogenital cancer, urothelial carcinoma, uterine cancer, vaginal cancer, and Wilms' tumor, in a patient in need thereof, comprising administering to the patient a compound represented by the following structural formula:

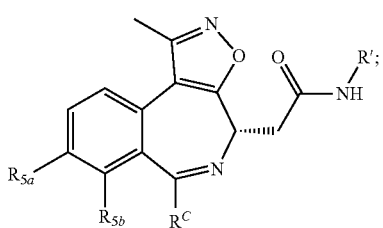

or a pharmaceutically acceptable salt thereof, wherein:
$R_{5a}$ is selected from hydrogen, halo, and alkoxy;
$R_{5b}$ is selected from hydrogen, halo, and alkyl;
$R^C$ is selected from phenyl, heteroaryl, and saturated heterocyclyl, wherein the group represented by $R^C$ is optionally substituted with 1 to 2 substituents independently selected from halo, —CN, alkyl, alkoxy, haloalkoxy, haloalkyl, and carbamyl; and
R' is selected from hydrogen, alkyl, and alkoxyalkyl.

14. The method of claim 13, wherein $R_{5a}$ is selected from hydrogen, chloro, and methoxy.

15. The method of claim 13, wherein $R_{5b}$ is selected from hydrogen, chloro, and methyl.

16. The method of claim 13, wherein $R_{5a}$ and $R_{5b}$ are simultaneously hydrogen.

17. The method of claim 13, wherein $R^C$ is selected from 4-chlorophenyl, 4-cyanophenyl, 4-fluorophenyl, pyridin-4-yl, 4-trifluoromethylphenyl, 5-chloropyridin-2-yl, 4-carbamylphenyl, 3-methoxyphenyl, 4-methoxyphenyl, 4-trifluoromethoxyphenyl, 2-methyl-4-chlorophenyl, and morpholin-4-yl.

18. The method of claim 13, wherein R' is selected from hydrogen, ethyl, and 2-methoxyethyl.

19. The method of claim 13, wherein the cancer is acute myelogenous leukemia, diffuse large B-cell lymphoma, Hodgkin's lymphoma, non-Hodgkin's lymphoma, T-cell lymphoma, primary central nervous system lymphoma, or multiple myeloma.

20. A method of treating a cancer selected from acute myelogenous leukemia, adenocarcinoma, adenoid cystic carcinoma, adult T-cell leukemia/lymphoma, bladder cancer, blastoma, bone cancer, breast cancer, Burkitt's lymphoma, brain cancer, carcinoma, myeloid sarcoma, cervical cancer, colorectal cancer, diffuse large B-cell lymphoma, Hodgkin's lymphoma, non-Hodgkin's lymphoma, T-cell lymphoma, primary central nervous system lymphoma, esophageal cancer, follicular lymphoma, gastrointestinal cancer, glioblastoma multiforme, glioma, gallbladder cancer, gastric cancer, head and neck cancer, intestinal cancer, kidney cancer, laryngeal cancer, leukemia, lung cancer, liver cancer, small cell lung cancer, non-small cell lung cancer, mesothelioma, midline carcinoma, multiple myeloma, neuroblastoma, ocular cancer, optic nerve tumor, oral cancer, ovarian cancer, pituitary tumor, prostate cancer, pancreatic cancer, pharyngeal cancer, renal cell carcinoma, rectal cancer, sarcoma, skin cancer, soft tissue sarcoma, spinal tumor, small intestine cancer, stomach cancer, testicular cancer, thyroid cancer, throat cancer, urogenital cancer, urothelial carcinoma, uterine cancer, vaginal cancer, and Wilms' tumor, in a patient in need thereof, comprising administering to the patient a compound represented by the following structural formula:

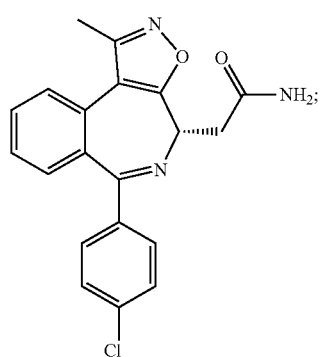 [SMILES: Cc1noc2c1-c1ccccc1C(c1ccc(Cl)cc1)=N[C@H]2CC(N)=O]

or a pharmaceutically acceptable salt thereof.

21. The method of claim 20, wherein the cancer is acute myelogenous leukemia, diffuse large B-cell lymphoma, Hodgkin's lymphoma, non-Hodgkin's lymphoma, T-cell lymphoma, primary central nervous system lymphoma, or multiple myeloma.

* * * * *